US012258631B2

(12) United States Patent
Stengel et al.

(10) Patent No.: US 12,258,631 B2
(45) Date of Patent: *Mar. 25, 2025

(54) RNA AND DNA ANALYSIS USING ENGINEERED SURFACES

(71) Applicant: ALIDA BIOSCIENCES, INC., San Diego, CA (US)

(72) Inventors: Gudrun Stengel, San Diego, CA (US); Hua Yu, San Diego, CA (US); Andrew Price, San Diego, CA (US); Jerome Santos, San Diego, CA (US); Yu-Hsien Hwang-Fu, San Diego, CA (US); Byron Purse, San Diego, CA (US)

(73) Assignee: ALIDA BIOSCIENCES INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/343,028

(22) Filed: Jun. 28, 2023

(65) Prior Publication Data

US 2023/0416828 A1 Dec. 28, 2023

Related U.S. Application Data

(63) Continuation of application No. PCT/US2022/080452, filed on Nov. 23, 2022.

(60) Provisional application No. 63/388,036, filed on Jul. 11, 2022, provisional application No. 63/282,808, filed on Nov. 24, 2021.

(51) Int. Cl.
*C12Q 1/6883* (2018.01)
*C12N 9/22* (2006.01)
*C12N 15/10* (2006.01)
*C12Q 1/48* (2006.01)
*C12Q 1/6806* (2018.01)
*C12Q 1/6853* (2018.01)
*C12Q 1/6874* (2018.01)

(52) U.S. Cl.
CPC .......... *C12Q 1/6883* (2013.01); *C12N 9/22* (2013.01); *C12N 15/1065* (2013.01); *C12Q 1/485* (2013.01); *C12Q 1/6806* (2013.01); *C12Q 1/6853* (2013.01); *C12Q 1/6874* (2013.01)

(58) Field of Classification Search
CPC .............................. C12Q 1/68; C12N 15/1065
See application file for complete search history.

(56) References Cited

U.S. PATENT DOCUMENTS

| 5,683,874 | A | * | 11/1997 | Kool | ................... | C12N 15/1135 536/23.1 |
| 5,731,171 | A | * | 3/1998 | Bohlander | ............. | C12Q 1/686 435/6.14 |
| 11,773,425 | B2 | * | 10/2023 | Stengel | ................ | C12Q 1/6804 435/6.1 |
| 2002/0192787 | A1 | | 12/2002 | Hillman | | |
| 2003/0186344 | A1 | * | 10/2003 | Holmes | .............. | G01N 33/5308 435/7.92 |
| 2005/0136414 | A1 | | 6/2005 | Gunderson | | |
| 2006/0008807 | A1 | * | 1/2006 | O'Hara | .............. | C12N 15/1003 435/6.14 |
| 2006/0204988 | A1 | * | 9/2006 | Fassbender | .......... | C12Q 1/6827 435/6.12 |
| 2006/0276426 | A1 | * | 12/2006 | Auwerx | ................. | G01N 33/74 435/254.2 |
| 2008/0076156 | A1 | * | 3/2008 | Inouye | ................... | C07K 14/31 435/69.7 |
| 2008/0241818 | A1 | * | 10/2008 | Lappalainen | .......... | C12Q 1/705 435/5 |
| 2009/0181373 | A1 | * | 7/2009 | Li | ........................ | C12Q 1/6853 435/6.12 |
| 2010/0081134 | A1 | * | 4/2010 | Mirkin | ................. | C12Q 1/6816 435/7.1 |

(Continued)

FOREIGN PATENT DOCUMENTS

| WO | 2018204854 A1 | 11/2018 |
| WO | 2020072829 A2 | 4/2020 |
| WO | 2022115608 A1 | 6/2022 |

OTHER PUBLICATIONS

Arul et al, Sample multiplexing strategies in quantitative proteomics. Analytical Chemistry 91:178-189 (Year: 2019).*
Chiu et al.Antibody structure and function: the basis for engineering therapeutics Antibodies 8, 55 antib8040055 (Year: 2019).*
Feederle et al., Antibodies specific for nucleic acid modifications. RNA Biology14(9): 1089-1098 (Year: 2017).*
Kando et al.Journal of Nucleic Acids Article ID 543531 (7 pgs. ) (Year: 2010).*
Luo et al., DNA N6-methyladenine: a new epigenetic mark in eukaryotes? Nature Review | Molecular Cell Biology 16 : 705 (Year: 2015).*

(Continued)

*Primary Examiner* — Ethan C Whisenant
(74) *Attorney, Agent, or Firm* — Rothwell, Figg, Ernst and Manbeck, P.C.

(57) ABSTRACT

Provided herein are compositions and methods for the multiplexed profiling of RNA and DNA modifications across transcriptomes and genomes, respectively. The methods combine molecular recognition of non-canonical features (e.g., base modifications, backbone modifications, lesions, and/or structural elements) of a target nucleic acid with a step of writing the information from this recognition event into the neighboring genetic sequence of the target nucleic acid using a barcode. The resultant barcoded nucleic acids are then converted into sequencing libraries and read by DNA/RNA sequencing methods. This step reveals the sequence of the barcode, which is correlated with the non-canonical feature in the target nucleic acid(s). The high throughput profiling methods described herein allow for identification and/or localization of one or more modifications in a target nucleic acid. The methods also allow for identification of the nature and location of several or all DNA/RNA modifications in parallel.

30 Claims, 57 Drawing Sheets

Specification includes a Sequence Listing.

(56) References Cited

U.S. PATENT DOCUMENTS

| | | | |
|---|---|---|---|
| 2013/0115272 A1* | 5/2013 | de Fougerolles | A61K 48/0066 424/490 |
| 2013/0344508 A1 | 12/2013 | Schwartz | |
| 2014/0004569 A1* | 1/2014 | Lambowitz | C12P 19/34 435/91.21 |
| 2015/0299784 A1* | 10/2015 | Fan | C12N 15/1075 506/4 |
| 2015/0376608 A1* | 12/2015 | Kaper | C12N 15/1093 506/26 |
| 2016/0024160 A1* | 1/2016 | Tota | C07K 14/43595 536/23.5 |
| 2017/0067905 A1 | 3/2017 | Wang | |
| 2018/0044724 A1* | 2/2018 | Fan | C12Q 1/6855 |
| 2019/0376929 A1 | 12/2019 | Adelman | |
| 2020/0102604 A1 | 4/2020 | Tosato | |
| 2020/0131567 A1* | 4/2020 | Kennedy | C12N 15/10 |
| 2020/0355673 A1 | 11/2020 | Moellering | |
| 2020/0377875 A1* | 12/2020 | Ares | C12Y 207/07052 |
| 2020/0399679 A1* | 12/2020 | Ellington | C12N 11/12 |
| 2021/0024977 A1* | 1/2021 | Song | C12N 9/22 |
| 2021/0054018 A1* | 2/2021 | Murray | C12P 19/30 |
| 2021/0164021 A1* | 6/2021 | Hogers | C12Q 1/6806 |
| 2021/0164992 A1* | 6/2021 | Mohr | G01N 33/6866 |
| 2021/0340596 A1* | 11/2021 | Meltzer | G01N 33/54313 |
| 2021/0355483 A1* | 11/2021 | Chee | G01N 33/68 |
| 2022/0064631 A1* | 3/2022 | Barna | C12N 15/1093 |
| 2022/0111019 A1 | 4/2022 | Kelly | |
| 2022/0298542 A1 | 9/2022 | Stengel | |
| 2022/0298543 A1 | 9/2022 | Stengel | |
| 2023/0121437 A1 | 4/2023 | Gao | |
| 2023/0133188 A1* | 5/2023 | Frischmuth | A61K 39/12 424/185.1 |
| 2023/0265484 A1* | 8/2023 | Kirschner | C40B 20/04 435/6.1 |
| 2023/0295723 A1* | 9/2023 | Fan | C12Q 1/6806 |
| 2023/0332213 A1* | 10/2023 | Henikoff | C12N 15/1082 |
| 2023/0348910 A1* | 11/2023 | Yang | C12N 15/11 |

OTHER PUBLICATIONS

Loomis et al., In Vitro Transcribed mRNA Vaccines with Programmable Stimulation of Innate Immunity. Bioconjugate Chemistry 29:3072 (Year: 2018).*

Matsuzawa et al., Development and validation of monoclonal antibodies against N6-methyladenosine for the detection of RNA modifications. PLOS one (Oct. 2019) 0223197, 15 pgs (Year: 2019).*

Meyer, KD., Meyer DART-seq. Nature Methods 16:1275-1280 (Year: 2019).*

Mora et al., Next generation ligand binding assays-review of emerging technologies' capabilities to enhance throughput and multiplexing. The AAPS Journal 16(6) :1175 (Year: 2014).*

Reddington et al., Secrets of a covalent interaction for biomaterials and biotechnology: SpyTag and SpyCatcher. Current Opinions in Chemical Biology (Year: 2015).*

Shao et al., NAD tagSeq for transcriptome-wide identification and characterization of NAD+-capped RNAs. Nature Protocols 15 :2813-2836 Year: 2020).*

Shendure et al., DNA sequencing at 40 : past, present and future. Nature 550:345-353 (Year: 2019).*

Xu et al. Structural basis for selective binding of m6A RNA by the YTHDC1 Yth domain. Nature Chemical Biology 10:927 (Year: 2014).*

Kaya-Okur et al., Cut&Tag for efficient epigenomic profiling of small samples and single cells. Nature Communications 12:795 (Year: 2019).*

Hatice S. Kaya-Okur et al: "Cut&Tag for efficient epigenomic profiling of small samples and single cells", Nature Communications, vol. 10, No. 1, (2019), 10 pgs.

Ay-Berthomieu, "What is Cut&Tag and How Does it Work? "Comprehensive Guide to Understanding and Using Cut&Tag Assays, Nov. 24, 2020, XP093029939, Retrieved from the Internet: URL:https://www.activemotif.com/blog-cut-t ag [retrieved on Mar. 8, 2023], 16 pgs.

International Search Report issue in PCT/US2022/080452, dated Mar. 23, 2023, 4 pgs.

Stoilov et al., "YTH: a new domain in nuclear proteins" Trends in Biomedical Sciences 27(10) 495 (Year: 2002).

Reznikoff, William. "Transposon Tn5" Annual Reviews in Genetics 42:269 (Year: 2008).

Kramer et al., "Photo-cross-linking and high-resolution mass spectrometry for assignment of RNA-binding sites in RNA-binding proteins" Nature Methods 11(10):1064 (Year: 2014).

Iglesias et al., "Ribosomal RNA N-glycosylase Activity Assay of Ribosome-inactivating Proteins" bio-protocol 7(06): p. 1 (Year: 2017).

Fossat et al., "C to U RNA editing mediated by APOBEC1 requires RNA-binding protein RBM47" EMBO Reports 15(8) (Year: 2018).

Patil et al., "Reading m6A in the Transcriptome: m6A-Binding Proteins" in Cell Biology 28(2):113 (Year: 2018).

Zhang et al., "Single-base mapping of m6A by an antibody-independent method" Science Advances 5: eaaz0250 (Year: 2019).

Office Action issued in U.S. Appl. No. 17/706,470 dated Dec. 15, 2022, 16 pgs.

Meyer et al., "Comprehensive Analysis of mRNA Methylation Reveals Enrichment in 3'UTRs and near Stop Condons", Cell, 149 (7), 2012, 1635-1646.

Saini et al.,"When secondary comes first—The importance of non-canonical DNA structures", Biochimie 95: pp. 117-123 (Year: 2013).

Suseela et al., "Far-red fluorescent probes for canonical and non• canonical nucleic acid structures: current progress and future implications", Chem. Soc. Rev. 47:pp. 1098-1131 (Year: 2018).

Iyer et al., "Barcoded oligonucleotides ligated on RNA amplified for multiplex and parallel in-situ analyses" bioRxiv preprint posted online on Mar. 20, 2018 (Year: 2018), 49 pgs.

Jin et al., "Sensitive and specific miRNA detection method using SplintR ligase", Nucleic Acids Research 44(13) : e116 (Year: 2016), 14 pgs.

Kingsmore, SF, "Multiplexed protein measurement: technologies and applications of protein and antibody arrays", Nature Reviews Drug Discovery 5: pp. 310-321 (Year: 2006).

Kubo et al., "A Novel, Sensitive, and Specific Assay for Abasic Sites, the Most Commonly Produced DNA Lesion" Biochemistry 31: pp. 3703-3708 (Year: 1992).

Kumar, et al. "Quantitative Multiplexed ChIP Reveals Global Alterations that Shape Promoter Bivalency in Ground State Embryonic Stem Cells", (2019), Cell Reports 28, 3274-3284.

Office Action issued in U.S. Appl. No. 17/706,493 dated Dec. 22, 2022, 18 pgs.

Office Action dated Mar. 12, 2024 issued in corresponding U.S. Appl. No. 18/343,014. (19 pages).

Weiguo Cao; "Endonuclease V: an unusual enzyme for repair of DNA deamination"; Cellular and Molecular Life Sciences; 2013; vol. 70, pp. 3145-3156. (12 pages)

Morita et al; "Human endonuclease V is a ribonuclease specific for inosine-containing RNA"; Nature Communications; Aug. 5, 2013; pp. 1-10. (10 pages).

Final Office Action dated Jul. 25, 2024 issued in related U.S. Appl. No. 18/343,014. (26 pages).

Song et al., "An all-to-all approach to the identification of sequence-specific readers for epigenetic DNA modifications on cytosine", Nature Communications, 12, 795, 2021, pp. 1-16 (16 pages).

Blanc et al., "Use of in vivo biotinylated GST fusion proteins to select recombinant antibodies", ALTEX-Alternatives to animal experimentation, 31(1), 2014, pp. 37-42 (6 pages).

Otieno et al., "Bioconjugation of Antibodies and Enzyme Labels onto Magnetic Beads", Methods in Enzymology, vol. 571, 2016, pp. 135-150 (16 pages).

Hutsell et al., "High-affinity immobilization of proteins using biotin- and GST-based coupling strategies", Methods Mol Biol., NIH Public Access, 627:75-90, 2010 (16 pages).

(56) References Cited

OTHER PUBLICATIONS

Fenstermaker et al., "A Proximity Ligation-Based Method to Detect RNA-DNA Association", Methods Mol Biol., HHS Public Access, 2008: 121-129, 2019 (9 pages).

* cited by examiner

Single-Stranded Ligation
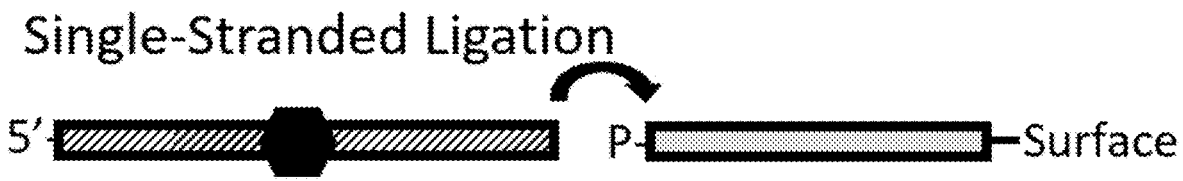
FIG. 2A
Splinted Ligation
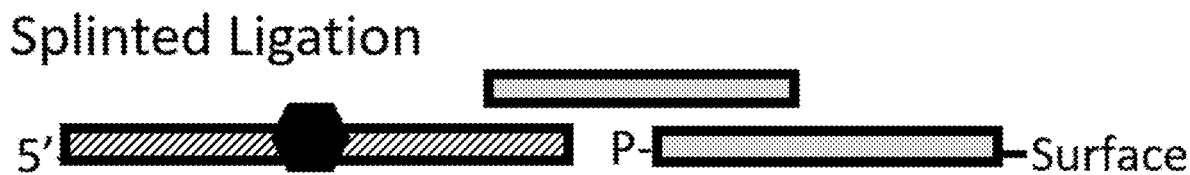
FIG. 2B
Splinted Extension
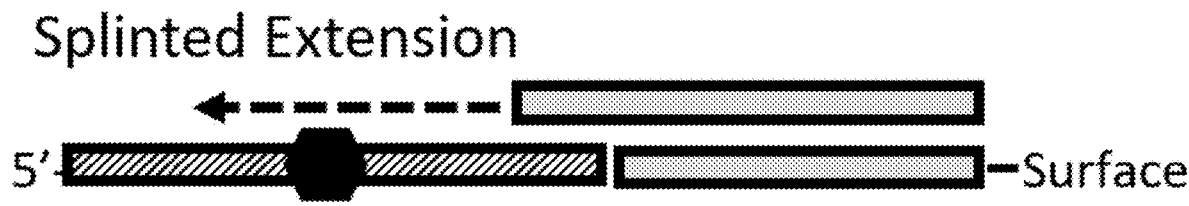
FIG. 2C
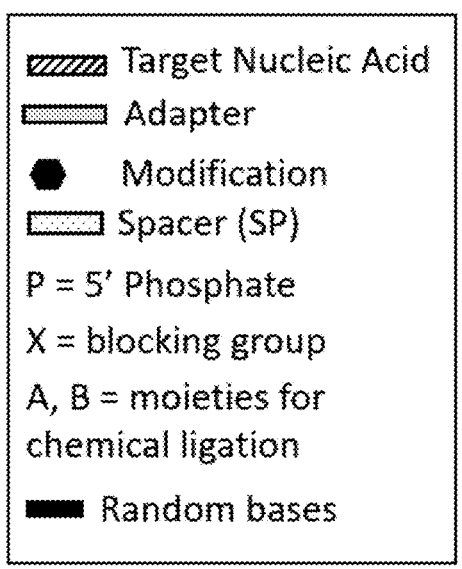

Chemical ligation

Bidirectional primer extension

Random priming

The barcode identifies the type of RNA modification and localizes it to the transcript. The base resolution corresponds to the length of the RNA fragment.

Legend

- Universal Forward Primer (UFP)
- Universal Reverse Primer (URP)
- Modification encoding barcode (MBC)
- Unique Molecular Identifier (UMI)
- Cleavage Site (CLS)
- Spacer (SP)

FIG. 12A Type A: Universal cap

UFP or URP

FIG. 12B Type B: Adapter for library preparation by circularization

    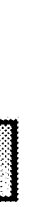

UFP   CLS   URP   UMI   MBC

FIG. 12C Type C: Adapter for barcode transfer by ligation reactions

UFP or  UMI  MBC
URP

FIG. 12D   Type D: Adapter for barcode transfer by primer extension
For a single barcoding event
SP   MBC   UMI   UFP
For multiple barcoding events
SP1   MBC   UMI   SP2

Tn5ME-B

5'-GTCTCGTGGGCTCGGAGATGTGTATAAGAGACAG
(SEQ ID NO: 14)     3'-TCTACACATATTCTCTGTC
                         ME  (SEQ ID NO: 15)

ME  (SEQ ID NO: 16)
CTGTCTCTTATACACATCT
GACAGAGAATATGTGTAGACTGCGACGGCTGCT-5'
                         (SEQ ID NO: 17)
Tn5ME-A

FIG. 13

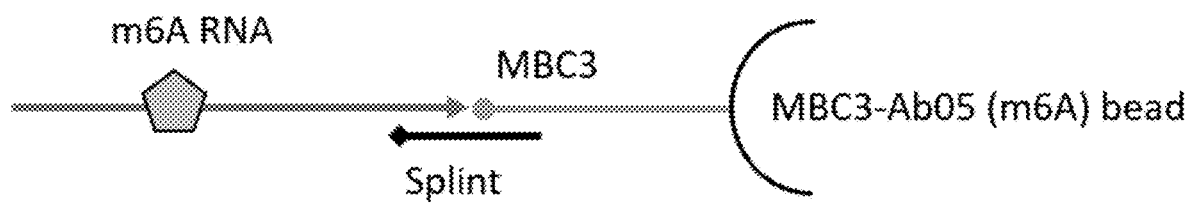
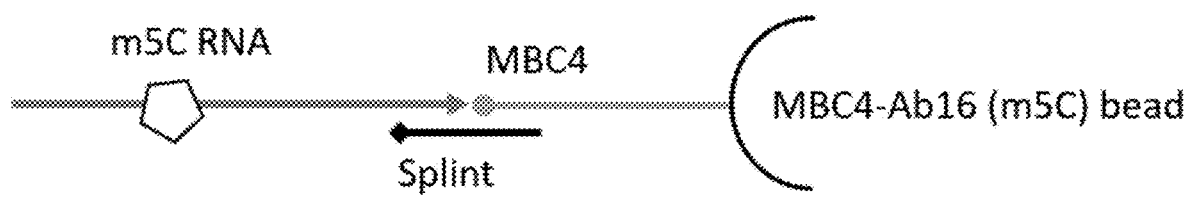
Splints
7-6 MBC3   AAAGCTGCACTCA/3SpC3/ (SEQ ID NO: 18)
7-6 MBC4   ATATAGGCACTCA/3SpC3/ (SEQ ID NO: 19)
7-3 MBC3   AAAGCTGCAC/3SpC3/ (SEQ ID NO: 20)
7-3 MBC4   ATATAGGCAC/3SpC3/ (SEQ ID NO: 21)
FIG. 20A

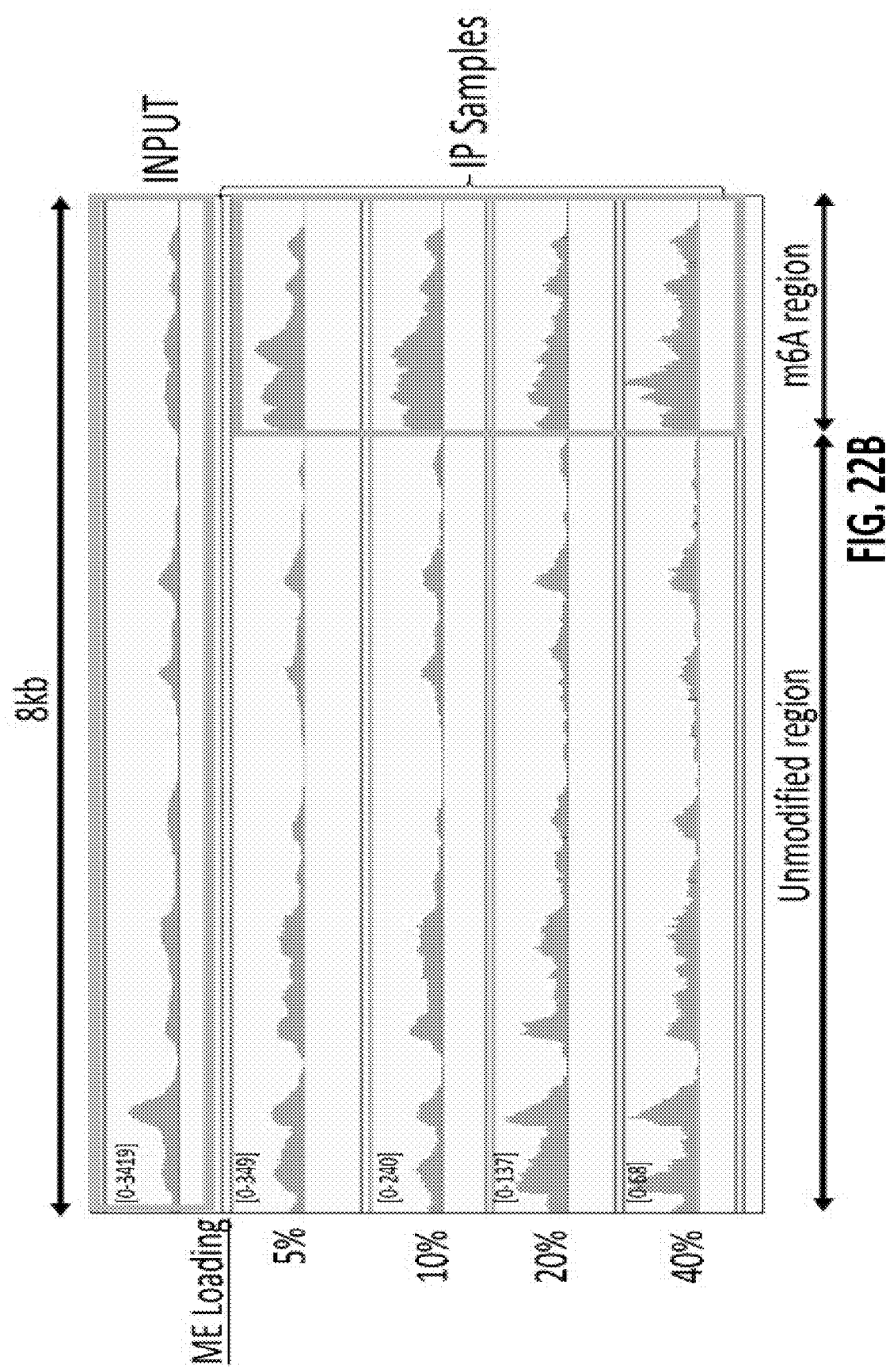

SEQUENCE LISTING

```
Sequence total quantity: 52
SEQ ID NO: 1            moltype = DNA   length = 45
FEATURE                 Location/Qualifiers
source                  1..45
                        mol_type = other DNA
                        organism = synthetic construct
modified_base           38
                        mod_base = OTHER
                        note = Uracil
SEQUENCE: 1
aattagtnnn agatcggaag agcacacgtc tatatattat atata              45
```

```
SEQ ID NO: 2            moltype = DNA   length = 53
FEATURE                 Location/Qualifiers
source                  1..53
                        mol_type = other DNA
                        organism = synthetic construct
modified_base           7
                        mod_base = OTHER
                        note = Uracil
SEQUENCE: 2
atatattata taagacgt gtgctcttcc gatctnnnca ctgatcactc agt          53

SEQ ID NO: 3            moltype = DNA   length = 45
FEATURE                 Location/Qualifiers
source                  1..45
                        mol_type = other DNA
                        organism = synthetic construct
modified_base           38
                        mod_base = OTHER
                        note = Uracil
SEQUENCE: 3
atcagtgnnn agatcggaag agcacacgtc tatatattat atata                 45

SEQ ID NO: 4            moltype = DNA   length = 45
FEATURE                 Location/Qualifiers
source                  1..45
                        mol_type = other DNA
                        organism = synthetic construct
modified_base           38
                        mod_base = OTHER
                        note = Uracil
SEQUENCE: 4
aaagctgnnn agatcggaag agcacacgtc tatatattat atata                 45

SEQ ID NO: 5            moltype = DNA   length = 45
FEATURE                 Location/Qualifiers
source                  1..45
                        mol_type = other DNA
                        organism = synthetic construct
modified_base           38
                        mod_base = OTHER
                        note = Uracil
SEQUENCE: 5
atataggnnn agatcggaag agcacacgtc tatatattat atata                 45

SEQ ID NO: 6            moltype = DNA   length = 20
FEATURE                 Location/Qualifiers
misc_feature            18..20
                        note = rna
source                  1..20
                        mol_type = other DNA
                        organism = synthetic construct
misc_feature            1..17
                        note = dna
SEQUENCE: 6
agacgtgtgc tcttccgggg                                             20

SEQ ID NO: 7            moltype = DNA   length = 19
FEATURE                 Location/Qualifiers
source                  1..19
                        mol_type = other DNA
                        organism = synthetic construct
SEQUENCE: 7
ctgtctctta tacacatct                                              19

SEQ ID NO: 8            moltype = DNA   length = 70
FEATURE                 Location/Qualifiers
source                  1..70
                        mol_type = other DNA
                        organism = synthetic construct
SEQUENCE: 8
aatgatacgg cgaccaccga gatctacacn nnnnnnntcg tcggcagcgt cagatgtgta  60
taagagacag                                                        70

SEQ ID NO: 9            moltype = DNA   length = 24
FEATURE                 Location/Qualifiers
source                  1..24
                        mol_type = other DNA
                        organism = synthetic construct
```

| | | |
|---|---|---|
| misc_feature | 1..21 | |
| | note = dna | |
| misc_feature | 22..24 | |
| | note = rna | |

SEQUENCE: 9
agacgtgtgc tcttccgatc tggg                                        24

| | | |
|---|---|---|
| SEQ ID NO: 10 | moltype = AA   length = 139 | |
| FEATURE | Location/Qualifiers | |
| source | 1..139 | |
| | mol_type = protein | |
| | organism = synthetic construct | |

SEQUENCE: 10
MSYYHHHHHH DYDIPTTENL YFQGAMVDTL SGLSSEQGQS GDMTIEEDSA THIKFSKRDE    60
DGKELAGATM ELRDSSGKTI STWISDGQVK DFYLYPGKYT FVETAAPDGY EVATAITFTV   120
NEQGQVTVNG KATKGDAHI                                               139

| | | |
|---|---|---|
| SEQ ID NO: 11 | moltype = AA   length = 13 | |
| FEATURE | Location/Qualifiers | |
| source | 1..13 | |
| | mol_type = protein | |
| | organism = synthetic construct | |

SEQUENCE: 11
AHIVMVDAYK PTK                                                    13

| | | |
|---|---|---|
| SEQ ID NO: 12 | moltype = DNA   length = 19 | |
| FEATURE | Location/Qualifiers | |
| source | 1..19 | |
| | mol_type = other DNA | |
| | organism = synthetic construct | |

SEQUENCE: 12
ctgtctctta tacacatct                                              19

| | | |
|---|---|---|
| SEQ ID NO: 13 | moltype = DNA   length = 59 | |
| FEATURE | Location/Qualifiers | |
| source | 1..59 | |
| | mol_type = other DNA | |
| | organism = synthetic construct | |
| modified_base | 8 | |
| | mod_base = OTHER | |
| | note = Uracil | |

SEQUENCE: 13
tttgtgatgc gatgaactca gagtgcttnn nnnnnnnnnn agatgtgtat aagagacag    59

| | | |
|---|---|---|
| SEQ ID NO: 14 | moltype = DNA   length = 34 | |
| FEATURE | Location/Qualifiers | |
| source | 1..34 | |
| | mol_type = other DNA | |
| | organism = synthetic construct | |

SEQUENCE: 14
gtctcgtggg ctcggagatg tgtataagag acag                             34

| | | |
|---|---|---|
| SEQ ID NO: 15 | moltype = DNA   length = 19 | |
| FEATURE | Location/Qualifiers | |
| source | 1..19 | |
| | mol_type = other DNA | |
| | organism = synthetic construct | |

SEQUENCE: 15
tctacacata ttctctgtc                                              19

| | | |
|---|---|---|
| SEQ ID NO: 16 | moltype = DNA   length = 19 | |
| FEATURE | Location/Qualifiers | |
| source | 1..19 | |
| | mol_type = other DNA | |
| | organism = synthetic construct | |

SEQUENCE: 16
ctgtctctta tacacatct                                              19

| | | |
|---|---|---|
| SEQ ID NO: 17 | moltype = DNA   length = 33 | |
| FEATURE | Location/Qualifiers | |
| source | 1..33 | |
| | mol_type = other DNA | |
| | organism = synthetic construct | |

SEQUENCE: 17
gacagagaat atgtgtagac tgcgacggct gct                              33

| | | |
|---|---|---|
| SEQ ID NO: 18 | moltype = DNA   length = 13 | |
| FEATURE | Location/Qualifiers | |

```
source                          1..13
                                mol_type = other DNA
                                organism = synthetic construct
SEQUENCE: 18
aaagctgcac tca                                                              13

SEQ ID NO: 19                   moltype = DNA  length = 13
FEATURE                         Location/Qualifiers
source                          1..13
                                mol_type = other DNA
                                organism = synthetic construct
SEQUENCE: 19
atataggcac tca                                                              13

SEQ ID NO: 20                   moltype = DNA  length = 10
FEATURE                         Location/Qualifiers
source                          1..10
                                mol_type = other DNA
                                organism = synthetic construct
SEQUENCE: 20
aaagctgcac                                                                  10

SEQ ID NO: 21                   moltype = DNA  length = 10
FEATURE                         Location/Qualifiers
source                          1..10
                                mol_type = other DNA
                                organism = synthetic construct
SEQUENCE: 21
atataggcac                                                                  10

SEQ ID NO: 22                   moltype = DNA  length = 15
FEATURE                         Location/Qualifiers
source                          1..15
                                mol_type = other DNA
                                organism = synthetic construct
SEQUENCE: 22
aaaaaaaaaa aaaaa                                                            15

SEQ ID NO: 23                   moltype = DNA  length = 39
FEATURE                         Location/Qualifiers
source                          1..39
                                mol_type = other DNA
                                organism = synthetic construct
SEQUENCE: 23
agacgtgtgc tcttccgatc tnnncagctt tcactcagt                                  39

SEQ ID NO: 24                   moltype = DNA  length = 19
FEATURE                         Location/Qualifiers
source                          1..19
                                mol_type = other DNA
                                organism = synthetic construct
SEQUENCE: 24
agatgtgtat aagagacag                                                        19

SEQ ID NO: 25                   moltype = DNA  length = 39
FEATURE                         Location/Qualifiers
source                          1..39
                                mol_type = other DNA
                                organism = synthetic construct
SEQUENCE: 25
agacgtgtgc tcttccgatc tnnncagctt tcactcagt                                  39

SEQ ID NO: 26                   moltype = DNA  length = 39
FEATURE                         Location/Qualifiers
source                          1..39
                                mol_type = other DNA
                                organism = synthetic construct
SEQUENCE: 26
agacgtgtgc tcttccgatc tnnncctata tcactcagt                                  39

SEQ ID NO: 27                   moltype = DNA  length = 39
FEATURE                         Location/Qualifiers
source                          1..39
                                mol_type = other DNA
                                organism = synthetic construct
SEQUENCE: 27
agacgtgtgc tcttccgatc tnnngatccc tcactcagt                                  39

SEQ ID NO: 28                   moltype = DNA  length = 25
```

```
FEATURE              Location/Qualifiers
source               1..25
                     mol_type = other DNA
                     organism = synthetic construct
modified_base        25
                     mod_base = OTHER
                     note = locked nucleotide
misc_feature         1..22
                     note = dna
misc_feature         23..24
                     note = rna
SEQUENCE: 28
ctacacgacg ctcttccgat ctggg                                              25

SEQ ID NO: 29        moltype = DNA   length = 25
FEATURE              Location/Qualifiers
source               1..25
                     mol_type = other DNA
                     organism = synthetic construct
misc_feature         23..25
                     note = rna
misc_feature         1..22
                     note = dna
SEQUENCE: 29
ctacacgacg ctcttccgat ctggg                                              25

SEQ ID NO: 30        moltype = DNA   length = 30
FEATURE              Location/Qualifiers
source               1..30
                     mol_type = other DNA
                     organism = synthetic construct
misc_feature         1..27
                     note = dna
misc_feature         28..30
                     note = rna
SEQUENCE: 30
ctacacgacg ctcttccgat ctnnnnnggg                                         30

SEQ ID NO: 31        moltype = RNA   length = 22
FEATURE              Location/Qualifiers
source               1..22
                     mol_type = other RNA
                     organism = synthetic construct
SEQUENCE: 31
ctacacgacg ctcttccgat ct                                                 22

SEQ ID NO: 32        moltype = DNA   length = 17
FEATURE              Location/Qualifiers
source               1..17
                     mol_type = other DNA
                     organism = synthetic construct
SEQUENCE: 32
agacgtgtgc tcttccg                                                       17

SEQ ID NO: 33        moltype = DNA   length = 39
FEATURE              Location/Qualifiers
source               1..39
                     mol_type = other DNA
                     organism = synthetic construct
modified_base        32
                     mod_base = OTHER
                     note = deoxy Uracil
SEQUENCE: 33
cagctttnnn agatcggaag agcacacgtc ttatatata                               39

SEQ ID NO: 34        moltype = DNA   length = 51
FEATURE              Location/Qualifiers
source               1..51
                     mol_type = other DNA
                     organism = synthetic construct
modified_base        45
                     mod_base = OTHER
                     note = deoxy Uracil
SEQUENCE: 34
cctatatnnn agatcggaag agcacacgtc ttaatattta atattatata t                 51

SEQ ID NO: 35        moltype = DNA   length = 48
FEATURE              Location/Qualifiers
```

```
                        source                  1..48
                                                mol_type = other DNA
                                                organism = synthetic construct
SEQUENCE: 35
agacgtgtgc tcttccgatc tnnnnnnnna ctaattttttt tttttttvn                      48

SEQ ID NO: 36           moltype = DNA   length = 49
FEATURE                 Location/Qualifiers
source                  1..49
                        mol_type = other DNA
                        organism = synthetic construct
SEQUENCE: 36
ctacacgacg ctcttccgat ctnnnnnnnn nnnngacacc acactcagt                       49

SEQ ID NO: 37           moltype = DNA   length = 49
FEATURE                 Location/Qualifiers
source                  1..49
                        mol_type = other DNA
                        organism = synthetic construct
SEQUENCE: 37
ctacacgacg ctcttccgat ctnnnnnnnn nnnntcaagc gcactcagt                       49

SEQ ID NO: 38           moltype = DNA   length = 49
FEATURE                 Location/Qualifiers
source                  1..49
                        mol_type = other DNA
                        organism = synthetic construct
SEQUENCE: 38
ctacacgacg ctcttccgat ctnnnnnnnn nnnnagcgat tcactcagt                       49

SEQ ID NO: 39           moltype = DNA   length = 66
FEATURE                 Location/Qualifiers
source                  1..66
                        mol_type = other DNA
                        organism = synthetic construct
SEQUENCE: 39
caagcagaag acggcatacg agatnnnnnn nngtctcgtg ggctcggaga tgtgtataag           60
agacag                                                                     66

SEQ ID NO: 40           moltype = DNA   length = 70
FEATURE                 Location/Qualifiers
source                  1..70
                        mol_type = other DNA
                        organism = synthetic construct
SEQUENCE: 40
aatgatacgg cgaccaccga gatctacacn nnnnnnntcg tcggcagcgt cagatgtgta           60
taagagacag                                                                 70

SEQ ID NO: 41           moltype = DNA   length = 66
FEATURE                 Location/Qualifiers
source                  1..66
                        mol_type = other DNA
                        organism = synthetic construct
SEQUENCE: 41
caagcagaag acggcatacg agatnnnnnn nngtctcgtg ggctcggaga tgtgtataag           60
agacag                                                                     66

SEQ ID NO: 42           moltype = DNA   length = 31
FEATURE                 Location/Qualifiers
source                  1..31
                        mol_type = other DNA
                        organism = synthetic construct
misc_feature            31
                        note = linked to 5-prime end of SEQ ID NO 43 via 18-atom
                         hexa-ethyleneglycol spacer
SEQUENCE: 42
aattagtnnn agatcggaag agcacacgtc t                                         31

SEQ ID NO: 43           moltype = DNA   length = 14
FEATURE                 Location/Qualifiers
source                  1..14
                        mol_type = other DNA
                        organism = synthetic construct
misc_feature            1
                        note = linked to 3-prime end of SEQ ID NO 42 via 18-atom
                         hexa-ethyleneglycol spacer
modified_base           7
                        mod_base = OTHER
                        note = Uracil
```

-continued

```
SEQUENCE: 43
atatattata tata                                                         14

SEQ ID NO: 44           moltype = DNA   length = 14
FEATURE                 Location/Qualifiers
source                  1..14
                        mol_type = other DNA
                        organism = synthetic construct
misc_feature            14
                        note = linked to 5-prime end of SEQ ID NO 45 via 18-atom
                          hexa-ethyleneglycol spacer
modified_base           7
                        mod_base = OTHER
                        note = Uracil
SEQUENCE: 44
atatattata tata                                                         14

SEQ ID NO: 45           moltype = DNA   length = 39
FEATURE                 Location/Qualifiers
source                  1..39
                        mol_type = other DNA
                        organism = synthetic construct
misc_feature            1
                        note = linked to 3-prime end of SEQ ID NO 44 via 18-atom
                          hexa-ethyleneglycol spacer
SEQUENCE: 45
agacgtgtgc tcttccgatc tnnncactga tcactcagt                              39

SEQ ID NO: 46           moltype = DNA   length = 31
FEATURE                 Location/Qualifiers
source                  1..31
                        mol_type = other DNA
                        organism = synthetic construct
misc_feature            31
                        note = linked to 5-prime end of SEQ ID NO 47 via 18-atom
                          hexa-ethyleneglycol spacer
SEQUENCE: 46
atcagtgnnn agatcggaag agcacacgtc t                                      31

SEQ ID NO: 47           moltype = DNA   length = 14
FEATURE                 Location/Qualifiers
source                  1..14
                        mol_type = other DNA
                        organism = synthetic construct
misc_feature            1
                        note = linked to 3-prime end of SEQ ID NO 46 via 18-atom
                          hexa-ethyleneglycol spacer
modified_base           7
                        mod_base = OTHER
                        note = Uracil
SEQUENCE: 47
atatattata tata                                                         14

SEQ ID NO: 48           moltype = DNA   length = 31
FEATURE                 Location/Qualifiers
source                  1..31
                        mol_type = other DNA
                        organism = synthetic construct
misc_feature            31
                        note = linked to 5-prime end of SEQ ID NO 49 via 18-atom
                          hexa-ethyleneglycol spacer
SEQUENCE: 48
aaagctgnnn agatcggaag agcacacgtc t                                      31

SEQ ID NO: 49           moltype = DNA   length = 14
FEATURE                 Location/Qualifiers
source                  1..14
                        mol_type = other DNA
                        organism = synthetic construct
misc_feature            1
                        note = linked to 3-prime end of SEQ ID NO 48 via 18-atom
                          hexa-ethyleneglycol spacer
modified_base           7
                        mod_base = OTHER
                        note = Uracil
SEQUENCE: 49
atatattata tata                                                         14

SEQ ID NO: 50           moltype = DNA   length = 31
```

```
FEATURE          Location/Qualifiers
source           1..31
                 mol_type = other DNA
                 organism = synthetic construct
misc_feature     31
                 note = linked to 5-prime end of SEQ ID NO 51 via 18-atom
                   hexa-ethyleneglycol spacer
SEQUENCE: 50
atataggnnn agatcggaag agcacacgtc t                                       31

SEQ ID NO: 51    moltype = DNA  length = 14
FEATURE          Location/Qualifiers
source           1..14
                 mol_type = other DNA
                 organism = synthetic construct
misc_feature     14
                 note = linked to 3-prime end of SEQ ID NO 50 via 18-atom
                   hexa-ethyleneglycol spacer
modified_base    7
                 mod_base = OTHER
                 note = Uracil
SEQUENCE: 51
atatattata tata                                                          14

SEQ ID NO: 52    moltype = DNA  length = 59
FEATURE          Location/Qualifiers
source           1..59
                 mol_type = other DNA
                 organism = synthetic construct
modified_base    8
                 mod_base = OTHER
                 note = Uracil
SEQUENCE: 52
tttgtgatgc gatgaactca gagtgcttnn nnnnnnnnnn agatgtgtat aagagacag         59
```

RNA AND DNA ANALYSIS USING ENGINEERED SURFACES

CROSS-REFERENCE TO RELATED APPLICATIONS

This application is a continuation of PCT International Patent Application No. PCT/US2022/080452, filed on Nov. 23, 2022, which claims priority to, and the benefit of U.S. Provisional Appl. No. 63/282,808, filed on Nov. 24, 2021 and U.S. Provisional Appl. No. 63/388,036, filed on Jul. 11, 2022, the disclosures of which are incorporated herein by reference in their entireties.

FEDERAL FUNDING SUPPORT CLAUSE

This invention was made with US government support from grant number 1R43HG012170-01 awarded by the National Human Genome Research Institute. The US government has certain rights in the invention.

FIELD

The instant disclosure relates generally to the identification and analysis of epitranscriptomic, epigenetic and other modifications to or noncanonical features of the structures of nucleic acids, including RNA and DNA.

SEQUENCE LISTING

The instant application contains a Sequence Listing XML which has been submitted electronically and is hereby incorporated by reference in its entirety. Said Sequence Listing XML, created on Jun. 26, 2023, is named 5371-102US4.xml and is 63,725 bytes in size.

BACKGROUND

Epigenetic changes, including chemical alterations of nucleotides, are widespread and play a major role in biological processes such as gene expression, gene silencing, and response to DNA damage. Likewise, chemical modifications of RNA, known as epitranscriptomic modifications, frequently occur within cells during or after transcription. RNA modifications play vital roles in the initiation translation, translation error rates, alternative splicing, RNA stability and folding and trafficking.

A wide variety of illnesses, behaviors, and other health indicators have been correlated with epigenetic changes in DNA, including cancers of almost all types, cognitive dysfunction, and respiratory, cardiovascular, reproductive, autoimmune, and neurobehavioral illnesses. However, little is known about the distribution of epigenetic changes throughout the genome, particularly in relation to health and disease. Some functions for epitranscriptomic modifications are known, but many are not, owing substantially to a lack of analytical methods for locating and quantifying these modifications in the entirety of cellular RNA. Currently, almost nothing is known about correlative levels of epitranscriptomic RNA modifications and their changes in cells because of a lack of robust, accessible methods for profiling a substantial number of these modifications simultaneously.

Combinations of chemical derivatization methods, molecular recognition (typically using antibodies, both for enrichment and detection), and sequencing by reverse transcription have provided profiling methods for a limited number of DNA and RNA modifications. However, these methods lack high sensitivity, cause some nucleic acid degradation/fragmentation, and often cannot be used to identify the location of the modifications at a single-base resolution. Moreover, these methods are not amenable to the multiplexed detection of several DNA or RNA modifications concurrently. Existing methods for sequencing common epitranscriptomic RNA modifications often give conflicting findings both in terms of the number of detected modifications (different by more than an order of magnitude) and the location of the modifications.

Accordingly, there is a need in the art for improved compositions and methods for identifying, analyzing, quantifying, and locating DNA and RNA modifications. Such advancements would pave the way for discovery of key regulatory mechanisms of biology in health and disease, and the development of new treatment paradigms in medicine.

BRIEF SUMMARY

Provided herein are compositions and methods for the identification and analysis of epitranscriptomic, epigenetic and other chemical modifications to the structures of nucleic acids, including RNA and DNA. The instant disclosure provides highly parallelized, sensitive, accurate, and high-throughput methods for profiling a potentially unlimited number of DNA and/or RNA modifications simultaneously.

Provided herein is a composition comprising: i) a substrate, ii) a binding domain coupled to the substrate via a first linker, and iii) an adapter coupled to the substrate via a second linker, wherein the binding domain binds specifically to a non-canonical feature of a DNA or an RNA; wherein the adapter comprises a nucleic acid barcode sequence unique to the non-canonical feature.

Also provided herein is a composition comprising i) a substrate, ii) a secondary recognition element coupled to the substrate, iii) an adapter coupled to the secondary recognition element, and iv) a binding domain, wherein the binding domain is configured to bind specifically to a non-canonical feature of a DNA or an RNA, and wherein the binding domain is immobilized by the secondary recognition element; wherein the adapter comprises a nucleic acid barcode sequence unique to the non-canonical feature. In some aspects, the composition comprises a plurality of secondary recognition elements wherein the plurality of secondary recognition elements comprises secondary recognition elements that are different from each other, wherein the adapter is coupled to one of the plurality secondary recognition elements and the binding domain is coupled to a different secondary recognition element. In some aspects, the composition comprises a plurality of secondary recognition elements, wherein the adapter is coupled to one of the plurality secondary recognition elements and the binding domain is coupled to another instance of the same secondary recognition element.

Also provided herein is a composition comprising i) a substrate, ii) a secondary recognition element coupled to the substrate, iii) a binding domain coupled to the substrate via a linker, iv) an adapter coupled to the substrate via the secondary recognition element, wherein the binding domain is configured to bind specifically to a non-canonical feature of a DNA or an RNA, and wherein the adapter comprises a nucleic acid barcode sequence unique to the non-canonical feature.

Also provided herein is a composition comprising i) a substrate, ii) a binding domain coupled to the substrate via a first linker or a secondary recognition element, iii) mosaic end (ME) adapters coupled to the substrate via a second linker or secondary recognition element, and iv) a transposase, wherein the transposase is loaded to the immobilized ME adapters, wherein the binding domain binds specifically to a non-canonical feature of a DNA or an RNA, wherein at least one of the ME adapters comprises a nucleic acid barcode sequence unique to the non-canonical feature; or i) the substrate, ii) the binding domain coupled to the substrate via a linker or secondary recognition element, and iii) the transposase coupled to the binding domain, wherein the transposase is loaded to ME adapters, wherein the binding domain binds specifically to a non-canonical feature of a DNA or an RNA, wherein at least one of the ME adapters comprises a nucleic acid barcode sequence unique to the non-canonical feature.

Also provided herein is a composition comprising: i) a substrate, ii) a plurality of secondary recognition elements coupled to the substrate, iii) an adapter coupled to one of the plurality of secondary recognition elements, and iv) a binding domain coupled to another one of the plurality of secondary recognition elements, wherein the binding domain binds specifically to a non-canonical feature of a DNA or an RNA, and wherein the adapter comprises a nucleic acid barcode sequence unique to the non-canonical feature bound specifically by the binding domain.

Also provided herein is a complex comprising one or more of the compositions comprising a binding domain described herein, and a target nucleic acid bound to the binding domain.

Also provided herein are methods of manufacturing the compositions and conjugates disclosed herein and depicted in the drawings.

Also provided herein is a method for analyzing a plurality of target nucleic acids, the method comprising: (i) contacting a solution comprising a plurality of target nucleic acids with a composition described herein, wherein a target nucleic acid comprising the non-canonical feature binds to the binding domain; (ii) performing one of the following: (a) transferring the nucleic acid barcode to a target nucleic acid comprising the non-canonical feature to generate a barcoded target nucleic acid or (b) generating a barcoded copy of the target nucleic acid comprising the non-canonical feature; (iii) amplifying the barcoded target nucleic acids; and (iv) sequencing the barcoded target nucleic acids, wherein steps (i) and (ii) are performed sequentially or concurrently. In some aspects, an adapter with 3' degenerate bases primes the target nucleic acid randomly. In some aspects, step (ii) further comprises introducing a modification-specific barcode, wherein the 3' end of the adapter is extended by reverse transcriptase or a DNA polymerase.

Also provided herein is a method for analyzing a plurality of target nucleic acids, the method comprising: (i) contacting a solution comprising a plurality of target nucleic acids with a composition described herein, wherein a target nucleic acid comprising the non-canonical feature binds to the binding domain; (ii) performing one of the following: (a) transferring the nucleic acid barcode to a target nucleic acid comprising the non-canonical feature to generate a barcoded target nucleic acid or (b) generating a barcoded copy of the target nucleic acid comprising the non-canonical feature; (iii) amplifying the barcoded target nucleic acids; and (iv) sequencing the barcoded target nucleic acids, wherein steps (i) and (ii) are performed sequentially or concurrently. In some aspects, an adapter with a 3' spacer' sequence binds site-specifically to a synthetic spacer sequence displayed by the target nucleic acid. In some aspects, step (ii) further comprises introducing a modification-specific barcode, wherein one or both 3' ends are extended by reverse transcriptase or a DNA polymerase.

Also provided herein is a method for analyzing a plurality of target nucleic acids, the method comprising (i) contacting a solution comprising a plurality of target nucleic acids with a composition described herein, wherein a target nucleic acid comprising the non-canonical feature binds to the binding domain; (ii) performing one of the following: (a) transferring the nucleic acid barcode to a target nucleic acid comprising the non-canonical feature to generate a barcoded target nucleic acid, or (b) generating a barcoded copy of the target nucleic acid comprising the non-canonical feature; (iii) amplifying the barcoded target nucleic acids; and (iv) sequencing the barcoded target nucleic acids, wherein steps (i) and (ii) are performed sequentially or concurrently.

Also provided herein is a method for analyzing a plurality of target nucleic acids, the method comprising: (i) providing a plurality of target nucleic acids by reverse transcribing target RNA molecules to form DNA-RNA heteroduplex molecules or providing target double-stranded DNA molecules; (ii) contacting a solution comprising the plurality of target nucleic acids with a composition described herein, wherein a target nucleic acid comprising the non-canonical feature binds to the binding domain; (iii) transferring, using transposase, two adapters, at least one of them comprising the nucleic acid barcode, to a double-stranded target nucleic acid comprising the non-canonical feature to generate barcoded target nucleic acids, (iv) amplifying the barcoded target nucleic acids; and (v) sequencing the barcoded target nucleic acids, wherein steps (ii) and (iii) are performed concurrently or sequentially.

Also provided herein is a method for detecting a plurality of non-canonical features in a plurality of target nucleic acids, the method comprising: (i) contacting a solution comprising the plurality of target nucleic acids with a plurality of compositions described herein, wherein the number of the plurality of compositions contacted in step (i) is equal to or greater than the number of non-canonical features, wherein the binding domains of the plurality of compositions each bind to different non-canonical features of a DNA or RNA or wherein multiple binding domains bind to the same non-canonical feature of a DNA or RNA; and wherein the adapters of the plurality of compositions each comprise a nucleic acid barcode sequence unique to the non-canonical feature bound specifically by the binding domain of that composition or unique to the binding domain; (ii) performing one of the following: (a) transferring the nucleic acid barcode sequences of each of the plurality of compositions to a plurality of target nucleic acids, or (b) generating barcoded copies of the plurality of target nucleic acids; (iii) amplifying the barcoded target nucleic acids; and (iv) sequencing the barcoded target nucleic acids. In some aspects, the transferring includes adapter transfer by transposase.

Also provided herein is a method for detecting a plurality of non-canonical features in a plurality of target nucleic acids, the method comprising: (i) providing a microarray, beads, and/or a fluidics device comprising a plurality of compositions as described herein, wherein the number of the plurality of compositions provided in step (i) is equal to or greater than the number of non-canonical features, wherein the binding domains of the plurality of compositions each bind to different non-canonical features of a DNA or RNA or wherein multiple binding domains bind to the same non-canonical feature of a DNA or RNA; and wherein the adapters of the plurality of compositions each comprise a nucleic acid barcode sequence unique to the non-canonical feature bound specifically by the binding domain of that composition or unique to the binding domain; (ii) contacting the plurality of target nucleic acids with the plurality of compositions and performing one of the following: (a) transferring the nucleic acid barcode sequences of each of the plurality of compositions to a plurality of target nucleic acids, or (b) generating barcoded copies of the plurality of target nucleic acids; (iii) amplifying the barcoded target nucleic acids; and (iv) sequencing the barcoded target nucleic acids. In some aspects, the transferring includes adapter transfer by transposase.

These and other aspects of the invention will be apparent upon reference to the following detailed description, drawings, claims, embodiments, procedures, compounds, and/or compositions and associated background information and references, which are hereby incorporated in their entirety.

BRIEF DESCRIPTION OF THE DRAWINGS

In FIG. 1A, DNA adapters and binding domains are both covalently attached to the surface using the same or orthogonal chemistry. Linkers may be included to increase the flexibility and accessibility of the surface-bound molecules. In FIG. 1B, the adapters are attached to a secondary recognition element that binds to the RNA specific binding domain, for example an RNA specific primary antibody that is immobilized via protein G, A or L, or a secondary antibody. FIG. 1C illustrates the use of a different secondary recognition element for adapter immobilization, for example, a layer of biotinylated adapter molecules bound to streptavidin. In this example, the binding domain is immobilized via a linker. Alternatively, both the binding domain and the adapters may be immobilized via streptavidin, or the adapter may be covalently coupled to the substrate while the binding domain is bound to secondary recognition element. FIG. 1D illustrates the use of two different secondary recognition elements for the immobilization of the binding domain and the adapters. For example, an antibody binding domain may be immobilized to the substrate via protein G, and biotinylated adapters may be immobilized to the substrate via streptavidin. FIG. 1E illustrates two antibody species immobilized on a substrate via protein G. One antibody species is labeled with adapters and does not bind nucleic acids, whereas the other antibody species is specific to a non-canonical feature of nucleic acids and is unlabeled. FIG. 1F shows immobilization of a binding domain on a surface, wherein the binding domain is coupled to a nucleic acid that is complementary to a capture sequence. When the capture sequence is immobilized on the substrate (e.g., via a linker), it hybridizes to the nucleic acid sequence coupled to the binding domain, resulting in immobilization of the binding domain on the substrate. In this example, the adapters comprise cleavage sites for releasing target RNA or cDNA from the surface after it has been enzymatically connected to a surface-tethered adapter. Cleavage may occur within a uracil modified adapter using USER enzyme, or cleavage may occur within a 8-oxoguanine modified adapter using FpG enzyme, or it may be part of a linker, for example, a photocleavable PC or disulfide linker. FIG. 1G shows a substrate exhibiting mosaic end (ME) adapters for transposition in proximity of a binding domain. Each Tn5 transposase dimer is loaded with two adapter molecules. DNA library preparation by tagmentation includes Tn5 dimers that are loaded with ME adapters with a forward and reverse primer site, respectively. FIG. 1H shows an alternative method for linking Tn5 molecules in proximity of an antibody binding domain. Dimers of Tn5-protein A fusion proteins are loaded with ME adapters and bound to the antibody via affinity binding of protein A to the Fc region of the antibody.

FIGS. 2A-2G illustrate different methods for attaching an adapter to an RNA molecule or its corresponding cDNA. FIG. 2A depicts ligation between the 3'OH of RNA (acceptor) and a 5'-phosphate (donor) of DNA or RNA, as catalyzed by T4 RNA ligase 1. Related illustrative formats include the ligation of pre-adenylated RNA or DNA donor to an RNA acceptor by T4 RNA ligase 2, and the ligation of a 3'phosphate of RNA to a 5'OH of RNA by RtcB ligase. Two single-stranded DNA fragments can be ligated by CircLigase. FIG. 2B illustrates the ligation of a nicked structure by T4 RNA ligase 2. The donor and acceptor may both be RNA, or the donor may be DNA. Nicks in double-stranded DNA may be sealed by T4 DNA ligase. FIG. 2C illustrates splint extension using a reverse transcriptase with the target RNA acting as the template. This format generates barcoded cDNA. In FIG. 2D, the target RNA acts as a primer and is appended with a barcode. Extension by a DNA polymerase requires the ligation of a short spacer sequence (SP) of known sequence. In some aspects, the present disclosure also includes the methods including multiple, sequential barcode transfers, e.g., wherein the barcode gets directly attached to the target nucleic acid. An adapter with two spacer regions such that shown in FIG. 2D is an example of an adapter suitable for such a repeat barcoding step. A reverse transcriptase may extend the adapter as shown in FIG. 2G, thereby synthesizing a cDNA copy of the RNA target. FIG. 2E shows barcoding by double-stranded ligation either of blunt of sticky ended DNA by T4 DNA ligase. FIG. 2F describes chemical ligation happening between two chemical moieties A and B. Chemical moiety A is part of a short spacer that is ligated onto the RNA target to prime it for chemical ligation.

FIG. 4A depicts different bead types combined in a pool, whereby each bead types captures and barcodes a specific RNA modification. Beads may be collected by filtration in a fritted column, or by magnetization. FIG. 4B illustrates the use of a DNA array for surface-mediated barcoding and for capture of the binding domains. Each spot of the array features at least one uniquely barcoded adapter and captures only one type of binding domain via hybridization to a DNA tag displayed by the binding domain. In figure FIG. 4C, monoclonal patches of co-immobilized barcodes and binding domains are integrated into a microfluidics chip forming individual channels. Each channel contains the immobilized barcodes and binding domains for one DNA/RNA modification or non-canonical feature. The analyte is supplied by sample splitting.

FIGS. 12A-12D are schematics showing the architecture of various DNA adapters. FIG. 12A shows an adapter comprising either a UFP or a URP. FIG. 12B shows an adapter which may be used for library preparation by circularization. FIG. 12C shows an adapter which may be used for barcode transfer by ligation. FIG. 12D shows adapters which may be used for single or multiple barcode transfers by primer extension. The spacer may be a specific sequence or comprise random bases. As shown in the legend, "UFP" is an abbreviation for universal forward primer, "URP" is an abbreviation for universal reverse primer, "MBC" is an abbreviation for modification-encoding barcode, "UMI" is an abbreviation for unique molecular identifier, and "CLS" is an abbreviation for cleavage site. "SP" is an abbreviation for spacer.

FIG. 13 shows illustrative mosaic end adapter molecules (ME and ME'). Shown is the product of transposition, wherein the grey lines are a piece of DNA and the sequences the ME and ME' adapters. Each transposase loads two adapters (in this example Tn5ME-/ME and Tn5ME-B/ME)

and they are ligated to either end of a ds-DNA. The following sequences are depicted:

| SEQ ID NO: | |
|---|---|
| 14 | GTCTCGTGGGCTCGGAGATGTGTATAAGAGACAG |
| 15 | TCTACACATATTCTCTGTC |
| 16 | CTGTCTCTTATACACATCT |
| 17 | GACAGAGAATATGTGTAGACTGCGACGGCTGCT |

FIGS. 14A-14G show the association and dissociation curves of different antibodies measured by Biolayer Interferometry (BLI). The solid lines describe antibody binding to degenerate RNA oligos with a central modified base. The dotted lines describe antibody binding to an unmodified RNA oligo of the same length.

Figure 15A:
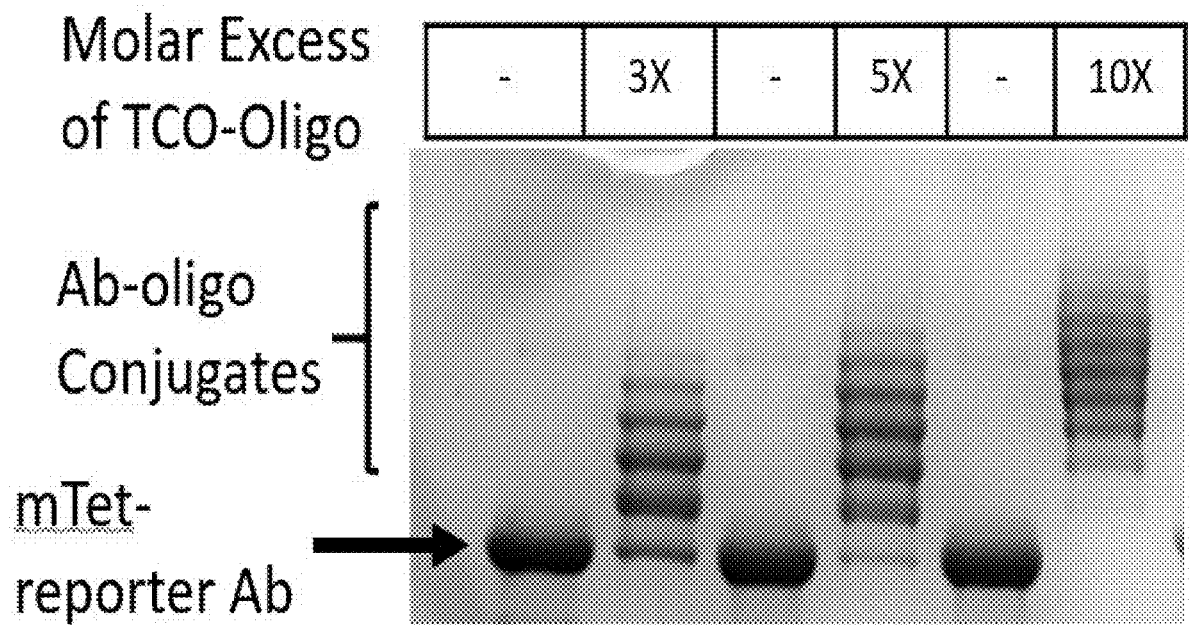

FIG. 15A depicts the products generated by labeling reporter antibodies with different amounts of adapter oligo and separated by denaturing gel electrophoresis. The reaction produces a distribution of labeling stoichiometries. The average labeling stoichiometry increases with an increasing molar excess of oligo over antibody.

Figure 15B:
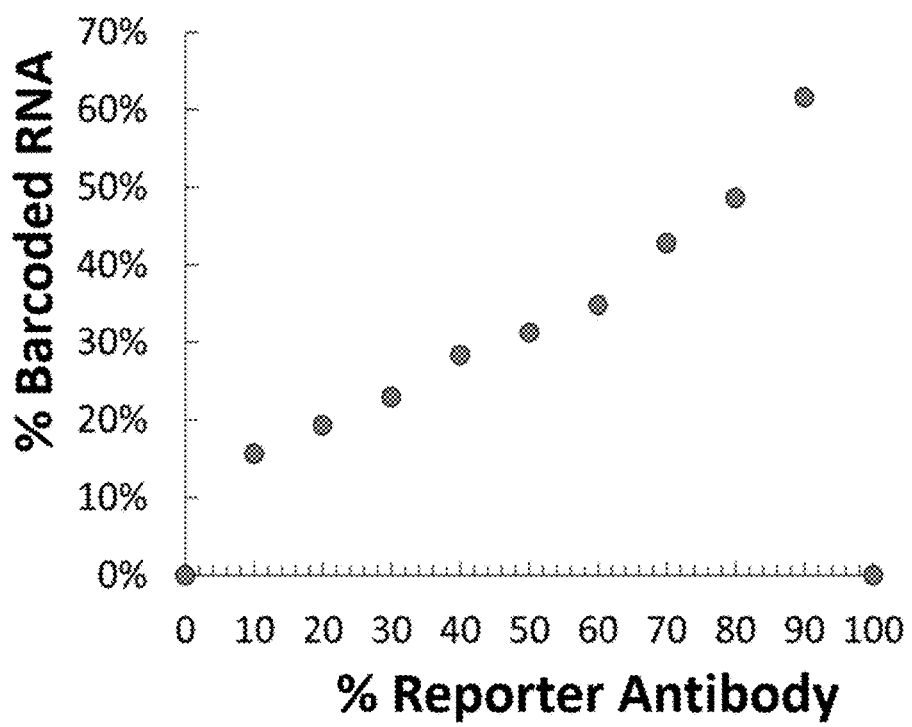

FIG. 15B describes the increase in barcoding yield as the number of reporter antibodies on the surface increases. The data are generated by loading mixtures of RNA modification specific and reporter antibodies on beads, followed by immunoprecipitation of modified RNA with a terminal dye label and initiation of the barcoding reaction. Barcoding is quantitated by denaturing gel electrophoresis of the eluted RNA and densitometry of the gel bands.

Figure 15C:
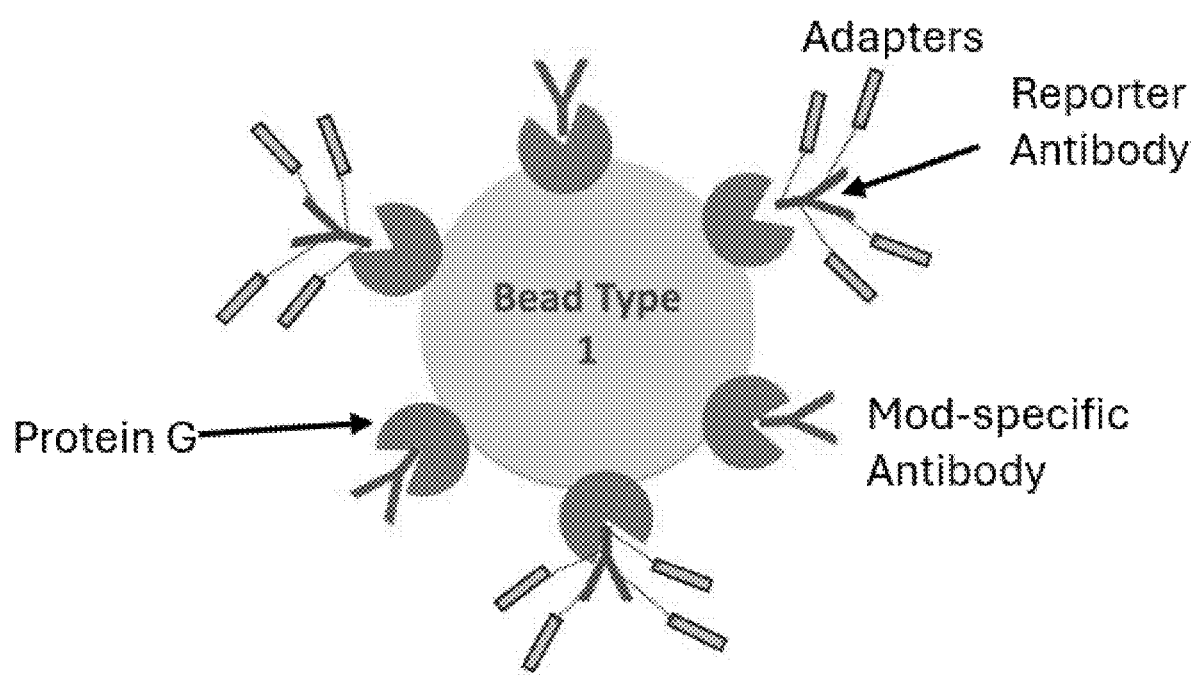

FIG. 15C schematically illustrates the composition of a "monoclonal" bead. Antibodies are immobilized on the bead surface by affinity binding to protein G. A monoclonal bead exhibits a single RNA modification specific antibody and a single adapter sequence that is indicative of the antibody. To barcode immunoprecipitated RNA effectively, the adapters need to be present at a density that allows for an interaction between the RNA and adapter molecules.

Figure 16:
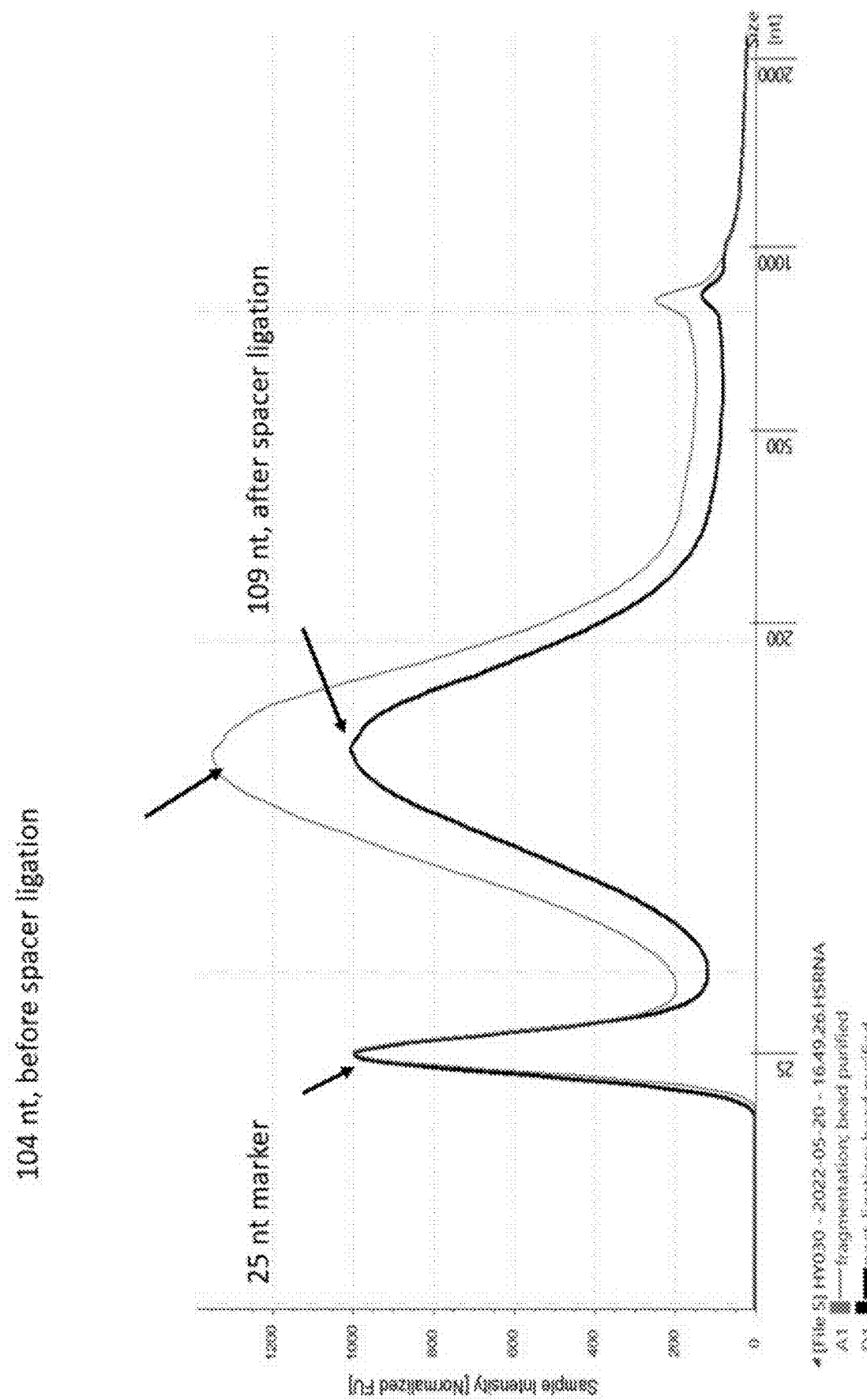

FIG. 16 shows the analysis of fragmented RNA before and after spacer ligation using capillary electrophoresis. The size of the fragments is normally distributed around 104 and 109 nucleotides, respectively.

Figure 17A:
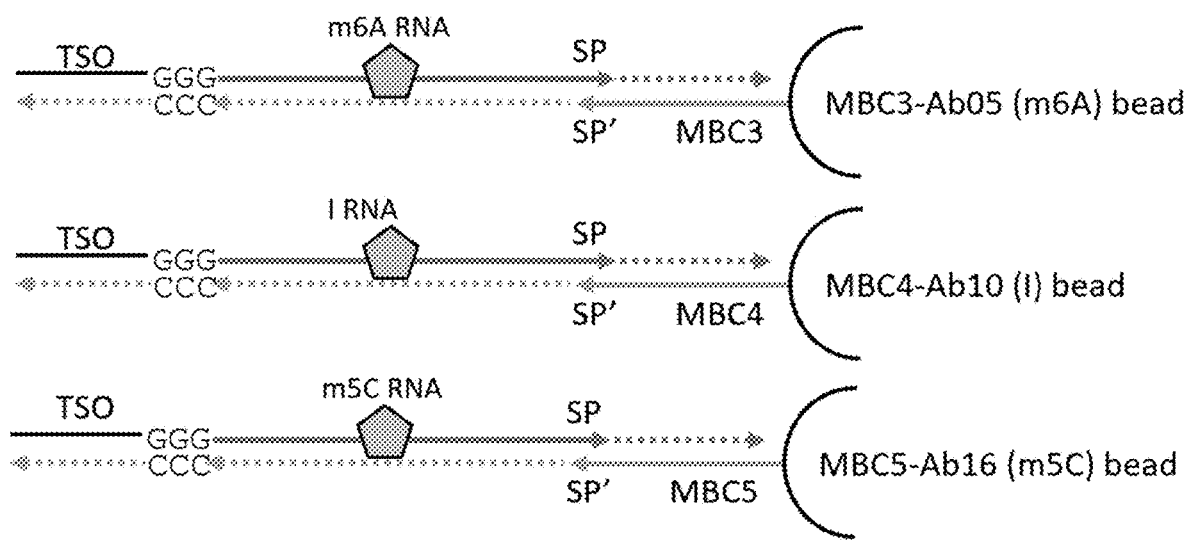
Figure 17B:
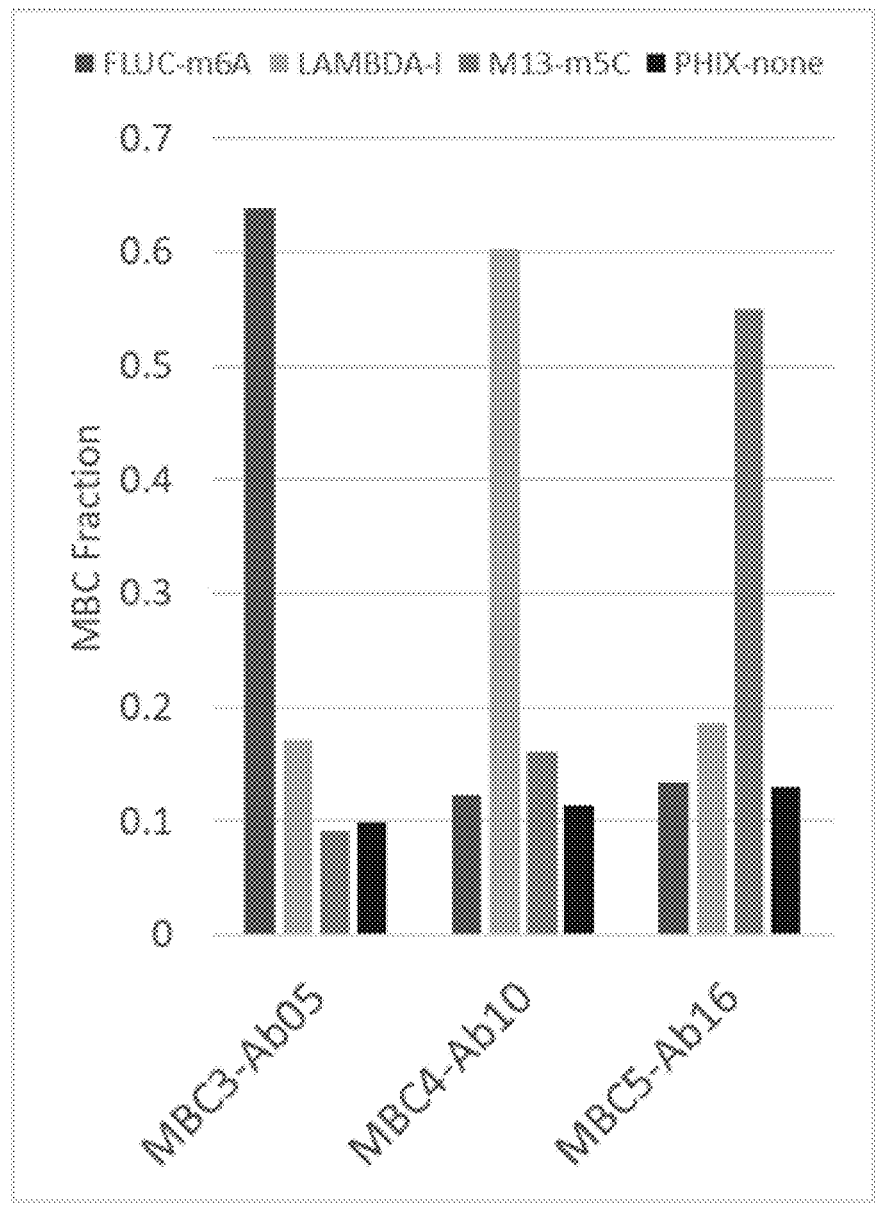
Figure 17C:
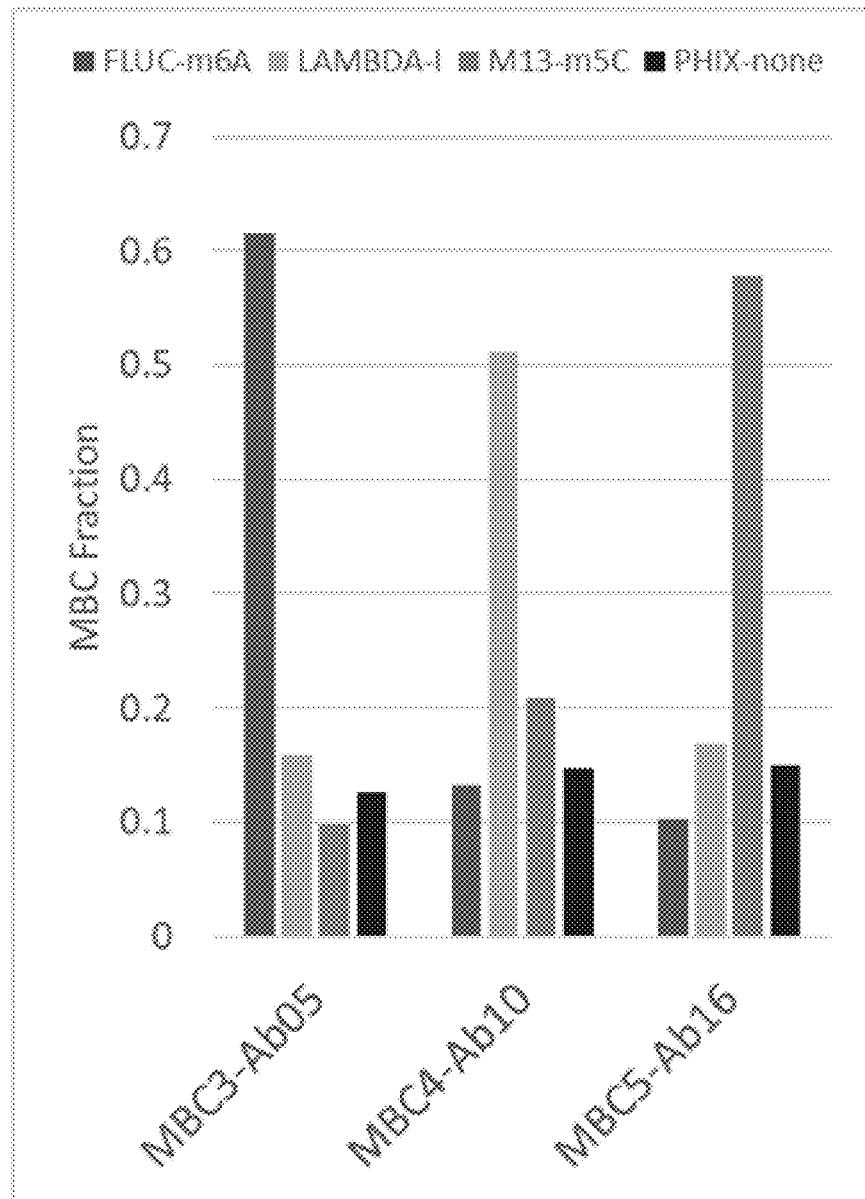
Figure 18A:
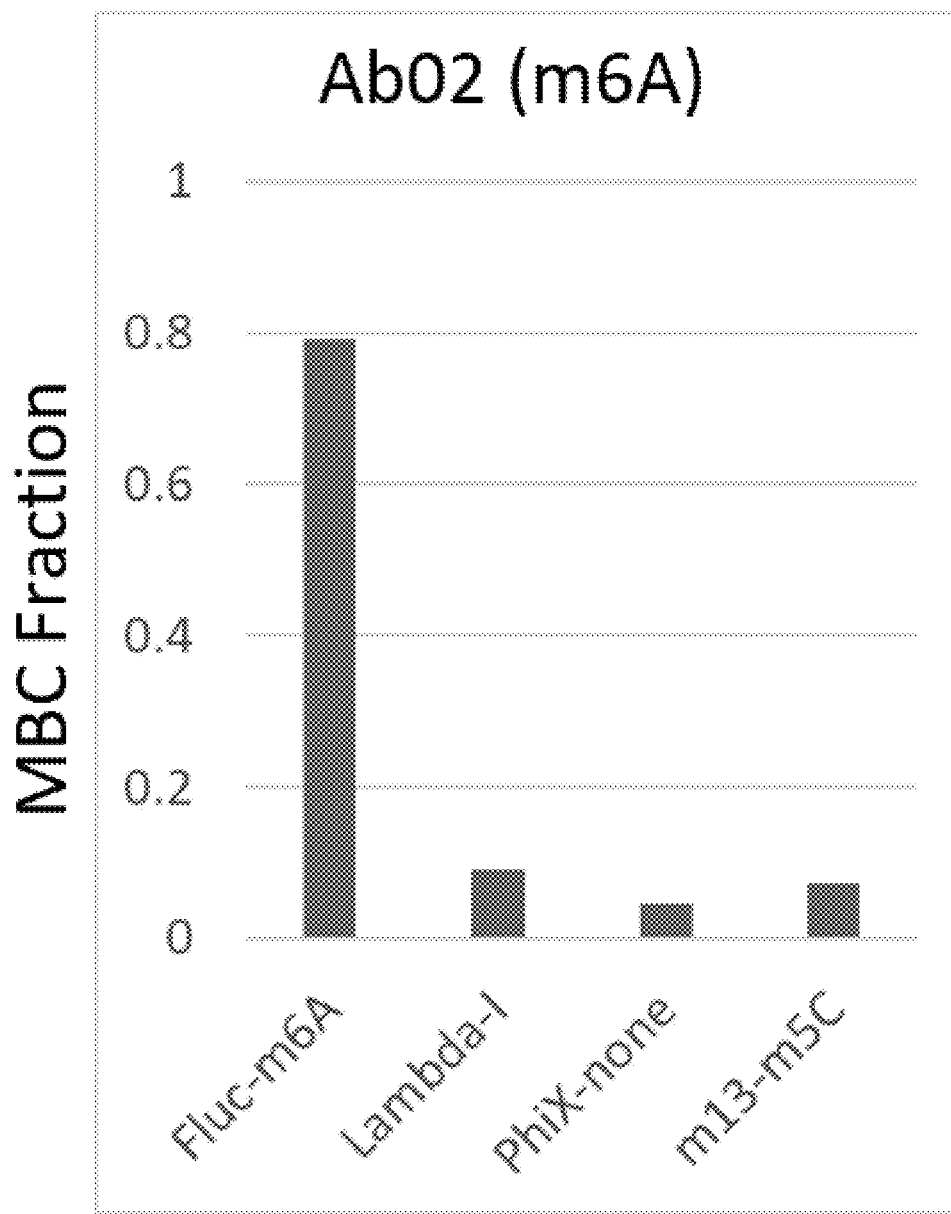
Figure 18B:
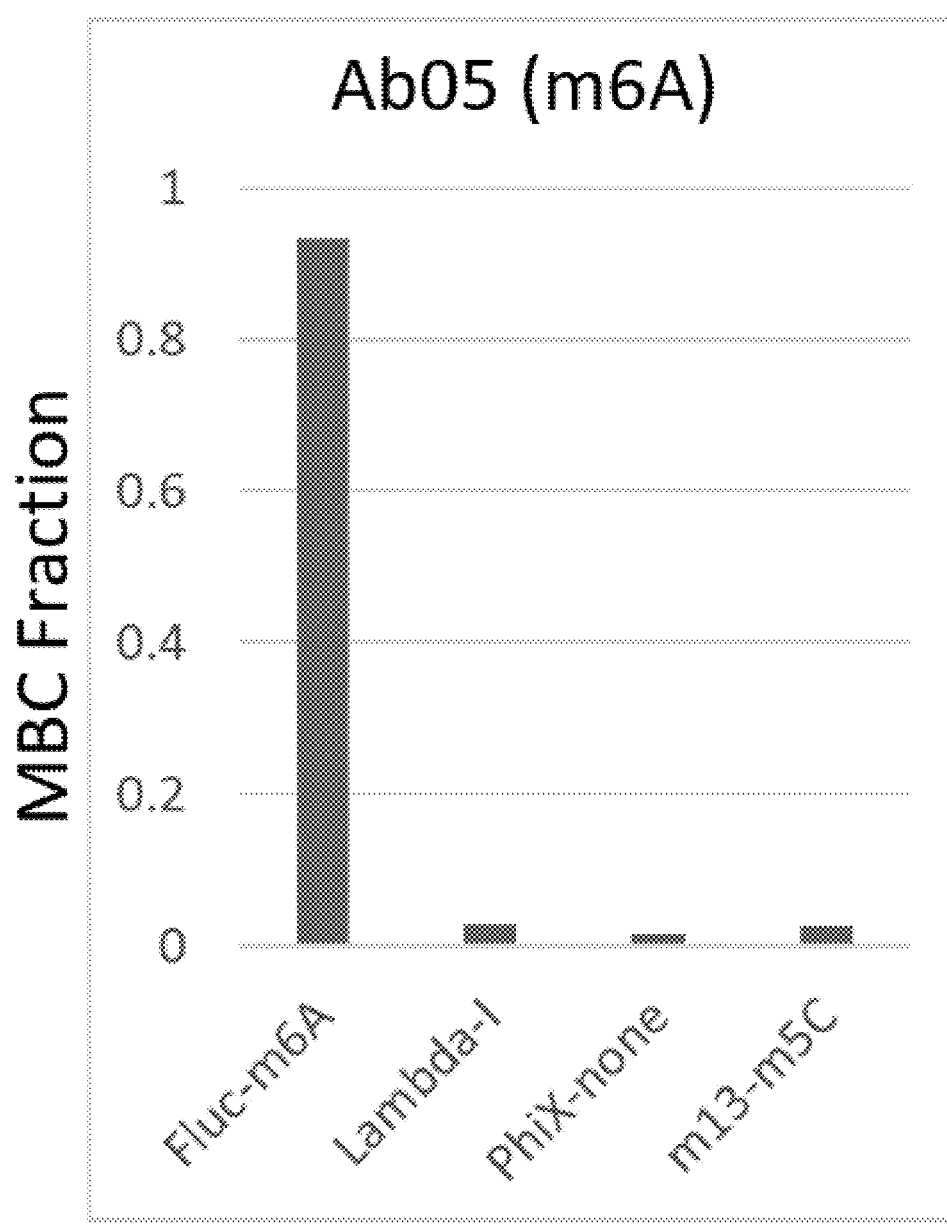
Figure 18C:
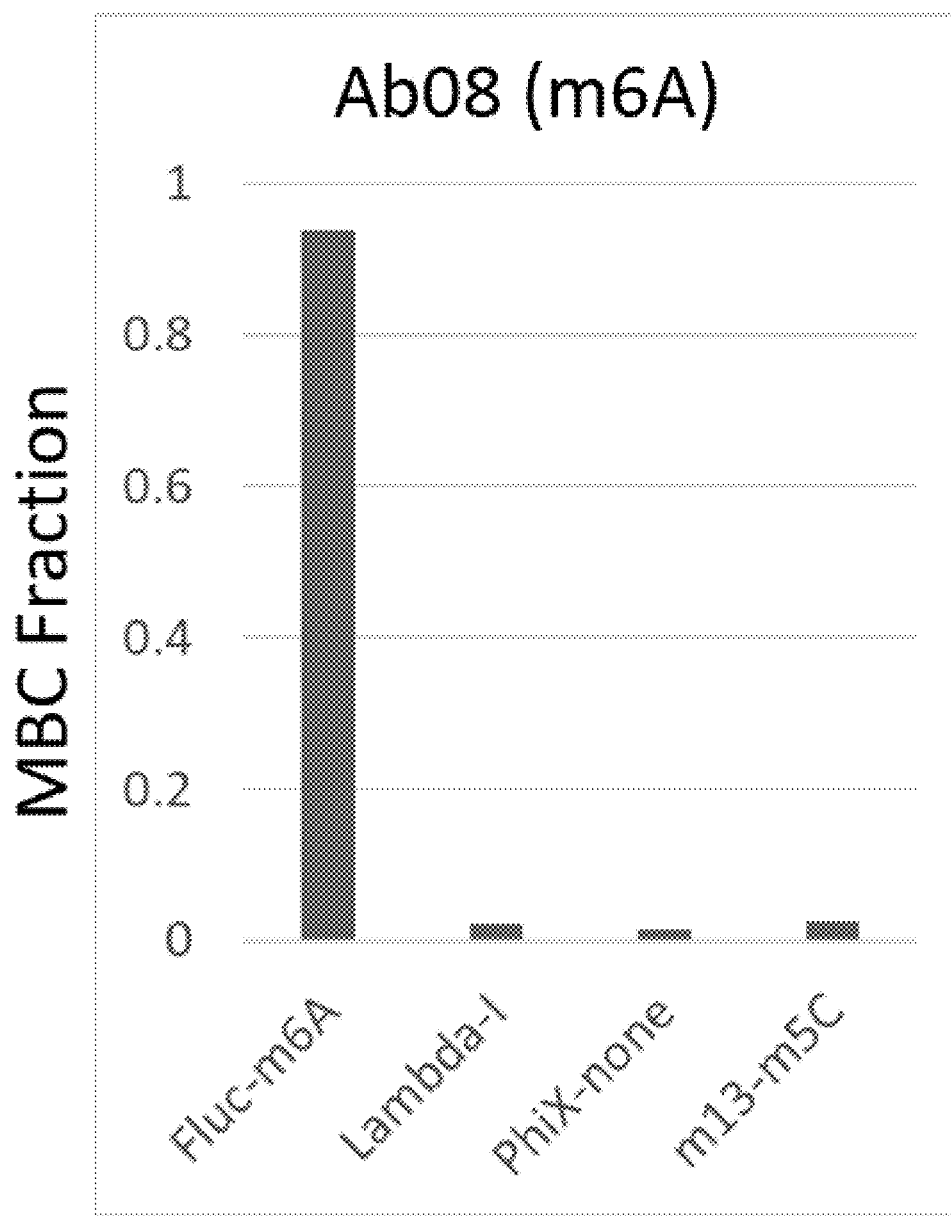
Figure 18D:
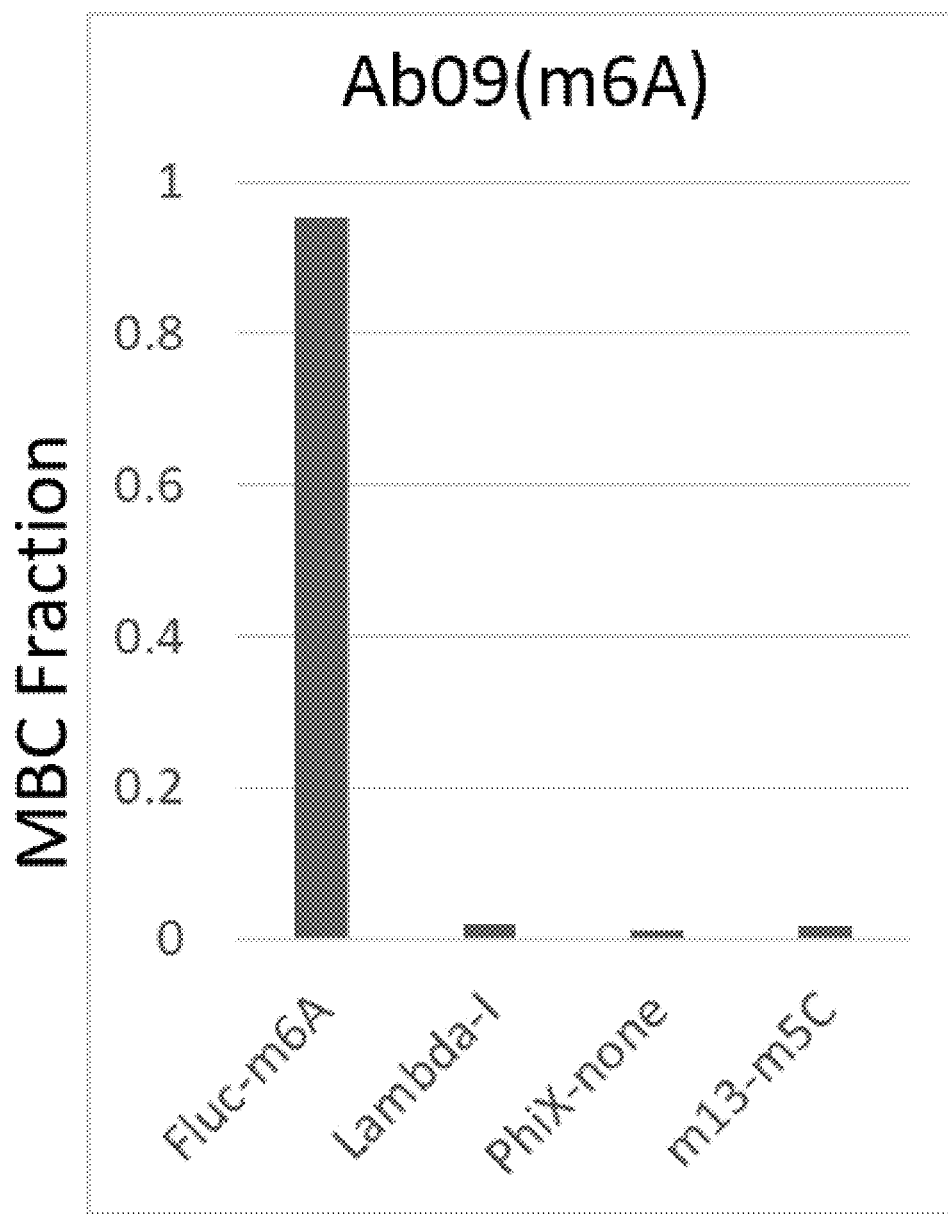
Figure 18E:
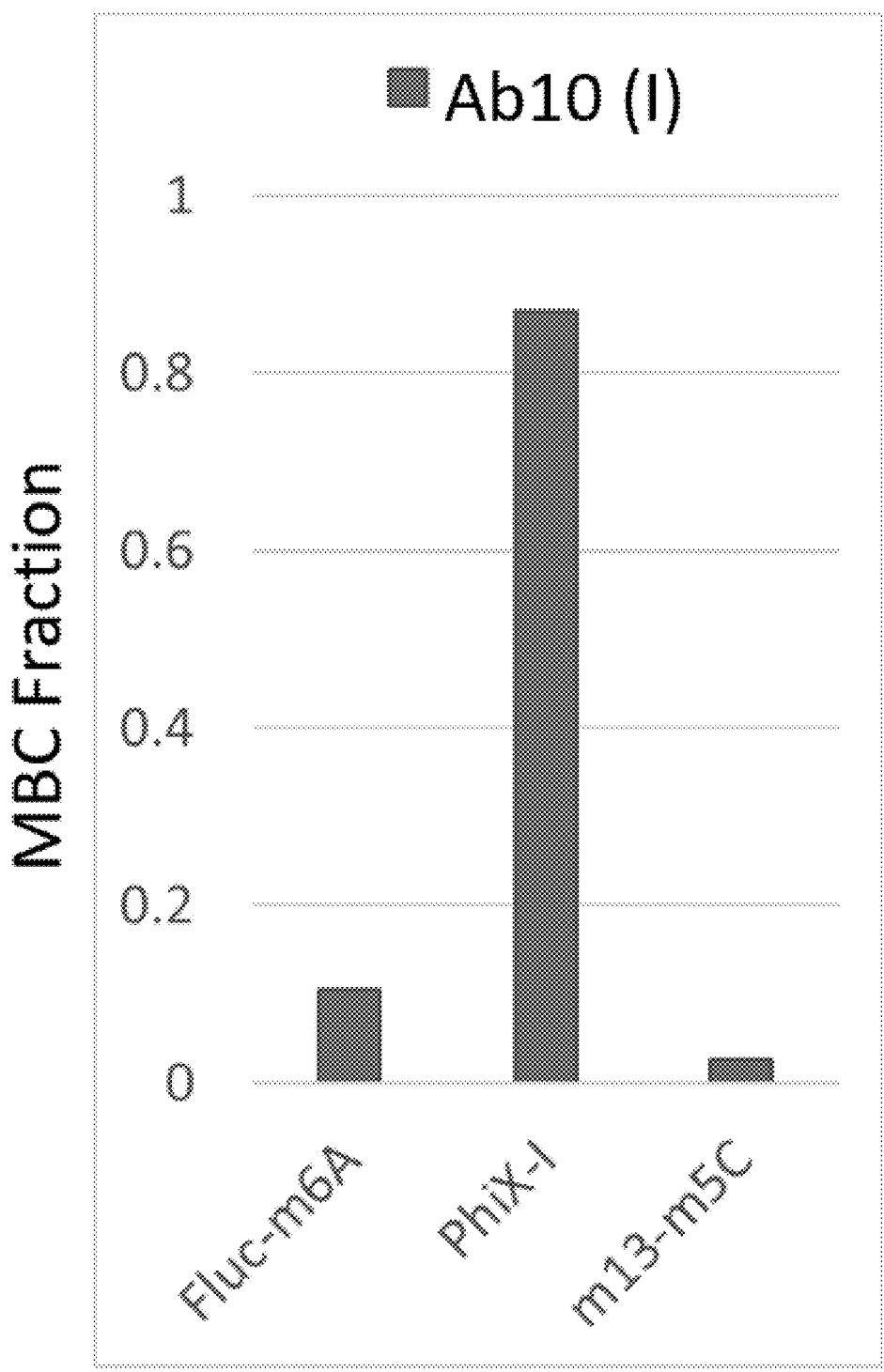
Figure 18F:
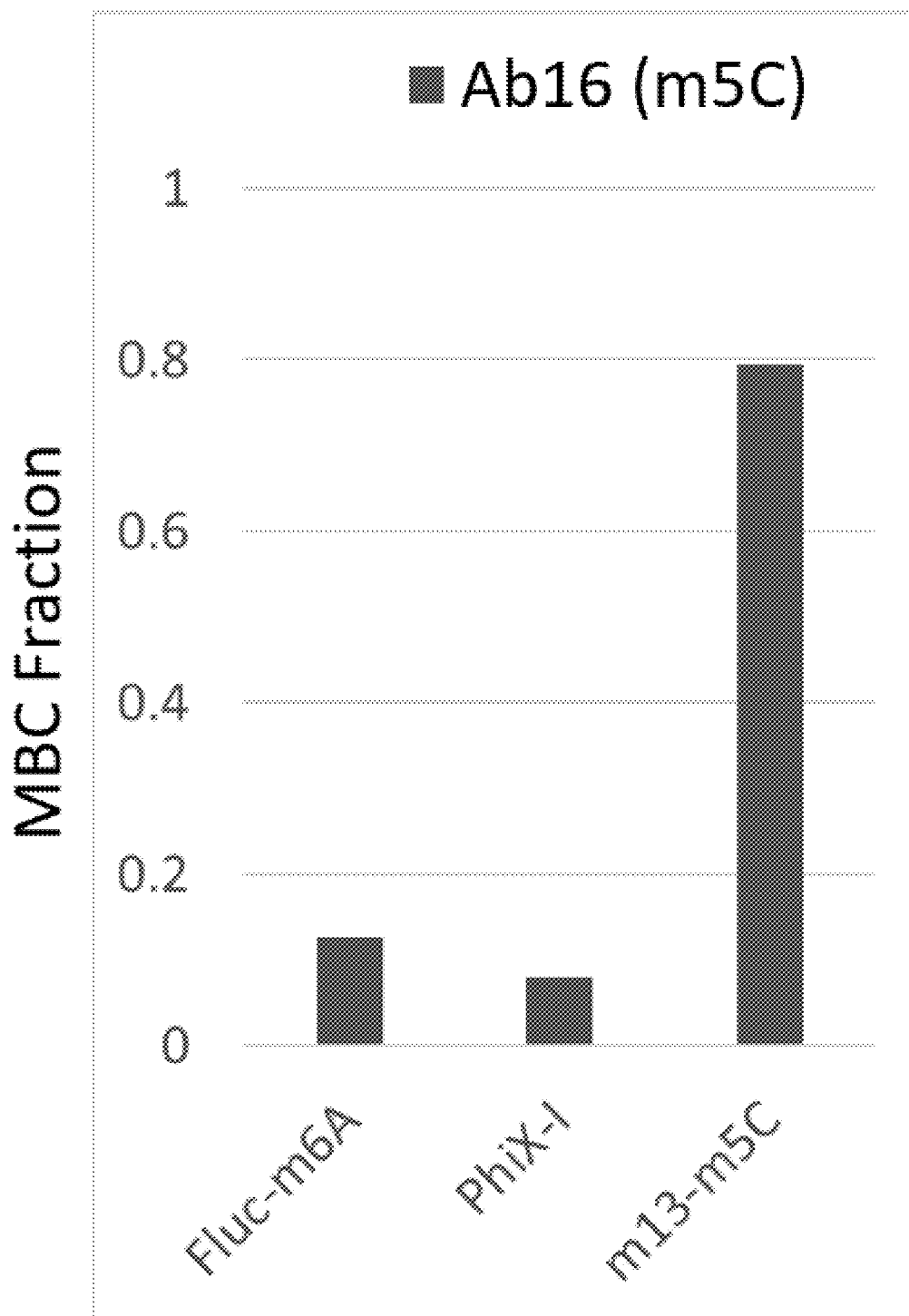
Figure 18G:
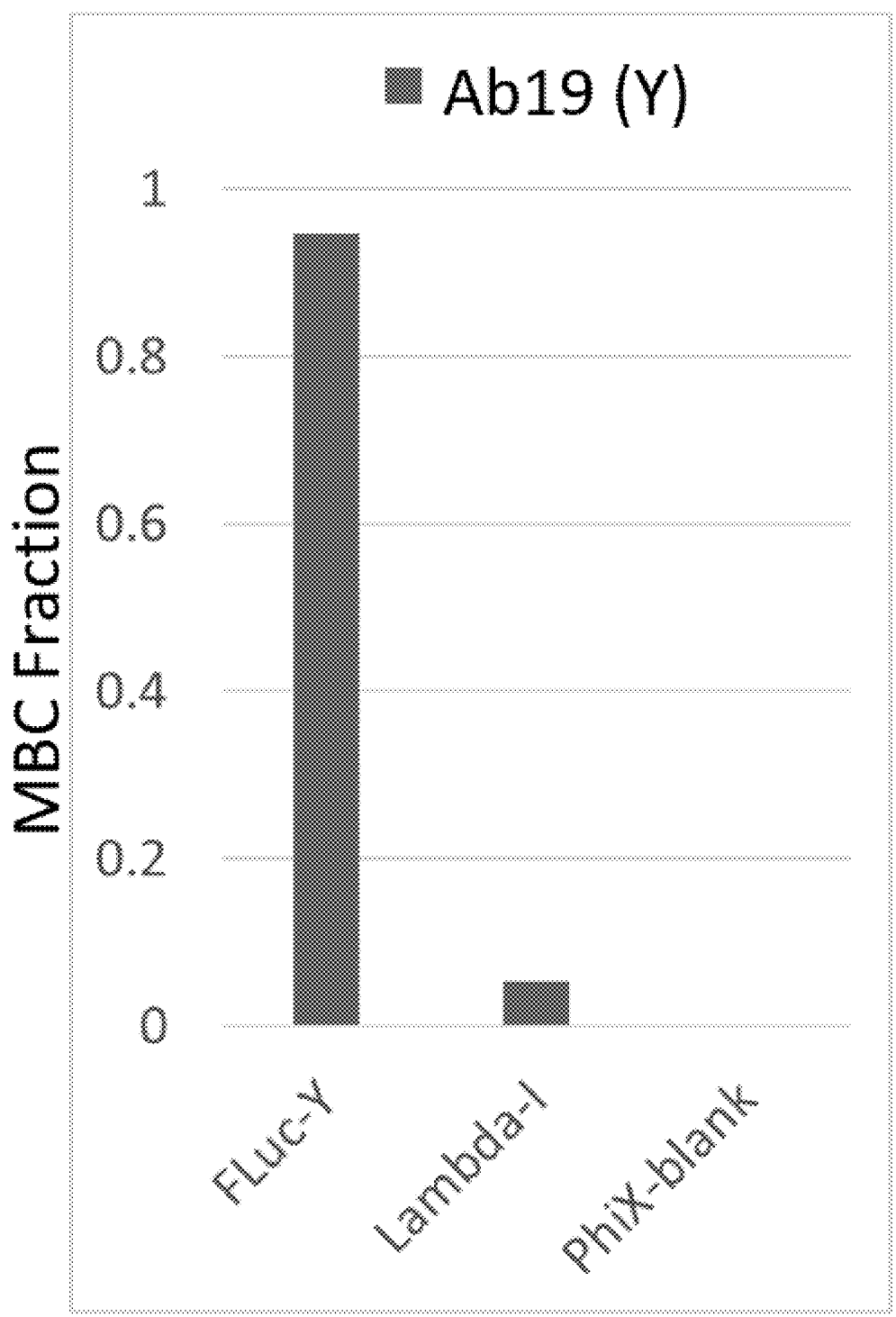

FIG. 17A depicts the molecular architecture of barcoding by reverse transcription. A 3-plex experiment contains three bead types. One bead type exhibits an m6A antibody and m6A specific adapter (MBC3-Ab05 (m6A)), the second bead type exhibits an inosine antibody and inosine specific adapter (MBC4-Ab10 (I)) and the third bead type exhibits a m5C antibody and m5C specific adapter (MBC5-Ab16 (m5C)). Spacer hybridization (SP-SP') between the target RNA and the adapter enables the bidirectional extension by reverse transcriptase, thereby copying the modification barcode (MBC) and producing cDNA. Including a template switching oligo (TSO) in the reverse transcription reaction attaches the second sequencing adapter. FIGS. 17B and 17C summarize the sequencing results obtained for a 3-plex experiment using modified RNA obtained by in vitro transcription (IVT) from four different genomes in the presence of the indicated modified nucleotide. The experiment summarized in FIG. 17B used SuperScript IV reverse transcriptase, whereas FIG. 17C used Maxima Minus reverse transcriptase. The normalized fraction of each MBC is plotted for each genome to indicate the modifications.

FIGS. 18A-18G depict the sequencing results of single-plex experiments that employ a single bead type and a target pool comprising modified IVT RNA from four different genomes. The purpose of the experiment was to compare the efficiency of barcoding by different antibodies. The MBC fraction associates an RNA modification with the correct genome. The antibodies are indicated on top of the plots, together with the modification target.

Figure 19A:
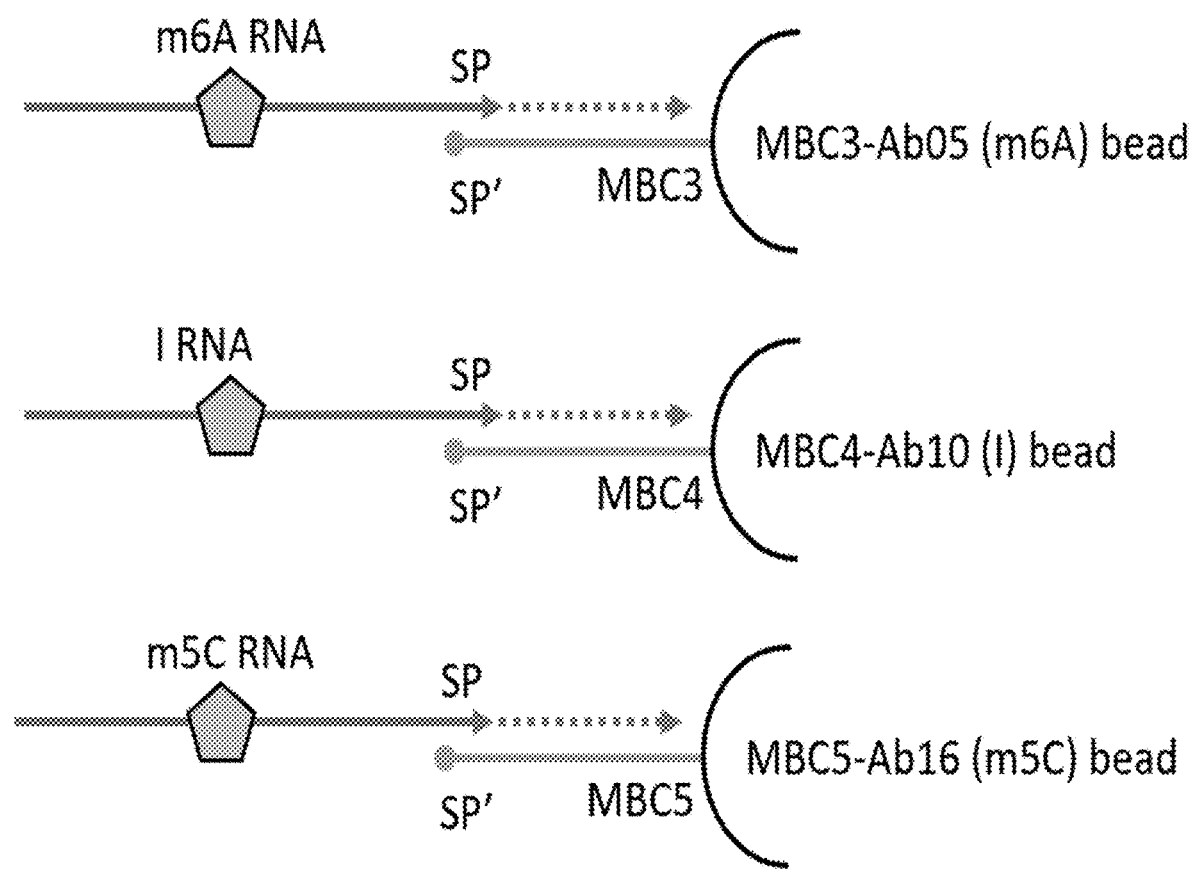
Figure 19B:
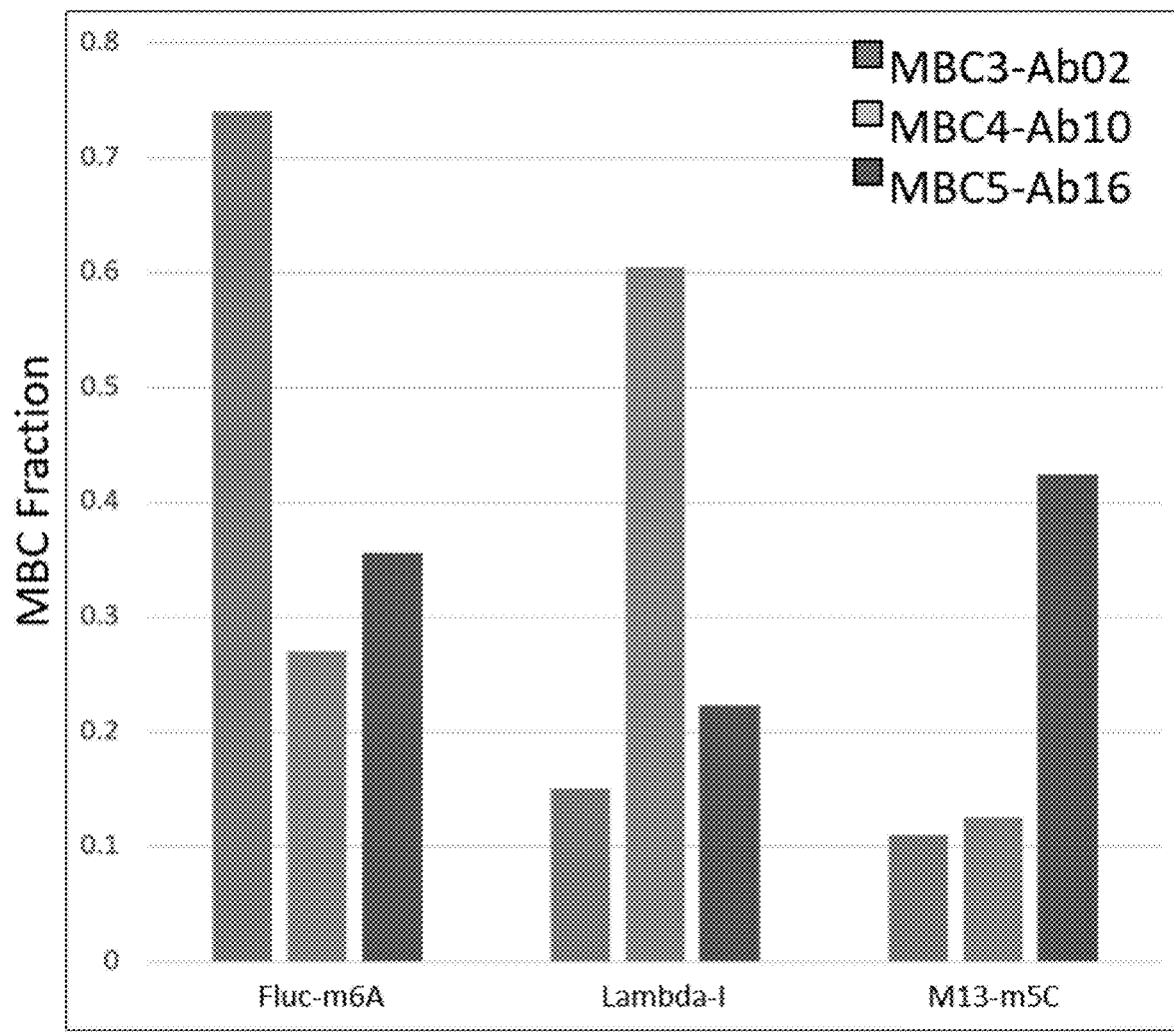

FIG. 19A illustrates the nucleic acid architectures required for barcoding with a DNA polymerase. The bead nomenclature is like in FIG. 17A, except that the 3' end of the adapter is blocked to prevent extension (light grey dot) of the bottom strand. FIG. 19B reports the associated sequencing data. The RNA modification is indicated by the barcode that amounts to the majority fraction.

Figure 20B:
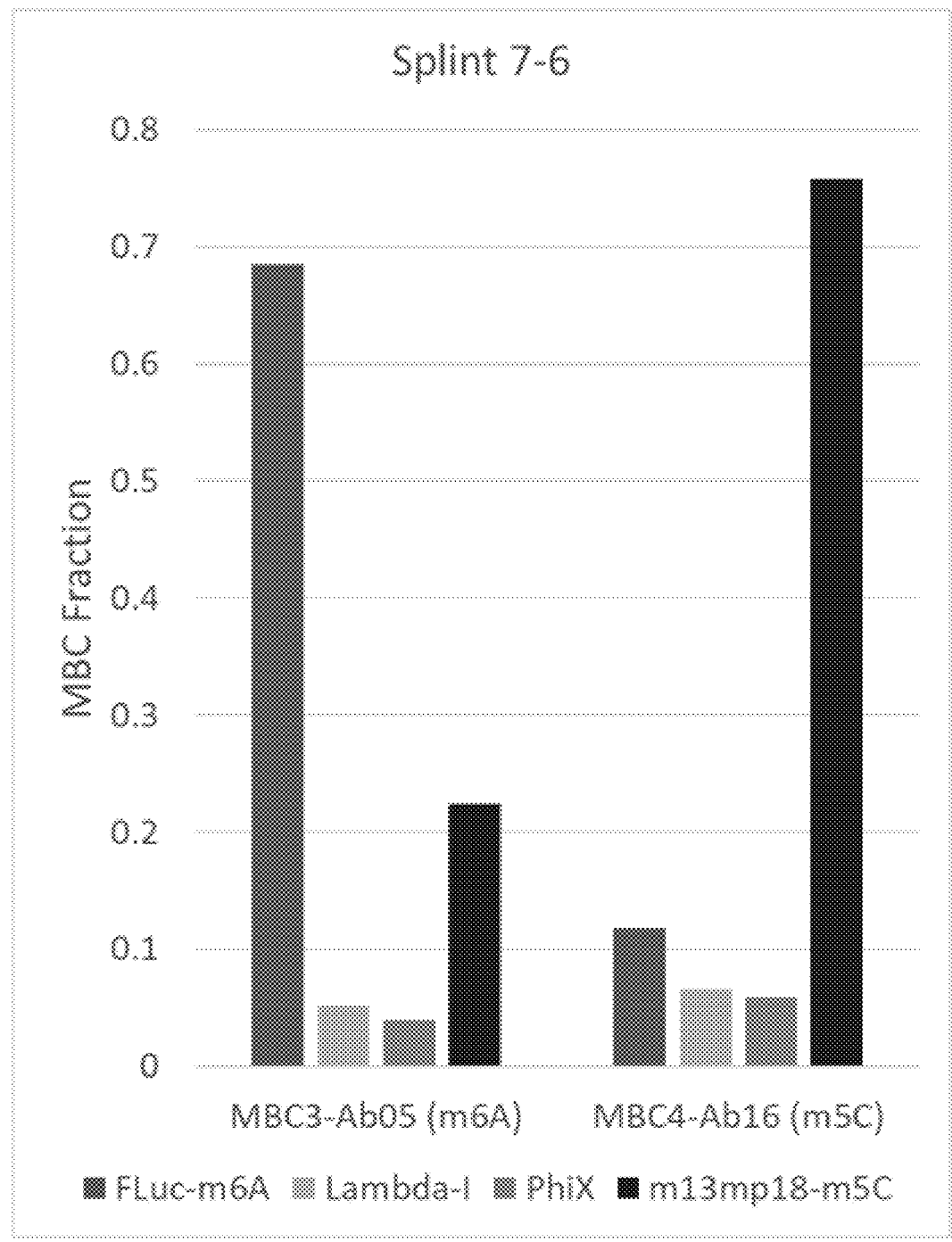
Figure 20C:
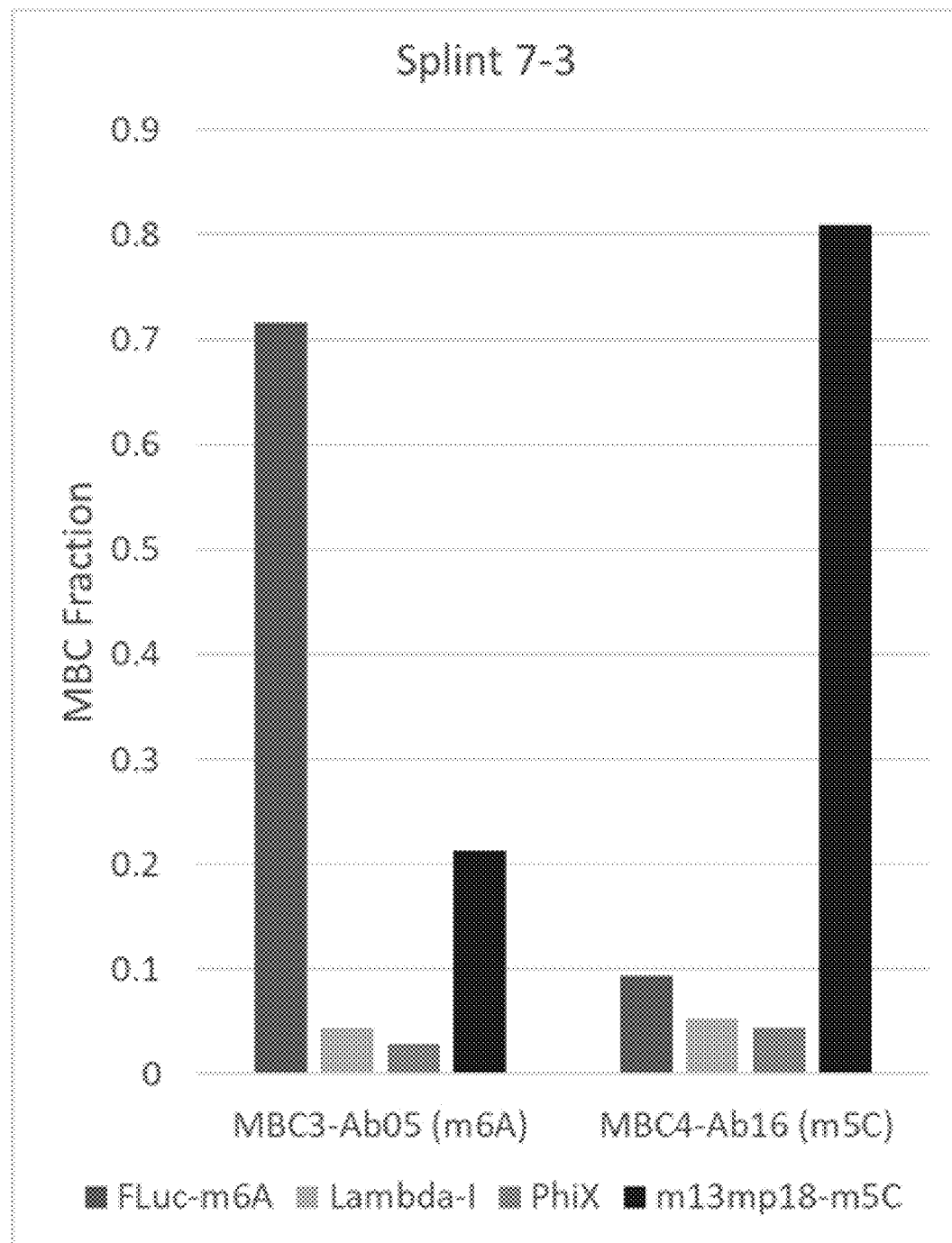

FIG. 20A introduces splint ligation as barcoding method. The splint (black line) bridges the RNA target and the adapter. A ligase seals the gap and connects the adapter to the RNA target. Two different bead types are shown, targeting m6A and m5C. FIGS. 20B-20C summarize the corresponding sequencing data illustrating the simultaneous detection of m6A and m5C. The portion of the splint that hybridizes to the adapter is 7 nt in length, whereas the RNA target facing portion is either 6 (7-6 splint) or 3 nts (7-3 splint) long.

The following sequences are depicted:

| SEQ ID NO: | |
|---|---|
| 18 | AAAGCTGCACTCA/3SpC3/ |
| 19 | ATATAGGCACTCA/3SpC3 |
| 20 | AAAGCTGCAC/3SpC3/ |
| 21 | ATATAGGCAC/3SpC3/ |

Figure 21A:
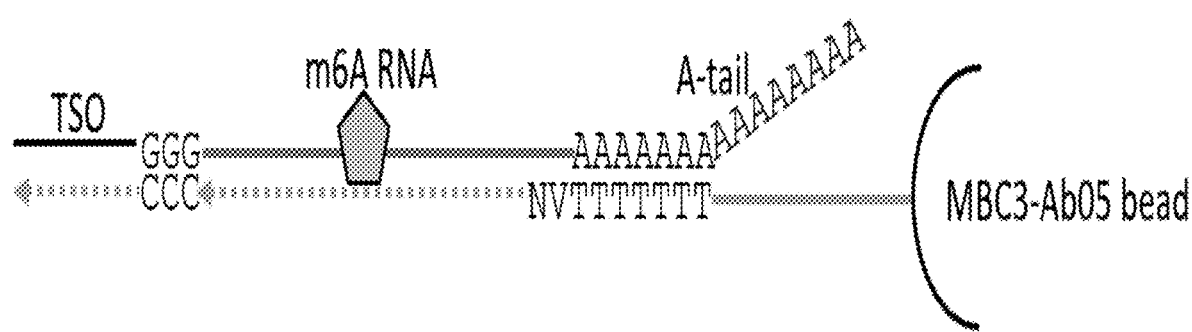
Figure 21B:
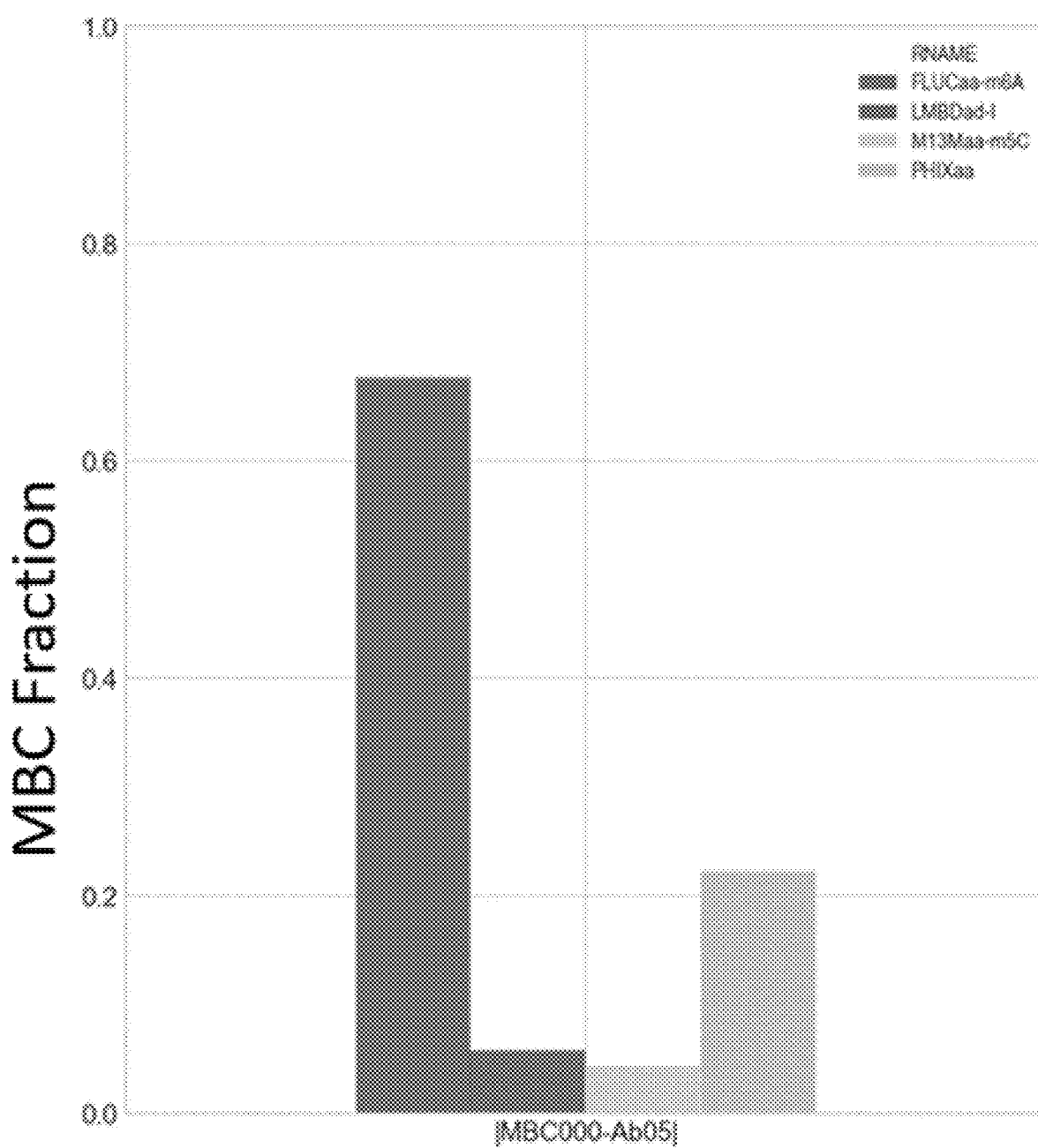

FIG. 21A presents an alternative to ligating a universal spacer to the RNA target. To poise the RNA for barcoding by primer extension, the RNA is A-tailed (poly-A tail (AAAAAAAAAAAAAAA (SEQ ID NO: 22)) and hybridized to an adapter sequence ending in the sequence NVTTTTTTT. Reverse transcription and template switching are performed as described above. FIG. 21B demonstrates the proof of concept for a single-plex data set.

Figure 22A:
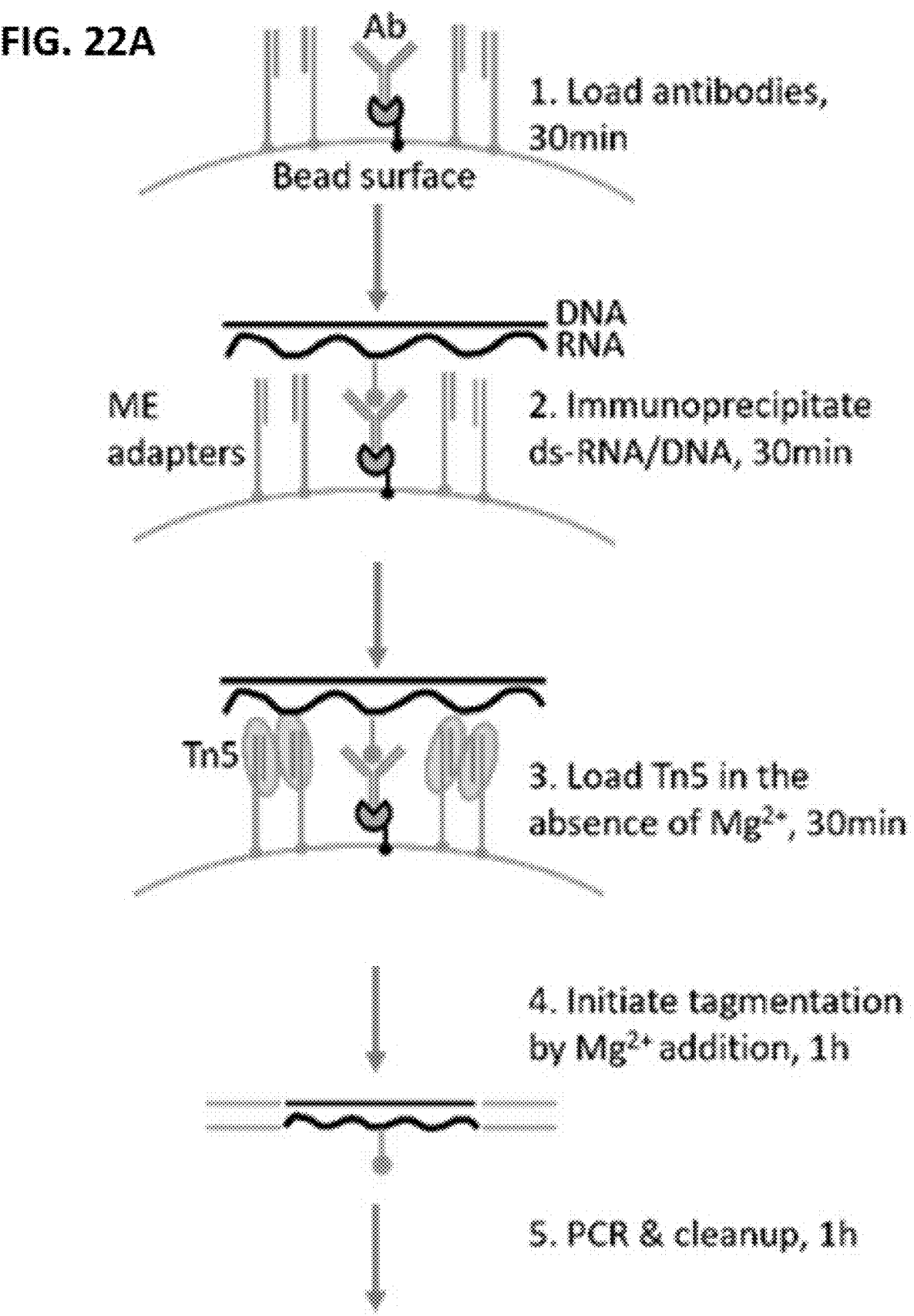

FIG. 22A illustrates a rapid method for profiling RNA modifications using Tn5 transposase for barcoding. To generate a substrate for transposition, RNA is reverse transcribed into a DNA/RNA heteroduplex. The surface (e.g., a bead) comprises antibodies and ME adapters loaded thereon. The heteroduplex is immunoprecipitated onto the surface displaying the antibodies and adapters. After washing the beads, Tn5 transposase is loaded to the ME adapters in the absence of $Mg^{2+}$. Then $Mg^{2+}$-containing tagmentation buffer is added to trigger insertion of the adapters into the captured DNA-RNA duplex that is securely captured on the beads. Gap filling followed by PCR completes the library preparation workflow. FIG. 22B is a coverage plot obtained for an experiment that employed an m6A-specific bead and a target pool comprising modified IVT RNA from four different genomes. The plot shows significant enrichment of the m6A containing fragments, attesting to the selective tagmentation of m6A modified RNA.

Figure 23A:
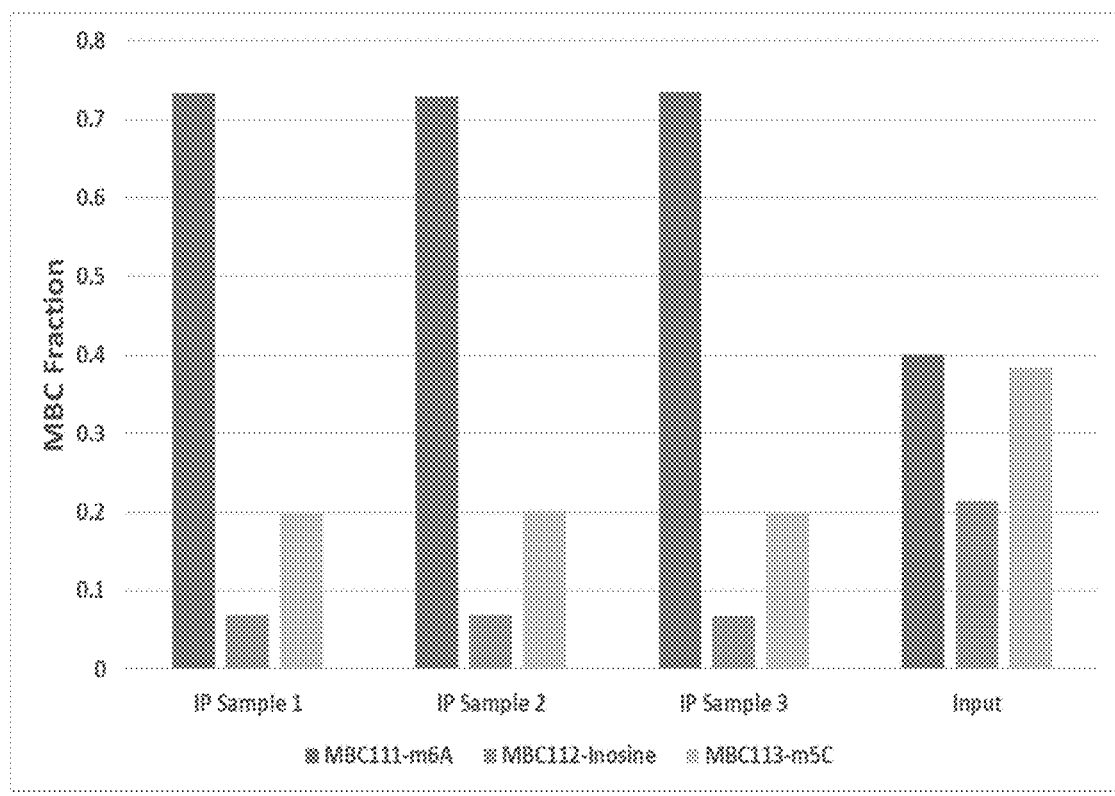
Figure 23B:
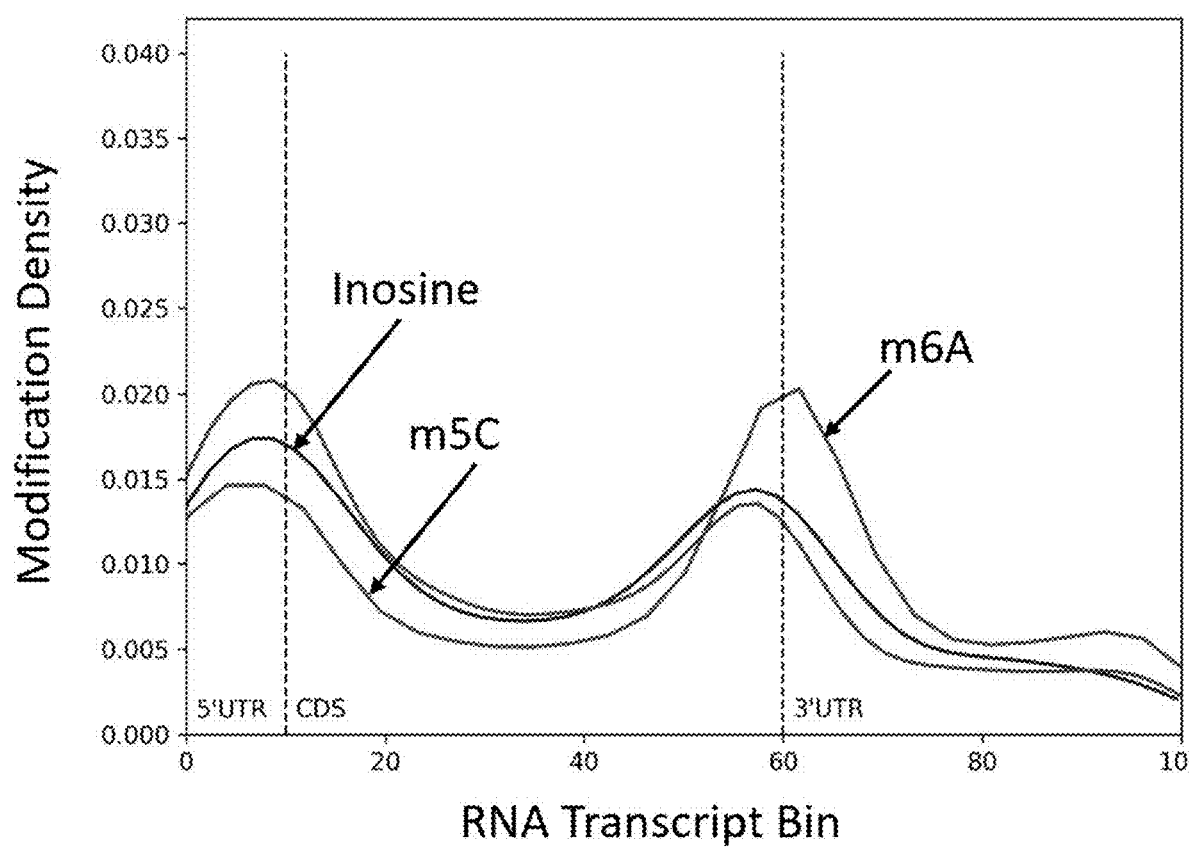

FIG. 23A shows the global barcode representation, as measured by MBC fraction, for technical triplicates of barcoded IP RNA and a non-enriched (input) sample. FIG. 23B shows the location of called peaks within genes. FIG.

23C shows the number of peaks called for each modification and each replicate sample in a Venn diagram.

Figure 24A:
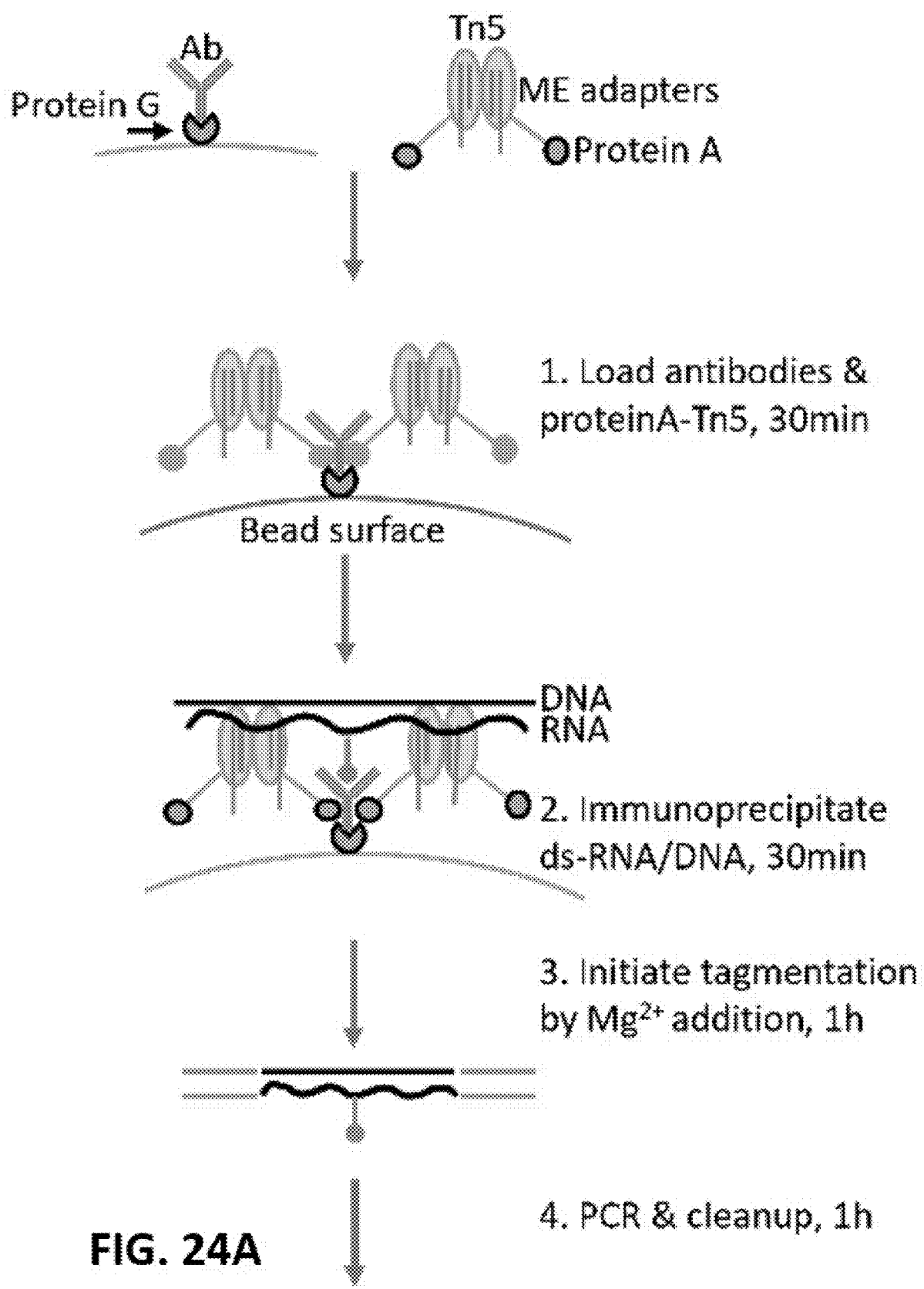
Figure 24B:
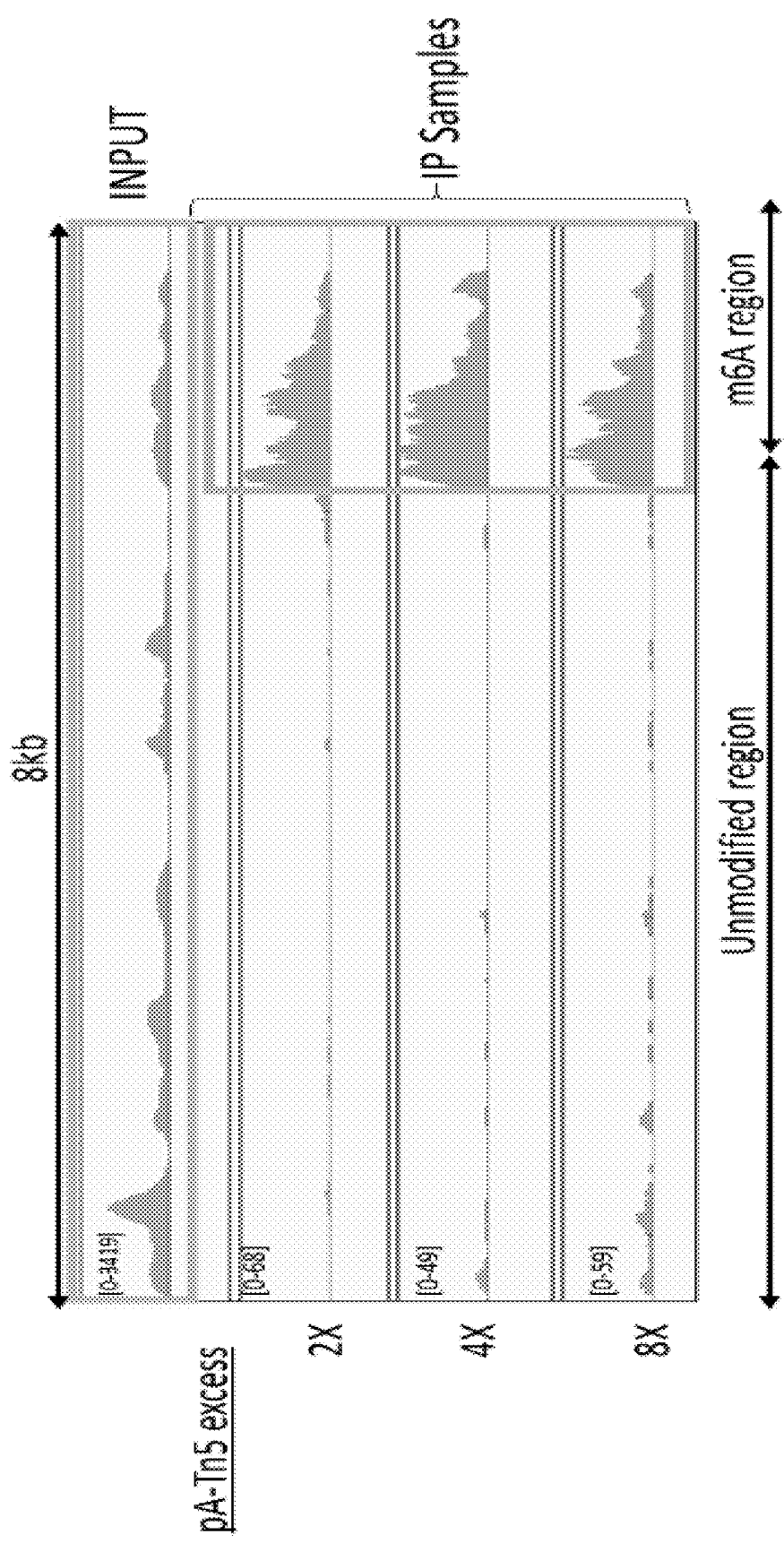

FIG. 24A shows a method of using an immobilized conjugate comprising an antibody and proteinA-Tn5 fusion protein for the tagmentation of DNA/RNA heteroduplexes. The surface (e.g., a bead) comprises protein G coupled thereto and binding a conjugate comprising an antibody and protein A-Tn5 molecules. Each Tn5 dimer is loaded with a pair of mosaic-end (ME) adapters, both containing a barcode. To generate a substrate for transposition, RNA is reverse transcribed into a DNA/RNA heteroduplex and allowed to immunoprecipitate on the bead. The beads were washed and a $Mg^{2+}$-containing tagmentation buffer is added to initiate the tagmentation reaction. The tagmented DNA/RNA heteroduplexes are gap filled and PCR amplified. Library preparation is then performed to complete the workflow. FIG. 24B compares the read coverage plots for the input (control) and the immunoprecipitated samples obtained for an experiment that targeted m6A.

DETAILED DESCRIPTION

Provided herein are compositions and methods for the multiplexed profiling of RNA and DNA modifications across transcriptomes and genomes, respectively. The methods combine molecular recognition of non-canonical features (e.g., base modifications, backbone modifications, lesions, and/or structural elements) of a target nucleic acid with a step of writing the information from this recognition event into the neighboring genetic sequence of the target nucleic acid using a barcode. The resultant barcoded nucleic acids are then converted into sequencing libraries and read by, for example, DNA/RNA sequencing methods or other methods. This step reveals the sequence of the barcode, which is correlated with the non-canonical feature in the target nucleic acid(s). Sequencing may also allow for localization of the non-canonical feature in the target nucleic acid(s). The high throughput profiling methods described herein allow for identification of the nature and location of several or all DNA/RNA modifications in parallel. These methods also allow for determination of abundance and stoichiometry of the DNA/RNA modifications.

In some embodiments, the disclosed methods are used to not only identify the modification on the target nucleic acid, but also to localize the modification on the target nucleic acid with a resolution as high as 1 base.

The present invention is described more fully hereinafter using illustrative, non-limiting embodiments, and references to the accompanying figures. This invention may, however, be embodied in many different forms and should not be construed as to be limited to the embodiments set forth below. Rather, these embodiments are provided so that this disclosure is thorough and conveys the scope described herein to those skilled in the art.

Unless otherwise defined, all technical and scientific terms used herein have the same meaning as commonly understood by one of ordinary skill in the art to which this disclosure belongs. The terminology used in the detailed description herein is for the purpose of describing particular embodiments only and is not intended to be limiting.

All publications, patent applications, patents, GenBank/Uniprot or other accession numbers and other references mentioned herein are incorporated by reference in their entirety for all purposes.

Definitions

The following terms are used in the description herein and the appended claims.

The singular forms "a," "an" and "the" are intended to include the plural forms as well, unless the context clearly indicates otherwise.

Furthermore, the term "about" as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features described herein can be used in any combination. Moreover, in some embodiments, any feature or combination of features set forth herein can be excluded or omitted. To illustrate further, if, for example, the specification indicates that a particular DNA base can be selected from A, T, G and/or C, this language also indicates that the base can be selected from any subset of these base(s) for example A, T, G, or C; A, T, or C; T or G; only C; etc., as if each such subcombination is expressly set forth herein. Moreover, such language also indicates that one or more of the specified bases can be disclaimed. For example, in some embodiments the nucleic acid is not A, T or G; is not A; is not G or C; etc., as if each such possible disclaimer is expressly set forth herein.

As used herein, the terms "reduce," "reduces," "reduction" and similar terms mean a decrease of at least about 10%, about 15%, about 20%, about 25%, about 35%, about 50%, about 75%, about 80%, about 85%, about 90%, about 95%, about 97% or more.

As used herein, the terms "increase," "improve," "enhance," "enhances," "enhancement" and similar terms indicate an increase of at least about 10%, about 15%, about 20%, about 25%, about 50%, about 75%, about 100%, about 150%, about 200%, about 300%, about 400%, about 500% or more.

The term "epigenetic change" is used herein to refer to a phenotypic change in a living cell, organism, etc., that is not encoded in the primary sequence (i.e., A, T, C, and G) of that cell's or organism's DNA. Epigenetic changes may include, for example, chemical alterations of nucleotides and/or histones (i.e., the proteins involved in coiling and packaging DNA in the nucleus). Illustrative DNA nucleotide modifications include the common epigenetic marker 5-methylcytidine (5mC) and its oxidation products 5-hydroxymethylcytidine (5hmC), 5-formylcytidine (5fC), 5-carboxymethylcytidine (5caC). 5mC is well known for its role in gene silencing, and a growing body of evidence suggests metabolic function for the oxidized intermediates 5hmC, 5fC, and 5caC on the pathway for demethylation of 5mC. Additional metabolically relevant DNA modifications include oxidized, alkylated, dimerized, cross-linked, and other chemically modified nucleotides associated with DNA damage. Such DNA modifications are relevant to understanding toxicity, but their distribution across the genome when damage occurs is not well understood. DNA modifications may have additional regulatory roles, for example as participants in G-quadruplex dynamics in promoter and other regions of the genome.

The term "epitranscriptomic change" is used herein to refer to a chemical modification of RNA that occurs during or after transcription. More than 170 distinct RNA modifications are known, including chemical changes to the nucleobases and to ribose and the phosphodiester backbone. RNA modifications are found in all types of RNA, including mRNA, tRNA, rRNA, lncRNA, miRNA, and they may alter cellular phenotypes by changing RNA structure and dynamics and/or by changing the molecular recognition of the RNA by other biological molecules such as proteins. Naturally occurring chemical RNA modifications of the epitranscriptome regulate a broad spectrum of functions in RNA metabolism, including RNA processing, splicing, polyadenylation, editing, structure, stability, localization, translation initiation, and gene expression. The epitranscriptome differs across cell types, metabolic conditions, and states of health, playing vital (but poorly understood) roles in the differentiation of cellular phenotype and function and helping to explain the dramatic phenotypic differences between cells of the same organism that possess an identical primary genetic sequence. Changes in the epitranscriptome are correlated with disease. For example, mRNA and ncRNA modifications are known to regulate spatiotemporal gene expression changes during cancer stem cell differentiation, thereby playing an orchestrating role in disease progression. Additionally, RNA modifications are strongly suspected of being a key mechanism by which RNA viruses (e.g. Coronaviridae and Flaviviridae) subvert the host and evade the innate immune system.

The term "genome" refers to all the DNA in a cell or population of cells, or a selection of specific types of DNA molecules (e.g., coding DNA, noncoding DNA, mitochondrial DNA, or chloroplast DNA.) The term "transcriptome" refers to all RNA molecules produced in one or a population of cells, or a selection of specific types of RNA molecules (e.g., mRNA vs. ncRNA, or specific mRNAs within an mRNA transcriptome) contained in a complete transcriptome. In some embodiments, a transcriptome comprises multiple different types of RNA, such as coding RNA (i.e., RNA that is translated into a protein, e.g., mRNA) and non-coding RNA. A non-limiting list of various types of RNA molecules found in a transcriptome, all of which may contain modified nucleosides, includes: 7SK RNA, signal recognition particle RNA, antisense RNA, CRISPR RNA, Guide RNA, long non-coding RNA, microRNA, messenger RNA, piwi-interacting RNA, repeat-associated siRNA, retrotransposon, ribonuclease MRP, ribonuclease P, ribosomal RNA, small Cajal body-specific RNA, small interfering RNA, smY RNA, small nucleolar RNA, small nuclear RNA, and trans-acting siRNA.

As used herein, the term "non-canonical feature" of a nucleic acid means a feature of a nucleic acid that is separate and distinct from its primary sequence. For example, a non-canonical feature may be a chemical modification to a DNA or RNA base, or to a DNA or RNA backbone. In some embodiments, a non-canonical feature may be a structural sequence, such as a hairpin or a loop. Other illustrative non-canonical structures include, but are not limited to, Z-DNA structures, G-quadruplexes, triplexes, I-motifs, bulges, abasic sites, triplexes, three-way junctions, cruciform structures, tetraloops, ribose zippers, pseudoknots, etc. Nucleic acids, including DNAs and RNAs, may comprise numerous non-canonical features. The frequency of these modifications varies widely depending on RNA and type of feature, although clusters of modifications may occur. In some embodiments, non-canonical features may result from DNA and/or RNA damage. The terms "non-canonical feature" and "modification" may be used interchangeably herein, as will be understood in context by a person of ordinary skill in the art.

As used herein, the term "target nucleic acid" refers to a nucleic acid comprising one or more non-canonical features. The binding domains described herein may bind to a target nucleic acid when the binding domain of the molecule recognizes the non-canonical feature.

As used herein, the term "substrate" will be used to refer to any solid support. For example, a substrate may be a bead, chip, plate, slide, dish, gel, tube, flowcell, matrix, array, microfluidics device or component thereof, well, cartridge or 3-dimensional polymer matrix. As described herein, the binding domains described herein may be coupled to one or more substrates, and a substrate may be coupled to one or more binding domains. Additionally, the adapters described herein may be coupled to one or more substrates, and a substrate may be coupled to one or more adapters. Substrates may be formed from a variety of materials. In some embodiments, the substrate is a resin, a membrane, a fiber, or a polymer. In some embodiments, the substrate comprises sepharose, agarose, cellulose, polystyrene, polymethacrylate, and/or polyacrylamide. In some embodiments, the substrate comprises a polymer, such as a synthetic polymer. A non-limiting list of synthetic polymers includes: poly (ethylene)glycol, polyisocyanopeptide polymers, polylactic-co-glycolic acid, poly(F-caprolactone) (PCL), polylactic acid, poly(3-hydroxybutyrate-co-3-hydroxyvalerate) (PHBV), chitosan and cellulose.

As used herein, the term "barcode" refers to a synthetically produced nucleic acid. Unique barcodes may be assigned to specific nucleic acid modifications, to allow for specific identification of those modifications in the methods described herein. Accordingly, a barcode is "unique" to a non-canonical modification if it is used specifically to identify that modification in one or more of the methods described herein. Barcodes may be produced using methods known in the art, such as solid phase oligonucleotide synthesis. In some embodiments, a barcode may be a DNA barcode (i.e., it may comprise a DNA sequence). In some embodiments, a barcode may comprise a synthetic DNA structure, such as a peptide nucleic acid (PNA) or a locked nucleic acid (LNA). In some embodiments, the synthetic DNA structure may comprise one or more modified bases. In some embodiments, a barcode may be an RNA barcode (i.e., it may comprise an RNA sequence). Barcodes may be any length, such as a length in the range of about 4 to about 150 nucleotides. In some embodiments, a barcode is about 4 to about 20 nucleotides in length, such as about 4, about 5, about 6, about 7, about 8, about 9, about 10, about 11, about 12, about 13, about 14, about 15, about 16, about 17, about 18, about 19, or about 20 nucleotides in length. Typically, a barcode will comprise a rationally designed sequence that is not found in the genome of any known organism. However, in some embodiments, a barcode may comprise a known sequence. For example, the sequence of the barcode may comprise a signature associated with a pathogen or other biological material. In some embodiments, a barcode may comprise a sequence configured to facilitate a sequencing reaction. The terms "barcode" and "adapter" may sometimes be used interchangeably herein. As will be understood in the art, an adapter may, in some embodiments, consist of a barcode. In some embodiments, an adapter may comprise a barcode and one or more additional elements as described below and as shown in FIG. 12A-12D.

The term "amplify," when used in reference to a nucleic acid, means producing copies of that nucleic acid. Nucleic acids may be amplified using, for example, polymerase chain reaction (PCR). Alternative methods for nucleic acid amplification include helicase-dependent amplification (HAD), recombinase polymerase amplification (RPA), loop mediated isothermal amplification (LAMP), nucleic acid sequence-based amplification (NASBA), self-sustained sequence replication (3SR), and rolling circle amplification (RCA).

As used herein the term "coupled" may be used to describe two or more components that are associated with one other. For example, a first component coupled to a second component may be bound covalently or non-covalently thereto, or otherwise linked.

As used herein the term "intra-complex adapter transfer" or "intra-complex barcode transfer" refers to transfer of an adapter and/or barcode to a target nucleic acid (e.g., a DNA or an RNA), while a binding domain and adapter are bound thereto. Thus, in this context, the term "complex" refers to a complex formed between the target nucleic acid, the binding domain, and its cognate adapter.

As used herein, the terms "crosstalk", "barcode crosstalk", and similar terms refer to the off-target transfer of a nucleic acid barcode. For example, barcode crosstalk may occur when the barcode of an adapter is transferred to a nucleic acid that is not bound to the binding domain of the nucleic acid binding molecule.

The term "DNA address" refers to a DNA or RNA sequence and/or its complement that is used as a programmable binding element, to facilitate a specific binding event. For example, a deaminase may be coupled to a DNA or RNA sequence (i.e., a first DNA address) that binds to a target DNA or RNA sequence (e.g., a second DNA address), directing the deaminase thereto.

A "nucleic acid lesion" such as a "DNA lesion" or a "RNA lesion" is a chemical modification of the nucleic acid that may occur as a result of endogenous processes and/or exogeneous agents. For example, DNA lesions may be caused by oxidative damage (e.g. 8-oxoguanine), reaction with electrophiles and alkylating agents including those present in charred meats and in tobacco smoke (benzo[a] pyrene adducts and alkylated nucleobases), UV damage (cyclobutane pyrimidine dimers and 6-4 pyrimidine-pyrimidine photoproducts), metal complexation (mercury complexes and platinated crosslinks). DNA lesions occurring due to endogenous processes occur frequently it is estimated that they occur around 50,000 times per day in each cell. DNA lesions are typically repaired by a variety of repair enzymes or bypassed by lesion bypass polymerases during replication of the genetic code, the latter process causing mutation. Mutations that confer unnatural cell growth and proliferation are drivers of cancer. Mutations are readily detected by conventional DNA sequencing, but the lesions themselves cannot be detected using standard DNA sequencing workflows. Lesions are not distributed uniformly throughout the genome, and the efficacy of repair is tied to DNA locus and cell state. Moreover, the most common cancer chemotherapeutics (cisplatin, gemcitabine, etc.) induce DNA damage, so mapping DNA damage across the human genome offers enormous potential to understand aging and cancer etiology and to improve the effectiveness and lower the toxicity of cancer chemotherapeutics.

Surface Architectures and Compositions

Described herein are compositions comprising adapters and binding domains for identifying non-canonical features on nucleic acids. The compositions described herein comprise different surface architectures of binding domains and adapters spatially separated on a substrate.

In some embodiments, a binding domain described herein is coupled to a substrate. In some embodiments, a binding domain is directly coupled to a substrate. In some embodiments, a binding domain is coupled to a linker wherein the linker is coupled to a substrate. In some embodiments, the binding domain is covalently bound to the substrate. In some embodiments, the binding domain is non-covalently bound to the substrate.

In some embodiments, an adapter described herein is coupled to a substrate. In some embodiments, an adapter is directly coupled to a substrate. In some embodiments, an adapter is coupled to a linker wherein the linker is coupled to a substrate. In some embodiments, an adapter is covalently bound to the substrate. In some embodiments, an adapter is non-covalently bound to the substrate.

Figure 1A:
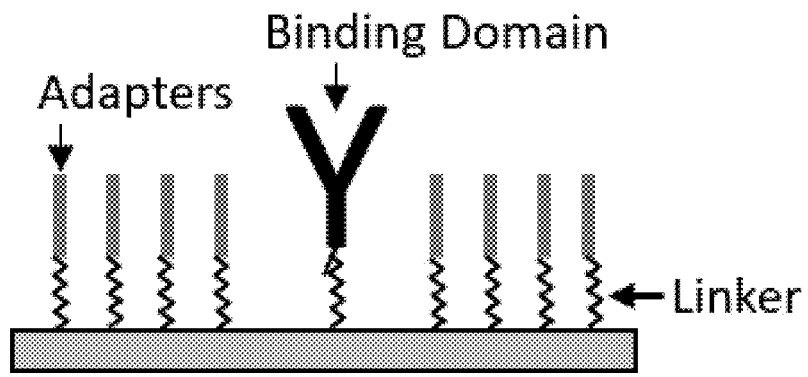
FIGS. 1A-1H illustrate different molecular architectures for coupling a DNA adapter and binding domain to a surface (e.g. a substrate). In an illustrative embodiment, the DNA adapter comprises an RNA modification specific barcode that is transferred to the target RNA for the purpose of identifying the modification.

In some embodiments, the disclosure provides compositions comprising a substrate, an adapter, and a binding domain. In some embodiments, the composition comprises a substrate, a binding domain, and an adapter as depicted in FIG. 1A. In some embodiments, a composition comprises a binding domain directly coupled to the substrate and an adapter directly coupled to the substrate. In some embodiments, a composition comprises a binding domain coupled to the substrate via a linker and an adapter directly coupled to the substrate. In some embodiments, a composition comprises a binding domain directly coupled to the substrate and an adapter coupled to the substrate via a linker. In some embodiments, a composition comprises a binding domain coupled to a substrate via a first linker and an adapter coupled to the same substrate via a second linker.

In some embodiments, a composition comprises:
i) a substrate,
ii) a binding domain coupled to the substrate via a first linker, and
iii) an adapter coupled to the substrate via a second linker.

In some aspects, the binding domain binds specifically to a non-canonical feature of a DNA or an RNA; and the adapter comprises a nucleic acid barcode sequence unique to the non-canonical feature bound specifically by the binding domain.

In some embodiments, the disclosure provides compositions comprising a secondary recognition element, a substrate, a binding domain, and an adapter.

In some aspects, the invention of the present disclosure includes one or more methods of manufacturing the compositions and conjugates disclosed herein and depicted in the drawings. In one aspect, the methods include coupling one or more adapters directly or indirectly to a substrate, and coupling one or more binding domains directly or indirectly to a substrate, wherein any indirect couplings may be via a linker. See, e.g., FIG. 1A.

In one aspect, the methods of manufacturing include coupling one or more secondary recognition elements directly or indirectly to a substrate, and binding one or more binding domains directly or indirectly to the one or more secondary recognition elements, and coupling one or more adapters directly or indirectly to the one or more secondary recognition elements, wherein any indirect couplings may be via a linker. See, e.g., FIG. 1B.

In one aspect, the methods of manufacturing include coupling one or more secondary recognition elements directly or indirectly to a substrate, and coupling one or more binding domains directly or indirectly to the substrate, and coupling one or more adapters directly or indirectly to the one or more secondary recognition elements or coupling one or more adapters directly or indirectly to the substrate, wherein any indirect couplings may be via a linker. See, e.g., FIG. 1C. In one aspect, the methods of manufacturing include coupling one or more secondary recognition elements directly or indirectly to a substrate, and coupling one or more binding domains directly or indirectly to the secondary recognition elements, and coupling one or more adapters directly or indirectly to the substrate, wherein any indirect couplings may be via a linker.

In one aspect, the methods of manufacturing include coupling two or more types of secondary recognition elements directly or indirectly to a substrate, and binding one or more binding domains directly or indirectly to at least one type of the secondary recognition elements, and coupling one or more adapters directly or indirectly to the one or more secondary recognition elements, wherein any indirect couplings may be via a linker. See, e.g., FIG. 1D.

In one aspect, the methods of manufacturing include coupling one or more secondary recognition elements directly or indirectly to a substrate, and binding two or more binding domains directly or indirectly to the secondary recognition elements, and coupling one or more adapters directly or indirectly to some of the binding domains such that one binding domain species is labeled with adapters and does not bind nucleic acids, whereas one or more other binding domain species are specific to a non-canonical feature of nucleic acids and are unlabeled, wherein any indirect couplings may be via a linker. See, e.g., FIG. 1E.

In one aspect, the methods of manufacturing include coupling two or more different types of cleavable adapters directly or indirectly to a substrate, and coupling one or more capture molecules directly or indirectly to the substrate, and providing one or more binding domains coupled to a nucleic acid that is complementary to a capture sequence of the capture molecule such that the nucleic acid that is complementary to a capture sequence hybridizes with the capture molecule, wherein any indirect couplings may be via a linker. See, e.g., FIG. 1F.

In one aspect, the methods of manufacturing include forming a transposome comprising a transposase dimer loaded with two Mosaic End (ME) containing adapter molecules, coupling the transposome directly or indirectly to a substrate, and coupling one or more secondary recognition elements directly or indirectly to the substrate, and binding one or more binding domains directly or indirectly to the secondary recognition element(s), wherein any indirect couplings may be via a linker. See, e.g., FIG. 1G. In one aspect, the methods of manufacturing include forming a transposome comprising a transposase dimer loaded with two Mosaic End (ME) containing adapter molecules, coupling the transposome directly or indirectly to a substrate, and coupling one or more binding domains directly or indirectly to the substrate, wherein any indirect couplings may be via a linker.

In one aspect, the methods of manufacturing include coupling a secondary recognition element directly or indirectly to a substrate, fusing Tn5 to protein A to form Tn5-protein A fusion proteins, forming dimers of the fusions proteins, loading the dimers of Tn5-protein A fusion proteins with ME adapters, binding a binding domain to the secondary recognition element, binding the protein A of the fusion proteins to the binding domain (e.g., to the Fc region of an antibody), wherein any indirect couplings may be via a linker. See, e.g., FIG. 1H. In one aspect, the methods of manufacturing include coupling a secondary recognition element directly or indirectly to a substrate, fusing Tn5 to protein A to form Tn5-protein A fusion proteins, forming dimers of the fusions proteins, loading the dimers of Tn5-protein A fusion proteins with ME adapters, coupling a binding domain directly or indirectly to the substrate, binding the protein A of the fusion proteins to the binding domain (e.g., to the Fc region of an antibody), wherein any indirect couplings may be via a linker.

Figure 1B:
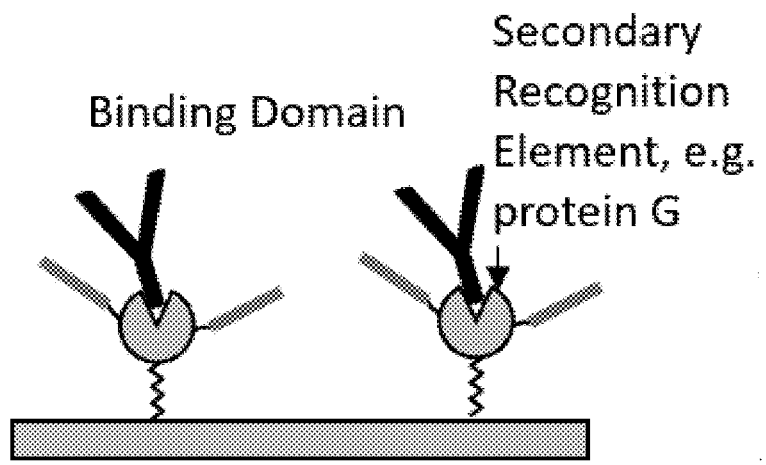
Figure 1C:
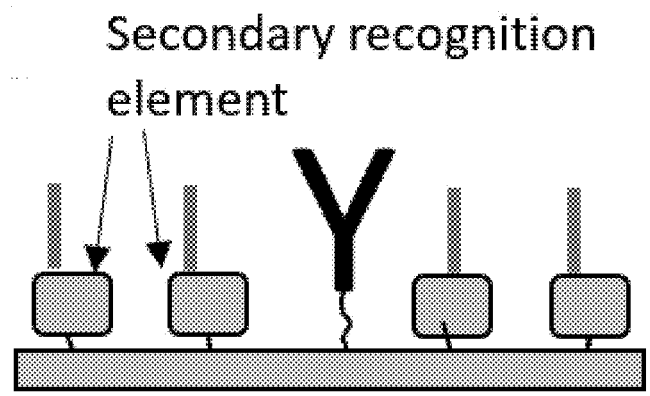

In some embodiments, a composition comprises a secondary recognition element, a substrate, a binding domain, and an adapter, wherein the adapter is coupled to the secondary recognition element as depicted in FIG. 1B. In some embodiments, a composition comprises a secondary recognition element, a substrate, a binding domain, and an adapter, wherein the adapter is coupled to the secondary recognition element as depicted in FIG. 1C. In some embodiments, a composition comprises a secondary recognition element directly coupled to a substrate (FIG. 1C). In some embodiments, a composition comprises a secondary recognition element indirectly coupled to a substrate, for example via a linker (FIG. 1B). In some embodiments, a composition comprises a secondary recognition element directly coupled to a substrate and an adapter directly coupled to the secondary recognition element. In some embodiments, a composition comprises a secondary recognition element coupled to a substrate via a linker and an adapter directly coupled to the substrate. In some embodiments, a composition comprises a secondary recognition element coupled to a substrate via a first linker and an adapter coupled to the substrate via a second linker.

In some embodiments, a composition comprises:
i) a substrate,
ii) a secondary recognition element coupled to the substrate,
iii) an adapter coupled to the secondary recognition element, and
iv) a binding domain.

In some aspects, the binding domain binds specifically to a non-canonical feature of a DNA or an RNA, and wherein the binding domain is immobilized by the secondary recognition element; and the adapter comprises a nucleic acid barcode sequence unique to the non-canonical feature bound specifically by the binding domain.

In some embodiments, a secondary recognition element is capable of binding to a single binding domain. In some embodiments, a secondary recognition element is capable of binding to multiple different types of binding domains. In some aspects, a secondary recognition element may be a streptavidin, avidin, neutravidin, or analogous molecule. In some aspects, a secondary recognition element may be protein G, protein A, protein L, a variant thereof or an antibody.

In some embodiments, a composition comprises:
i) a substrate,
ii) a secondary recognition element coupled to the substrate,
iii) an adapter coupled to the secondary recognition element, and
iv) a binding domain.

In some aspects, the binding domain is configured to bind specifically to a non-canonical feature of a DNA or an RNA, and wherein the binding domain is immobilized by the secondary recognition element and the adapter comprises a nucleic acid barcode sequence unique to the non-canonical feature. In some aspects, the composition alternatively or further comprises an adapter coupled to the substrate directly or via a linker.

In some embodiments, the composition comprises a plurality of secondary recognition elements wherein the plurality of secondary recognition elements comprises secondary recognition elements that are different from each other, wherein the adapter is coupled to one of the plurality of secondary recognition elements and the binding domain is coupled to a different secondary recognition element.

In some embodiments, the composition comprises a plurality of secondary recognition elements, wherein the adapter is coupled to one of the plurality of secondary recognition elements and the binding domain is coupled to another instance of the same secondary recognition element.

In some embodiments, a composition comprises:
i) a substrate,
ii) a secondary recognition element coupled to the substrate,
iii) a binding domain coupled to the substrate via a secondary recognition element,
iv) an adapter coupled to the substrate via a linker.

In some embodiments, the binding domain is configured to bind specifically to a non-canonical feature of a DNA or an RNA, and the adapter comprises a nucleic acid barcode sequence unique to the non-canonical feature.

In some embodiments, a composition comprises:
i) a substrate,
ii) a secondary recognition element coupled to the substrate,
iii) a binding domain coupled to the substrate via a linker,
iv) an adapter coupled to the substrate via the secondary recognition element, In some embodiments, the binding domain is configured to bind specifically to a non-canonical feature of a DNA or an RNA, and the adapter comprises a nucleic acid barcode sequence unique to the non-canonical feature.

Figure 1D:
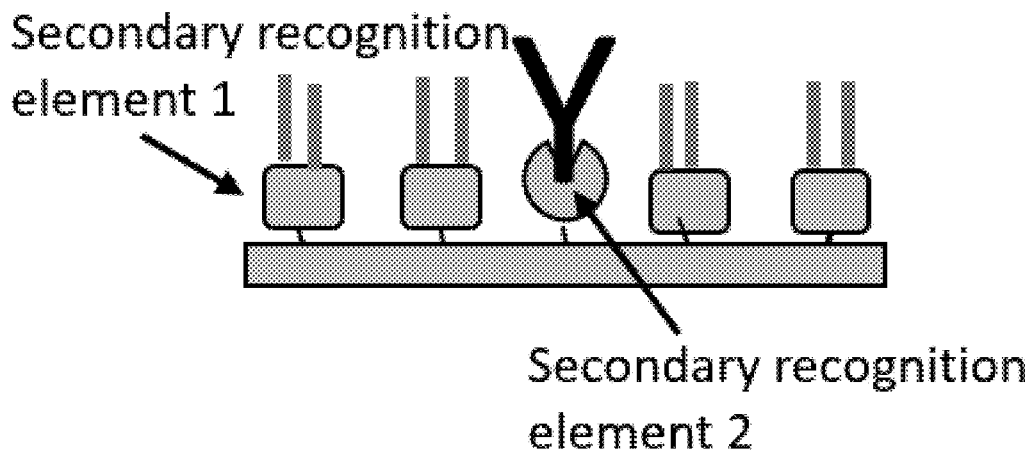

In some embodiments, a composition comprises a substrate, a capture molecule, an adapter, and a binding domain. In some embodiments, a composition comprises a substrate, a capture molecule, an adapter, and a binding domain as depicted in FIG. 1F. In some embodiments, the binding domain is immobilized by the capture molecule.

In some embodiments, a composition comprises:
i) a substrate,
ii) a capture molecule coupled to the substrate,
iii) an adapter coupled to the substrate, and
iv) a binding domain immobilized to the substrate via the capture molecule.

In some embodiments, the capture molecule is a capture molecule as depicted in FIG. 1F. In some embodiments, the capture molecule is coupled directly to the substrate. In some embodiments, the capture molecule is coupled to the substrate via a linker. In some embodiments, a capture molecule is an oligonucleotide, such as an oligonucleotide that can capture the binding domain by binding to a complementary oligonucleotide sequence coupled thereto. In some embodiments, a capture molecule is an polyethylene glycol, with pendant Click chemistry groups such as DBCO, azido, alkyne, mTET or TCO.

In some embodiments, the capture molecule can effect capture of the binding domain by a covalent or non-covalent mechanism. For example, covalent capture may be achieved by using a biorthogonal chemistry (such as DBCO/azido, alkyne/azido, mTet/TCO etc). A non-covalent capture may be achieved by a protein-based capture molecule that targets a specific binding site on the binding domain.

In some embodiments, a composition comprises:
i) a substrate,
ii) a capture molecule coupled to the substrate,
iii) an adapter coupled to the substrate, and
iv) a binding domain,
wherein the binding domain binds specifically to a non-canonical feature of a DNA or an RNA, and wherein the binding domain is immobilized by the capture molecule;
wherein the adapter comprises a nucleic acid barcode sequence unique to the non-canonical feature bound specifically by the binding domain.

In some aspects, the present disclosure includes a composition comprising:
i) a substrate,
ii) a binding domain coupled to the substrate via a first linker or a secondary recognition element, and
iii) mosaic end (ME) adapters coupled to the substrate via a second linker or secondary recognition element, and
iv) a transposase,
wherein the transposase is loaded to the immobilized ME adapters,
wherein the binding domain binds specifically to a non-canonical feature of a DNA or an RNA,
wherein at least one of the ME adapters comprises a nucleic acid barcode sequence unique to the non-canonical feature.

In some aspects, the present disclosure includes a composition comprising:
i) a substrate,
ii) a binding domain coupled to the substrate via a linker or secondary recognition element, and
iii) transposase coupled to the binding domain,
wherein the transposase is loaded to ME adapters,
wherein the binding domain binds specifically to a non-canonical feature of a DNA or an RNA,
wherein at least one of the ME adapters comprises a nucleic acid barcode sequence unique to the non-canonical feature.

In some embodiments, a composition comprises a substrate, a binding domain coupled to the substrate via a first linker or is bound to a secondary recognition element that is directly or indirectly bound to the substrate, an mosaic end (ME) adapter coupled to the substrate via a second linker, and a transposase, wherein the transposase is loaded to the ME adapter, wherein the binding domain binds specifically to a non-canonical feature of a DNA or an RNA, wherein the adapter comprises a nucleic acid barcode sequence unique to the non-canonical feature bound specifically by the binding domain. See, e.g., FIG. 1G. In some embodiments, the transposase is Tn5 transposase. FIG. 1H shows dimers of Tn5-protein A fusion proteins loaded with ME adapters and bound to the antibody via affinity binding of protein A to the Fc region of the antibody. In some embodiments, a composition comprises a substrate, a plurality of secondary recognition elements coupled to the substrate, an adapter coupled to one of the plurality of secondary recognition elements, and a binding domain coupled to another one of the plurality of secondary recognition elements, wherein the binding domain binds specifically to a non-canonical feature of a DNA or an RNA, and wherein the adapter comprises a nucleic acid barcode sequence unique to the non-canonical feature bound specifically by the binding domain. See, e.g., FIG. 1D. In some aspects, a composition comprises a bead as a substrate, e.g., as shown in FIG. 15C. According to any of the composition aspects disclosed herein, a composition may include a 1-, 2-, 3-, 4-, 5-, 6-, 7-, 8-, 9-, 10-, 11-, 12-, 13-, 14, or 15-fold excess of adapter over binding domain. Such a ratio provides efficient barcoding yield while minimizing side products.

Also provided herein are compositions comprising one or more binding domains of the disclosure. In some embodiments, a composition comprises two or more different binding domains. For example, the composition may comprise a first binding domain that binds to a first non-canonical feature, and a second binding domain that binds to a second non-canonical feature. In some embodiments, the composition may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 71, 80, 90, 100, 125, 150, 175, or 200 or more different types of binding domains.

Also provided herein are compositions comprising one or more binding domains and one or more adapters, wherein each adapter comprises a nucleic acid barcode sequence unique to the non-canonical feature bound specifically by each binding domain. For example, in a composition comprising two binding domains and two adapters, the first adapter comprises a nucleic acid barcode sequence unique to the non-canonical feature bound specifically by the first binding domain, and the second adapter comprises a nucleic acid barcode sequence unique to the non-canonical feature bound specifically by the second binding domain.

In some embodiments, a composition herein comprises one or more substrates. In some embodiments, a composition comprises two substrates. In some embodiments, the composition comprises one, two, three, four, five, or more substrates.

The compositions described herein may further comprise, in some embodiments a base editing enzyme. In some embodiments, the base editing enzyme is an adenosine deaminase, a cytosine deaminase, a glycosylase, a methylase, a demethylase, or a dioxygenase. In some embodiments, the base editing enzyme is an enzyme that removes a base, e.g., a glycosylase. The base editing enzyme may be coupled, for example, to the binding domain. Having a base editing enzyme coupled to the binding domain brings the enzyme into proximity with a target nucleic acid bound to the binding domain. The base editing enzyme may then edit the target nucleic acid. After the nucleic acid is amplified and sequenced, the location of the edited base may be determined and used to gauge the location at which the binding domain bound to the target nucleic acid (i.e., the location of a non-canonical feature on the garget nucleic acid.

In some embodiments, the base editing enzyme is covalently coupled to the binding domain. For example, the base editing enzyme may be fused to the binding domain (i.e., as a fusion protein). In some embodiments, the base editing enzyme may be covalently coupled to the binding domain via a linker that is fused to both the base editing enzyme and the binding domain. In some embodiments, the base editing enzyme is coupled to the binding domain via a targeting moiety. The targeting moiety may be selected from, for example, a peptide tag, a protein tag, a secondary antibody, a nucleic acid sequence, or a biorthogonal reactive group. In one illustrative embodiments, a base editing enzyme may be coupled to a secondary antibody, wherein the secondary antibody recognizes the binding domain (e.g., a primary antibody). In some embodiments, the targeting moiety is a protein A, protein L, or protein G. In some embodiments, the targeting moiety is a nucleic acid coupled to the base editing enzyme, wherein the nucleic acid coupled to the base editing enzyme is complementary to a nucleic acid coupled to the binding domain.

In some embodiments, the compositions described herein comprise one or more carriers, excipients, buffers, etc. The compositions may have a pH of about 0.5, about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, about 10.0, about 10.5, about 11.0, about 11.5, about 12.0, about 12.5, about 13.0, about 13.5, or about 14.0. In some embodiments, the compositions are pharmaceutical compositions.

Adapters

As used herein, the term "adapter" refers to any short nucleic acid sequence that can be coupled to the end of a DNA or RNA molecule and that confers some functionality. For example, in some embodiments, an adapter may facilitate sequencing and/or identification of a DNA or RNA molecule. In some embodiments, an adapter is a DNA, an RNA or a mixed DNA and RNA sequence. In some examples, the nucleic acid adapter comprises backbone modifications, e.g., one or more backbone modifications selected from locked nucleic acid (LNA), peptide nucleic acid (PNA), glycol nucleic acid (GNA), phosphorothioate, 2'-fluoro-ribose, 2'-methoxy-ribose, phosphorodithioate, methylphosphonate, phosphoramidate, guanidinopropyl phosphoramidate, triazole, guanidinium, morpholino, threose nucleic acid (TNA) or hexitol nucleic acid (HNA).

In some embodiments, the adapter comprises a 5' phosphate. In some embodiments, the adapter comprises a 3' phosphate. In some embodiments, the adapter comprises a 5' phosphate and a 3' phosphate. In some embodiments, an adapter is single-stranded. In some embodiments, an adapter is double-stranded. In some embodiments, a double-stranded adapter may comprise a single-stranded adapter hybridized to a complementary oligonucleotide.

In some embodiments, an adapter may be cleavable. For example, the adapter may comprise one or more cleavage sites. The cleavage site may comprise, for example, one or several uracil bases, a sequence recognized by an enzyme (e.g., a restriction enzyme or other nuclease), or a synthetic chemical moiety. In some embodiments, an adapter is cleavable as depicted in FIG. 1F. In some embodiments, the linker is cleaved by chemical or enzymatic cleavage using for example, disulfides, a Cathepsin B cleavage site, or photocleavage. In some embodiments, adapters are cleaved at a site within the adapter. For example, at a restriction site (requires double-strand formation), using a uracil/USER enzyme, using a 8-oxoG/FpG enzyme, or via a photocleavable phosphate backbone modification.

In some embodiments, an adapter comprises a universal forward primer (UFP). In some embodiments, an adapter comprises a universal reverse primer (URP). In some embodiments, an adapter comprises a UFP and a URP. In some embodiments, an adapter consists of a UFP or a URP. The UFP and URP sequences are DNA sequences that do not occur naturally and allow for selective amplification of only those sequences that were introduced into a target nucleic acid (or copy thereof). During sequencing, the UFP and/or URP are annealed to the DNA target, to provide an initiation site for the elongation of a new DNA molecule (i.e., a copy thereof). A list of illustrative UFPs and URPs can be found at the world wide web address Islabs.com/resources/universal-primer-list. In some embodiments, universal primer sequences used in the adapters (and transferred to the target nucleic acid) are compatible with established DNA sequencing platforms and may be used to introduce surface adapters such as Illumina P5 and P7 in downstream PCR reactions.

In some embodiments, an adapter may comprise a barcode, such as a modification encoding barcode (MBC). An MBC is a short, unique nucleic acid sequence. Each MBC is used in connection with a specific epigenetic or epitranscriptomic modification, to help with the identification and/or analysis thereof. For example, an MBC may be used in an adapter that is coupled to a binding domain that is specific for a particular non-canonical feature. In some embodiments, an adapter may consist of a barcode. In some embodiments, an adapter may consist of an MBC.

In some embodiments, an adapter may comprise a unique molecular identifier (UMI). A UMI consists of a short, random sequence that has $4^{[UMI\ Length]}$ unique variants. For example, a 10-base long UMI can encode 1,048,576 ($4^{10}$) unique molecules. UMIs are used for the absolute quantification of sequencing reads to correct for PCR amplification bias and errors. For example, an RNA sample may contain 100 copies of transcript A and 100 copies of transcript B. After PCR amplification, 1M copies of transcript A and 2M of transcript B may be detected because transcript B amplifies more efficiently. UMI tagging, however, links 100 unique UMIs to A and 100 unique UMIs to B. When using a UMI for transcript A, 10,000 copies of 100 UMI variants will be detected, and for transcript B 20,000 copies of 100 UMI variants will be detected. Counting the number of UMI variants instead of counting the number of reads provides the absolute number of molecules.

In some embodiments, an adapter comprises one or more unnatural nucleobases. In some embodiments, the one or more unnatural nucleobases are independently selected from a G clamp (9-(2-aminoethoxy)-3H-benzo[b]pyrimido[4,5-e][1,4]oxazin-2(10H)-one), tC (3H-benzo[b]pyrimido[4,5-e][1,4]oxazin-2(10H)-one), $tC^O$(3H-benzo[b]pyrimido[4,5-e][1,4]oxazin-2(10H)-one), inosine, Super T (5-hydroxybutynl-2'-deoxyuridine), Super G (8-aza-7-deaz-aguanosine), uracil, or 8-oxo-G.

In some embodiments, the adapter comprises 2 or more random bases at its 3' end, e.g., 1, 2, 3, 4, 5, 6, 7, 8, 9, 10, 11, 12, 13, 14, 15, 16, 17, 18, 19, 20, or more, or 2-12, or 3-8, or 4-6 random bases at its 3' end. In some aspects, the disclosure includes a method of random priming the RNA to introduce the barcode using such random bases. This method eliminates the need for ligating a spacer sequence to the target nucleic acid, prior to the barcoding step.

In some aspects, adapter comprises 3' or 5' blocking groups. In some aspects, the 3' or 5' blocking groups are independently selected from a dideoxyribose, a phosphate, an inverted base, or a linker.

FIG. 12A-12D illustrate exemplary nucleic acid adapter architectures, and the legend provides a description of each element used therein. These adapters are labeled Type A, Type B, Type C, and Type D for ease of reference.

The adapters shown in FIG. 12A (Type A) represent minimal adapters that may comprise either a UFP or a URP sequence. Type A adapters do not contain any sequence that can be used for identification or analysis of a non-canonical nucleic acid feature, but are instead used for library construction. In some embodiments, Type A adapters are coupled to nucleic acid molecules that do not comprise a non-canonical feature. In some embodiments, Type A adapters are coupled to nucleic acid molecules that do contain a non-canonical feature after introducing a barcoded adapter to the other end of the target nucleic acid. For example, Type A adapters may be used to cap and prepare a nucleic acid for PCR amplification after one or more barcodes have been added.

The adapters shown in FIG. 12B-12D each comprise an MBC, which is specific for one non-canonical DNA/RNA feature (e.g., a modified base). As shown in FIG. 12B, Type B adapters may be used for library preparation workflows that involve circularization of cDNA. They comprise a cleavage site (CLS). Cleavage of Type B adapters may be performed prior to PCR amplification. As shown in FIG. 12C, Type C adapters lack the CLS and contain only one universal primer region. Type C adapters may be used, for example, in barcode transfer by ligation reactions. They may be combined with methods for second strand synthesis, such as template switching oligonucleotides according to Smart-Seq technology or another adapter ligation. As shown in FIG. 12D, Type D adapters are specifically designed for encoding by primer extension. Type D adapters may comprise one 3'-terminal spacer (SP) or two spacer regions (e.g. SP1, SP2) at either ends. The reaction is initiated by ligating a short spacer region (SP) onto the 3' end of the target nucleic acid and binding of a Type D adapter with complementary spacer. The spacer may be universal across all nucleic acid-binding molecules and cycles, unique to each type of nucleic acid-binding molecule, or unique to each cycle of barcoding. In some embodiments, a spacer is 3, 4, 5, 6, 7, 8, 9, 10, 11, 12, 13, 14, 15, 16, 17, 18, 19, or 20 nucleotides in length. In some embodiments, a spacer is 6 nucleotides in length. In some embodiments, a spacer is 7 nucleotides in length. In some embodiments, a spacer is 8 nucleotides in length. Type D adapters may be used, for example, in a single barcode transfer by primer extension reactions, or for multiple, sequential barcode transfers. Multiple cycles of barcoding may be used to interrogate only one, or a subset of non-canonical features in each cycle. For example, the first encoding cycle may employ nucleic acid binding molecules specific for m5C. The second encoding cycle may employ nucleic acid binding molecules specific for m6A. The third encoding cycle may employ nucleic acid binding molecules specific to inosine, etc. In another embodiment, the first cycle may interrogate m5C and m6A, and the second cycle may interrogate inosine. In another embodiment, the first encoding cycle may interrogate all non-canonical features, and the second encoding cycle may interrogate all non-canonical features for a second time.

In some embodiments, an adapter comprises a UFP, a URP, or a UFP and a URP. In some embodiments, an adapter comprises a UFP and/or a URP, and also comprises an MBC. In some embodiments, an adapter comprises a UFP and/or a URP, an MBC, and a UMI. In some embodiments, and adapter comprises a UFP and/or a URP, a MBC, a UMI, and a CLS. In some embodiments, an adapter comprises a UFP and/or a URP, a MBC, a UMI, a CLS, and a SP. In some embodiments, an adapter comprises a UFP, a CLS, a URP, a UMI, and an MBC. In some embodiments, an adapter comprises a UFP, a UMI, and an MBC. In some embodiments, an adapter comprises a URP, a UMI, and an MBC. In some embodiments, an adapter comprises a first SP, an MBC, a UMI, and a second SP.

The adapters described herein may, in some embodiments, comprise one or more linkers, such as linkers which help link the binding domain to the adapter. The linkers may comprise polyethylene glycol, hydrocarbons, peptides, DNA, or RNA. The linkers may vary in length. Longer linkers may be used in situations where a non-canonical feature of a DNA or RNA is located far from the 5' or 3' end of a nucleic acid sequence. Shorter linkers may be used in situations where a non-canonical feature of a DNA or RNA is located relatively close to a 5' or a 3' end of a nucleic acid sequence.

In some embodiments, the adapters, or a linker sequence contained therein, are cleavable. For example, the adapters may comprise one or more cleavage sites. The adapter may be chemically, photochemically or enzymatically cleavable. The cleavage sites may comprise, for example, one or several uracil bases, a sequence recognized by an enzyme (e.g., a restriction enzyme or other nuclease), or a synthetic chemical moiety, for example disulfides, carbonate ester, hydrazones, cis-aconityl, or β-glucuronide.

As described in further detail below, adapters may be fused to a single- or double-stranded target nucleic acid (e.g., a DNA or RNA) using a barcode transfer reaction.

In some embodiments, barcoding by primer extension comprises appending a 3'poly-rA tail to an RNA target. The 3'poly-rA tail is appended by polyadenylation using any known poly (A) polymerase (e.g. *E. coli* poly (A) polymerase). In some embodiments, the RNA target is incubated with poly (A) polymerase and a competitor poly-dT oligonucleotide. Co-treatment with a poly (A) polymerase and a competing poly-dT oligonucleotide controls the length of the appended 3'poly-rA tail. In some examples, a mixture of ATP and ddATP may be used as substrates in an A-tailing reaction to control the length of the A-tail. Typically, polyadenylation yields a mean 3'poly-rA tail length of about 150 bases. In some embodiments, the length of the 3'poly-rA tail is about 5, about 10, about 15, about 20, about 25, about 30, about 35, about 40, about 45, about 50, about 55, or about 60 bases in length.

In some embodiments, primer extension comprises appending a 3'poly-U tail to an RNA target. The 3'poly-U tail is appended by polyuridylation using any known poly (U) polymerase (e.g. *Schizosaccharomyces pombe* Cid1). In some embodiments, the length of the 3'poly-U tail is about 5, about 10, about 15, about 20, about 25, about 30, about 35, about 40, about 45, about 50, about 55, or about 60 bases in length.

In some embodiments, an adapter comprises any one of SEQ ID NOs: 1-5 as provided in Table 4. In some embodiments, an adapter comprises the sequence of SEQ ID NO: 1. In some embodiments, an adapter comprises the sequence of SEQ ID NO: 2. In some embodiments, an adapter comprises the sequence of SEQ ID NO: 3. In some embodiments, an adapter comprises the sequence of SEQ ID NO: 4. In some embodiments, an adapter comprises the sequence of SEQ ID NO: 5. In some embodiments, the adapter comprises an adapter as shown in Table 4, or a sequence having 1, 2, 3, 4, or 5 amino acid substitutions relative thereto.

In some embodiments, an adapter described herein comprises a 5'-amine moiety (5AmMC6). In some embodiments an adapter comprises a 3' amino moiety (3AmMO). In some embodiments, an adapter comprises an 18-atom hexa-ethyleneglycol spacer (iSp18). In some embodiments, an adapter comprises a single uracil surrounded by filler AT repeats for release from the substrate surface by USER enzyme (NEB) cleavage. In some embodiments, an adapter comprises an 8 base barcode.

In some embodiments, an adapter described herein is functionalized to a substrate with TCO-PEG4-NHS Ester. In some embodiments, an adapter is immobilized on a substrate using Protein G, A, or L.

TABLE 4

Adapters

| Description | Sequence | SEQ ID NO |
|---|---|---|
| 5'end is phosphorylated (5Phos) to enable enzymatic ligation, followed by a 7b barcode (underlined) that indicates the RNA modification, a unique molecular identifier of at least 3 bases (NNN, wherein N is any nucleotide), the Illumina adapter (bold), an 18-atom hexa-ethyleneglycol spacer (iSp18), a single uracil surrounded by filler AT repeats for release from the surface by USER enzyme (NEB) cleavage, and a 3' amino moiety (3AmMO) for surface coupling. | AATTAGTNNNAGATCGGAAGAGCACAC GTCTATATATUATATATA /5Phos/AATTAGTNNNAGATCGGAAGAGC ACACGTCT (SEQ ID NO: 42)/iSp18/ATATATUATATATA/3AmMO/ (SEQ ID NO: 43) | 1<br><br>42 & 43 |
| 5AmMC6 is a 5'-amine moiety followed by a single uracil (bold) surrounded by filler AT repeats for release from the surface by USER enzyme (NEB) cleavage, an 18-atom hexa-ethyleneglycol spacer (iSp18), the Illumina adapter (bold), a unique molecular identifier of at least 3 bases (NNN, wherein N is any nucleotide), an 7b barcode (underlined) that indicates the RNA modification, and an 8bp spacer (italics). | ATATATUATATATAAGACGTGTGCTCTT CCGATCTNNNCACTGATCACTCAGT /5AmMC6/ATATATUATATATA (SEQ ID NO: 44)/iSp18/AGACGTGTGCTCTTCCGATCT NNNCACTGATCACTCAGT (SEQ ID NO: 45) | 2<br><br>44 & 45 |
| 5'end is phosphorylated (5Phos) to enable enzymatic ligation, followed by an 7b barcode (underlined) that indicates the RNA | ATCAGTGNNNAGATCGGAAGAGCACAC GTCTATATATUATATATA | 3 |

TABLE 4-continued

Adapters

| Description | Sequence | SEQ ID NO |
|---|---|---|
| modification, a unique molecular identifier of at least 3 bases (NNN, wherein N is any nucleotide), the Illumina adapter (bold), an 18-atom hexa-ethyleneglycol spacer (iSp18), a single uracil surrounded by filler AT repeats for release from the surface by USER enzyme (NEB) cleavage, and a 3' amino moiety (3AmMO). | /5Phos/ATCAGTGNNNAGATCGGAAGAGC ACACGTCT (SEQ ID NO: 46)/iSp18/ATATATUATATATA/3AmMO/ (SEQ ID NO: 47) | 46 & 47 |
| 5'end is phosphorylated (5Phos) to enable enzymatic ligation, followed by an 7b barcode (underlined) that indicates the RNA | AAAGCTGNNNAGATCGGAAGAGCACAC GTCTATATATUATATATA | 4 |
| modification, a unique molecular identifier of at least 3 bases (NNN, wherein N is any nucleotide), the Illumina adapter (bold), an 18-atom hexa-ethyleneglycol spacer (iSp18), a single uracil surrounded by filler AT repeats for release from the surface by USER enzyme (NEB) cleavage, and a 3' amino moiety (3AmMO). | /5Phos/AAAGCTGNNNAGATCGGAAGAGC ACACGTCT (SEQ ID NO: 48)/iSp18/ATATATUATATATA/3AmMO/ (SEQ ID NO: 49) | 48 & 49 |
| 5'end is phosphorylated (5Phos) to enable enzymatic ligation, followed by an 7b barcode (underlined) that indicates the RNA | ATATAGGNNNAGATCGGAAGAGCACAC GTCTATATATUATATATA | 5 |
| modification, a unique molecular identifier of at least 3 bases (NNN, wherein N is any nucleotide), the Illumina adapter (bold), an 18-atom hexa-ethyleneglycol spacer (iSp18), a single uracil surrounded by filler AT repeats for release from the surface by USER enzyme (NEB) cleavage, and a 3' amino moiety (3AmMO). | /5Phos/ATATAGGNNNAGATCGGAAGAGC ACACGTCT (SEQ ID NO: 50)/iSp18/ATATATUATATATA/3AmMO/ (SEQ ID NO: 51) | 50 & 51 |
| Lower case: mosaic end Bold: mosaic end prime The series of N's represents the barcode sequence Italics: primer site In example 7, below, Tn5 ligates the same adapters to both ends of the target nucleic acid. These adapters may later be cleaved and replaced by Illumina adapters. | 5'-BiotinTEG-Spacer18-TTTGTGAUGC*GATGAACTCAGAGTGCTT* NNNNNNNNNNNNagatg tgtataagagacag-3' (SEQ ID NO: 13) Hybridized to: 5'-Phos-CTGTCTCTTATACACATCT (SEQ ID NO: 16) | 12 & 13 |
| MBC-111 | /5Biosg//iSp18//iSp18//iSp18//iSp18/CTACAC GACGCTCTTCCGATCTNNNNNNNNNNNN GACACCACACTCAGT | 36 |
| MBC-112 | /5Biosg//iSp18//iSp18//iSp18//iSp18/CTACAC GACGCTCTTCCGATCTNNNNNNNNNNNN TCAAGCGCACTCAGT | 37 |
| MBC-113 | /5Biosg//iSp18//iSp18//iSp18//iSp18/CTACAC GACGCTCTTCCGATCTNNNNNNNNNNNN AGCGATTCACTCAGT | 38 |

TABLE 4-continued

Adapters

| Description | Sequence | SEQ ID NO |
|---|---|---|
| ME adapter | CAAGCAGAAGACGGCATACGAGAT-NNNNNNNN-GTCTCGTGGGCTCGGAGATGTGTATAAGAGACAG | 39 |
| ME adapter | AATGATACGGCGACCACCGAGATCTACAC-NNNNNNNN-TCGTCGGCAGCGTCAGATGTGTATAAGAGACAG | 40 |

Binding Domains

As used herein, the term "binding domain" refers to any nucleic acid, polypeptide, etc. that binds to a non-canonical feature of a target nucleic acid, such as a modified nucleoside. The term "binding domain" may be used interchangeably herein with the terms "binder," "recognition element," "antibody," etc., as will be understood from context by those of skill in the art. In some embodiments, a binding domain binds to a non-canonical feature of a target nucleic acid. In some embodiments, the binding domain does not bind to any nucleic acid features flanking the non-canonical feature. In some embodiments, a binding domain binds to both (i) a non-canonical feature of a target nucleic acid, and (ii) one or more nucleic acid features flanking the non-canonical feature (e.g., a nucleobase, a sugar, a phosphate, or a combination thereof). In some embodiments, the binding domain may bind a conserved sequence motif. For example, $m^6A$ often occurs in the following motif: GG($m^6A$)CT. Accordingly, when a binding domain binds to $m^6A$, it may also bind to one or more of the nucleic acids (e.g., GG or CT) that are adjacent thereto. As another example, a binding domain may bind to all or part of the anticodon loop of tRNA.

The binding domains described herein, bind specifically to a non-canonical feature of a DNA or an RNA. The binding domains described herein may be any protein, nucleic acid, or fragment or derivative thereof that is capable of recognizing and binding to a non-canonical feature of a target nucleic acid. For example, in some embodiments, the binding domain comprises an antibody, an aptamer, a reader protein, a writer protein, an eraser protein, endonuclease V, an engineered macromolecule scaffold, an engineered protein scaffold, or a selective covalent capture reagent, or a fragment or derivative thereof. In some aspects, the binding domain comprises a catalytically inactive variant of a writer or eraser protein. In some aspects, the reader protein is NUDT16, YTHDC1, YTHDC2, YTHDF1, YTHDF2, or a fragment or derivative thereof. In some aspects, the writer protein is a DNMT protein, a NAT10 protein, a METTL protein, a TRM protein, a BMT protein, a DUS protein, a PUS protein, a ADAR protein or a NSUN protein, or a fragment or derivative thereof. In some aspects, the writer protein is DNTM1, DNTM3A/B, NAT10, METTL3, METTL8, METTL14, METTL16, TRM, BMT, DUS2, PUS, or NSUN2, or a fragment or derivative thereof. In some aspects, the eraser protein is a FTO protein, a ALKBH protein, or a TET protein, or a fragment or derivative thereof. In some aspects, the eraser protein is FTO, ALKBH3, or ALKBH5, or a fragment or derivative thereof. In some embodiments, the binding domain comprises an IgG antibody, an antigen-binding fragment (Fab), a single chain variable fragment (scFv), or a heavy or light chain single domain ($V_H$ and $V_L$). In some embodiments, the binding domain comprises a heavy-chain antibody (hcAb) or the $V_H$H domain of a hcAb (nanobody). In some embodiments, the binding domain comprises an engineered protein scaffold such as an adnectin, an affibody, an affilin, an anticalin, an atrimer, an avimer, a bicyclic peptide, a centyrin, a cys-knot, a darpin, a fynomer, a kunitz domain, an obody or a pronectin.

IgG antibodies are the predominant isotype of immunoglobulins. IgGs comprise two identical heavy chains and two identical light chains that are covalently linked and stabilized through disulfide bonds. IgGs recognize an antigen via the variable N-terminal domains of the heavy ($V_H$) and the light ($V_L$) chain and six complementarity determining regions (CDRs). Antibodies that bind to some modified DNA and RNA bases are available commercially. For example, several companies sell antibodies specific for 5-methylcytidine (m5C), 5-hydroxymethylcytidine (hm5C), or N6-methyladenosine (m6A), including Active Motif and Sigma. Eurogentec S.A. (Belgium) sells a monoclonal antibody that binds to m5C. Monoclonal antibodies that bind to inosine are commercially available, e.g., from Diagenode. Megabase Research Products (USA) sells rabbit polyclonal sera that bind to m5C 6-methyladenosine and 7-methylguanosine. Abcam (USA) sells recombinant antibodies against the RNA modifications m6A, ac4C, m1A, m2,2G, m4C, m2A, m6,6A and m8A. Antibodies that bind to modified bases can be developed according to methods known and practiced by persons of ordinary skill in the art. In some embodiments, the antibodies may be monoclonal antibodies, polyclonal antibodies, or functional fragments or variants thereof. The term "antibody" as used herein covers any specific binding substance having a binding domain with the required specificity. Thus, this term covers antibody fragments, derivatives, functional equivalents, and homologues of antibodies, including any polypeptide comprising an immunoglobulin binding domain, whether natural or synthetic, monoclonal or polyclonal. Chimeric molecules comprising an immunoglobulin binding domain, or equivalent, fused to another polypeptide are also included.

In some embodiments, the binding domain may comprise a nanobody. Nanobodies comprise a single variable domain ($V_H$H) of heavy chain antibodies, as produced by camelids and several cartilaginous fish. The $V_H$H domain comprises three CDRs that are enlarged compared to the CDRs of IgG antibodies, and provide a sized antigen-interacting surface that is similar in size compared to that of IgGs (i.e., about 800 Å$^2$). Nanobodies bind antigens with similar affinities as IgG antibodies, and offer several advantages relative thereto: they are smaller (15 kDa), less sensitive to reducing environments due to fewer disulfide bonds, more soluble, and devoid of post-translational glycosylation. Nanobodies can be produced in bacterial expression systems, and they are therefore amenable to affinity and specificity maturation by phage and other display techniques. Other advantages include improved thermal stability and solubility, and straightforward approaches to site-specific labeling. Due to their small size, nanobodies can form convex paratopes making them suitable for binding difficult-to-access antigens. Illustrative methods for producing nanobodies include immunizing the respective animal (e.g., a llama) with the antigen of interest, by further evolving an existing naïve library, or by a combination thereof.

In some embodiments, the binding domain comprises a reader protein, a writer protein or an eraser protein. A "reader protein" is a protein that selectively recognizes and binds specific chemical modifications on a DNA or RNA. A "writer protein" is a protein that adds specific chemical modifications to a DNA or RNA. An "eraser protein" is an enzyme which removes specific chemical modifications from a DNA or RNA. In some embodiments, the binding domain comprises a fragment or derivative of a reader protein, a writer protein, or an eraser protein. In some embodiments, the binding domain comprises an engineered form of a reader, writer, or eraser protein, such as a form which has been engineered to retain nucleic acid binding but lacks any enzymatic activity. In some embodiments, the binding domain comprises a catalytically inactive variant of a writer or eraser protein. Illustrative reader, writer, and eraser proteins that may be used in the binding domains described herein are listed in Table 1 and Table 2. Additional reader, writer, and eraser proteins are listed at the following world wide web address: rnawre.bio2db.com.

TABLE 1

Reader, writer, and eraser proteins

| Type | Family | Specific Protein Examples |
|---|---|---|
| Writer | Methyltransferase | METTL3, TRMT, NSUN2, NSUN6, ALKBH8, RNMT, DMNT1, BCDIN3D, BMT5 |
| | H/ACA ribonucleoprotein complex subunit DKC1; catalyzes pseudouridylation of rRNA | DKC1 |
| | RNA cytidine acetyltransferase; catalyzes formation of N4-acetylcytidine (ac4C) | NAT10 |
| | tRNA dimethylallyltransferase; catalyzes formation of N6-(dimethylallyl)adenosine (i6A) | TRIT1 |
| | Catalyzes the synthesis of dihydrouridine, a modified base, in various RNAs, such as tRNAs, mRNAs and some long non-coding RNAs | DUS3L |
| | Catalyzes the formation of pseudouridine at position 39 in the anticodon stem and loop of transfer RNAs | PUS3 |
| Eraser | Demethylases of the ALKBH family | FTO, ALKBH3, ALKBH5 |
| Reader | YTH domain proteins | YTHDC1, YTHDC2, YTHDF1, YTHDF2 |
| | THO complex subunit 4 | ALYREF |

TABLE 2

RNA modifying proteins, RNA modifications produced thereby, and relation to cancer development

| Nt. | RNA Modification | RNA-modifying proteins | Site-specific position & RNA species | Associated Cancer |
|---|---|---|---|---|
| A | m1A | TRMT6 (W) | A58 tRNA-Met | Gastrointestinal Cancer (Onc) |
| | | | mRNA | Gastrointestinal Cancer (Onc) |
| | | TRMT10C (W) | A9 tRNA mitchondrial | Gastrointestinal Cancer (Onc) |
| | | TRMT61A (W) | A58 tRNA | Gastrointestinal Cancer (Onc) |
| | | | mRNA | Gastrointestinal Cancer (Onc) |
| | | ALKBH1 (E) | A58 tRNA | Cervix Cancer (Onc) |
| | | ALKBH3 (E) | mRNA (5'UTR near Start Codon) | Pancreatic Cancer (Onc) Breast Cancer (Onc) Ovarian Cancer (Onc) |
| | | | A58 tRNA | Cervix Cancer (Onc) |

TABLE 2-continued

RNA modifying proteins, RNA modifications produced thereby, and relation to cancer development

| Nt. | RNA Modification | RNA-modifying proteins | Site-specific position & RNA species | Associated Cancer |
|---|---|---|---|---|
| A | ms2i6A | CDK5RAP1 (W) | A37 tRNA mitochondrial | Breast Cancer (Onc) |
| A | i6A | TRIT1 (W) | A37 tRNA-SelenoCys | Melanoma (Onc) Lung Cancer (TS) |
| A | m6A | METTL3 (W) | mRNA (5'UTR, ORF, 3'UTR) | Gastric Cancer Endometrial Cancer (TS) Glioblastoma (TS) Breast Cancer (Onc) Hepatocarcinoma (Onc) AML (Onc) |
| | | FTO (E) | mRNA | Glioblastoma (Onc) Cervix Cancer (Onc) AML (Onc) Melanoma (Onc) Gastric Cancer (Onc) Breast Cancer (Onc) |
| | | ALKBH5 (E) | mRNA | Pancreatic Cancer (TS) AML (TS) Glioblastoma (Onc) Breast Cancer (Onc) |
| | | YTHDC2 (R) | mRNA | Colorectal Cancer (Onc) |
| | | YTHDF2 (R) | mRNA | Pancreatic Cancer (Dual Effect) Hepatocarcinoma (Onc) Prostate Cancer (Onc) |
| C | m3C | METTL6 (W) | C32 tRNA-Ser | Breast Cancer (Onc) Lung Cancer (Onc) |
| | | METTL8 (W) | mRNA | Hepatocarcinoma (TS) |
| | | ALKBH1 (E) | C32 tRNA | Hepatocarcinoma (Onc) |
| | | | C34 tRNA mitochondrial | Hepatocarcinoma (Onc) Cervix Cancer (Onc) |
| | | ALKBH3 (E) | C32, C47 tRNA | Cervix Cancer |
| C | m5C | NSUN1 (W) | C4447 rRNA-28S | Leukemia (Onc) |
| | | NSUN2 (W) | C34, C47, C48, C49, C50 tRNA | Ovarian Cancer (TS) |
| | | | mRNA | Skin Cancer (TS) Squamous-Cell Carcinoma (Onc) Breast Cancer (Onc) Bladder Cancer (Onc) |
| | | NSUN3 (W) | C34 tRNA mitochondrial | Non-Small Cell Lung Cancer |
| | | NSUN4 (W) | C841 rRNA-12S | Breast and Prostate Cancer |
| | | NSUN5 (W) | C3782 rRNA-28S | Glioblastoma (TS) |
| | | DNMT2 (W) | C38 tRNA-Asp | Colorectal Cancer (Onc) |
| C | ac4C | NAT10 (W) | C12 tRNA-Leu/Ser | Ovaric Cancer |
| | | | mRNA (ORF) | Hepatocarcinoma |
| | | | C1337 rRNA-18S | Colorectal Cancer (Onc) |
| G | m7Gpp(pN) | RNMT (W) | mRNA (5'Cap) | Breast Cancer (Onc) |
| | | NUDT16 (E) | mRNA (5'Cap) | T-ALL (TS) |
| G | m7G | METTL1 (W) | G46 tRNA miRNA | Hepatocarcinoma Lung Cancer (TS) |
| | | BUD23 (W) | G1639 rRNA-18S | Metastasis in p53+ tumours (Onc) |
| G | m2,2G | TRMT1 (W) | G26 tRNA | Breast Cancer |
| G | m2G | TRMT11 (W) | G6, G10, G26 tRNA | Prostate Cancer |
| G | Q | TGT (W) | G34 tRNA-Asn/Asp/His/Tyr | T-Cell Lymphoma (TS) Colon Cancer (Onc) |

TABLE 2-continued

RNA modifying proteins, RNA modifications produced thereby, and relation to cancer development

| Nt. | RNA Modification | RNA-modifying proteins | Site-specific position & RNA species | Associated Cancer |
|---|---|---|---|---|
| G | yW (and derivatives) | TYW2 (W) | G37 tRNA-Phe | Head and Neck (Onc) |
|   |   |   |   | Breast Cancer (Onc) |
| U | m5U | TRMT2A (W) | U54 (tRNA) | Breast Cancer (TS) |
| U | ncm5U | ELP3 (W) | U34 tRNA-Lys/Gln/Glu | Breast Cancer (Onc) |
| U | mcm5U | ELP3 (W) | U34 tRNA-Lys/Gln/Glu | Breast Cancer (Onc) |
|   |   | ALKBH8 (W) |   |   |
| U | mcm5s2U | CTU1 (W) | U34 tRNA-Lys/Gln/Glu | Breast Cancer (Onc) |
|   |   |   |   | Melanoma (Onc) |
|   |   | CTU2 (W) |   | Breast Cancer (Onc) |
|   |   |   |   | Melanoma (Onc) |
|   |   | ELP3 (W) |   | Breast Cancer (Onc) |
|   |   | ALKBH8 (W) |   | Breast Cancer (Onc) |
| U | D | DUS2 (W) | U20 tRNA | Lung Cancer |
| U | Ψ | DKC1 (W) | rRNA (~36 sites in 18S, ~57 sites in 28S) | X-Linked Dyskeratosis congenita |
|   |   |   |   | Prostate Cancer (Onc) |
|   |   |   |   | Breast Cancer (Onc) |
|   |   |   |   | Hepatocarcinoma (Onc) |
|   |   |   |   | Lung Cancer (Onc) |
| Others | Nm | Fibrillarin (W) | rRNA (41 sites in 18S, 67 sites in 28S. U14 and G75 in 5.8S) | Breast Cancer (Onc) |
|   |   | HENMT1 (W) | piRNA | Testicular tumours |
| Others | m(pN) | BCDIN3D (W) | miRNA (5'Cap) | Breast Cancer (Onc) |
|   |   | MePCE (W) | 7SK RNA | Breast Cancer (Onc) |
| Editing | A-to-I | ADAR1 (W) | mRNA | Hepatocarcinoma (Onc) |
|   |   |   |   | Colorectal Cancer (Onc) |
|   |   |   |   | Gastric Cancer (Onc) |
|   |   |   |   | Esophageal Cancer (Onc) |
|   |   |   |   | Glioblastoma (Onc) |
|   |   |   |   | Lung Cancer (Onc) |
|   |   |   | miRNA | Leukemia (Onc) |
|   |   | ADAR2 (W) | mRNA | Gastric Cancer (Onc) |
| Editing | C-to-U | APOBEC1 (W) | mRNA | Hepatocarcinoma (Onc) |
|   |   | APOBEC3G (W) | mRNA | Hepatocarcinoma (Onc) |

Legend: W: Writer, E: Eraser, R: Reader, TS: Tumor suppressor, Onc: Oncogene. RNA modifications: m1A: 1-methyladenosine, ms2i6A: 2-methylthio-N6-isopentenyl-adenosine, i6A: N6-isopentenyladenosine, m6A: N6-methyladenosine, m3C: 3- methylcytosine, m5C: 5-methylcytosine, ac4C: N4-acetylcytosine, m7Gpp (pN): 7-methylguanosine cap, m7G: 7-methylguanosine internal, m2,2G: N2,N2,-di- methylguanosine, m2G: N2-methylguanosine, Q: queuosine, yW et al.: Wybutosine and derivatives, m5U: 5-methyluridine, ncm5U: 5-carbamoyl-methyluridine, mcm5U: 5-methoxycarbonyl-methyluridine, mcm5s2U: 5-methoxy-carbonylmethyl-2-thiouridine, D: dihydrouridine, Ψ: pseudouridine, Nm: 2'-O-Methylnucleotide, m(pN): 5' phosphate monomethylation, A-to-I: Deamination of Adenosine, C-to-U: Deamination of Cytosine. RNA modifying enzymes: ADAR1-3: Adenosine Deaminase RNA Specific 1-3, ALKBH1/3/5/8: AlkB Homolog 1/3/5/8, APOBEC1/3G: Apolipoprotein B mRNA Editing Enzyme Catalytic Subunits 1/3G, BCDIN3D: BCDIN3 Domain Containing RNA Methyltransferase, BUD23: RRNA Methyltransferase And Ribosome Maturation Factor, CDK5RAP1: CDK5 Regulatory Subunit Associated Protein 1, CMTR1/2: Cap Methyltransferase 1/2, CTU1/2: Cytosolic Thiouridylase Subunit 1/2, DKC1: Dyskerin Pseudouridine Synthase 1, DNMT2: tRNA Aspartic Acid Methyltransferase 1, DUS2: Dihydrouridine Synthases 2, ELP3: Elongator Acetyltransferase Complex Subunit 3, FTO: FTO Alpha-Ketoglutarate Dependent Dioxygenase, HENMT1: HEN Methyltransferase 1, METTL1/2/3/6/8/14/16: Methyltransferase Like-1/2/3/6/8/16, NAT10: N-Acetyltransferase 10, NSUN1-5: NOP2/Sun RNA Methyltransferase 1-5, NUDT16: Nudix Hydrolase 16, RNMT: RNA Guanine-7 Methyltransferase, TGT: Queuine TRNA-Ribosyltransferase Catalytic Subunit 1, TRIT1: tRNA Isopentenyltransferase 1, TRMT1/2A/2B1/5/6/10C/11/61A/61B/112: tRNA Methyltransferase Subunits, TYW2: tRNA-YW Synthesizing Protein 2 Homolog.

In some embodiments, the binding domain comprises a reader protein. In some embodiments, the binding domain comprises a reader protein selected from NUDT16, YTHDC1, YTHDC2, YTHDF1 or YTHDF2. NUDT is the U8 snoRNA-decapping enzyme (see, e.g., Uniprot Accession No. Q96DE0). YTHDC1 is a regulator of alternative splicing that specifically recognizes and binds N6-methyladenosine (m6A)-containing RNAs (see, e.g., Uniprot Accession No. Q96MU7). YTHDC2 is the 3'-5' RNA helicase (see, e.g., Uniprot Accession No. Q9H6S0). YTHDF1 specifically recognizes and binds N6-methyladenosine (m6A)-containing mRNAs, and regulates their stability (see, e.g., Uniprot Accession No. Q9BYJ9). YTHDF2 specifically recognizes and binds N6-methyladenosine (m6A)-containing mRNAs, and regulates their stability (see, e.g., Uniprot Accession No. Q9Y5A9). In some embodiments, the binding domain comprises a fragment or derivative of NUDT16, YTHDC1, YTHDC2, YTHDF1 or YTHDF2.

In some embodiments, the binding domain comprises a writer protein. In some embodiments, the binding domain comprises a writer protein selected from DNTM1, DNTM3A/B, NAT10, METTL3, METTL8, METTL15, TRM, BMT, DUS2, PUS, and NSUN2. DNMT1 and DNTM3A/B are DNA (cytosine-5)-methyltransferases. NAT10 is the RNA cytidine acetyltransferase (see, e.g., Uniprot Accession No. Q9H0A0). METTL3 is the N6-adenosine-methyltransferase catalytic subunit (see, e.g., Uniprot Accession No. Q86U44). NSUN2 is the RNA cytosine C(5)-methyltransferase (see, e.g., Uniprot Accession No. Q08J23). In some embodiments, the binding domain comprises a writer protein that is a fragment or derivative of NAT10, METTL3, or NSUN2. In some aspects, the writer protein is a DNMT protein, a NAT10 protein, a METTL protein, a TRM protein, a BMT protein, a DUS protein, a PUS protein, a ADAR protein or a NSUN protein, or a fragment or derivative thereof.

In some embodiments, the binding domain comprises an eraser protein. In some embodiments, the binding domain comprises an engineered eraser protein selected from FTO, ALKBH3, and ALKBH5. FTO is the alpha-ketoglutarate-dependent dioxygenase (see, e.g., Uniprot Accession No. Q9C0B1). ALKBH3 is the alpha-ketoglutarate-dependent dioxygenase alkB homolog 3 (see, e.g., Uniprot Accession No. Q96Q83). ALKBH5 is the RNA demethylase (see, e.g., Uniprot Accession No. Q6P6C2). In some embodiments, the binding domain comprises a writer protein that is a fragment or derivative of FTO, ALKBH3, or ALKBH5.

Binding domains may be selected and/or engineered to bind to any non-canonical feature of a DNA or RNA. For example, the non-canonical feature may be a modified base, a modified backbone, or a structural element. In some embodiments, the binding domain may bind to two or more non-canonical features.

In some embodiments, the binding domain binds to a modified base and/or nucleoside. In some embodiments, the binding domain contacts at least one, at least two, or at least three modified nucleosides. In some embodiments, the binding domain contacts at least one modified nucleoside. In some embodiments, the binding domain contacts at least one modified nucleoside and one or more nucleotides adjacent thereto. Exemplary modified nucleosides that may occur in humans and other organisms are provided in Table 3A. Modified nucleosides that are known to occur in humans are listed in Table 3B. Additional modified bases and nucleosides are listed at the world wide web address genesilico.pl/modomics/modifications.

TABLE 3A

Modified nucleosides

| Modified nucleosides | Nucleic Acid in which it typically occurs* |
|---|---|
| 5-methyldeoxycytidine | DNA |
| 5-methylcytidine | RNA |
| 5-hydroxymethyldeoxycytidine | DNA |
| 5-hydroxymethylcytidine | RNA |
| 5-formyldeoxycytidine | DNA |
| 5-formylcytidine | RNA |
| 1-methyladenosine | RNA |
| 6-methyladenosine | RNA, DNA |
| 6-methyldeoxyadenosine | RNA, DNA |
| 7-methylguanosine | RNA |
| 2,7,2'-methylguanosine | RNA |
| Pseudouridine | RNA |
| 1-methyl-3-(3-amino-3-carboxypropyl) pseudouridine | RNA |
| 1-methylpseudouridine | RNA |
| 2-thiouridine | RNA |
| 2'-O-methyluridine | RNA |
| 5-(carboxyhydroxymethyl) uridine methyl ester | RNA |
| 5-carbamoylmethyluridine | RNA |
| 5-carboxymethylaminomethyluridine | RNA |
| 5-methoxycarbonylmethyl-2-thiouridine | RNA |
| 5-methoxycarbonylmethyluridine | RNA |
| 5-methylaminomethyl-2-selenouridine | RNA |
| 5-methyluridine | RNA |
| 5-taurinomethyluridine | RNA |
| 2'-O-methylcytidine | RNA |
| 3-methylcytidine | RNA |
| N4-acetylcytidine | RNA |
| 1-methylguanosine | RNA |
| 2'-O-methylguanosine | RNA |
| 7-methylguanosine | RNA |
| N2,N2-dimethylguanosine | RNA |
| N2-methylguanosine | RNA |
| wybutosine | RNA |
| 2-methylthio-N6-isopentenyladenosine | RNA |
| 2-methylthio-N6-threonylcarbamoyladenosine | RNA |
| 2 -O-methyladenosine | RNA |
| N6-formyladenosine | RNA |
| N6-isopentenyladenosine | RNA |
| inosine | RNA |

*As will be understood by those of skill in the art, a modified base/nucleoside that typically occurs in an RNA may sometimes occur in a DNA, and a modified base/nucleoside that typically occurs in a DNA may sometimes occur in an RNA.

TABLE 3

Modified nucleosides occurring in humans

| Symbol | Modified Nucleoside | Symbol | Modified Nucleoside |
|---|---|---|---|
| Cm | 2'-O-methylcytidine | cmo$^5$U* | uridine 5-oxyacetic acid |
| m$^3$C | 3-methylcytidine | chm$^5$U | 5-carboxyhydroxymethyluridine |
| m$^4$C | N4-methylcytidine | mcm$^5$s$^2$U | 5-methoxycarbonylmethyl-2-thiouridine |
| m$^5$C | 5-methylcytidine | mcmo$^5$U* | uridine 5-oxyacetic acid methyl ester |
| m$^4$4C* | N4,N4-dimethylcytidine | mchm$^5$U | 5-(carboxyhydroxymethyl)uridine methyl ester |
| m$^5$Cm* | 5,2'-O-dimethylcytidine | cmnm$^5$Um* | 5-carboxymethylaminomethyl-2'-O-methyluridine |

TABLE 3-continued

Modified nucleosides occurring in humans

| Symbol | Modified Nucleoside | Symbol | Modified Nucleoside |
|---|---|---|---|
| $m^4 4Cm^*$ | N4,N4,2'-O-trimethylcytidine | $acp^3U$ | 3-(3-amino-3-carboxypropyl)uridine |
| $f^5C$ | 5-formylcytidine | $acp^3Um^*$ | 3-(3-amino-3-carboxypropyl)methyluridine |
| $f^5Cm$ | 5-formyl-2'-O-methylcytidine | Am | 2'-O-methyladenosine |
| $hm^5C$ | 5-hydroxymethylcytidine | $m^1A$ | 1-methyladenosine |
| $ac^4C$ | N4-acetylcytidine | $m^2A^*$ | 2-methyladenosine |
| $ac^4Cm^*$ | N4-acetyl-2'-O-methylcytidine | $m^6A$ | N6-methyladenosine |
| Y | Pseudouridine | $m^8A$ | C8-methyladenosine |
| D | Dihydrouridine | $m^1Am^*$ | 1,2'-O-dimethyladenosine |
| Um | 2'-O-methyluridine | $m^6Am$ | N6,2'-O-dimethyladenosine |
| $m^3U$ | 3-methyluridine | $m^28A^*$ | 2,8-dimethyladenosine |
| $m^5U$ | 5-methyluridine | $m^62A$ | N6,N6-dimethyladenosine |
| Ym | 2'-O-methylpseudouridine | $m^66A$ | N6,N6-dimethyladenosine |
| $m^1Y$ | 1-methylpseudouridine | $m^66Am^*$ | N6,N6,2'-O-trimethyladenosine |
| $m^3Y^*$ | 3-methylpseudouridine | $hn^6A^*$ | N6-hydroxynorvalylcarbamoyladenosine |
| $m^5D^*$ | 5-methyldihydrouridine | $i^6A$ | N6-isopentenyladenosine |
| $m^3Um^*$ | 3,2'-O-dimethyluridine | I | Inosine |
| $m^5Um^*$ | 5,2'-O-dimethyluridine | Im | 2'-O-methylinosine |
| $s^2Um$ | 2-thio-2'-O-methyluridine | $m^1I$ | 1-methylinosine |
| $m^5s^2U$ | 5-methyl-2-thiouridine | Gm | 2'-O-methylguanosine |
| $nm^5U^*$ | 5-methylaminouridine | $m^1G$ | 1-methylguanosine |
| $mnm^5U^*$ | 5-methylaminomethyluridine | $m^2G$ | N2-methylguanosine |
| $f^5U$ | 5-formyl-uridine | $m^7G$ | 7-methylguanosine |
| $f^5Um^*$ | 5-formyl-O-methyluridine | $m^1Gm^*$ | 1,2'-O-dimethylguanosine |
| $ho^5U$ | 5-hydroxyuridine | $m^2Gm^*$ | N2,2-O-dimethylguanosine |
| $ncm^5U$ | 5-carbamoylmethyluridine | $m^22G$ | N2,N2-dimethylguanosine |
| $ncm^5Um^*$ | 5-carbamoylmethyl-2'-O-methyluridine | $m^27G$ | N2,7-dimethylguanosine |
| $mcm^5U$ | 5-methoxycarbonylmethyluridine | PreQ1* | 7-aminomethyl-7-deazaguanosine |
| $mo^5U$ | 5-methoxyuridine | $m^22Gm^*$ | N2,N2,2-O-trimethylguansine |

In some embodiments, the binding domain binds to one or more of the following modified nucleosides: 3-methylcytidine (m3C), 5-methylcytidine (m5C), $N^4$-acetylcytidine (ac4C), Pseudouridine (Ψ), 1-methyladenosine (m1A), $N^6$-methyladenosine (m6A), Inosine (I), 7-methylguanosine (m7G), 7-methylguanosine (m7G)-Cap, Dihydrouridine (D), 3-methyluridine (m3U), 5-methyluridine (m5U), 1-methylguanosine (m1G), $N^2$-methylguanosine (m2G), 5-methyldeoxycytidine (m5dC), $N^4$-methyldeoxycytidine, 5-hydroxymethylcytidine (5-hmC), 5-hydroxymethyldeoxycytidine (5hmdC), 5-carboxydeoxycytidine (5cadC), 5-carboxycytodine (5caC), 5-formylcytidine (5fC), 5-formyldeoxycytidine (5fdC), 6-methyldeoxyadenosine, $N^7$-methylguanosine (m7G), 2,7,2'-methylguanosine, ribose methylation (Nm), N2,N2-dimethyl guanosine ($m^2_2G$), 5-carbamoylmethyl-2'-O-methyluridine (ncm5Um), 5-methoxycarbonylmethyluridine (ncm5mU), 5-methoxycarbonylmethyl-2-thiouridine (mem5s2U), queuosine (Q), 2-thiouridine (s2U), 5-taurinomethyluridine (τm5U), 5-taurinomethyl-2-thiouridine (τm5s2U), N6-isopentenyladenosine (I6A), 2-methylthio-N6-threonyl carbamoyladenosine (ms2t6A).

In some embodiments, the non-canonical feature is: 3-methylcytidine (m3C), 5-methylcytidine (m5C), $N^4$-acetylcytidine (ac4C), Pseudouridine (Ψ), 1-methyladenosine (m1A), $N^6$-methyladenosine (m6A), Inosine (I), 7-methylguanosine (m7G), 7-methylguanosine (m7G)-Cap, Dihydrouridine (D), 3-methyluridine (m3U), 5-methyluridine (m5U), 1-methylguanosine (m1G), $N^2$-methylguanosine (m2G), 5-methyldeoxycytidine (m5dC), $N^4$-methyldeoxycytidine, 5-hydroxymethylcytidine (5-hmC), 5-hydroxymethyldeoxycytidine (5hmdC), 5-carboxydeoxycytidine (5cadC), 5-carboxycytodine (5caC), 5-formylcytidine (5fC), 5-formyldeoxycytidine (5fdC), 6-methyldeoxyadenosine, $N^7$-methylguanosine (m7G), 2,7,2'-methylguanosine, or ribose methylation (Nm).

In some embodiments, the binding domain binds to a nucleic acid lesion resulting from naturally occurring oxidative or ultra-violet light-induced damage, or bulky adduct formation or base alkylation by exogeneous agents. In some embodiments, the nucleic acid lesion is the lesion is 8-oxo-guanine (8-oxoG), one or more abasic sites, cis-platin crosslinks, benzo(a)pyrene diol epoxide (BPDE)-adducts, cyclobutene pyrimidine dimers (CPD), pyrimidine-pyrimidone (6-4) photoproduct (6-4PP), 6-O-methylguanine ($O^6$-MedG), or 06-(Carboxymethyl)-2'-deoxyguanosine (O6-CMdG). In some embodiments, the non-canonical feature is a nucleic acid lesion resulting from naturally occurring oxidative or ultra-violet light-induced damage, or bulky adduct formation or base alkylation by exogeneous agents. In some embodiments, the nucleic acid lesion is the lesion is 8-oxo-guanine (8-oxoG), one or more abasic sites, cis-platin crosslinks, benzo(a)pyrene diol epoxide (BPDE)-adducts, cyclobutene pyrimidine dimers (CPD), pyrimidine-pyrimidone (6-4) photoproduct (6-4PP), 6-O-methylguanine ($O^6$-MedG), or O6-(Carboxymethyl)-2'-deoxyguanosine (O6-CMdG).

In some embodiments, the binding domain binds to a structural element. The structural element may be, for example, a hairpin or a loop. Other illustrative structural elements include, but are not limited to, Z-DNA structures, G-quadruplexes, triplexes, I-motifs, bulges, abasic sites, triplexes, three-way junctions, cruciform structures, tetraloops, ribose zippers, pseudoknots, etc. In some embodiments, a plurality of compositions is provided, wherein each composition comprises a binding domain, and wherein each binding domain binds to a different type of non-canonical feature. This allows for a multiplexing approach, wherein numerous non-canonical features can be detected simultaneously.

The binding domains described herein may specifically bind RNAs or may specifically bind DNAs. In some embodiments, the binding domain binds to both RNAs and DNAs. In some embodiments, the binding domain specifically binds to a double stranded nucleic acid with one or more non-canonical features. In some embodiments, the binding domain specifically binds to a single stranded nucleic acid with one or more non-canonical features.

Figure 3:
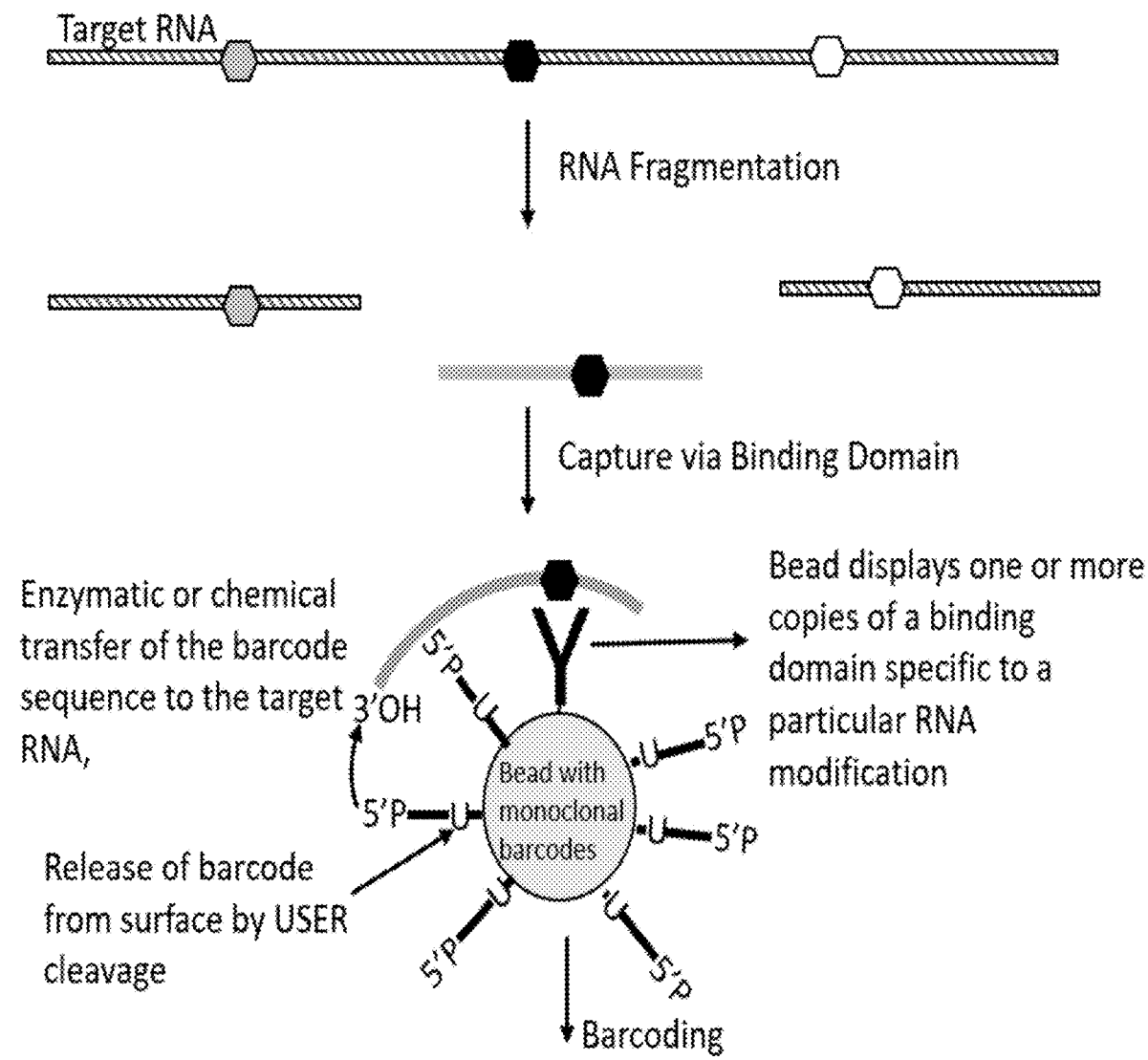
FIG. 3 illustrates a general overview of RNA profiling using engineered surfaces (e.g., a bead). A plurality of RNA strands is chemically fragmented. Modified RNA fragments (modifications indicated using hexagons) are enriched on the surface via the interaction with RNA modification specific binding domains. A plurality of beads may be used, such that each bead type exhibits copies of the same binding domain and barcodes. The reaction may contain any number of bead types to interrogate any number of RNA modifications. Transferring a barcode to the target RNA translates the RNA modification into a DNA code. Sequencing of the cDNA library provides the modification status for each RNA fragment.
Figure 3:
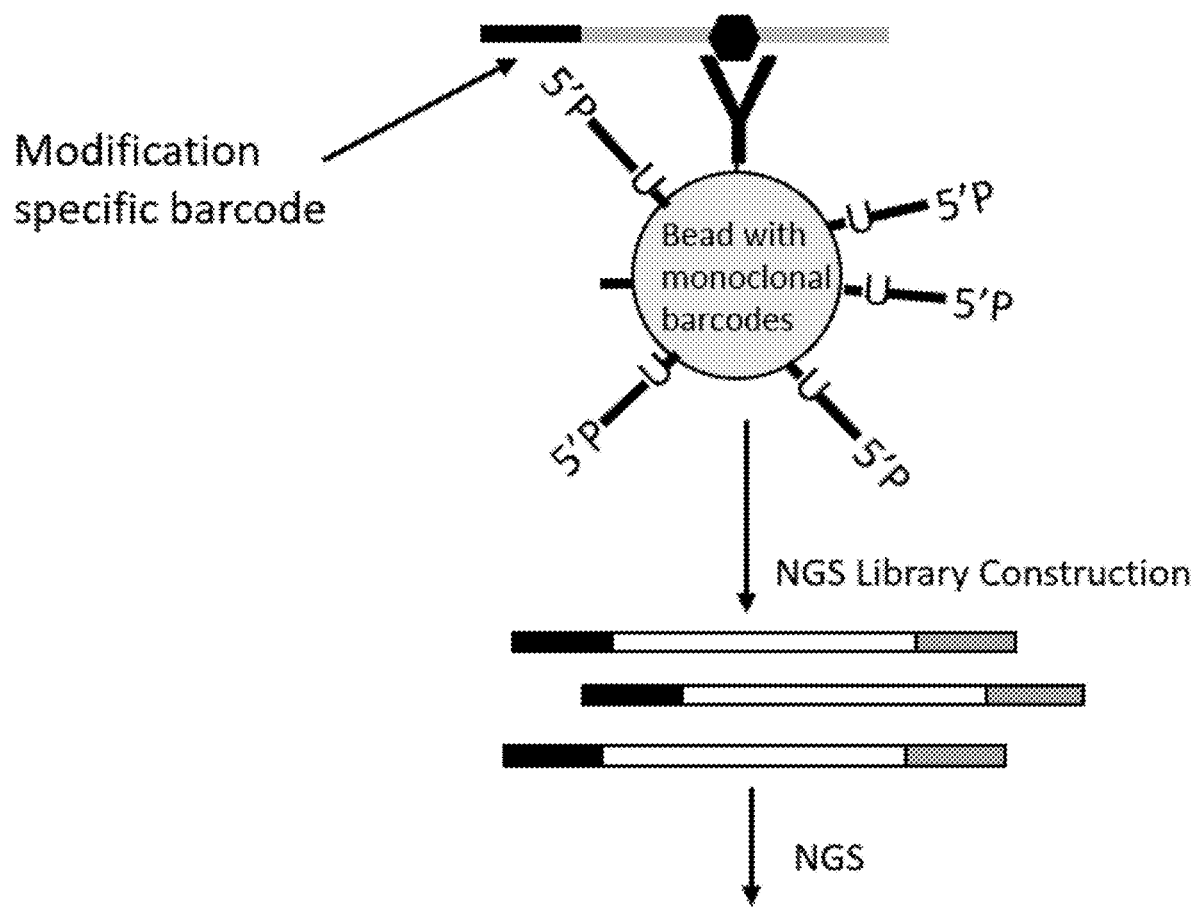
Figure 5:
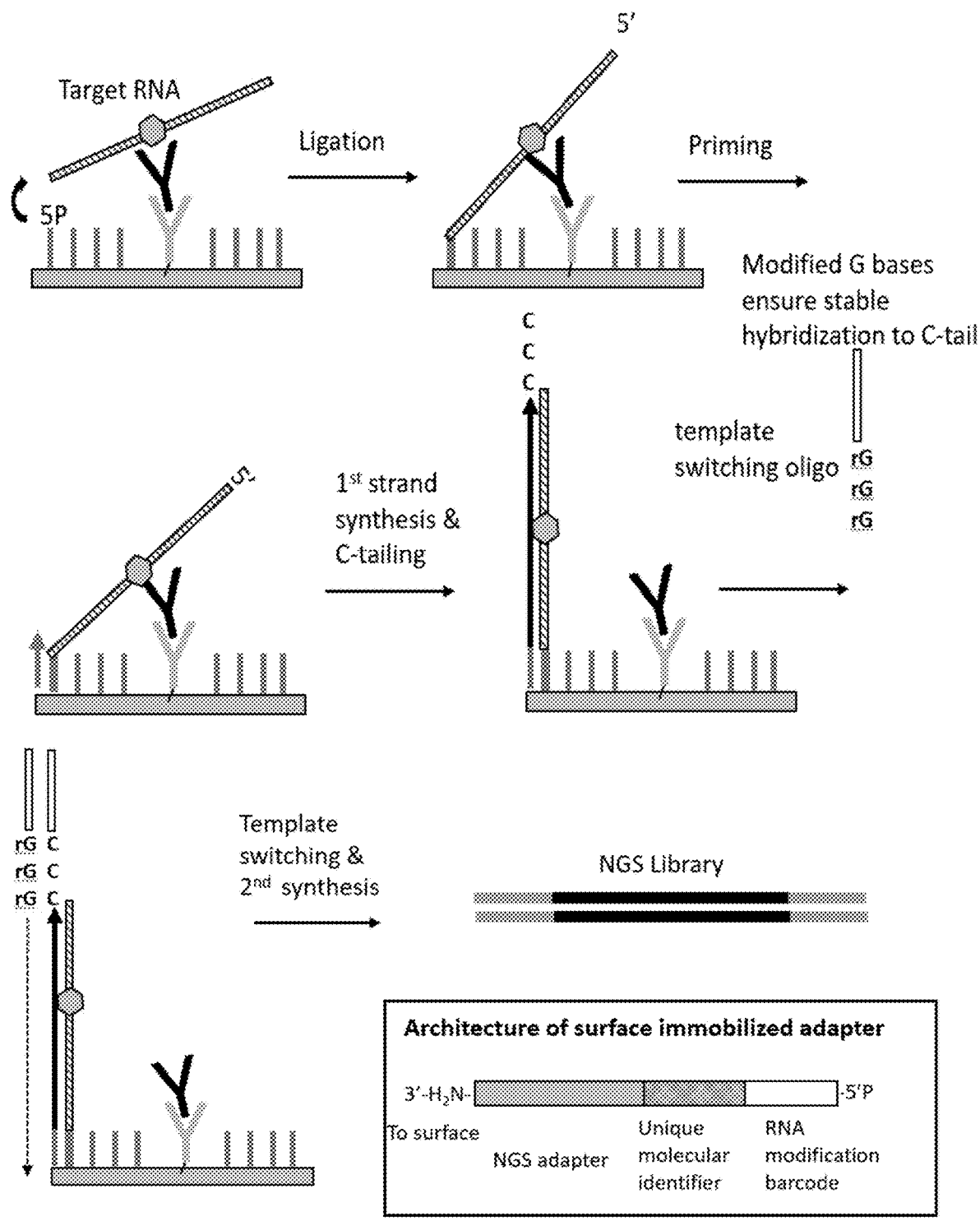
FIG. 5 illustrates a complete RNA modification profiling workflow utilizing 3'-immobilized adapters and barcoding by ligation. Workflow steps include modification specific RNA capture, barcoding by single stranded ligation, first strand cDNA synthesis and second strand synthesis by template switching. The DNA adapter contains a 3' amine for surface immobilization, a universal priming site, a unique molecular identifier, a modification specific barcode and a 5' phosphate.

In some embodiments, binding of a binding domain to a non-canonical feature of a target nucleic acid positions the DNA adapter in proximity to the 5' or 3' terminus of the target nucleic acid. For example, FIG. 3 depicts a target nucleic acid bound to a binding domain, which positions the adapter in proximity to the 3' end of the target nucleic acid. FIG. 5 depicts a binding domain immobilized on a secondary recognition element wherein a target nucleic acid is bound to the binding domain, which positions the adapter in proximity to the 3' end of the target nucleic acid. In some embodiments, a target nucleic acid is bound to a binding domain, which positions the adapter in proximity to the 3' end of the target nucleic acid. In some embodiments, a target nucleic acid is bound to a binding domain, which positions the adapter in proximity to the 5' end of the target nucleic acid.

Binding domains may be made using standard molecular biology, protein engineering and/or chemistry techniques.

Adapters (e.g., adapters comprising a linker) may be coupled to the substrate using several different methods. In some embodiments, adapters may be covalently coupled to a secondary recognition element or intermediary protein by random tagging (see, e.g., FIG. 1B and FIG. 1E). For example, a NHS-activated residue on the adapter may be reacted with one or more amine groups of surface exposed protein lysine residues of a secondary recognition element or intermediary protein. Similarly, maleimide-activated adapters can be reacted with native or engineered cysteines of a secondary recognition element or intermediary protein. As will be understood by those of skill in the art, the number of adapters tethered to a secondary recognition element or intermediary protein will depend on the number of reactive lysine or cysteine residues, respectively, and the choice of reaction conditions. In some embodiments, adapters may be non-covalently coupled to a secondary recognition element (see, e.g., FIG. 1C and FIG. 1D). For example, 5'-biotinylated adapters may be coupled to substrate-anchored streptavidin, avidin, neutravidin or a variant thereof.

Figure 1E:
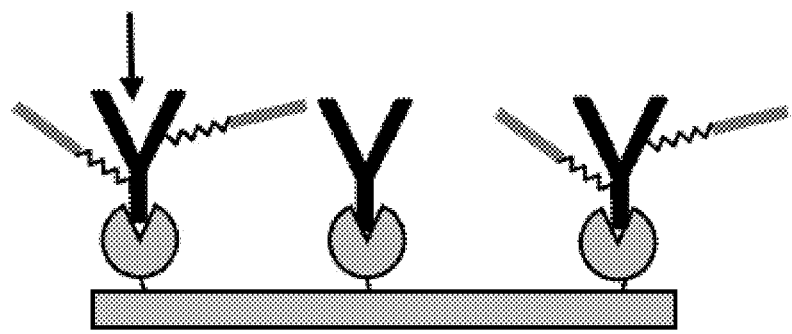
Figure 1F:
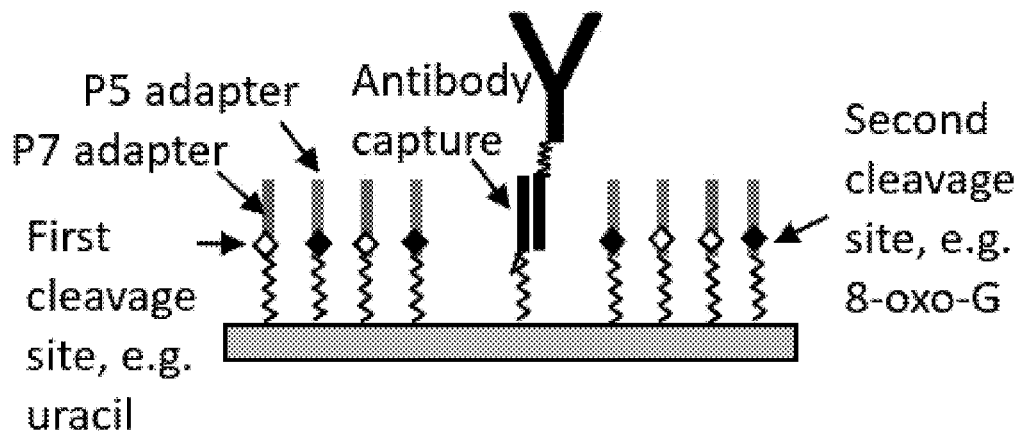

Site-selective coupling methods can also be used to couple adapters to secondary recognition elements (see, e.g., FIG. 1B and FIG. 1E). Site-selective methods can also be used for coupling Tn5 transposase to binding domains (see, e.g., FIG. 1H) or for coupling nucleic acid editing enzymes to binding domains (see, e.g., FIG. 10). Site-specific coupling avoids impacting the function of binding domains, secondary recognition elements or intermediary proteins and allows for reproducible material production. Site-selective internal tagging of a secondary recognition element or intermediary protein can be achieved by genetic incorporation of unnatural amino acid using cell lines with engineered aminoacyl-tRNA synthetase/tRNA pairs. The incorporated unnatural amino acids exhibit moieties that can undergo bio-orthogonal reactions. Commonly used are amino acids that bear moieties that can undergo copper-catalyzed azide alkyne cycloadditions (CuAAC), photoactivated 1,3-dipolar cycloadditions, strain-promoted azide alkyne cycloadditions (SPAAC) or inverse electron-demand Diels-Alder cycloadditions (IEDDA). An illustrative, versatile method for C- or N-terminal or internal tagging of binding domains, secondary recognition elements or intermediary proteins involves the use of protein or peptide-tags. Protein-tags such as SNAP-tag, Halo-tag, Spy-tag, Snoop-tag, Isopeptag, Dog-tag, Sdy-tag, Clip-tag are small proteins or peptides that can be cloned into any protein gene to express a binding domain, secondary recognition element or intermediary protein as protein-tag fusion protein. Such protein-tags may self-catalyze covalent bond formation with a specific peptide or substrate. For example, SpyCatcher is a 113-residue protein that recognizes SpyTag, a 13-residue peptide that can be readily coupled to any DNA sequence. Depending on the molecular weight of the binding domain, secondary recognition element or intermediary protein, a smaller peptide-tag may be preferred. Peptide-tags are typically 10-12 amino acids long and act in enzyme-mediated coupling reactions. Examples of enzyme-mediated reactions for coupling a secondary recognition element or intermediary protein to an adapter include but are not limited to: (a) the use of biotin-ligase to link AP-peptide labeled binding domain and biotin-DNA (e.g., biotin-linkers), (b) the use of lipoic acid ligase to link LAP-peptide labeled secondary recognition elements and lipoic acid-DNA (e.g., lipoic acid-linkers), (c) the use of tubulin tyrosine ligase to link Tub-tag labeled secondary recognition elements and tyrosine-modified DNA (e.g., tyrosine-modified linkers), (d) the use of Sortase-A, which reacts with LPxTG peptide and glycine-modified DNA (e.g., glycine-modified linkers), and more. In some embodiments, a Tn5 transposase-protein A fusion protein may be generated and bound to the Fc region of an RNA modification specific antibody (see, e.g., FIG. 1H). In some embodiments, ADAR enzyme, an adenosine deaminase, may be genetically fused to protein L and bound to the Fc region of an RNA modification specific antibody (see, e.g., FIG. 10). In some embodiments, SpyTag may be genetically engineered into a binding domain and SpyCatcher may be genetically engineered into a nucleic acid editing enzyme or Tn5 transposase. Mixing the SpyTag modified binding domain and the SpyCatcher modified nucleic acid editing enzyme, will produce a covalent conjugate comprising a binding domain and a nucleic acid editing enzyme, as used for marking the position of a non-canonical feature. Mixing the SpyTag modified binding domain and Tn5 transposase produces a covalent conjugate comprising a binding domain and Tn5 transposase, as used for barcoding by enzymatic transposition. In addition, a group of metal ion recognition tags and small molecule binding motifs may be used. Another variant of peptide tagging is to redirect the endogenous cellular machinery to introduce aldehydes into recombinant proteins. The method exploits formylglycine-generating enzyme (FGE), which converts cysteine co-translationally to formylglycine (FGly) within a conserved 13-residue consensus sequence. The resulting aldehyde tag can be readily modified with reactive amines that are tethered to DNA.

In some embodiments, the adapter may be coupled to a secondary recognition element or intermediary protein via bioorthogonal chemistry. In some embodiments, the secondary recognition element or intermediary protein comprises a DNA oligonucleotide which facilitates coupling of the barcode. DNA oligonucleotides are readily commercially available with amino, azido, biotin and alkyne modification.

Alkyne and azido oligos can be coupled to unnatural amino acids in a copper-catalyzed azide-alkyne cycloaddition or a strain-promoted azide-alkyne cycloaddition. Amino-oligonucleotide may be reacted with formylglycine, which can be introduced into the secondary recognition element or intermediary protein by the formylglycine-generating enzyme (FGE) within a 13aa conserved sequence.

Once the binding domains described herein bind to a target nucleic acid, a complex is formed. In some embodiments, the binding domain of the complex may be covalently linked to the target nucleic acid. For example, the binding domain may be chemically and/or photochemically linked to the target nucleic acid.

Secondary Recognition Elements

A secondary recognition element is an antibody, protein, or peptide used to tether a binding domain described herein to the surface of a substrate. In some embodiments, a secondary recognition element described herein is coupled to a linker wherein the linker is coupled a substrate. In some embodiments, a secondary recognition element binds to an antibody binding domain. In some embodiments, a secondary recognition element is a protein G, protein L, protein A, protein AG, protein AL, protein LG or an antibody. In some embodiments, the antibody is a species-specific antibody. In some embodiments, the species-specific antibody is select from, but not limited to mouse, rat, rabbit, human, or non-human primate.

In some embodiments, an adapter is coupled to a secondary recognition element. For example, in some embodiments the secondary recognition element is an antibody, and an adapter is coupled to the Fc region of the antibody. Adapters may be coupled to the lysines of proteins using N-hydroxysuccinimidyl ester (NHS ester). Adapters may be conjugated to cysteine of proteins using maleimide or iodoacetyl groups. Adapters may be reacted with the carbohydrate groups of antibodies or of other glycosylated proteins. In some embodiments, one adapter is coupled to a secondary recognition element. In some embodiments, two adapters are coupled to a secondary recognition element. In some embodiments, a plurality of adapters is coupled to a secondary recognition element.

In some embodiments, a secondary recognition element is a protein. In some embodiments, the secondary recognition element is a peptide tag. Example peptide tags include, but are not limited to Flag, Avi, HA, His, Myc, and Strep-tag. In some embodiments, the secondary recognition element is a covalent peptide tag. Example peptide tags include, but are not limited to a Spy Tag, Snoop Tag, or Dog Tag. In some embodiments, the secondary recognition element is a protein tag. Example protein tags include, but are not limited to MBD, CLIP, and Halo.

In some embodiments, a secondary recognition element is an avidin protein, for example streptavidin, neutravidin or related variants. For example, a substrate may be coated with streptavidin and co-functionalized with biotin-labeled adapters and biotinylated protein G, where protein G is further coupled to an antibody binding domain.

Adapter/Barcode Transfer Reactions

The binding domains described herein may be used to transfer an adapter to a target nucleic acid, such as an adapter comprising a barcode. Thus, in some embodiments, the binding domains described herein may be used to transfer a barcode to a target nucleic acid. The barcode may be a MBC, i.e., a barcode that is unique to the non-canonical feature bound specifically by the binding domain. A target nucleic acid to which an adapter has been transferred is referred to herein as a "labeled target nucleic acid," a "labeled target" or similar terms. A target nucleic acid to which a barcode has been transferred is referred to herein as a "barcoded target nucleic acid," a "barcoded target" or similar terms. A reaction in which an adapter is transferred to a target nucleic acid is referred to herein as an "adapter transfer reaction." Similarly, a reaction in which a barcode is transferred to a target nucleic acid is referred to herein as a "barcode transfer reaction."

The goal of adapter/barcode transfer is covalent attachment of the adapter/barcode to a target nucleic acid molecule, or to a copy of the target nucleic acids molecule. For example, in some embodiments, a barcode is chemically or enzymatically ligated to the 5' or 3' end of the target nucleic acid. In some embodiments, barcoding is accomplished by extending the 3' end of a nucleic acid by a DNA polymerase, RNA polymerase or reverse transcriptase, using the adapter as a template for introducing a barcode. In some embodiments, the 3' ends of the target nucleic acid and of the adapter, respectively, hybridize and are extended simultaneously by a reverse transcriptase. In some embodiments, an adapter with degenerate bases at the 3' end may randomly prime a DNA or RNA target and be extended by a DNA polymerase or reverse transcriptase. The labeled/barcoded nucleic acid molecule may, in some embodiments, be sequenced in downstream steps. In some embodiments, a copy of the labeled target nucleic acid may be sequenced. FIG. 2A-2G provides examples of adapter/barcode transfer reactions.

The enzymes used for adapter transfer differ for DNA and RNA target nucleic acids and depend on the adapter architecture. Adapter/barcode transfer to a target DNA may be performed using one or more enzymes, such as T4 DNA ligase, CircLigase, Klenow fragment, Bst DNA polymerase, or Bsu DNA polymerase. Adapter/barcode transfer to a target RNA may be performed using, for example T4 RNA ligase 1, T4 RNA ligase 2, or RtcB ligase. A reverse transcriptase may be used to simultaneously copy the barcode and synthesize cDNA. This reaction may be catalyzed by M-MLV reverse transcriptase, AMV reverse transcriptase, or a group II intron-encoded reverse transcriptase, e.g. Induro™ Reverse Transcriptase (NEB). Some commercial M-MLV mutants, such as Superscript II RT (Thermo Fisher), Superscript IV RT (Thermo Fisher) and Maxima H Minus RT (Thermo Fisher) are capable of catalyzing template switching reactions, which may be used to introduce a second adapter after barcode transfer (see, e.g., FIG. 5 and FIG. 6).

For example, FIG. 5 illustrates ligation of a single-stranded DNA adapter (e.g., an adapter comprising or consisting of a barcode) to single-stranded target nucleic acid. In some embodiments wherein the target nucleic acid is an RNA, the adapter comprises a 5' phosphate, and is catalyzed by T4 RNA ligase 1. Alternatively, the adapter may be 5'-pre-adenylated and transferred by T4 RNA ligase 2 to obviate the need for ATP and limit the reaction to a single turnover. Alternatively, an unphosphorylated adapter may be used, and may be transferred to 3'-phosphorylated RNA using RtcB ligase. In some embodiments wherein the target nucleic acid is a DNA, the adapter/barcode may be transferred in a reaction catalyzed by CircLigase.

Figure 6:
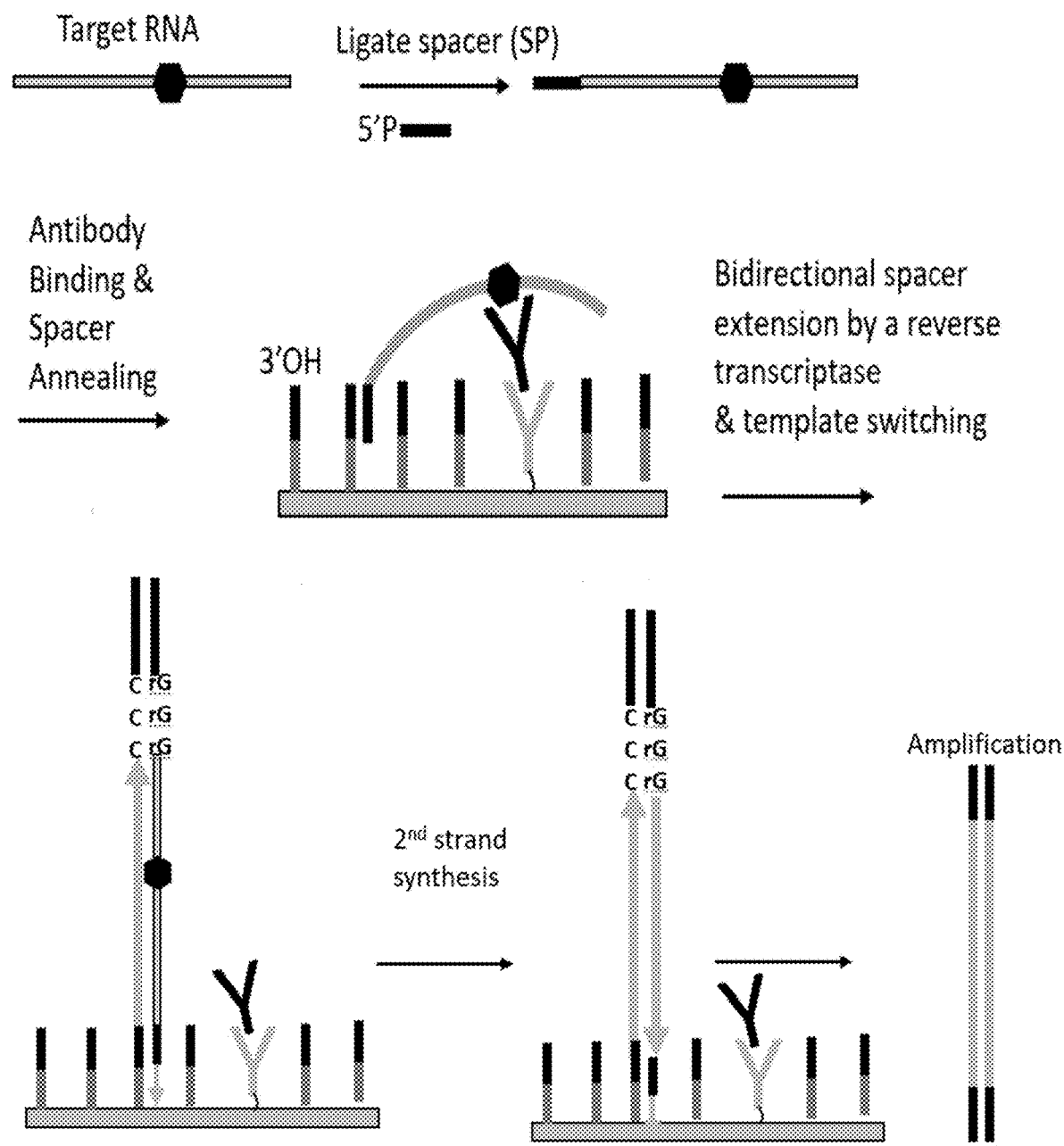
FIG. 6 illustrates a complete RNA modification profiling workflow utilizing 5'immobilized adapters and barcoding by primer extension. In this non-limiting example, a short spacer (SP) is ligated upstream. The spacer is complementary to the surface-bound adapter and annealing of the RNA target to the surface bound adapter creates a priming site for reverse transcriptase. To ensure RNA modification-specific pull down of the target, the spacer interaction is weak and not stable on its own in the absence of antibody binding. Simultaneous binding to the antibody and to the spacer is depicted. The DNA adapter comprises a 5' amine for surface immobilization, a universal priming site, a unique molecular identifier, a modification specific barcode and a 3' spacer. Extending the surface-bound adapter by reverse transcriptase in the presence of a template switching oligo creates a barcoded first strand cDNA and introduces a second sequencing adapter, attaching the cDNA covalently to the surface. The amplification of the cDNA is either performed in a separate reaction by PCR using the bead as an input, or in situ on the surface (as depicted in FIG. 7 and FIG. 8, respectively).
Figure 6:
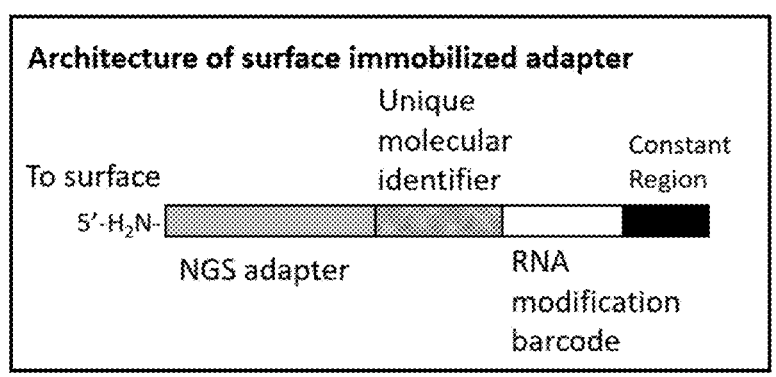

FIG. 6 illustrates barcoding by a reverse transcriptase. Ligation of a universal spacer sequence (SP) enables hybridization of the target RNA to the adapter while the binding domain captures an RNA modification. Hybridization occurs in the configuration illustrated in FIG. 2G. A reverse transcriptase extends the 3' end of the RNA, thereby copying the modification barcode. Simultaneously, the enzyme extends the 3' end of the adapter, thereby generating cDNA. Including a template switching oligo in the reaction introduces a universal region of choice, for example, an Illumina sequencing adapter.

Splint ligation may also be used to transfer an adapter/barcode to a target nucleic acid. In splint ligation, a bridging DNA or RNA oligonucleotide is used to bring two nucleic acids together, which may be joined by one or more enzymes. For example, splint ligation of two RNAs (e.g., a target RNA and an adapter/barcode) may be carried out using T4 ligase 1, and a bridging RNA oligonucleotide complementary to the RNAs. For example, the splinted nucleic acid construct shown in FIG. 2B may be created by using splint ligation. SplintR ligase may be used to connect the 3' end of RNA to 5'-pDNA when annealed to either DNA or RNA complements. If the target molecule is DNA, splinted DNA ligation may be performed using enzymes like T4 DNA ligase, T3 DNA ligase, T7 DNA ligase or E. coli DNA ligase.

Splint extension is another methods that may be used to transfer an adapter/barcode to a target nucleic acid. A "splint" is a sequence that spans a ligation junction. The splint may exhibit random bases or universal synthetic bases to facilitate binding to a target nucleic acid of unknown sequence. FIG. 2C depicts adapter transfer by splint extension, wherein a copy of the sequence of the target nucleic acid molecule is made, using a double-stranded adapter with a 3' base overhang. The 3' base overhang may contain random bases or synthetic universal bases that base pair promiscuously. If the target nucleic acid molecule is RNA, this reaction may be catalyzed by a reverse transcriptase such as Avian Myeloblastosis Virus (AMV) Reverse Transcriptase and Moloney Murine Leukemia Virus (M-MuLV, MMLV). If the target molecule is DNA, the primer may be extended by any suitable DNA polymerase with or without 3'->5' exonuclease activity.

Figure 2D:
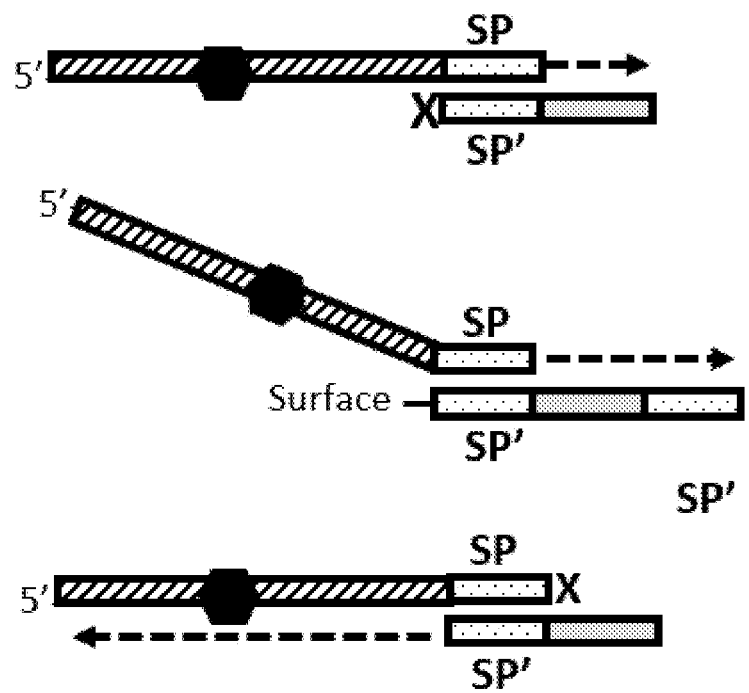
Figure 2E:
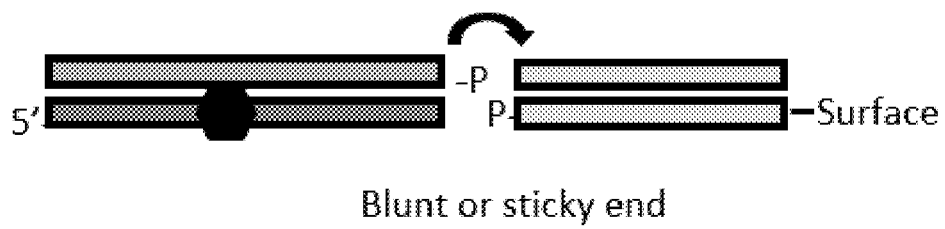
Figure 2F:
Figure 2G:
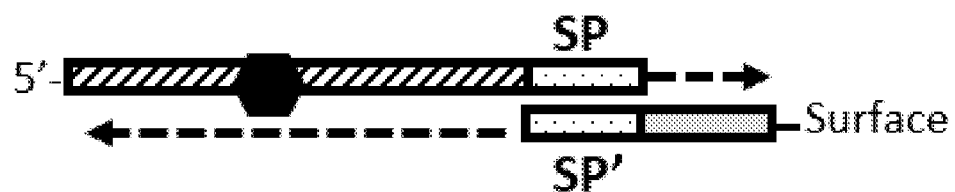
Figure 2H:
FIG. 2H is like FIG. 2G but does not rely on ligating a spacer sequence to the RNA target. The 3' end of the adapter exhibits degenerate bases to allow for random priming of the target RNA, followed by single or bi-directional primer extension to transfer the barcode.

In some embodiments, templated extension may be used to transfer an adapter/barcode to a target nucleic acid. FIG. 2G illustrates direct adapter transfer by primer extension, initiated by the hybridization of an adapter to a target RNA. Using a reverse transcriptase, the adapter and the target nucleic acid may be extended, hence, introducing the barcode to the target RNA and to the cDNA copy thereof ("bi-directional extension"). The adapter may hybridize via a short spacer sequence (SP) that can be ligated to the target nucleic acid upstream (FIG. 2G), or the adapter may hybridize randomly via degenerate bases that are part of the adapter sequence (FIG. 2H). Blocking groups at either one of the 3' ends controls whether primer extension is uni- or bi-directional. Uni-directional extension as depicted in FIG. 2D can be executed as part of a multi-cycle encoding process using an adapter with two spacer sequences, or as a single cycle. For DNA adapters/barcodes, the extension of the target nucleic acid may be catalyzed by a DNA polymerase, e.g. Klenow fragment, T7, T4 or Bst or Bsu DNA polymerase. In some embodiments, the barcoded nucleic acid produced is capped with a universal primer for downstream amplification as a last step.

Additionally, double-stranded ligation may also be used to transfer an adapter/barcode to a target nucleic acid. For example, FIG. 2E illustrates double-stranded ligation for adapter/barcode transfer. In some embodiments, the target nucleic acid molecule may be double-stranded DNA, or an RNA/DNA hybrid, and may have either a blunt or a sticky end. Blunt and sticky end ligation of double-stranded DNA may be catalyzed by T4, T3, T7 or E. coli ligase.

In some embodiments, chemical ligation may be used to transfer an adapter/barcode to a target nucleic acid.

Figure 9:
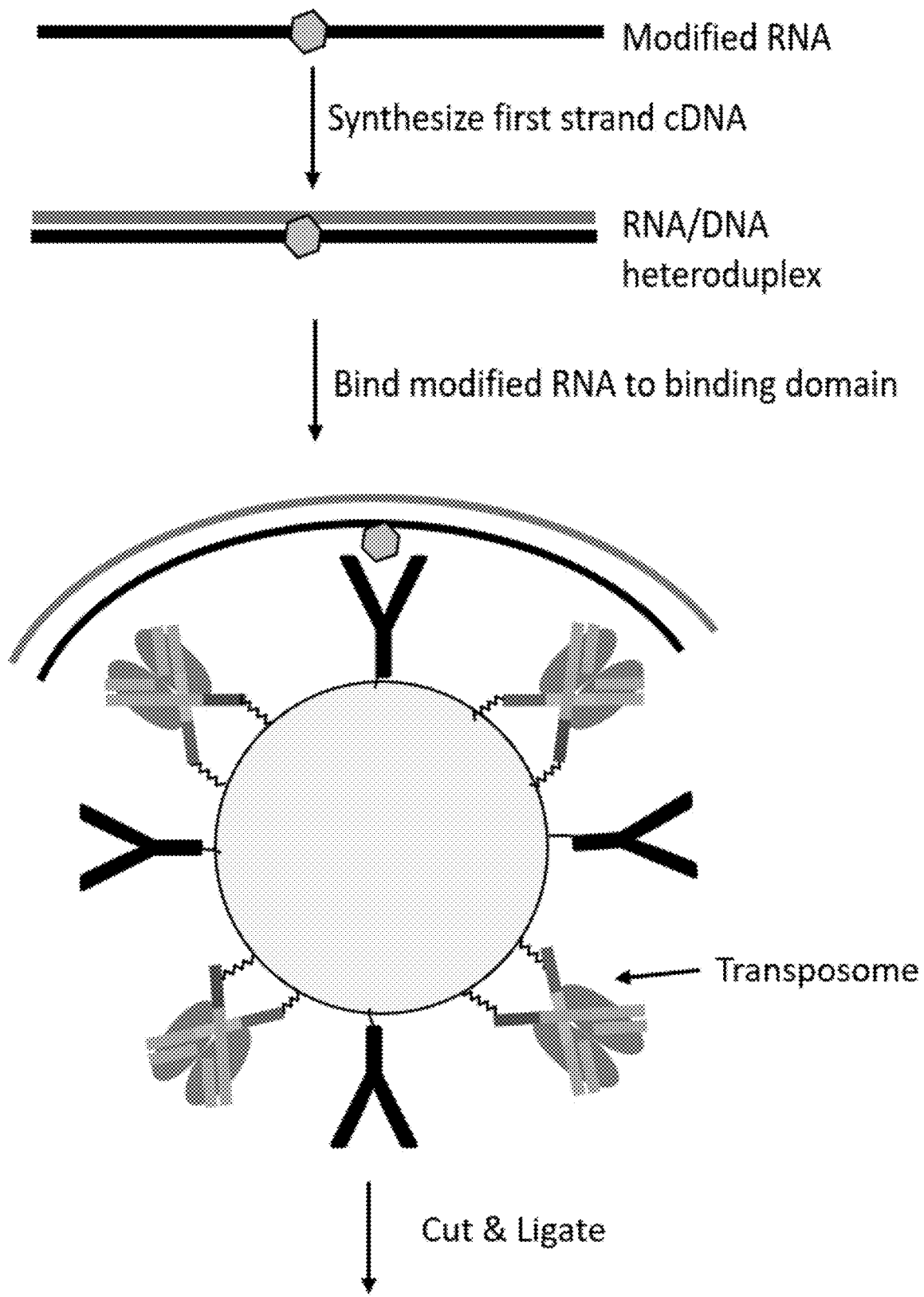
FIG. 9 illustrates a rapid method for profiling RNA modifications using Tn5 transposase for barcoding. To generate a substrate for transposition, RNA is reverse transcribed into a DNA/RNA heteroduplex. The heteroduplex is immunoprecipitated onto a surface (e.g., a bead) displaying antibodies and adapters with mosaic ends (ME). Transposomes, comprising Tn5 transpose molecules bound to the ME adapters, are assembled and Tn5 transposase inserts barcoded adapters in a one-step cut and paste mechanism in the presence of $Mg^{2+}$-ions. Gap fill followed by PCR completes the library preparation workflow.
Figure 9:
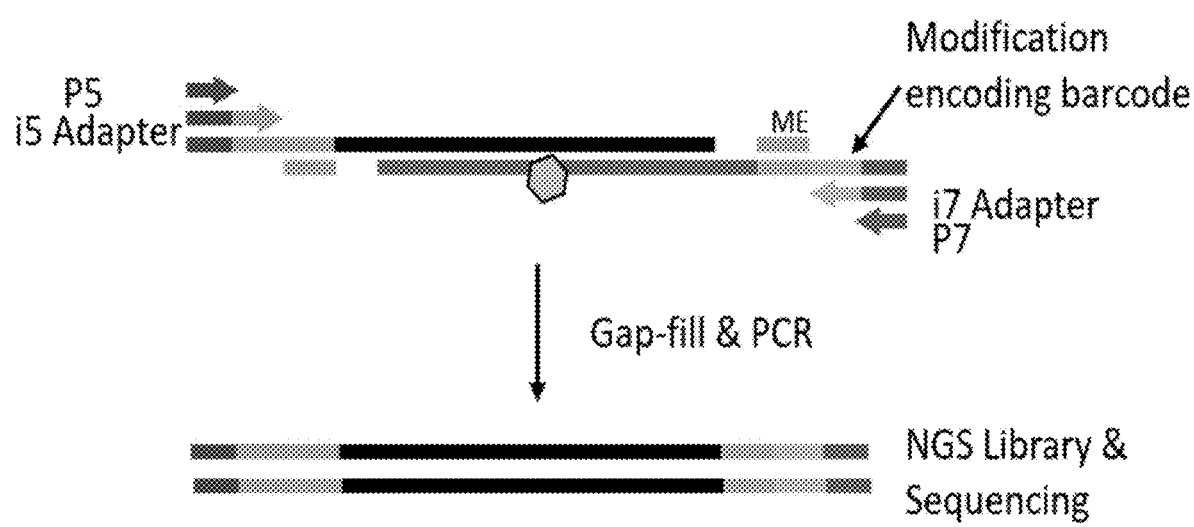

In some embodiments, target nucleic acids may be barcoded by enzymatic transposition using Tn5 transposase (FIG. 9 and FIG. 13). Using a one-step cut & ligate mechanism, Tn5 transposase inserts mosaic-end (ME) adapters into double-stranded nucleic acid targets. Suitable targets are genomic DNA or DNA/RNA heteroduplexes. ME adapters may comprise the 19 bp ME sequence, an MBC, a UMI and a universal sequence, such as a UFP or a URP. An illustrative example of the product of a transposition reaction is depicted in FIG. 13. Transposases form homodimers where each transposase monomer loads one ME adapter. Cutting a target nucleic acid and barcoding both liberated ends at the cut site requires two ME adapter loaded transposase dimers.

Methods for Facilitating Barcode Transfer to a Target Nucleic Acid Immobilized by a Binding Domain Adapter/barcode transfer may be facilitated by spatial arrangement of the molecules involved in the reaction (e.g., binding domain, adapter, secondary recognition element, and intermediate protein). Specifically, the transfer may be facilitated by positioning the molecules (e.g., adapters and binding domains), the target nucleic acids, and/or complexes comprising the binding domains bound to target nucleic acids, such that a binding domain bound to a target nucleic acid is in proximity to an adapter, allowing for adapter transfer to the target nucleic acids.

In some embodiments, the spatial arrangement can be achieved by surface immobilization. For example, the binding domains described herein may be immobilized by being coupled to a substrate (see FIG. 1A-1H). Most substrate formats may comprise only one type of binding domain. The format depicted in FIG. 1B, where the adapter is coupled to a secondary recognition element that is also coupled to the binding domain may further comprise at least two, at least three, at least four, at least five, or more types of binding domains, provided the binding domains are configured at single molecule spacing. Each "type" of binding domain binds to a different non-canonical feature and/or comprises a different barcode. In some embodiments, a binding domain is positioned on a substrate in proximity to an adapter, to allow for transfer of the adapter to a target nucleic acid bound to the binding domain. In some embodiments, a binding domain is positioned on a substrate in proximity to an adapter to allow for transfer of a copy of the adapter sequence to a target nucleic acid. For barcoding by ligation the adapter is transferred. However, for barcoding by primer extension a copy of the adapter is transferred. For example, the binding domain and the adapter are less than 200, 190, 180, 170, 160, 150, 140, 130, 120, 110, 100, 90, 80, 70, 60, 50, 40, 30, 20, 10, or 5 nm apart.

Exemplary substrates to which the binding domains, adapters, secondary recognition elements, and/or intermediary proteins may be coupled include, for example, beads, chips, plates, slides, dishes, or 3-dimensional matrices. In some embodiments, the substrate is a resin, a membrane, a fiber, or a polymer. In some embodiments, the substrate is a bead, such as a bead comprising sepharose, agarose, cellulose, polystyrene, polymethacrylate, and/or polyacrylamide. In some embodiments, the substrate is a magnetic bead. In some embodiments, the support is a polymer, such as a synthetic polymer. A non-limiting list of synthetic polymers includes: polystyrene, poly(ethylene)glycol, polyisocyanopeptide polymers, polylactic-co-glycolic acid, poly(ε-caprolactone) (PCL), polylactic acid, poly(3-hydroxybutyrate-co-3-hydroxyvalerate) (PHBV), chitosan and cellulose.

The molecules (e.g., binding domains, adapters, secondary recognition elements, and/or intermediary proteins) may be coupled directly to the surface of substrate. For example, molecules may be coupled directly to the substrate by one or more covalent or non-covalent bonds. In embodiments wherein the substrate is a 3D matrix or other 3D structure, the molecules may be coupled to multiple surfaces of the substrate.

In some embodiments, the nucleic acid-binding molecules may be coupled indirectly to the surface of the substrate. For example, the binding domain may be coupled to the surface of the substrate indirectly via a capture molecule, wherein the capture molecule is coupled directly to the substrate. The capture molecule may be any nucleic acid, protein, sugar, chemical linker, etc., that can bind or be linked to both the substrate and the binding domain and/or the adapter. In some embodiments, a capture molecule binds to a binding domain or to an adapter (e.g., to the linker of an adapter) to immobilize it on a substrate.

In some embodiments, a first adapter is separated from a second adapter on the surface of a substrate, so as to ensure that each adapter can only interact with one target nucleic acid (i.e., a target nucleic acid immobilized by a binding domain). In some embodiments, a binding domain and an adapter are arranged on the surface of a substrate, so as to ensure interaction between an adapter and a target nucleic acid bound to a binding domain. In some embodiments, an adapter is separated from a binding domain by at least 1 nm and at most 30 nm. For example, in some embodiments, an adapter and binding domain are separated by about 15 nm.

In some embodiments, multiple copies of an adapter are coupled to a substrate, at a density of approximately 1 adapter/5 nm$^2$ to about 1 adapter/50 nm$^2$, such as 1 adapter/20 nm$^2$. In some embodiments, multiple copies of a binding domain are coupled to a substrate, at a density of approximately 1 binding domain per 1000 nm$^2$ to about 1 binding domain per 15000 nm$^2$, such as 1 binding domain per 8000 nm$^2$.

In general, the goal of coupling a binding domain to a substrate is to ensure transfer of an adapter and/or a barcode to the target nucleic acid bound to the binding domain. FIGS. 1A-1H provide non-limiting examples of ways that binding domains and adapters may be coupled to, and immobilized on, a substrate. These examples are described in more detail below.

Coupling of a Binding Domain to a Substrate

In some embodiments, a binding domain is coupled directly or indirectly to a substrate. In some embodiments, a plurality of binding domains are immobilized on a substrate using site-specific chemistry. For example, in some embodiments, the binding domain comprises a site that allows it to be immobilized on a substrate. Coupling of a binding domain to the surface of a substrate may be facilitated by fusing self-catalyzing protein tags to the terminus of the binding domain (e.g., Spycatcher, sortase A, SNAP tag, Halo tag and CLIP tag). These protein tags on the binding domain may then be covalently reacted with their cognate reactive moieties on the surface of the substrate. For example, the Spycatcher protein may be engineered into a binding domain. Spytag forms a covalent linkage with a Spytag protein (a 13aa peptide). If Spytag is coupled to the surface of a substrate, a reaction between a Spycatcher-linked binding domain and Spytag will serve to covalently link the binding domain to the substrate. Similarly, a binding domain may be fused with a Sortase A tag, which could be used to react with pentaglycine coupled to a substrate surface. As another example, a binding domain may be fused with a SNAP tag, which could be used to react with O6-benzylguanine that is coupled to a substrate surface. In some embodiments, a binding domain may be fused with a CLIP tag, which could be used to react with O2-benzylcytosine that is coupled to a substrate surface. In some embodiments, a binding domain may be fused with a Halo tag, which could be used to react with an alkyl halide present on a substrate surface.

In some embodiments, the binding domain may comprise a biotin moiety. Such binding molecules may be immobilized on a substrate surface by a capture molecule that binds biotin (e.g., streptavidin).

Binding domains may be coupled to the substrate via Spytag-Spycatcher interactions. This can be accomplished by functionalizing a substrate with Spytag peptide at a suitable surface density using standard NHS chemistry. Spytag is a short 13aa peptide (AHIVMVDAYKPTK; SEQ ID NO: 11). Spycatcher is a 139 amino acid protein that can be genetically engineered into most binding domains: msyyhhhhhh dydipttenl yfqgamvdtl sglsseqgqs gdmtieedsa thikfskrde dgkelagatm elrdssgkti stwisdgqvk dfylypgkyt fvetaapdgy evataitfty neqgqvtvng katkgdahi (SEQ ID NO: 10). When exposing a Spycatcher-modified binding domain to a Spytag coated surface the C-terminus of Spytag and the N-terminus of Spycatcher react spontaneously and form an isopeptide bond, thereby immobilizing the binding domain.

Figure 1G:
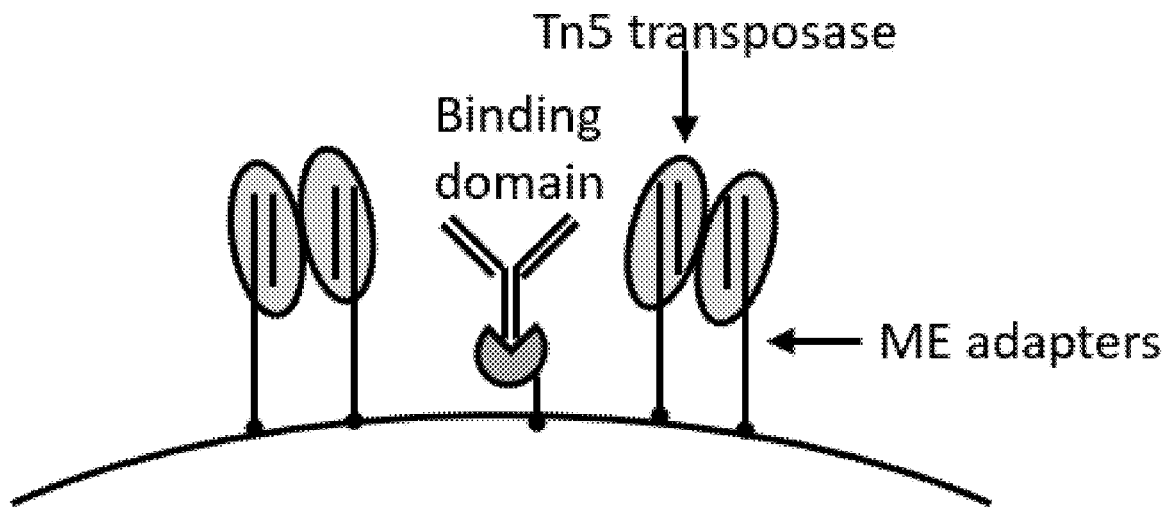
Figure 1H:
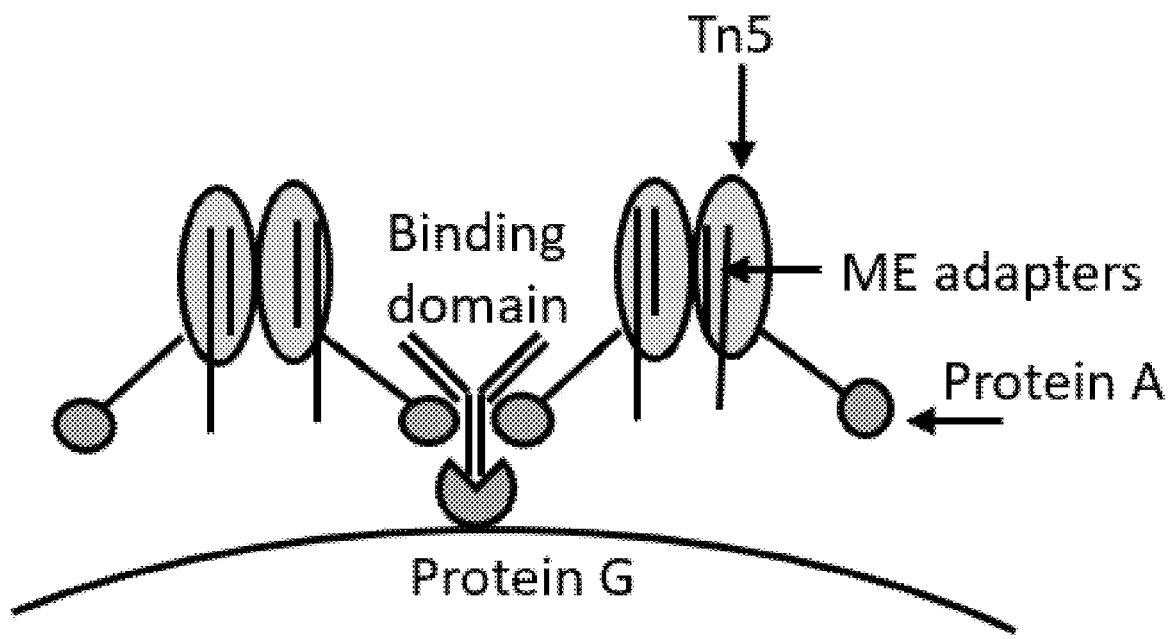

Commercial streptavidin and protein G beads are convenient substrates for immobilizing binding domains. In some embodiments, streptavidin beads are functionalized with a mixture of biotinylated adapters and biotinylated protein G. In a second step, protein G is further coupled to antibody binding domains by affinity binding (FIG. 1D). The surface density of biotinylated adapters and protein G can be adjusted to achieve high yielding and specific barcode transfer. In some embodiments, transposase beads may be prepared by coupling 5'biotinylated ME adapters to a streptavidin bead, followed by loading the ME adapters with Tn5 transposase (FIG. 1G). In some embodiments, protein G beads are functionalized by adapters using chemical conjugation of protein lysines and amino-modified adapters. In a second step, protein G is loaded with antibody binding domains (FIG. 1B). Here, the labeling stoichiometry of protein G with adapters must be controlled to maintain the ability of protein G to bind to antibodies. In some embodiments, transposase beads may be prepared from protein G beads by first loading an antibody binding domain, followed by binding a Tn5 transpoases-protein A fusion protein to the antibody (FIG. 1H).

Substrates

In some embodiments, the compositions herein comprise one substrate. In some embodiments, the compositions herein comprise two or more substrates. In some embodiments, a composition comprises a plurality of substrates wherein each substrate is formed from the same material. In some embodiments, a composition comprises a plurality of substrates wherein each substrate is formed from a different material. In some embodiments, the substrate is a bead, chip, plate, tube, slide, dish, gel, or 3-dimensional polymer matrix. Substrates may be formed from a variety of materials. In some embodiments, the substrate is a resin, a membrane, a fiber, or a polymer. In some embodiments, the substrate comprises sepharose, agarose, cellulose, polystyrene, polymethacrylate, and/or polyacrylamide. In some embodiments, the substrate comprises a polymer, such as a synthetic polymer. A non-limiting list of synthetic polymers includes: poly(ethylene)glycol, polyisocyanopeptide polymers, polylactic-co-glycolic acid, poly(F-caprolactone)

(PCL), polylactic acid, poly(3-hydroxybutyrate-co-3-hydroxyvalerate) (PHBV), chitosan and cellulose.

In some embodiments, a target nucleic acid is coupled indirectly to a substrate via a binding domain. In some embodiments, adapters are coupled to surface-activated beads comprising a binding domain. The surface-activated beads may exhibit epoxy, tosyl, carboxylic acid or amine groups for covalent linkage. Carboxy beads typically need to be reacted with carbodiimide to facilitate peptide bond formation, and amine beads typically require a bifunctional NHS-linker. In some embodiments, the surface of the bead is passivated to prevent non-specific binding. Passivation can be achieved, in some embodiments, by co-grafting poly-ethylene glycol (PEG) molecules with the same linkage chemistry. For example, binding domains and amino-terminated polyethylene glycol (PEG) is used such that, on average, most substrate sites will be occupied by PEG molecules that will serve to spatially distribute the binding domains. If an excess of PEG is used, the binding domains will be, on average, spatially separated from one another. The surface density of binding domains can be adjusted by altering the ratio of binding domains to PEG molecules.

In some embodiments, the beads are Sepharose beads made with mTet (tetrazine) and carboxy-PEG. A reduced ratio of mTet to carboxy-PEG reduces crosstalk between target nucleic acids. In some embodiments, the mTet:carboxy-PEG ratio is 1:500, 1:600, 1:700, 1:800, 1:900, 1:1000, 1:1100, 1:1200, 1:1300, 1:1400, 1:500, or 1:2000. In some embodiments, the mTet:carboxy-PEG ratio is 1:1000.

In some embodiments, a substrate comprises a plurality of the same binding domain. In some embodiments, a substrate comprises a plurality of the same adapter.

Nucleic Acid Analysis Methods

The compositions described herein (e.g. a composition comprising a binding domain, an adapter, and a substrate) may be used in various methods of analyzing nucleic acids, specifically for recognizing non-canonical features on target nucleic acids. This disclosure thus provides methods for analyzing non-canonical features on target nucleic acids, including methods for multiplexed profiling of RNA and DNA modifications across transcriptomes and genomes. In these methods, non-canonical features of an RNA or DNA are recognized by a binding domain. The adapter or part thereof (e.g., a barcode) is then transferred from the substrate to the target nucleic acid (i.e., to generate a labeled/barcoded target nucleic acid) or to a copy of the target nucleic acid. Because the barcode is unique to the particular non-canonical feature bound by the target nucleic acids, this step serves to write the information from the recognition event into the nucleic acid sequence of the target nucleic acid. The resultant barcoded target nucleic acid is then converted into a sequencing library and read by DNA/RNA sequencing methods. This step reveals the sequence of the barcode, which is correlated with the non-canonical feature in the target nucleic acid(s). Sequencing may also allow for localization of the non-canonical feature in the target nucleic acid(s). The high throughput profiling methods described herein allow for identification of several or all DNA/RNA modifications in parallel.

The methods described herein comprise a series of steps, as described below. As will be understood by those skilled in the art, in some embodiments, various steps may be omitted and/or performed in a different order.

Contacting the Binding Domains and the Target Nucleic Acids

In some embodiments, the methods described herein comprise a step of contacting a composition described herein (e.g. a substrate, a binding domain, and an adapter) with one or more target nucleic acids. The target nucleic acid(s) may comprise DNA, RNA, or a combination of DNA and RNA. The target nucleic acids may be, for example, isolated from a cell or tissue of an organism. In some embodiments, the target nucleic acids may be fragmented.

Contacting the compositions described herein with the target nucleic acid(s) may occur in solution. For example, a composition comprising one or more target nucleic acids may be contacted with one or more compositions comprising a substrate, a binding domain, and an adapter. In some embodiments, the contacting may occur in a dilute solution, so that only one binding domain may interact with each target nucleic acid.

In some embodiments, one or more binding domains may be coupled to a substrate, and one or more target nucleic acids may be contacted with the binding domains coupled to the substrate.

The target nucleic acids may be contacted with only one type of binding domain (i.e., to detect only one type of non-canonical feature), or in some embodiments, the target nucleic acids may be contacted with more than one type of binding domain, to detect multiple non-canonical features. For example, the target nucleic acids may be contacted with at least one, at least two, at least three, at least four, at least five, at least six, at least seven, at least eight, at least nine, at least ten, at least twenty, at least thirty, at least forty, at least fifty, at least sixty, at least seventy, at least eighty, at least ninety, at least one hundred, at least one-hundred and fifty, or at least two hundred or more different types of binding domains. In some embodiments, the target nucleic acids may be contacted with 1-5, 5-10, 10-25, 25-50, 50-100, 100-150, 150-175, 175-200, or more different types of binding domains. When multiple types of binding domains are used, the contacting may occur at the same time (i.e., the target nucleic acids are contacted with multiple binding domains recognizing different non-canonical features simultaneously), or the contacting may be sequential (i.e., the target nucleic acids are contacted with a first binding domain recognizing a first non-canonical feature, and then later contacted with a second binding domain recognizing a second non-canonical feature).

Barcode Transfer

Each binding domain binds specifically to a non-canonical feature of a target nucleic acid, an adapter coupled in close proximity to the binding domain enables interaction of either the 3' or the 5' end of the target nucleic acid with the adapter. The adapter (e.g., an adapter comprising or consisting of a barcode) may then be transferred to the target nucleic acid. In some embodiments, the adapter is coupled to the substrate by a cleavable linker. In some embodiments, when the adapter binds to the target nucleic acid, the adapter is released at the cleavage site. In some embodiments, the transferring occurs in an environment that substantially prevents off-target generation of barcoded nucleic acids. Such an environment may be, for example, an environment wherein the adapters and binding domains are at a defined density, where each binding domain and its cognate adapter occupy a defined space separate from a second binding domain and its cognate adapter (e.g. each binding domain and adapter pair are on a separate bead, spot, or array wherein they cannot interact with a second binding domain and adapter pair). In some embodiments, the transferring is performed by copying the target nucleic acid, to generate a labeled/barcoded copy of the target nucleic acid. For example, if an adapter comprising at least a barcode and a universal primer site is transferred to a target nucleic acid, polymerase chain reaction (PCR) may be used to generate a barcoded copy of the target nucleic acid.

Modification of the Target Nucleic Acid (or a Copy Thereof)

In some embodiments, the method may comprise a step of modifying the barcoded target nucleic acid(s) or a barcoded copy(ies) thereof. This modification may occur after the binding domain has been bound to the non-canonical feature, and in some embodiments, may occur after the barcode has been transferred to the target nucleic acid (or a barcoded copy of the target nucleic acid has been generated).

Modification is performed so that the position of the non-canonical feature is identifiable based on the primary nucleic acid sequence of the barcoded target nucleic acids, or the barcoded copies thereof, and may therefore be detected in downstream sequencing steps. Many different types of modifications may be used for this purpose. For example, in some embodiments, the modification may prevent polymerase bypass during copying of the target nucleic acid (or barcoded copy thereof).

In some embodiments, the modification is achieved, in part, by chemically modifying the binding domain. This may, in some embodiments, induce truncation during copying of the target nucleic acid, while the binding domain is bound thereto.

In some embodiments, the modification comprises photochemically linking the binding domain (or a fragment thereof, such as the binding domain) to the target nucleic acid (or barcoded copy thereof). Methods for photochemically linking a nucleic acid and a protein are known to those of skill in the art. For example, photochemical linkages may be induced by exposing complexes comprising a binding domain and a target nucleic acid to ultraviolet (UV) light.

In some embodiments, the modification comprises editing a base at or near, e.g., within 1 to 20 bases, the site where the binding domain is bound to the target nucleic acid. For example, the base may be edited using cytosine deaminase or adenosine deaminase. The base editing molecule may be coupled to the binding domain via a secondary recognition element. In some embodiments, cytosine deaminase may be genetically fused to protein A and bound to the Fc region of an antibody binding domain. In some embodiments, cytosine deaminase may be genetically fused to Spycatcher and bound to a Spytag-labeled binding domain. Adenosine deaminase converts an adenosine (A) to inosine (I), which amplification enzymes base pair with cytosine (C) introducing a thymine (T) to cytosine (C) mutation. Cytosine deaminase converts a cytosine (C) near the modification site to uracil (U), introducing a guanine (G) to adenosine (A) mutation. Another way to localize the non-canonical feature is to cleave uracil (U) subsequently by USER™ from NEB® (a mixture of the enzymes uracil deglycosylase and endonuclease VIII), which produces a truncated read.

Amplification and Sequencing

After a target nucleic acid (or barcoded copy thereof) has been modified, it may be amplified and then sequenced. This step reveals the sequence of the barcode, which is correlated with the non-canonical feature originally bound by the binding domain in the target nucleic acid(s). Sequencing may also reveal the length of a truncated fragment, which allows for localization of the non-canonical feature in the target nucleic acid(s). Sequencing may also reveal a mutation near the non-canonical feature, from which the location of the non-canonical feature can be derived informatically. The mutation may be a result of base editing with a deaminase enzyme, or it may result from an increased base insertion error rate of the enzyme that is used to copy past a non-canonical feature of the nucleic acid target (a DNA polymerase if the target is DNA, or a reverse transcriptase if the target is RNA). The non-canonical feature may naturally increase the enzymatic bypass error rate, or the effect may be amplified by chemically modifying the non-canonical feature.

Thus, in some embodiments, the method described herein may comprise a step of sequencing the barcoded target nucleic acids, or copies thereof. The sequencing step may be performed using any suitable method known in the art. For example, the sequencing may be performed using a next-generation sequencing (NGS) method, a massively parallel sequencing method, or a deep sequencing method. There are a number of NGS platforms that may be used with the methods of the instant disclosure. For example, Illumina® (Solexa®) sequencing works by simultaneously identifying DNA bases as each base emits a fluorescent signal and adding them to a nucleic acid chain. Roche® 454 sequencing is based on pyrosequencing, a technique which detects pyrophosphate release using fluorescence, after nucleotides are incorporated by a polymerase to a new strand of DNA. Ion Torrent (Proton/PGM sequencing) measures the direct release of protons (H+) from the incorporate of individual nucleotides by DNA polymerase.

In some embodiments, sequencing is not required to detect a target nucleic acid. For, example, the target nucleic acid may be detected using PCR. For example, PCR may be used to detect whether a target nucleic acid (e.g., a barcode) is present. In some embodiments, a target nucleic acid is detected using a fluorescent probe (e.g., a fluorescently-labeled hybridization probe). In some embodiments a target nucleic acid is detected using a microarray or other nucleic acid array.

In some embodiments, sequencing is not required to detect the addition of a barcode by a reaction mediated by the nucleic acid binding molecule. For example, the presence of a DNA/RNA modification may be confirmed by detecting the associated barcode using nucleic acid electrophoresis, a fluorescent hybridization probe, PCR, rolling circle amplification, LAMP or any other nucleic acid amplification method that can be triggered by the barcode.

Illustrative Methods for Identification and Quantification, of a Non-Canonical Feature on a Target Nucleic Acid In some embodiments, the methods described herein may be used to not only identify the modification (i.e., a non-canonical feature) on a target nucleic acid, but also to quantify the number of modifications present. In some embodiments, the methods described herein are used to identify the multiple modifications (i.e., a non-canonical features) on a plurality of target nucleic acids, and to quantify the number of each modification present.

In some embodiments, a method for detecting a non-canonical feature in a target nucleic acid comprises: (i) contacting the target nucleic acid with a composition as described herein; (ii) either (a) transferring the nucleic acid barcode to the target nucleic acids to generate barcoded target nucleic acid, or (b) generating a barcoded copy of the target nucleic acid; and (iii) detecting the presence of the barcode in the target nucleic acid or copy thereof.

In some embodiments, a method for detecting and or quantifying a two or more non-canonical features in plurality of target nucleic acids comprises: (i) contacting the target nucleic acids with at least two compositions, wherein each composition comprises a binding domain and an adapter; wherein the binding domain of each nucleic-acid binding molecule binds to a different non-canonical feature of a DNA or an RNA; wherein the adapter comprises a nucleic acid barcode sequence unique to the non-canonical feature bound specifically by each binding domain; (ii) either (a) transferring the nucleic acid barcode to the target nucleic acids to generate barcoded target nucleic acids, or (b) generating barcoded copies of the target nucleic acids; (iii) modifying the barcoded target nucleic acids or the barcoded copies thereof, such that the position of the non-canonical feature is identifiable based on the primary nucleic acid sequence of the barcoded target nucleic acids, or the barcoded copies thereof; and (vi) sequencing the barcoded target nucleic acids. In some embodiments, the method comprises amplifying the barcoded target nucleic acids or copies thereof prior to sequencing.

In some embodiments, a method for analyzing a plurality of target nucleic acids comprises: (i) contacting the target nucleic acids with a composition as described herein; (ii) either (a) transferring the nucleic acid barcode to the target nucleic acids to generate barcoded target nucleic acids, or (b) generating barcoded copies of the target nucleic acids; (iii) modifying the barcoded target nucleic acids or the barcoded copies thereof, such that the position of the non-canonical feature is identifiable based on the primary nucleic acid sequence of the barcoded target nucleic acids, or the barcoded copies thereof; and (vi) sequencing the barcoded target nucleic acids.

In some embodiments, any one or more of the foregoing steps are repeated at least once (e.g., at least twice, at least three times, at least four times, at least five times, at least six times, at least seven times, at least eight times, at least nine times, at least ten times, or more). In some aspects, one or more of the foregoing steps may be performed concurrently or sequentially. In some embodiments, the same or a different binding domain is used each time steps (i)-(iii) are repeated. In some embodiments, the method comprises amplifying the barcoded target nucleic acids or copies thereof prior to sequencing.

In some embodiments, an RNA sample comprising modified and unmodified RNA transcripts is provided. Each transcript of the RNA sample may or may not comprise a non-canonical feature. The RNA transcripts are then contacted with beads, wherein the beads are coupled, directly or indirectly, to binding domains specific for a non-canonical feature (i.e., the Type 1, Type 2, and Type III beads of FIG. 4A). The modified RNA molecules bind to the beads, whereas unmodified RNA remains in the supernatant. To be able to quantitate the level of RNA modifications, both fractions (substrate-bound and supernatant) may be processed and converted into sequencing libraries. Unmodified RNA molecules are capped on each end with adapters comprising a UFP and a URP, whereas the modified RNA molecules receive a barcode indicative of their modification (i.e., it is transferred from the adapter bound to the bead).

In some embodiments, the methods described herein comprise a substrate wherein the substrate is a bead. In some embodiments, the substrate is a pool of beads. In some embodiments, each bead comprises a different binding domain. In some embodiments, each bead comprises a different adapter. In some embodiments, each bead comprises a different binding domain and an adapter, wherein the adapter comprises a nucleic acid barcode sequence unique to the non-canonical feature bound specifically by the binding domain.

Provided herein are methods for measuring target genes comprising contacting a plurality of target genes with a substrate wherein the substrate is immobilized on a microarray. In some embodiments, the microarray is a spotted microarray. In some embodiments, the microarray is a printed microarray. An example of the microarray is that depicted in FIG. 4B. In some embodiments each spot on the microarray comprises a different binding domain and an adapter, wherein the adapter comprises a nucleic acid barcode sequence unique to the non-canonical feature bound specifically by the binding domain. In some embodiments, each spot on the microarray comprises a different composition described herein.

Provided herein are methods for measuring target genes comprising contacting a plurality of target genes with a substrate wherein the substrate is immobilized in a channel of a microfluidic device. In some embodiments, the microfluidic device comprises 1, 2, 3, 4, 5, 6, 7, 8, 9, 10, 20, 30, 40, or 50 channels. An example of a microfluidic device is that depicted in FIG. 4C. In some embodiments each channel of the microfluidic device comprises a different binding domain and an adapter, wherein the adapter comprises a nucleic acid barcode sequence unique to the non-canonical feature bound specifically by the binding domain. In some embodiments, each channel of the microfluidic device comprises a different composition described herein.

In some embodiments, the methods herein comprise analyzing a plurality of target nucleic acids. In some embodiments, the method comprises contacting a plurality of target nucleic acids with any composition described herein.

In some aspects, the present disclosure includes a method for analyzing a plurality of target nucleic acids, the method comprising:
(i) contacting a solution comprising a plurality of target nucleic acids with a composition of the present disclosure, wherein a target nucleic acid comprising the non-canonical feature binds to the binding domain;
(ii) performing one of the following: (a) transferring the nucleic acid barcode to a target nucleic acid comprising the non-canonical feature to generate a barcoded target nucleic acid, or (b) generating a barcoded copy of the target nucleic acid comprising the non-canonical feature;
(iii) amplifying the barcoded target nucleic acids; and
(iv) sequencing the barcoded target nucleic acids,
wherein steps (i) and (ii) are performed sequentially or concurrently.

In some aspects, the present disclosure includes a method for analyzing a plurality of target nucleic acids, the method comprising:
(i) contacting a solution comprising a plurality of target nucleic acids with a composition of the present disclosure, wherein a target nucleic acid comprising the non-canonical feature binds to the binding domain;
(ii) performing one of the following: (a) transferring the nucleic acid barcode to a target nucleic acid comprising the non-canonical feature to generate a barcoded target nucleic acid, or (b) generating a barcoded copy of the target nucleic acid comprising the non-canonical feature;
(iii) amplifying the barcoded target nucleic acids; and
(iv) sequencing the barcoded target nucleic acids,
wherein steps (i) and (ii) are performed sequentially or concurrently.

In some aspects, the present disclosure includes a method for analyzing a plurality of target nucleic acids, the method comprising:
(i) providing a plurality of target nucleic acids by reverse transcribing target RNA molecules to form DNA-RNA heteroduplex molecules or providing target double-stranded DNA molecules;
(ii) contacting a solution comprising the plurality of target nucleic acids with a composition of the present disclosure, wherein a target nucleic acid comprising the non-canonical feature binds to the binding domain;
(iii) transferring, using transposase, two adapters, at least one of them comprising the nucleic acid barcode, to a double-stranded target nucleic acid comprising the non-canonical feature to generate barcoded target nucleic acids,
(iv) amplifying the barcoded target nucleic acids; and
(v) sequencing the barcoded target nucleic acids,
wherein steps (ii) and (iii) are performed concurrently or sequentially.

In some aspects, the present disclosure includes a method for detecting a plurality of non-canonical features in a plurality of target nucleic acids, the method comprising:
(i) contacting a solution comprising the plurality of target nucleic acids with a plurality of compositions of the present disclosure;
wherein the number of the plurality of compositions contacted in step (i) is equal to or greater than the number of non-canonical features,
wherein the binding domains of the plurality of compositions each bind to different non-canonical features of a DNA or RNA or wherein multiple binding domains bind to the same non-canonical feature of a DNA or RNA; and
wherein the adapters of the plurality of compositions each comprise a nucleic acid barcode sequence unique to the non-canonical feature bound specifically by the binding domain of that composition or unique to the binding domain;
(ii) performing one of the following: (a) transferring the nucleic acid barcode sequences of each of the plurality of compositions to a plurality of target nucleic acids, or (b) generating barcoded copies of the plurality of target nucleic acids;
(iii) amplifying the barcoded target nucleic acids; and
(iv) sequencing the barcoded target nucleic acids.

In some embodiments, the transferring is adapter transfer by transposase.

In some aspects, the present disclosure includes a method for detecting a plurality of non-canonical features in a plurality of target nucleic acids, the method comprising:
(i) providing a microarray, beads, and/or a fluidics device comprising a plurality of compositions of the present disclosure;
wherein the number of the plurality of compositions provided in step (i) is equal to or greater than the number of non-canonical features,
wherein the binding domains of the plurality of compositions each bind to different non-canonical features of a DNA or RNA or wherein multiple binding domains bind to the same non-canonical feature of a DNA or RNA; and
wherein the adapters of the plurality of compositions each comprise a nucleic acid barcode sequence unique to the non-canonical feature bound specifically by the binding domain of that composition or unique to the binding domain;
(ii) contacting the plurality of target nucleic acids with the plurality of compositions and performing one of the following: (a) transferring the nucleic acid barcode sequences of each of the plurality of compositions to a plurality of target nucleic acids, or (b) generating barcoded copies of the plurality of target nucleic acids;
(iii) amplifying the barcoded target nucleic acids; and
(iv) sequencing the barcoded target nucleic acids.

Figure 4A:
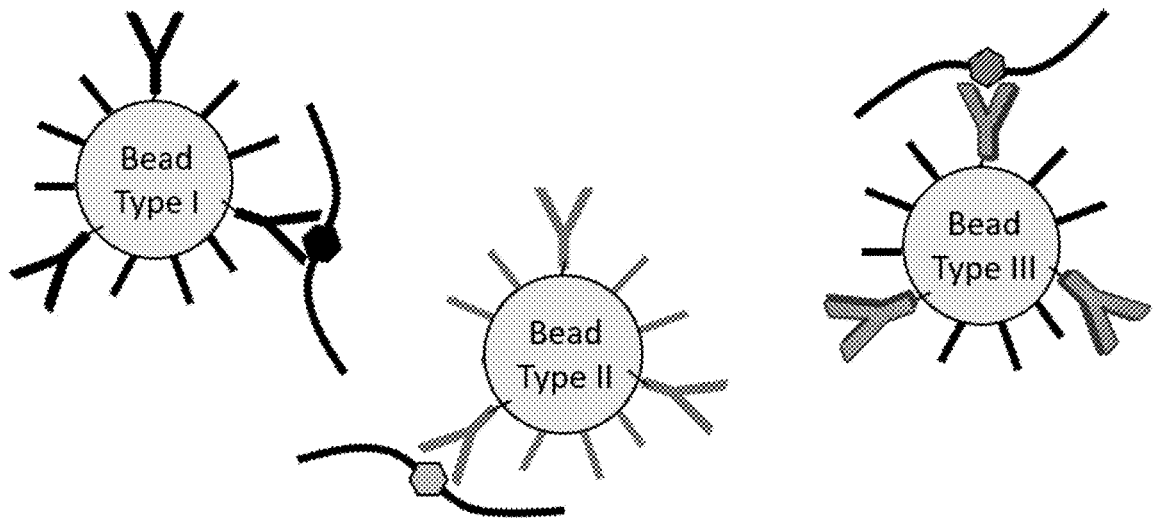
FIGS. 4A-4C illustrate several surface-based assay formats for the simultaneous interrogation of multiple non-canonical features (e.g., RNA modifications) on different strands in the same reaction. These formats aim to spatially segregate different types of binding domains and the associated barcodes and to expose them to the same analyte to enable multiplexed analysis.

In some embodiments, a method for analyzing a plurality of target nucleic acids comprises contacting a solution comprising a plurality of target nucleic acids with a plurality of compositions described herein, wherein the substrate of each composition is a bead as depicted in FIG. 4A.

In some embodiments, a method for analyzing a plurality of target nucleic acids comprises:
(i) contacting a microfluidic device with a solution comprising a plurality of target nucleic acids, wherein the microfluidic device comprises a plurality of channels, wherein each channel comprises a composition described herein wherein the adapter comprises a nucleic acid barcode sequence unique to the non-canonical feature bound specifically by the binding domain, and wherein each of the compositions bind a different non-canonical feature,
thereby binding a plurality of non-canonical features on the target nucleic acids,
(ii) either (a) transferring the nucleic acid barcode to the target nucleic acids to generate barcoded target nucleic acids, or (b) generating barcoded copies of the target nucleic acids; and,
(iii) amplifying the barcoded target nucleic acids; and,
(iv) sequencing the barcoded target nucleic acids.

Figure 4B:
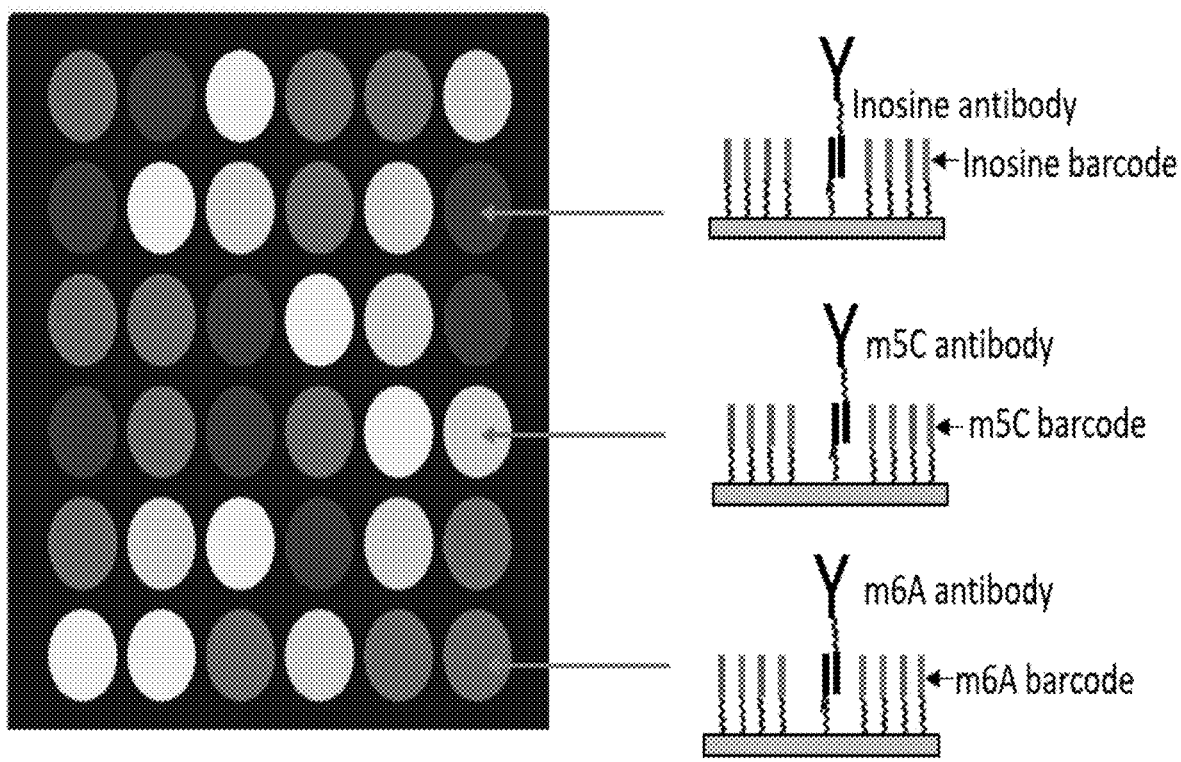

In some embodiments, a method for analyzing a plurality of target nucleic acids comprises contacting a solution comprising a plurality of target nucleic acids with a plurality of compositions described herein, wherein the substrate of each composition is immobilized on a microarray as depicted in FIG. 4B.

In some embodiments, a method for analyzing a plurality of target nucleic acids comprises:
(i) contacting a solution comprising the plurality of target nucleic acids with a plurality of compositions described herein, wherein each composition is immobilized on a microarray wherein the adapter comprises a nucleic acid barcode sequence unique to the non-canonical feature bound specifically by the binding domain; and wherein each of the compositions bind a different non-canonical feature, thereby binding a plurality of non-canonical features on the target nucleic acids,
(ii) either (a) transferring the nucleic acid barcode to the target nucleic acids to generate barcoded target nucleic acids, or (b) generating barcoded copies of the target nucleic acids,
(iii) amplifying the barcoded target nucleic acids; and,
(iv) sequencing the barcoded target nucleic acids.

Figure 4C:
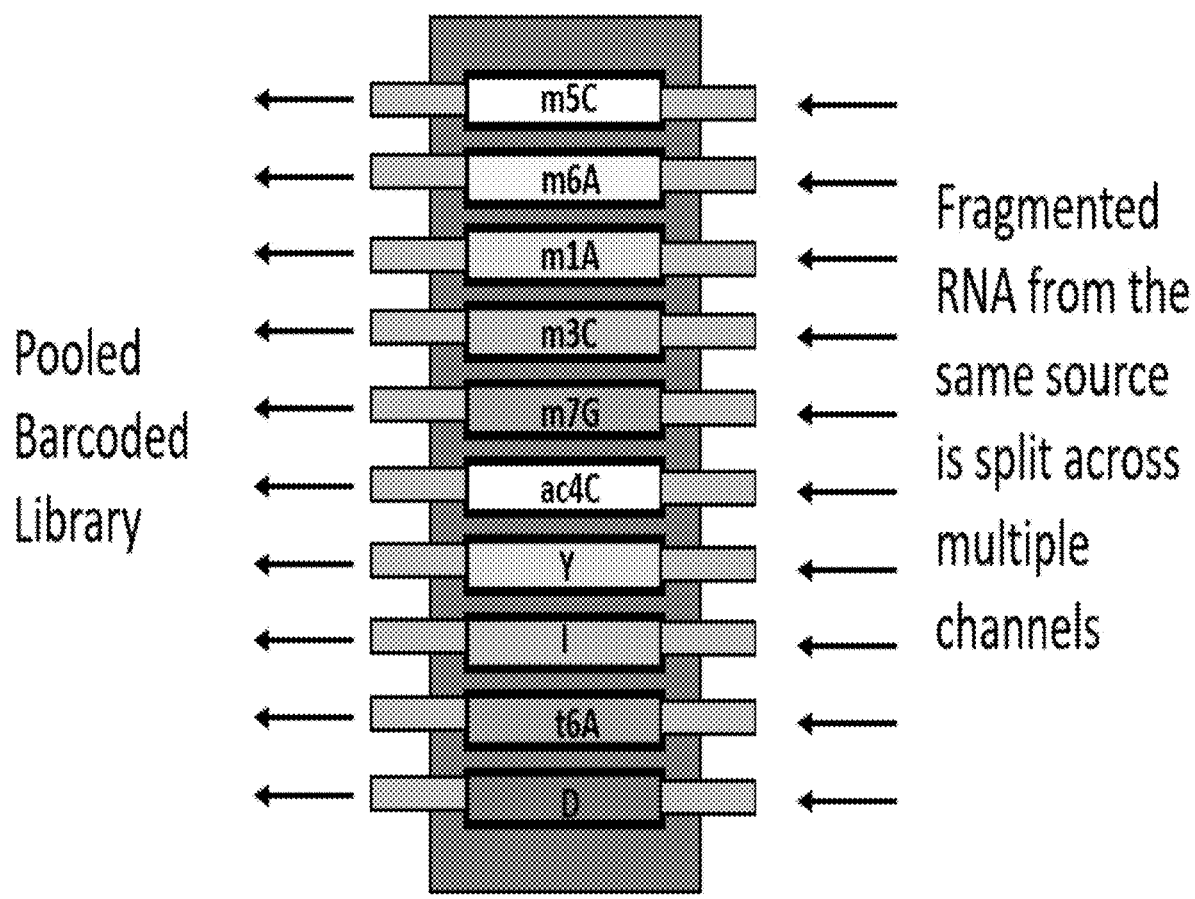

In some embodiments, a method for analyzing a plurality of target nucleic acids comprises contacting a solution comprising a plurality of target nucleic acids with a plurality of compositions described herein, wherein the substrate of each composition is immobilized in a channel of a microfluidic device as depicted in FIG. 4C.

A method for detecting a plurality of non-canonical features in a plurality of target nucleic acids, the method comprising:
(i) contacting a solution comprising the plurality of target nucleic acids with the plurality of compositions described herein;
wherein the binding domains of the plurality of compositions each bind to different non-canonical features of a DNA or RNA or wherein multiple binding domains bind to the same non-canonical feature of a DNA or RNA; and
wherein the number of the plurality of compositions contacted in step (i) is equal to or greater than the number of non-canonical features, wherein the adapters of the plurality of compositions each comprise a nucleic acid barcode sequence unique to the non-canonical feature bound specifically by the binding domain of that composition or unique to the binding domain;

(ii) performing one of the following:
(a) transferring the nucleic acid barcode sequences of each of the plurality of compositions to a plurality of target nucleic acids, or
(b) generating barcoded copies of the plurality of target nucleic acids;
(iii) amplifying the barcoded target nucleic acids; and
(iii) sequencing the barcoded target nucleic acids.

As such, the method makes it possible to detect the same modification with multiple binding domains, each exhibiting its own barcode.

In some embodiments, normalization probes (controls) may be spiked into the solution comprising target nucleic acids (surface bound, supernatant) to enable relative quantification. In addition, absolute quantification can be accomplished by counting unique molecular identifiers that may be present in the adapters. Many RNA modifications occur at low copy numbers. Accordingly, modified and unmodified fractions of target nucleic acids can be combined at a ratio that provides optimal sensitivity for the low copy number transcripts at a given sequencing depth. This approach allows for measuring the stoichiometry and abundance of an RNA modification. The "stoichiometry" is a relative number and is calculated as the number of copies of a particular locus that contain a non-canonical feature divided by all copies of this locus. The "abundance" is the absolute number of occurrences of a non-canonical feature of a nucleic acid at a given locus.

In some embodiments, a method for analyzing a plurality of target nucleic acids may comprise RNA profiling by barcode transfer by ligation, and localizing the non-canonical feature by cDNA truncation. One or more compositions described herein may then be added to the RNA sample. The binding domain of the composition recognizes the RNA modifications, and adapters (e.g., adapters containing DNA barcodes) are coupled to the ends of the RNA target. In some embodiments, to generate a mark that prevents reverse transcriptases from copying past the recognition element (i.e. the modification), the target RNA and the binding domain may be cross-linked (e.g., photochemically cross-linked). In some embodiments, a stopping point may be created without cross-linking by selecting and engineering for recognition elements that disrupt polymerase-RNA interactions and/or present additional reactive groups that can be engaged for the same purpose. Single-stranded adapter ligation may then be used to provide a primer binding site for reverse transcription, and cDNA may be synthesized by primer extension. The cDNA is synthesized such that the end of the transcript marks the position of the RNA modification. The resolution by which the modification may be localized will depend on the nature of the truncation mechanism.

cDNA molecules may be circularized. For example, cDNA molecules with Type B adapters may be circularized by Circligase. Cleavage of the circularized cDNAs releases linear cDNA fragments that are strand-specific and can be easily converted into a sequencing library using PCR amplification. Primers may be used to introduce additional adapter pieces, which are useful for downstream processes such as sequencing.

In some embodiments, a method for analyzing a plurality of target nucleic acids may be used to detect/quantify a single type of DNA or RNA modification per reaction. In some embodiments, a method for analyzing a plurality of target nucleic acids may be adapted for detecting multiple DNA or RNA modifications by sample splitting.

In some embodiments, a transposase is bound to a substrate, as described herein. In some embodiments, Tagmentation is used for barcoding. In some embodiments, Tagmentation is used for barcoding as depicted in FIG. 9. Transposases, enzymes used for tagmentation, exist in both prokaryotes and eukaryotes and catalyze the movement of defined DNA elements (transposon) to another part of the genome in a 'cut and paste' mechanism. The transposase molecules are loaded with double-stranded DNA adapters that are indicative of specific RNA modifications. Transposases bind double-stranded DNA adapters, and cut and insert these adapters by ligation to the 5' ends of a double-stranded DNA substrate. They do not tag 3' ends, and the arising gap can be filled by a polymerase reaction. In some embodiments, the transposases can use DNA/RNA heteroduplexes as substrates. Tagmentation reactions typically produce 30-200 nt long fragments and can be optimized by sample input. In some embodiments, binding domain-transposase conjugates are added to unfragmented total or enriched/depleted RNA. Upon recognizing a modified RNA base, the transposase inserts specific barcodes into the RNA/DNA duplex thereby also appending universal and reverse primer sites. Filling the gaps using appropriate polymerases completes library preparation. Tagmentation frames the site of RNA modification by specific barcodes and positional information will be obtained by engineering the transposase linker to a length that optimizes positional resolution. In some embodiments, the transpose is a Tn5 transposase.

Transposases are widely used in many biomedical applications. For example, an engineered, hyperactive Tn5 transposase from *E. coli* can bind to a double-stranded synthetic 19 bp mosaic end (ME)-recognition sequences that can be appended to any sequencing adapter. In some embodiments, the ME-adapter comprises CTGTCTCTTATACACATCT (SEQ ID NO: 16). In some embodiments, the ME-adapter comprises AGATGTGTATAAGAGACAG (SEQ ID NO: 24). In some embodiments, the ME-adapter comprises TTTGTGAUGCGAT-GAACTCAGAGTGCTTNNNNNNNNNNNNNA-GATGTGTATAAGAGA CAG; SEQ ID NO: 52, wherein the plurality of N's is the barcode. In some embodiments, the mosaic end comprising SEQ ID NO: 16 is hybridized to the ME-adapter comprising SEQ ID NO: 52. Each transposase molecule simultaneously loads two ME-tagged adapters. Tn5 transposase has been utilized for in vitro tagmentation reactions (simultaneously fragment and tag a target sequence with sequencing adaptors) using double-stranded DNA or RNA/DNA heteroduplexes as a substrate. The major advantage of tagmentation is that it reduces the amount of input nucleic acid and significantly simplifies the assay workflow. Tagmentation is commonly performed with picograms of DNA or RNA and has been successful for single cell approaches.

In some embodiments, a binding domain-enzyme conjugate comprises a binding domain that specifically binds RNA modifications, DNA modifications, or both RNA and DNA modifications, and which directs transposase to target nucleic acids. Conjugated to the modification specific binding domain, the transposase inserts specific barcodes into the RNA/DNA duplex thereby also appending universal and reverse primer sites. Tagmentation is magnesium ion dependent and tagmentation may be triggered by addition of magnesium ions. The length of the tagmented duplex depends on the reaction conditions and can be optimized to be as short as 30 base pairs. Thus, targeted tagmentation can detect DNA or RNA modifications with a base resolution of up to 30 base pairs.

In some embodiments, transposase may not be directly tethered or fused to the binding domain that recognizes the DNA/RNA modification. In some embodiments, the transposase may be tethered or fused to a peptide or protein domain that covalently or non-covalently binds to a structural element of the binding domain that recognizes the DNA/RNA modification. In some embodiments, the binding domain, for example an antibody, is genetically fused to a Spy-tag peptide, whereas transposase is genetically fused to SpyCatcher protein. Spy-tag and Spy-Catcher will spontaneously form a covalent bond and thus target transposase to the modification site. In some embodiments, transposase is genetically fused to protein A, G, or L. In some embodiments, transposase is genetically fused to protein A. In some embodiments, transposase is genetically fused to protein G. In some embodiments, transposase is genetically fused to protein L. Protein A, G, or L bind to specific regions of IgG antibodies and direct transposase activity to DNA or RNA modification-bound antibodies.

In some embodiments, transposase may bind to ME-tagged adapters that are covalently conjugated to the binding domain. The adapter may be present as a ME-tagged single strand and hybridization of the ME complement triggers loading of the transposase in situ. The binding domain may display two or more ME-adapter molecules to enable loading of the transposase with two adapters, which is necessary for tagmentation. In some embodiments, the ME-adapter molecules have the same sequence. In some embodiments, the ME-adapter molecules have different sequences. In some embodiments, the ME-adapter comprises a barcode specific to the DNA or RNA modification.

The methods described herein may be used to diagnose a disease, disorder, or condition. For example, in some embodiments, the methods may be used to diagnose cancer in a subject in need thereof. In some embodiments, the kits may be used to monitor a disease, disorder, or condition over time, such as in response to one or more treatments. For example, the kits may be used to monitor epigenetic and/or epitranscriptomic changes over time in a subject undergoing treatment for cancer (i.e., chemotherapy, radiation, etc.) In some embodiments, the methods may be used to analyze a cell or tissue from a subject in need thereof. For example, the methods may be used to detect non-canonical features in a cell or tissue isolated from a blood sample, a biopsy sample, an autopsy sample, etc.

In some embodiments, the methods may be used to detect and/or monitor epigenetic changes in cells used commercially for production of one or more products, such as cells used for industrial fermentation. In some embodiments, the methods may be used to detect and/or monitor epigenetic changes in a plant cell or tissue.

Kits for Analyzing Nucleic Acids

The compositions described herein can be provided in a kit (e.g., as a component of a kit). For example, the kit may comprise the composition, or one or more components thereof, and informational material. In some embodiments, the kit comprises two or more compositions described herein. The informational material can be, for example, explanatory material, instructional material, sales material, or other material regarding the methods described herein and/or the use of the composition. The informational material of the kit is not limited in form. In some embodiments, the informational material may include information regarding the production of the composition, molecular weight, concentration, expiration date, batch or production site information, and the like. In some embodiments, the informational material may comprise a list of disorders and/or conditions that may be diagnosed or evaluated using the kit.

In some embodiments, the composition may be provided in a suitable manner (e.g., in an easy-to-use tube, at a suitable concentration, etc.) for use in the methods described herein. In some embodiments, the kit may require some preparation or manipulation of the composition before use. In some embodiments, the composition is provided in a liquid, dried, or lyophilized form. In some embodiments, the composition is provided in an aqueous solution. In some embodiments, the composition is provided in a sterile, nuclease-free solution. In some embodiments, the composition is substantially free from any nucleic acids besides those that may comprise the molecule itself.

In some embodiments, the kit may comprise one or more syringes, tubes, ampoules, foil packages, or blister packs. The container of the kit can be airtight, waterproof (i.e., to prevent changes in moisture or evaporation), and/or comprise light shielding.

In some embodiments, the kit may be used to perform one or more of the methods described herein, such a method for analyzing a population of target nucleic acids. In some embodiments, the kit may be used to diagnose a disease, disorder, or condition. For example, in some embodiments, the kit may be used to diagnose cancer. In some embodiments, the kit may be used to monitor a disease, disorder, or condition over time, such as in response to one or more treatments. For example, the kit may be used to monitor epigenetic and/or epitranscriptomic changes over time in a subject undergoing treatment for cancer.

EXAMPLES

The following non-limiting examples further illustrate embodiments of the compositions and methods of the instant disclosure.

Example 1: Binding Domain Selection

Binding domains specific to pseudouridine, inosine, m5C and m6A are selected based on their association rates (on-rate) and dissociation rates (off-rate), as measured by Bio-Layer Interferometry (BLI). Initially, a screen of commercial antibodies is performed. The goal is to identify antibodies with minimal off-rates and high specificity.

A BLI instrument (Gator Prime) is equipped with protein G probes (Gator Bio, cat #160006). Protein G probes have the capacity to bind 0.02-2000 µg/mL of IgG antibodies of most isoforms. IgG antibodies are immobilized on a protein G probe (5 µg/µL antibody in phosphate buffered saline (PBS)) at a density corresponding to 1 nm shift of the BLI signal. Real-time on-rates of antigens are obtained by immersing the BLI probes in 1 to 250 nM solutions of RNA targets exhibiting one or more modifications. Off-rates are generated by moving the probes into PBS buffer without antigen. The same procedure is repeated with unmodified RNA strands. Depending on the molecular weight of the tested RNA analyte it may be necessary to amplify the signal by conjugating a high molecular weight reporter molecule to the RNA, for example by using a biotin-labeled RNA bound to streptavidin. The antibodies with the lowest off-rates and highest off-rate selectivity for the specific target (off-rate$_{specific}$/off-rate$_{unspecific}$) are selected for further characterization.

Example 2: Generation of Beads with Covalently Linked Antibodies and DNA Adapter Molecules This example outlines the preparation of a bead surface with covalently tethered antibodies and DNA adapters (FIG. 1A). The antibodies are site-specifically linked to preserve their activity and the density of antibodies and DNA adapters is independently tunable. A 10-fold excess of adapter over antibody provides efficient barcoding yield while minimizing side products.

Carboxylated, magnetic beads (Thermo Fisher, Dynabeads® M-270 Carboxylic Acid) are activated for amine coupling using standard 1-ethyl-3-(-3-dimethylaminopropyl) carbodiimide hydrochloride (EDC) chemistry. The EDC activated surface is functionalized with a ternary mixture of a passivating molecules (COOH-PEG4-Amine, Broadpharm cat #BP-20423), antibody reactive linkers (DBCO-PEG10-amine, Broadpharm cat #BP-24181) and DNA reactive linkers (mTET-PEG3-amine, Broadpharm cat #BP-26276). Antibodies are activated for DBCO coupling using site-click chemistry (Thermo Fisher, cat #S20026). Site-click chemistry introduces an azido group to the glycosylation sites of the Fc region of IgG antibodies. Amino-modified DNA adapters are functionalized with TCO-PEG4-NHS Ester (Broadpharm, cat #BP-22418).

To generate surfaces with 3'immobilized ligation barcodes, adapters of the following general architecture are used (SEQ ID NO: 1): /5Phos/AATTAGTNNNAGATCG-GAAGAGCACACGTCT (SEQ ID NO: 42)/iSp18/ATATATUATATATA(SEQ ID NO: 43)/3AmMO/). The 5' end is phosphorylated to enable enzymatic ligation, followed by a 7b barcode (underlined) that indicates the RNA modification, a unique molecular identifier of at least 3 bases (NNN, wherein N is any nucleotide), the Illumina adapter (bold), an 18-atom hexa-ethyleneglycol spacer (iSp18), a single uracil surrounded by filler AT repeats for release from the surface by USER enzyme (NEB) cleavage, and a 3' amino moiety (3AmMO).

Surfaces with 5' immobilized primer extension barcodes are prepared using the general architecture of SEQ ID NO: 2 (/5AmMC6/ATATATUATATATA (SEQ ID NO: 44)/iSp18/AGACGTGTGCTCTTCCGATCTNNNCACTGAT-CACTCAGT (SEQ ID NO: 45)), where 5AmMC6 is a 5'-amine moiety and the CACTCAGT sequence is a spacer for barcoding by primer extension.

The final functionalization of the bead is conducted stepwise. First, the azido-activated antibodies are immobilized at the DBCO sites, followed by filling the mTet sites with TCO-adapters.

Example 3: Preparation of Beads Displaying Adapter-Loaded Protein G and Antibodies This example describes an alternative to Example 2. Instead of immobilizing the DNA adapters directly to the bead surface, they are attached to protein G (FIG. 1B). Protein G also serves to anchor IgG antibodies via affinity binding.

The lysine residues of protein G on the surface of magnetic beads (Thermo Fisher) are labeled with S-HyNic linker (Vector Labs, cat #50-204-5741). Full length protein G isolated from *Streptococcus* is 63 kDa in size, whereby most commercial versions are engineered to be smaller (e.g., Abcam, Uniprot ID: P19909), while maintaining subnanomolar affinity for IgG antibodies. To protect the IgG binding site of protein G from functional damage, the HyNic reaction is conducted in the presence of a sacrificial IgG antibody that is eluted with 0.2M glycine pH 2 after labeling. The HyNic modification reacts rapidly with DNA adapters (e.g., SEQ ID NO: 1 or 2) whose amine group have been activated with S-4FB linker (Vector Labs, cat #50-204-5743).

Removal of the sacrificial antibody and loading of the desired RNA modification specific antibody completes the preparation of the bead.

Example 4: Preparation of a Planar Arrays of Antibodies

This example uses DNA microarray technology for the immobilization of antibodies on a planar surface via DNA hybridization probes (FIG. 1F and FIG. 4B). After patterning, the surface features 48 spots, with each spot presenting one RNA modification specific antibody, together with an RNA modification specific barcoded i7 adapter and a universal i5 Illumina adapter. In this example, the i7 adapter comprises a single uracil for cleavage with USER enzyme mix and the i5 adapter a single 8-oxoG for cleavage with FpG enzyme. The goal is to integrate the patterned surface into a flowcell to enable clonal amplification of the captured nucleic acid sequences followed by in situ sequencing. Selective cleavage of the forward or reverse strand are essential steps for strand linearization preceding read 1 and read 2, respectively. Mounting the flowcell on a Peltier element and connecting the flowcell to a pump driven fluidics system allows for controlling the temperature and automating liquid exchanges. These features will be utilized to build a fully automated library preparation workflow, as outlined in Example 6.

Microscope slides are patterned by ink jet printing of synthetic DNA probes, and the slides are incorporated into flowcells using common bonding procedures. The microscope slides feature 48 spots and each spot contains a mixture of three different oligonucleotides: a capture probe that is complementary to a DNA address attached to an antibody, and versions of the Illumina i5 adapter and i7 adapters. The i7 adapter exhibits an 8b spacer region at the 3' end to enable barcoding by primer extension according to FIG. 2D. The density of the DNA probes is experimentally optimized to facilitate barcoding. The RNA modification-specific antibodies are site-specifically labeled with an DNA address using site-click chemistry (Thermo Fisher). Antibodies are loaded onto the array by hybridization to the capture probes via their DNA address.

Example 5: RNA Modification Specific Barcoding by Ligation Using a Bead Pool

This example describes the workflow for profiling RNA modification using a bead pool prepared according to Example 2. Each bead type displays an antibody targeting one type of RNA modification and a matching DNA adapter whose barcode is transferred to the target RNA by ligation (FIG. 5). The identity of the barcode is determined by next-gen sequencing, which reveals the nature of the RNA modification.

Four different bead types are prepared: Bead type 1 displays a m6A antibody and a DNA adapter for barcoding by ligation (SEQ ID NO. 1). Three more bead types are generated with antibodies for m5C, pseudouridine, and inosine and DNA adapters with different barcodes (SEQ ID NOs 3-5). The beads are pooled and incubated with 100 ng RNA sample that has been chemically fragmented to an average size of 100b and dephosphorylated. After washing away unmodified RNA, the 3' ends of the modified RNA are ligated to the surface-bound adapters by the action of T4 RNA ligase 1. The DNA adapters are primed and first and second strand synthesis are performed in a single reaction containing dNTPs, DTT, a template switching oligonucleotide (AGACGTGTGCTCTTCCGrGrGrG, wherein r represents a ribonucleotide; SEQ ID NO. 6), SuperScript IV reverse transcriptase and an appropriate enzyme buffer. The resulting cDNA library is PCR amplified to introduce the complete Illumina adapters and sequenced.

Example 6: RNA Modification Specific Barcoding by Primer Extension with Subsequent Amplification on Flowcell This example employs the patterned array fabricated according to Example 4 for profiling of RNA modifications. The advantage of the patterned array is that it can be integrated into a fluidics system to enable a fully automated library prep workflow. In this example, we detect all 8 RNA modifications present in mRNA (m5C, m6A, m7G, m1A, m3C, ac4C, inosine, pseudouridine). For each of the modifications, the array exhibits a minimum of three spots with cognate antibodies.

Figure 7:
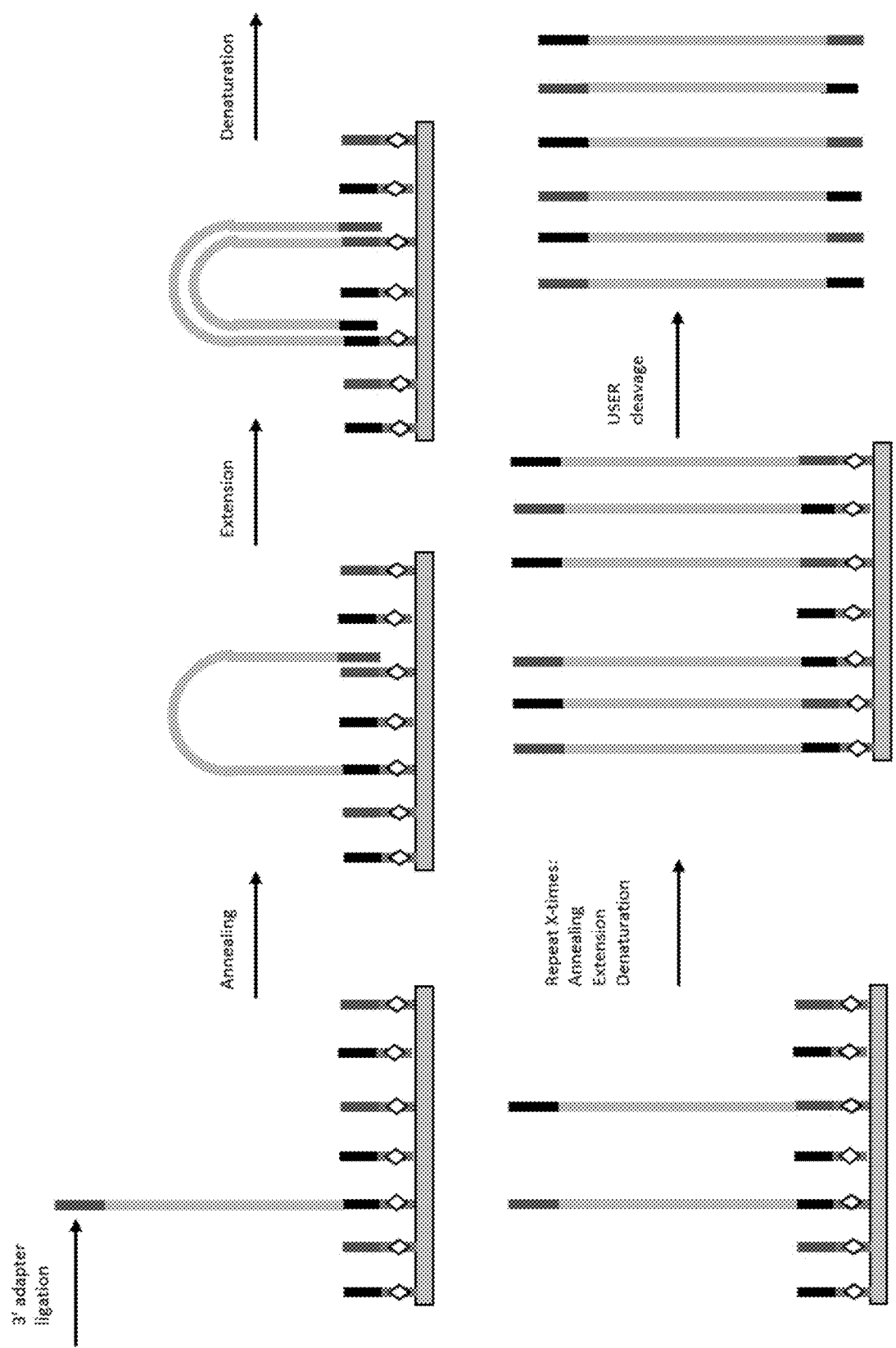
FIG. 7 shows a schematic of surface-based cDNA amplification, which can be used to form a cluster of identical copies of a target nucleic acid on a substrate. Analogous to solution PCR, the process employs temperature cycling to anneal, extend and melt DNA strands, resulting in exponential amplification. Surface-based amplification generates monoclonal clusters of identical copies of the initial cDNA strand. Each cluster is seeded by the recognition of a non-canonical feature by its binding domain, which is coupled to the substrate. The surface density of the binding domains is sparse to avoid merging of neighboring clusters. The initial cDNA strands are produced according to the workflow described in FIG. 6 using a surface that exhibits P5 and P7 primers. At low temperature, the cDNA strands anneal to the complementary surface primer. Extension of the primer by a DNA polymerase at medium temperature generates a copy of the parent strand. The resultant duplex is separated by heat and/or the addition of chaotropes setting the starting point for the next cycle. One or multiple clusters of identical copies may be formed. The methods of the present disclosure include in situ sequencing of the clusters of identical copies of target nucleic acids on the substrate.
Figure 8:
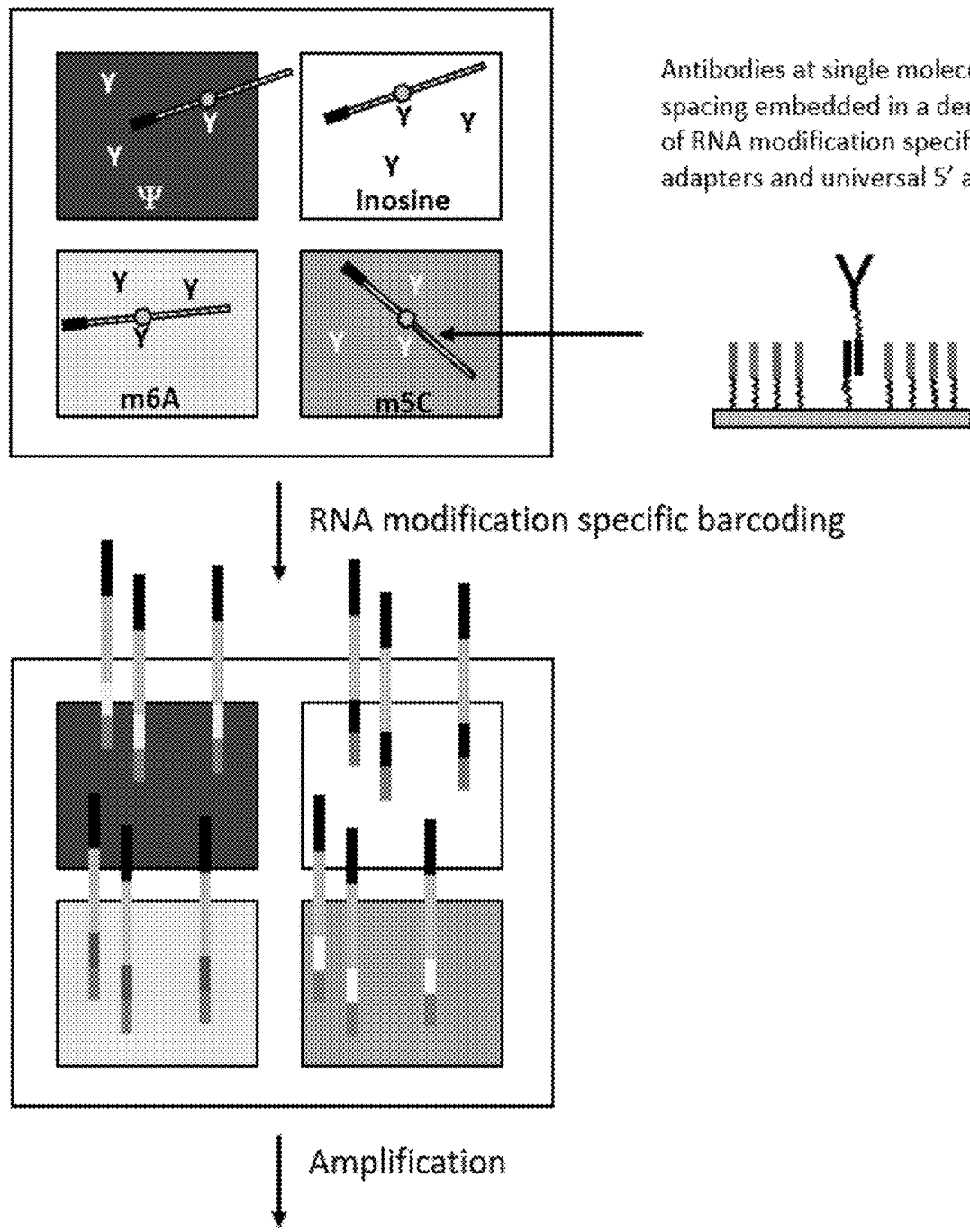
FIG. 8 illustrates a process for generating monoclonal cDNA clusters suitable for sequencing by synthesis, with each cluster representing a modified RNA strand. Fragmented RNA is partitioned and seeded on a flowcell based on the interaction of the RNA modification with the binding domains (See FIG. 6). The flowcell is segmented, whereby each segment targets a different modification. For example, to detect 10 modifications, the flowcell includes 10 regions modified with a suitable binding domain and adapter pair. The surface density of antibodies is low to prevent contamination with neighboring sequences during amplification. RNA strands are captured based on their modification, covalently linked to the surface and barcoded by primer extension, followed by clonal amplification (See FIG. 7). The clonally amplified barcoded cDNA is then linearized and directly sequenced using sequencing-by-synthesis (SBS) chemistry.
Figure 8:
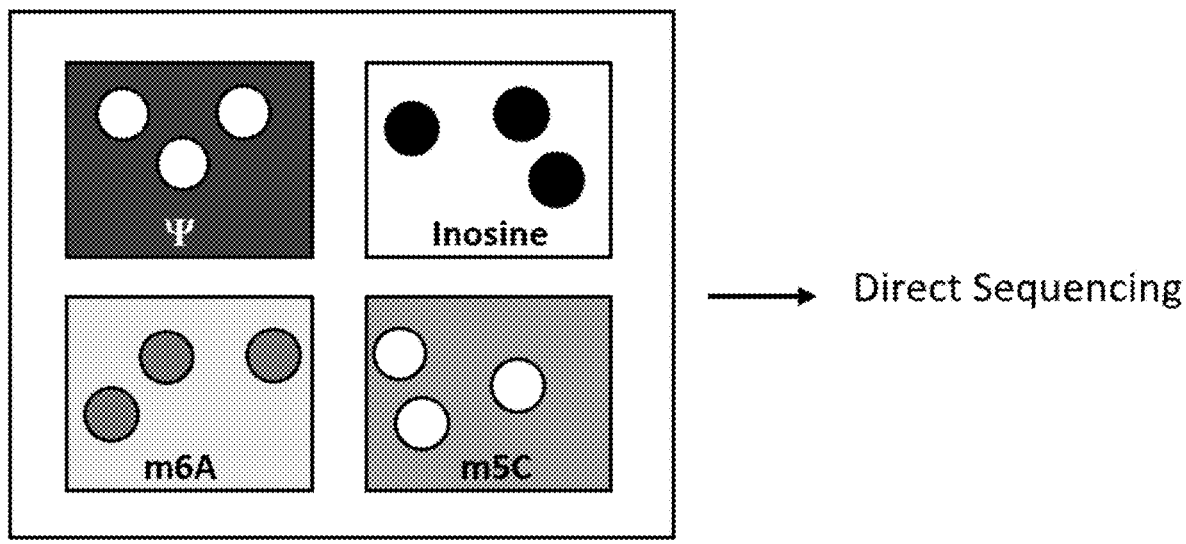

The RNA sample is chemically fragmented by treatment with magnesium chloride at 95C. The RNA fragments are dephosphorylated with shrimp alkaline phosphatase and T4 polynucleotide kinase. A 8b base spacer sequence is ligated onto the 3' end with T4 RNA ligase I. As the RNA solution is contacted with the antibody array, modified RNA strands are specifically captured by the antibodies, separating the RNA fragments into spots according to their modification. The 3'spacer of the RNA strands hybridizes to the Illumina i7 adapter, and the adapter is extended by Superscript IV reverse transcriptase generating a barcoded cDNA strand (FIG. 6). An i5 adapter complement is attached to the 3' end of the first strand by including a template-switching oligonucleotide in the reverse transcription reaction as described in Example 5. Treatment of the surface with 0.1 M sodium hydroxide hydrolyzes the RNA and strips off the antibodies. The DNA is amplified by temperature cycling in the presence of a thermostable DNA polymerase (e. g. Bst polymerase) (FIG. 7). The temperature protocol comprises three phases: (1) annealing of the DNA to the surface bound adapters at 37° C., (2) extension of the adapters at 60° C. and (3) denaturation at 60 to 95° C., depending on the presence of denaturants such as formamide, ethylene glycol, betaine or propane diol to lower the melting temperature. This process produces clonal copies of the barcoded cDNA. Conducting this process at low density of antibody generates spatially separated monoclonal clusters that are suitable for direct sequencing by synthesis (SBS) (FIG. 8).

Example 7: Barcoding of m6A-Modified RNA Using Immobilized Transposases

This example uses antibody-mediated pull down of RNA modifications followed by enzymatic transposition to introduce barcodes to a modified RNA fragment in a rapid one-step reaction (FIG. 9 and FIG. 22A).

Tagmentation is a well-established process for NGS library preparation and refers to the Mg-ion dependent "cut & ligate" activity of Tn5 transposases, enzymes that cleave double-stranded nucleic acids and ligate DNA adapters onto the ends of each cleaved target in a single step. Transposases bind selectively to a short, 19 bp "mosaic end (ME)" duplex, which can be appended to any DNA adapter for use in tagmentation.

In this example, the surface of beads is loaded with transposomes (FIG. 1G). A transposome consists of a transposase dimer loaded with two Mosaic End (ME) containing adapter molecules. As used herein, ME and ME' (Mosaic end and mosaic end prime, respectively) are used to describe the double-stranded sequence 5'-CTG TCT CTT ATA CAC ATC T-3' (SEQ ID NO: 7), which Tn5 transposase spontaneously binds to. This sequence can be fused to any DNA sequence, for example to a universal primer site, or to an Illumina adapter fragment (See, e.g., FIG. 13).

Streptavidin beads were loaded with an equimolar ratio of Illumina i5 and i7 ME adapters at 5, 10, 20 or 40% of the total loading capacity, alongside with m6A antibody (FIG. 1G) The sequence of the i7 ME adapter was: 5'Phos-CTGTCTCTTATACACATCT (SEQ ID NO: 16) hybridized to 5'biotin-CAAGCAGAAGACGGCATACGAGAT-NNNNNNNN-GTCTCGTGGGCTCG-GAGATGTGTATAAGAGACAG (SEQ ID NO: 41). The sequence of the i5 ME adapter was: 5'Phos-CTGTCTCT-TATACACATCT (SEQ ID NO: 16) hybridized to 5'biotin-AATGATACGGCGACCACCGAGATCTACAC-NNNNNNNN-TCGTCGGCAGCGTCAGATGTGTATAAGAGACAG (SEQ ID NO: 8). The ME sequence is shown in bold, whereas NNNNNNNN denotes the barcode.

After bead preparation, a mixture of unmodified and m6A-modified IVT RNA was reverse transcribed using Superscript IV reverse transcriptase. Subsequently, the reverse transcribed RNA sample was immunoprecipitated using the streptavidin beads with co-immobilized ME adapters and m6A antibody. After washing the beads, Tn5 transposase (Diagenode, cat. no. C01070010-10) was loaded to the ME adapters in binding buffer (50 mM HEPES pH 7.5, 300 mM NaCl, 0.1 mM EDTA, 0.05% Tween® (polysorbate)-20). The addition of $Mg^{2+}$-containing tagmentation buffer (10 mM Tris-HCl pH 8.5, 5 mM MgCl2, 10% DMF) triggered insertion of the adapters into the captured DNA-RNA duplex. In this format, the tagmentation product was securely captured on the beads, which served as an input for gap fill PCR (0.5 uM forward primer, 0.5 uM reverse primer, NEBNext Ultra II Q5 (cat. no. M0544X, New England Biolabs) for 17-19 cycles (5 min at 72° C., 2 min at 98° C., then n cycles of 10 sec at 98° C.-75 sec at 65° C., and final extension for 5 min at 65° C.). The DNA library was sequenced, followed by deconvoluting the barcodes and sequence alignment.

The coverage plot (FIG. 22B) shows significant enrichment of the m6A containing fragments, attesting to the selective tagmentation of m6A modified RNA. Loading the bead at 5 or 10% of the total binding capacity with ME adapters produced slightly better signal-to-noise of enrichment than higher ME densities and was associated with higher library preparation yields (not shown). This experiment demonstrates the feasibility of detecting m6A-modified RNA using beads with co-immobilized ME adapters and m6A antibody. Multiple RNA modifications can be detected by mixing several bead types, each exhibiting a single type of antibody and ME adapters with a barcode that encodes the antibody.

Example 8: Read-Phasing of Long RNA with Multiple m6A Modifications

Figure 10:
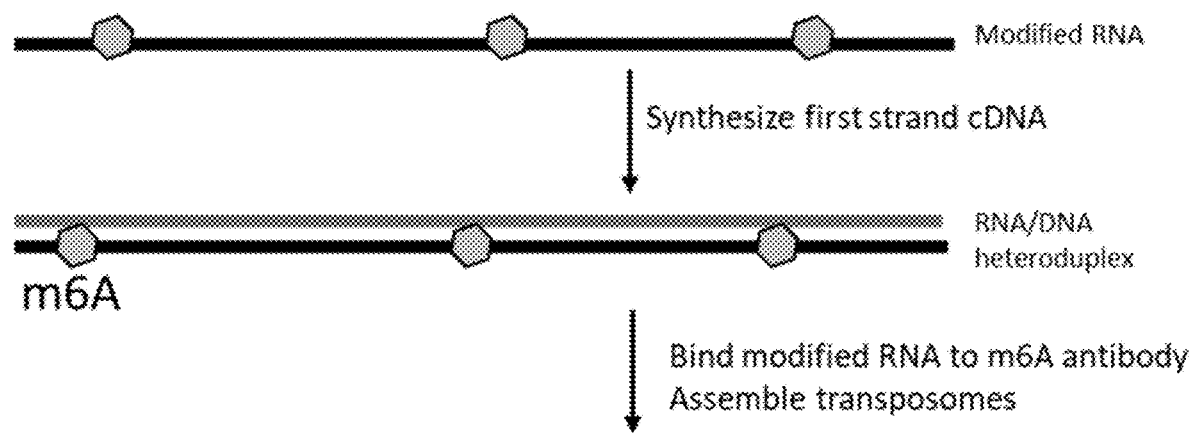
FIG. 10 illustrates a process for marking the position of multiple m6A modifications within the same RNA strand by base editing with ADAR enzyme. After position marking, individual RNA strands are barcoded by transposase as shown in FIG. 9. NGS (next-generation sequencing) reads that originate from the same parent RNA molecule share the same barcode. "A>I" refers to mutation of an adenine to an inosine, as catalyzed by ADAR enzyme.
Figure 10:
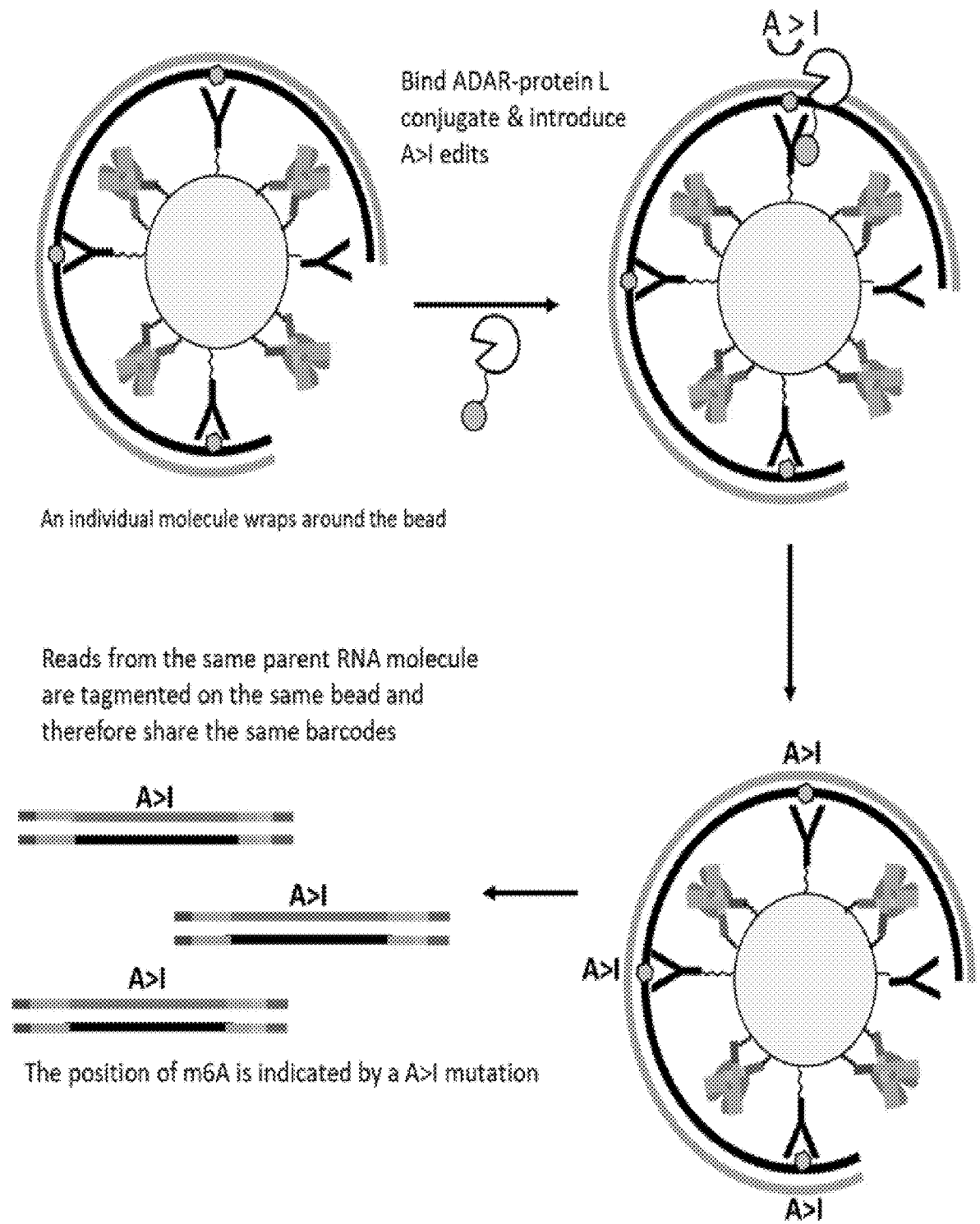

This example expands on Example 7 by introducing a base editing step to mark the position of multiple modifications of the same kind (FIG. 10).

Figure 11:
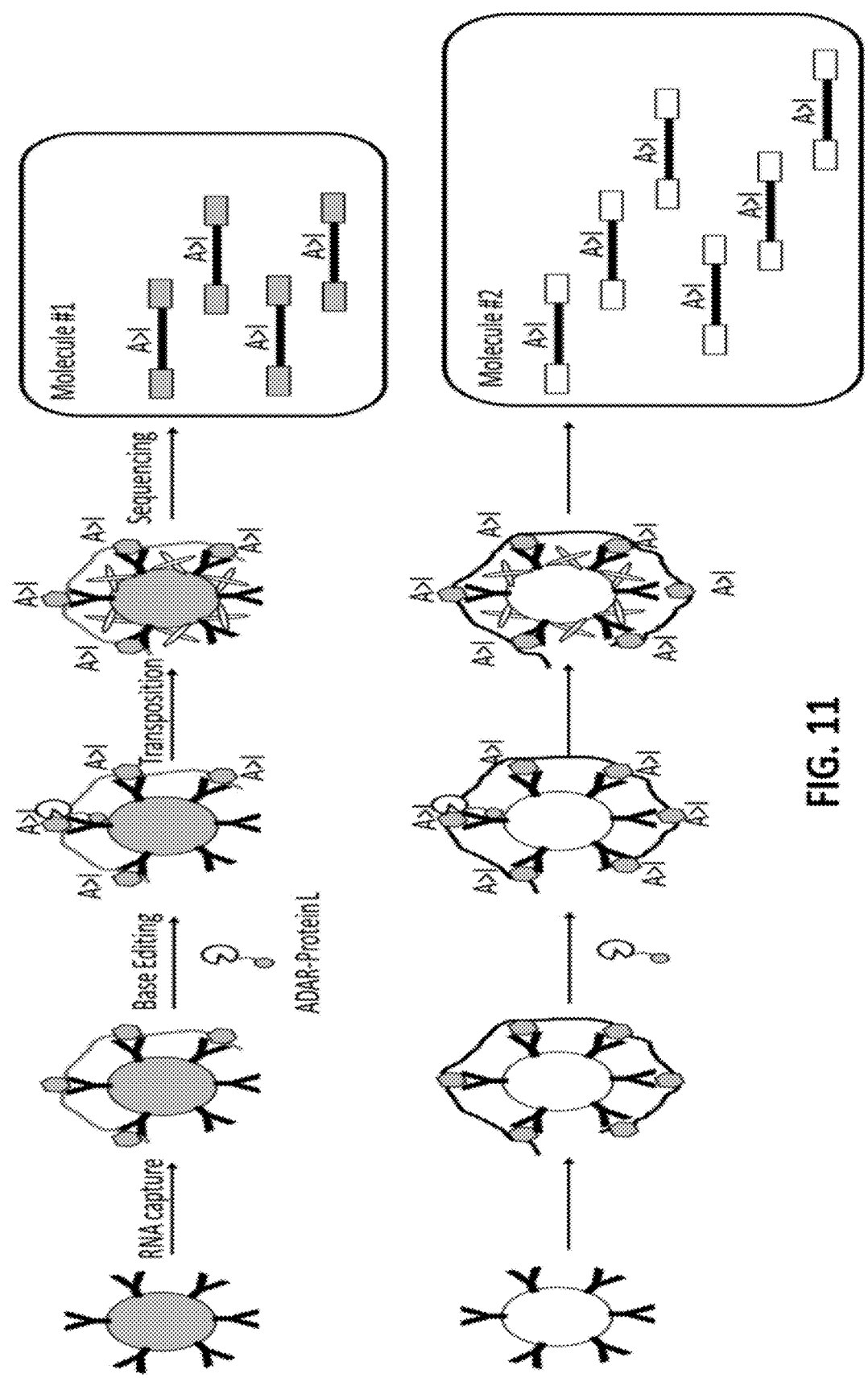
FIG. 11 illustrates the concept of long read phasing. Position marking and barcoding according to the process described in FIG. 10 allows for reconstructing long transcripts from short sequencing reads. To uniquely barcode each short nucleic acid fragment that originates from the same parent molecule, each bead exhibits a plurality of unique barcodes that indicates the RNA modification and the individual bead. The bead surface is small, capturing only a single full-sized parent molecule on average. Immobilized transposomes cut the parent molecule into short fragments, thereby inserting the bead-specific barcodes. Short reads are aligned to a reference genome and joined at junctions that exhibit the same barcode. "A>I" refers to mutation of an adenine to an inosine.
Figure 14A:
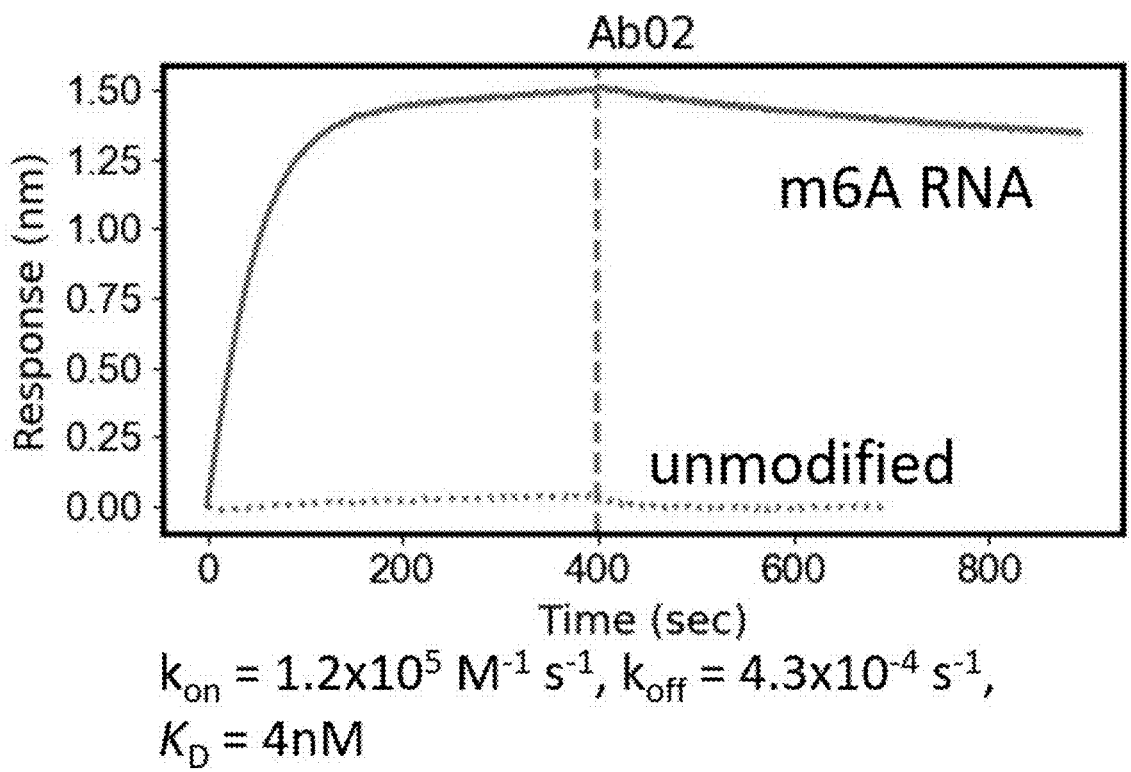
Figure 14B:
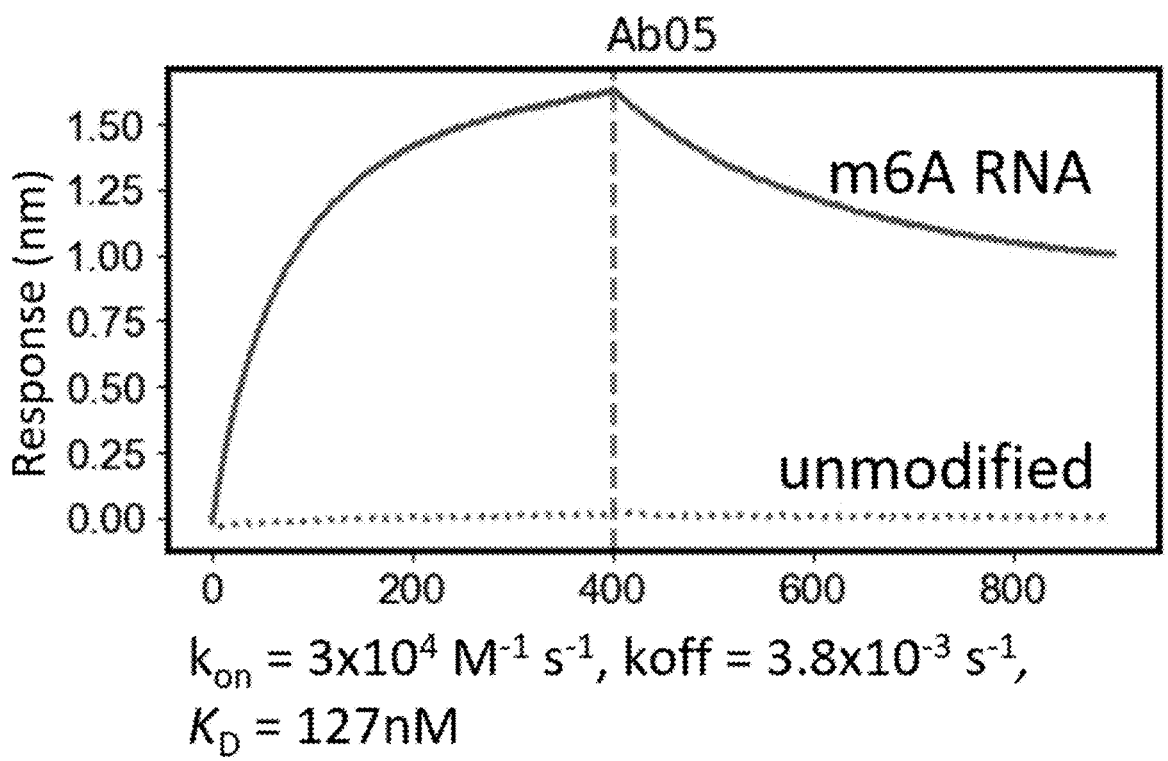
Figure 14C:
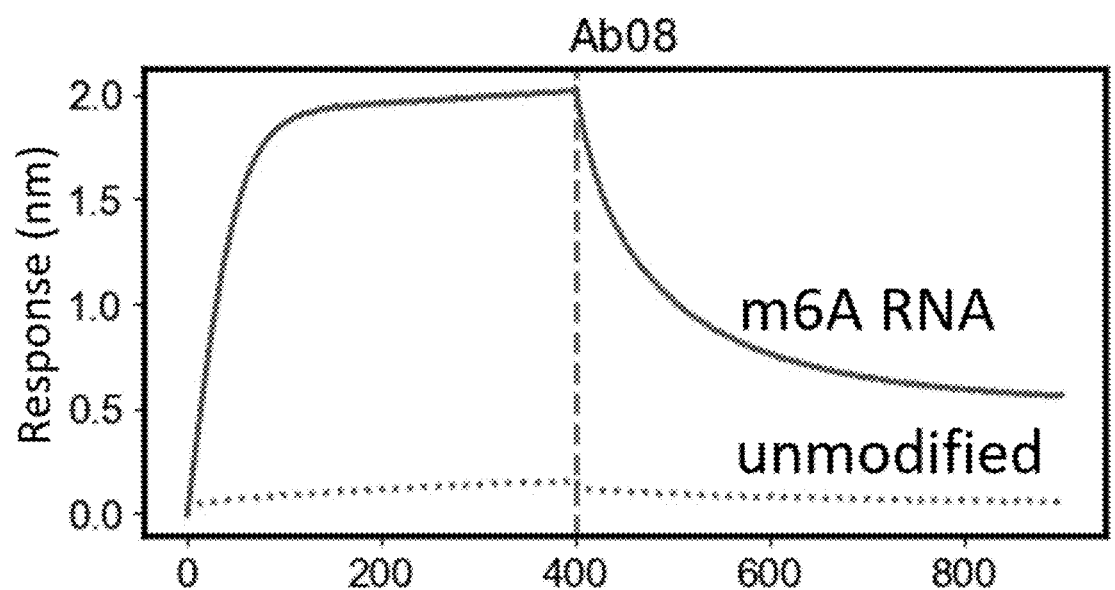
Figure 14D:
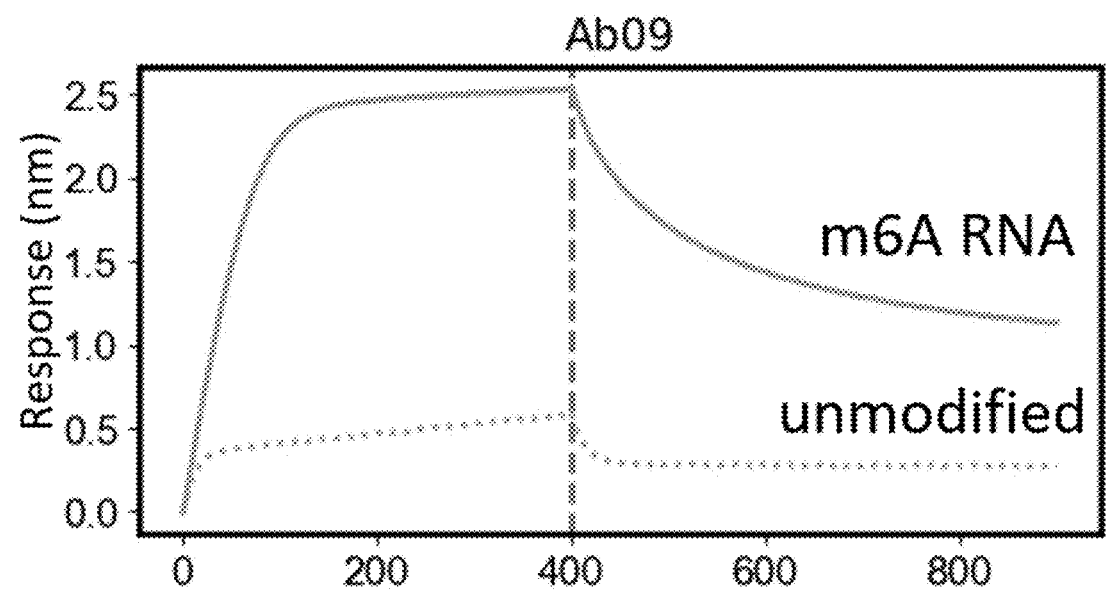
Figure 14E:
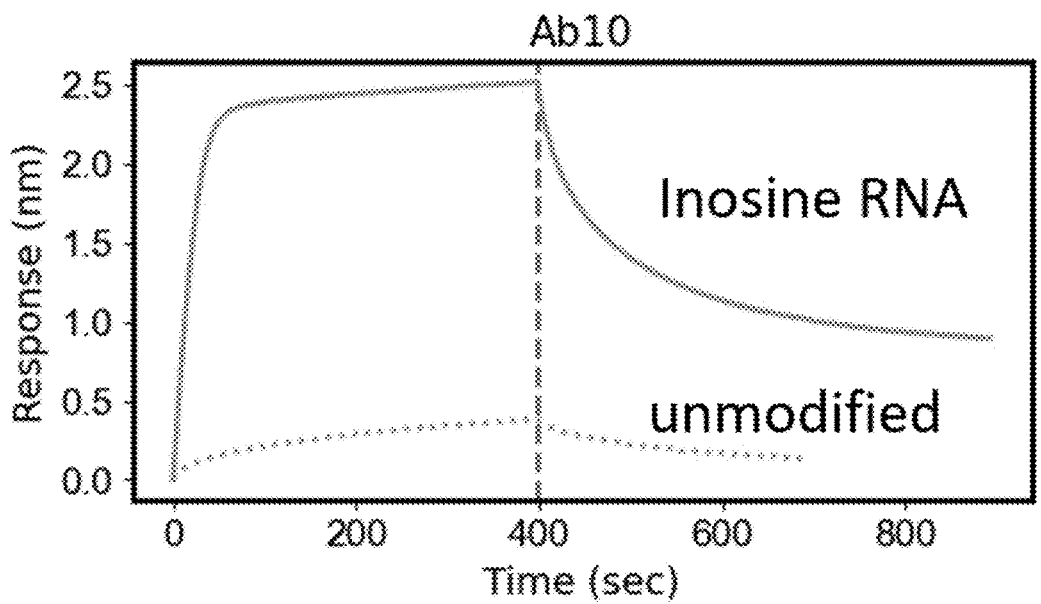
Figure 14F:
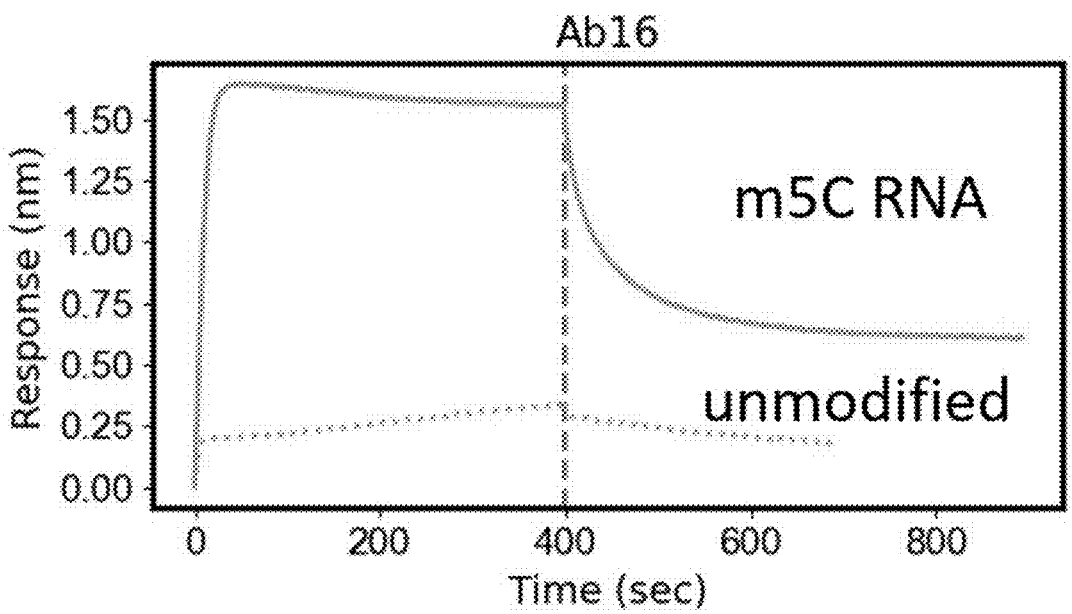
Figure 14G:
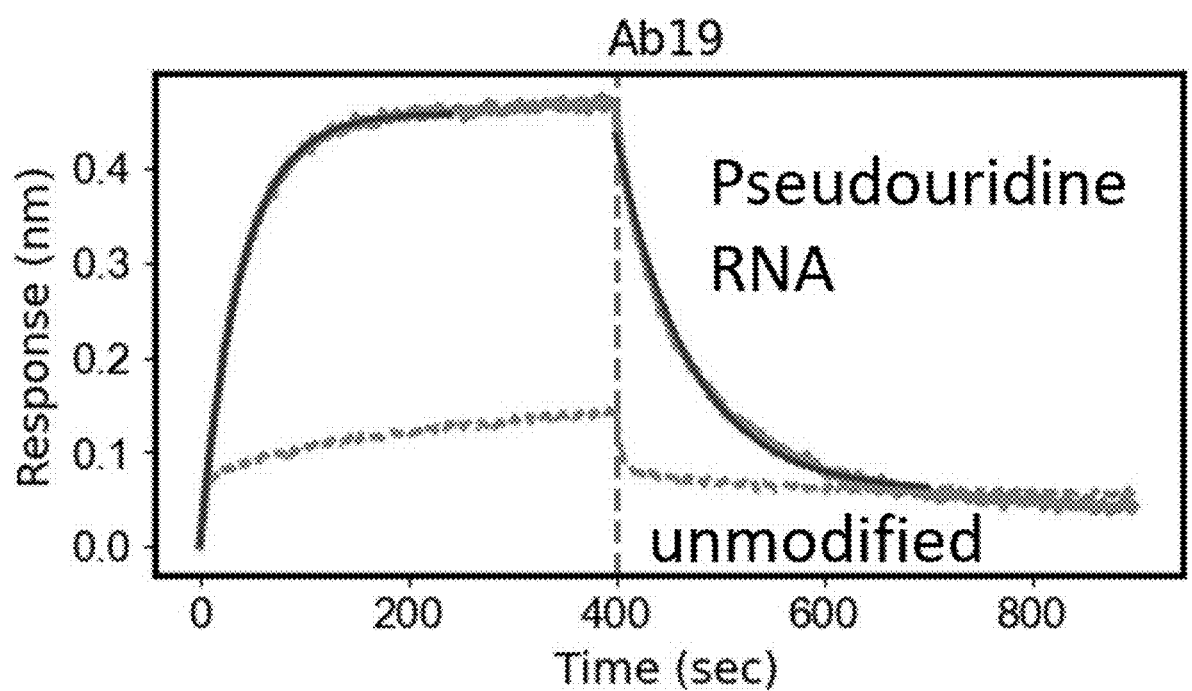

Full length RNA strands are reverse transcribed and captured by beads displaying m6A antibodies and biotin-labeled ME adapters. After washing, ADAR-Protein L conjugates are introduced. Protein L binds specifically and with high affinity to the light chain of IgG antibodies. ADAR enzyme edits double-stranded RNA and the DNA strand in DNA/RNA heteroduplex with a A>I (inosine) mutation. The linkage architecture of the ADAR-protein L conjugate is such that it confines ADAR activity to the direct proximity of the m6A modification. The Adenine to Inosine (A-to-I) mutation introduced by ADAR marks the position of m6A. After base editing, the transposomes are assembled by allowing Tn5 transposase to bind the surface-tethered ME adapters. Transposition tags sequencing identifies reads stemming from the same molecule with the same barcode, which allows for reconstructing long transcripts from short sequencing reads (FIG. 11).

Example 9: Binding Domain Selection

Binding domains specific to pseudouridine, inosine, m5C and m6A were selected based on their association rates (on-rate) and dissociation rates (off-rate), as measured by Bio-Layer Interferometry (BLI). Initially, a screen of commercial antibodies was performed. The goal was measuring the on- and off-rates of antibodies and to correlate their properties with performance in barcoding assays.

A BLI instrument (Gator Prime) was equipped with streptavidin probes (cat. no. 160002, Gator Bio). 5'biotinylated RNA oligos with a central m5C, inosine, m6A or pseudouridine base were immobilized at a sparse surface coverage to ensure the formation of 1:1 antibody:RNA complexes. An oligo without modified bases served as a negative control. Real-time on-rates of antigens were obtained by immersing the BLI probes in 1 to 250 nM solutions of antibodies. Off-rates were generated by moving the probes into PBS buffer without antibodies. The same procedure was repeated with unmodified RNA strands.

FIGS. 14A-14G show the on- and off-rates for several commercial antibodies directed against m6A, m5C, inosine and pseudouridine (Ab02 (m6A)=MA5-33030, Thermo Fisher; Ab05 (m6A)=345E11, Synaptic Systems; Ab08 (m6A)=Rb212B11, Synaptic Systems; Ab09 (m6A)=C15200082-50, Diagenode; Ab10 (inosine)=C15200251, Diagenode; Ab16 (m5C)=MA5-24694, Thermo Fisher; Ab19 (pseudouridine)=D347-3, MBL). On-rates for specific antigen binding range from $10^4$ to $10^5$ $M^{-1}$ $s^{-1}$, whereas off-rates are more variable between $10^{-4}$ and $10^{-2}$ $s^{-1}$. The corresponding dissociation constants $K_D$ are between 3.5 and 150 nM. Generally, negligible binding is observed for the negative oligo controls, confirming target specificity. Based on ELISA data, most antibodies bind unmodified RNA weakly with a $K_D$ that is 100-500-fold larger than that for the specific target.

All antibodies indicated in FIGS. 14A-14G are useful in antibody-mediated barcoding assays (see example 6), demonstrating the compatibility of the method with a range of antibody properties. Antibodies with nanomolar affinity are readily accessible by hybridoma technology, attesting to the versatility of the method. Low RNA target capture efficiency is observed for $K_D$ values above 150 nM, which is where we set the assay requirement.

Example 10: Preparation of Beads for Immunoprecipitation and Barcoding of Modified Nucleic Acids In this example, two types of IgG antibodies were loaded on magnetic protein G beads via affinity binding. One antibody specifically binds one type of nucleic acid modification. The other antibody has no nucleic acid binding activity but is labeled with DNA adapters (a reporter antibody) (FIG. 1E). Part of the adapter design is a modification barcode (MBC). In the examples below, nucleic acid modifications were detected by transferring the MBC to the target nucleic acid in an antibody-mediated reaction. The purpose of this bead architecture, and particularly of the reporter antibody, is displaying the DNA adapters in a spatial orientation that significantly facilitates transferring the barcode from the adapter to the target nucleic acid without needing to label the antibody directly (c.f. FIG. 1E). Beads were loaded such that each bead is "monoclonal", containing a single species of modification-specific antibody, and a single type of REPA bearing a unique MBC (FIG. 15C).

A reporter antibody was prepared by randomly labeling its lysine residues using a mTET-PEG5-NHS ester (cat. no. BP-22945, Broadpharm). Any IgG antibody without nucleic acid binding activity may be used, for example, a monoclonal anti-bovine serum albumin antibody (cat. no. MA1-82941, Thermo Fisher). The IgG subclass needs to be compatible with binding by protein G. Coupling of the mTET-NHS ester to the reporter antibody was performed in phosphate buffered saline (PBS) containing up to 1 mg of antibody and 30 mol equivalents of linker. The reaction was allowed to proceed at 25° C. for 12 hours and the resulting antibody-linker conjugates were purified by 7 kDA MWCO Zeba desalting columns (cat. no. 89882, Thermo Fisher) to remove excess linker. In a separate reaction, an adapter DNA oligo (for example, /5AmMC6/T/iSp18//iSp18//iSp18//iSp18/AGACGTGTGCTCTTCC-GATCTNNNCAGCTTTC ACTCAGT with 5AmMC6 being a 5' amino modification and iSp18 being a PEG spacer (SEQ ID NO: 23), Integrated DNA Technologies) was activated with a trans-cyclooctene (TCO)-PEG4-NHS ester (cat. no. BP-22418, Broadpharm) at 25° C. for 12 hours in PBS buffer. The final product was then purified via acetone precipitation. The iSp18 linker units provide both spatial flexibility and reach and are necessary for barcoding in the described format. The final adapter-labeled reporter antibody was prepared by incubating the mTET antibody with stoichiometric equivalents of TCO. Since the antibody is hyper-labeled with mTET, the final labeling ratio was determined by the molar equivalents of TCO-conjugated adapter, which reacts with quantitative yield. Analyzing the size of the resulting antibody-oligo conjugates by denaturing SDS gel electrophoresis shows how the labeling stoichiometry titrates proportionally with TCO-oligo excess (FIG. 15A). A 3.5× molar excess of TCO-oligo is ideal as it eliminates the occurrence of unmodified antibody, while preventing over-labeling that may interfere with protein G binding. This procedure generated reporter antibodies that displayed 2-3 adapters on average, regardless of IgG subtype and adapter sequence.

For a standard barcoding reaction, 2 uL of protein G Dynabeads (cat. no. 10004D, Thermo Fisher) were loaded with a total of 0.5 ug of a mixture containing the mod-specific and reporter antibodies. Antibodies were loaded in PBST for 30 min at room temperature and excess antibody is removed by three washes with PBST. Typically, a 50:50 mixture of nucleic acid specific and reporter antibody was used. Altering the ratio does not affect barcoding specificity significantly in the range from 20% to 80% of reporter antibody, but it changes the yield of barcoding. The barcoding yield, which is the ratio of the barcoded RNA molecules divided by the captured RNA molecules, increases as the surface density of reporter antibody increases, as measured by capture, barcoding, elution, and denaturing gel electrophoresis of dye-labeled modified RNA (FIG. 15B).

Example 11: Generation of In Vitro Transcribed RNA with Modified Bases as Truth Model This example describes the preparation of RNA targets with known modification content. The resulting modified RNA targets were used as truth sets in the barcoding experiments described below.

In vitro transcribed (IVT) RNA was synthesized using the HiScribe™ T7 High Yield RNA Synthesis Kit (cat. no. E2040S, New England Biolabs) following the vendor manual. Template DNA amplicons for the IVT reactions were generated by amplifying regions of genomic phage or bacterial DNA using primers with a T7 promotor sequence and purifying the amplicons using a PureLink™ PCR Purification Kit (cat. no. K310001, Thermo Fisher). The following genomes were used for T7-tagged amplicon generation (New England Biolabs): (DX174 Virion DNA (cat. no. N3023S), M13mp18 Single-stranded DNA (cat. no. N4040S), Lambda DNA (cat. no. N3011S) and FLuc Control Plasmid (cat. no. E2040S). IVT reactions were performed using T7 promotor exhibiting PCR amplicons as an input and substituting 10-50% of the natural NTP with a modified NTP, such as methyladenosine-5'-triphosphate (m6ATP, cat. no. N-1013-5, Trilink), inosine-5'-triphosphate (ITP, cat. no. N-1020, TriLink), 5-methylcytidine-5'-triphosphate (m5CTP, cat. no. N-1014, TriLink) or pseudouridine-5'-triphosphate (YTP, cat. no. N-1019, TriLink). IVT reactions were treated with DNAse I (cat. no. M0303S, New England Biolabs) to remove DNA template and purified using Monarch® RNA Cleanup Columns (cat. no. T2047L, New England Biolabs).

Using this procedure, a model target pool was generated consisting of IVT RNA originating from different genomes where each genome displays a different modification. For example, PhiX RNA was unmodified, Flue RNA contained m6A, M13mp18 RNA contained m5C and Lambda RNA contained inosine.

The model RNA pool with known modifications was used in barcoding experiments and sequenced. The specificity of barcoding is determined by aligning the reads of the immunoprecipitated and barcoded sample, counting the number of RNA fragments that display the correct modification barcode (MBC), and normalizing the results to the input sample.

Example 12: Preparing RNA Samples for Downstream Modification Analysis by Attaching a Universal Spacer Sequence This example provides a protocol for attaching a spacer sequence to a pool of RNA molecules. During proximity encoding, the spacer binds to the spacer' complement of the bead-anchored adapter and is extended by a DNA polymerase (FIG. 2D) or reverse transcriptase (FIG. 2G).

RNA was fragmented by incubating in 1× T4 RNA ligase I buffer (New England Biolabs) at 90C for 8-25 min. This treatment resulted in a fragment peak size of 60-150 bases. Subsequently, the 3' ends of RNA were dephosphorylated by addition of T4 Polynucleotide Kinase (cat. no. T4PK-200, MCLab) in the presence of RNase inhibitor (cat. no. AM2694, Thermo Fisher) at 37C for 30 min. Ligating a spacer poised the RNA for barcoding by primer extension, either by DNA polymerases or reverse transcriptases. The spacer was attached in a reaction containing 0.3 units/uL T4 RNA ligase I, 10 uM spacer (/5Phos/NNACTGAGTG), 1×T4 RNA ligase I buffer, 1 mM ATP, 1 mM DTT, 15% PEG-8000, 0.2 units/uL RNase inhibitor at 20 C for 1 hour. The spacer ligated RNA was ready to be used in barcoding assays after purification with 1×RNAClean XP beads (cat. no. A63987, Beckman Coulter). FIG. 16 shows the fragment size obtained after fragmenting a mixture of 1.5 kb IVT RNA fragments, followed by ligating a spacer. The addition of the spacer increased the apparent fragment size from 104 nt to 109 nt.

Example 13: Multiplexed Detection of m6A, Inosine and m5C Using Encoding by Reverse Transcription, Template Switching and Protein G Bead This example describes an end-to-end library preparation workflow with an integrated barcoding step for the detection of RNA modifications. Barcoding is accomplished by bidirectional extension of the RNA target and the adapter using a reverse transcriptase (FIG. 17A).

To detect m5C, m6A and inosine in an RNA sample, a minimum of three different bead types are required and prepared according to example 10. The first bead type displayed an anti-m6A (cat. no. 345E11, Synaptic Systems) and a reporter antibody conjugated to an adapter containing MBC-3 (/5AmMC6/T/iSp18//iSp18//iSp18//iSp18/AGACGTGTGCTCTTCCGATCTNNNCAGCTTTC ACTCAGT) (SEQ ID NO: 25). A second bead type exhibited an anti-inosine (cat. no. C15200251, Diagenode) and a reporter antibody conjugated to an adapter containing MBC-4 (/5AmMC6/T/iSp18//iSp18//iSp18//iSp18/AGACGTGTGCTCTTCCGATCTNNNCCTATATC ACTCAGT) (SEQ ID NO: 26). A third bead type featured an anti-m5C (cat. no. MA5-24694, Thermo Fisher) and a reporter antibody with an adapter containing MBC-5 (/5AmMC6/T/iSp18//iSp18//iSp18//iSp18/AGACGTGTGCTCTTCCGATCTNNNGATCCCTC ACTCAGT) (SEQ ID NO: 27).

The adapters contained the spacer' sequence (bold letters at the 3' end), the MBC (underlined), a UMI (NNN) and the i7 Illumina adapter (sequence 5' of the UMI).

Per sample, equal volumes of each loaded bead type were combined. The first assay step was an immunoprecipitation (IP) of the spacer ligated RNA prepared according to example 4. The bead pool, 0.5 to 50 ng of RNA, and 10 units/uL of RNase inhibitor were incubated in 1×PBST. After incubation, the beads are washed with PBST buffer and resuspended in 1× Superscript IV reverse transcription buffer (cat. no. 18090050, Thermo Fisher). Washing removed non-specifically bound RNA and preserved the specific RNA modification-antibody complexes. In the next step, an MBC containing i7 and a universal i5 adapter were added to the target RNA. In this step, a reverse transcriptase elongated the 3' end of the RNA targets, thereby copying the MBC and i7 adapter, and simultaneously synthesized cDNA by extending the 3' end of the adapter. For template switching, a reverse transcriptase with terminal deoxynucleotidyl transferase (TdT) activity was required such as the M-MLV mutants Superscript II or IV (cat. no 18064014 or 18090200, Thermo Fisher), Maxima H Minus (cat. no. EP0751, Thermo Fisher) or Smartscribe reverse transcriptase (cat. no. 18064014, Takara Bio). The TdT activity appends a C-tail to the end of the DNA/RNA heteroduplex and enables binding and copying of the template switching oligo (TSO) that comprises the Illumina i5 adapter and ends in three G bases.

The IP beads were added to the reverse transcription reaction (1×SSIV buffer, 0.5 u/uL Superase-In, 5 u/uL SSIV reverse transcriptase, 1 mM dNTPs, 2 uM template switching oligo, "TSO") and incubated for 15 min at 23C, followed by 60 min at 50C. Several versions of the TSO performed well, for example CTACACGACGCTCTTCCGATCTrGrG+G (rG is a riboG, +G is LNA-G) (SEQ ID NO: 28), CTACACGACGCTCTTCCGATCTrGrGrG (SEQ ID NO: 29), or CTACACGACGCTCTTCCGATCTNNNNNrGrGrG (SEQ ID NO: 30). After completion of the reaction, the supernatant was amplified by PCR using standard Illumina index primers (0.5 uM forward primer, 0.5 uM reverse primer, NEBNext Ultra II Q5 (cat. no. M0544X, New England Biolabs) for 10-13 cycles (30 sec at 98° C., then n cycles of 10 sec at 98° C., 75 sec at 65° C., and 5 min at 65° C.).

The library was sequenced, and RNA modifications were identified and localized to specific loci via bioinformatic deconvolution of the MBCs appended to each RNA fragment. FIG. 17B shows the sequencing results obtained for the described barcoding method using 5 ng of pooled IVT as input and SuperScript IV reverse transcriptase, FIG. 17C shows the same using Maxima Minus reverse transcriptase for encoding. In this example, the IVT RNA pool consisted of 70% unmodified PhiX RNA, 10% m6A-modified FLuc-RNA, 10% inosine-modified Lambda RNA and 10% m5C-modified M13 RNA. The plots show that most of each MBC was associated with the correct genome, whereby the SuperScript IV data set exhibited a better signal-to-noise ratio.

Example 14: Multiplexed Detection of m6A, Inosine and m5C Using a DNA Polymerase for Encoding This example describes a different version of barcoding by primer extension and offers an alternative to library preparation by template switching. As for barcoding by reverse transcription, the workflow requires ligating a spacer sequence to the RNA pool upstream. After immunoprecipitation of spacer-extended RNA, a DNA polymerase (Klenow fragment exo-) was used to append the barcode to the target RNA by primer extension of the top strand (FIG. 19A).

To detect m5C, m6A and inosine in an RNA sample, three different bead types were prepared as described in example 10. However, in this example, the 3' ends of the adapter sequences were blocked for extension, for example by /3SpC3/ (c.f. nomenclature by Integrated DNA Technologies). Bead loading and IP followed the same protocol as described in example 13. After the IP wash, the beads exhibiting the captured RNA were resuspended in 1× Klenow buffer (50 mM Tris pH7.9, 2 mM MgCl2, 50 mM NaCl, 0.1% Tween®-20) and combined with an equal volume of barcoding mix (200 uM dNTP, 0.5 units/uL Klenow fragment exo- (cat. no. KPIM-200, MCLAB), 50 mM Tris pH7.9, 2 mM MgCl2, 50 mM NaCl, 0.1% Tween®-20). The Klenow reaction was allowed to proceed at room temperature for 5 min. The barcoded RNA was eluted from the beads by incubation in water with 5 mM DTT and 1 mM EDTA for 5 min at 37C. The eluted RNA was added to a ligation reaction containing the i5 adapter (2 uM i5 RNA adapter (/5SpC3/rCrUrArCrArCrGrArCrGrCrUrCrUrUrCrCrGrArUrCrU) (SEQ ID NO: 31), 1XT4 RNA ligase buffer, 1 mM ATP, 10% PEG-8000, 0.5 u/uL Superase-in, 1 u/uL T4 Polynucleotide kinase, 1 u/uL T4 RNA ligase 1) and incubated for 1 hour at room temperature. After cleanup with 3× Ampure beads, the adapter ligated RNA was reverse transcribed (1 uM cDNA primer (AGACGTGTGCTCTTCCG) (SEQ ID NO: 32), 0.5 mM dNTP, 1×SSIV buffer, 5 mM DTT, 2 u/uL RNAseOUT, 10 u/uL SuperScript IV reverse transcriptase) for 10 min at 55 C. Optionally, the cDNA may be cleaned up by NaOH treatment, neutralization and 3× Ampure beads at this point, or used directly as input for index PCR (cDNA, 0.5 uM forward primer, 0.5 uM reverse primer, NEBNext Ultra II Q5) for 10-13 cycles (30 sec at 98° C., then n cycles of 10 sec at 98° C., 75 sec at 65° C., and 5 min at 65° C.).

Using this workflow, we screened the antibodies that were characterized by BLI (example 9 and FIGS. 14A-14G) in single-plex experiments, i.e. one bead type loaded with a modification specific antibody and a reporter antibody is exposed to an IVT RNA pool comprising m6A modified Flue RNA, inosine modified Lambda RNA and m5C labeled M13 RNA, and in some cases, unmodified PhiX RNA. For each antibody, at least 80% of the MBC was associated with the correct genome, based on sequencing analysis (FIGS. 18A-18G). Combining three bead types in a 3-plex reaction (FIG. 19A) produced a similar outcome, with a slightly elevated background compared to the corresponding single-plex reactions (FIG. 19B).

Example 15: Simultaneous Detection of m6A and m5C Using Splint Ligation for Encoding This example introduces the modification specific barcode by enzymatic ligation rather than by primer extension. Specifically, the example uses DNA splint ligation catalyzed by T4 DNA ligase (FIG. 20A).

In this example, the adapters were conjugated to the reporter antibody via 3'-amine groups and exhibit a 5'-phosphate for ligation (c.f. example 10). In addition, uracil bases were introduced to allow for cleavage of the adapter strand as needed. (MBC3: /5Phos/CAGCTTTNNNAGATCG-GAAGAGCACACGTCT/ideoxyU/ATATATA/iSp18//iSp18//iSp18//iSp18/T/3AmMO/(SEQ ID NO: 33); and MBC4: /5Phos/CCTATATNNNAGATCG-GAAGAGCACACGTCTTAATATTTAATAT/ideoxyU/ATA TAT/iSp18//iSp18//iSp18//iSp18/T/3AmMO/) (SEQ ID NO: 34).

Two bead types were prepared in total, one displaying a reporter antibody with MBC3 and Ab05 (m6A), the other displaying a reporter antibody with MBC4 and Ab16 (m5C). IP of spacer-modified RNA samples was conducted as described above. Barcoding was induced by adding the RNA loaded, washed beads to a ligation mix containing a mixture of splint oligonucleotides. The splints were designed such that one side hybridizes to the spacer region of the target RNA and the other side is complementary to the 7 nt long MBC3 or MBC4 of the adapters. One set of splints hybridizes to 6 bases of the spacer region (AAAGCTGCACTCA/3SpC3/ (7-6 MBC3) (SEQ ID NO: 18) and ATATAGGCACTCA/3SpC3/ (7-6 MBC4) (SEQ ID NO: 19), the other set binds to 3 bases of the spacer region (AAAGCTGCAC/3SpC3/ (7-3 MBC3) (SEQ ID NO: 20) and ATATAGGCAC/3SpC3/ (7-3 MBC4)) (SEQ ID NO: 21). Both sides of the splint, the length and sequence of the universal spacer and the adapter complements were tuned to discourage binding stabilization by mechanisms other than modification recognition by the antibody to ensure encoding by proximity ligation. While spacers and spacer complements were present during the IP step for workflows that rely on primer extension for encoding (i.e. those shown in FIG. 17A and FIG. 19A), this protocol adds the splints after IP, thus uncoupling IP from nucleic acid hybridization. For simultaneous detection of m6A and m5C, the ligation mix contained 0.5 uM of a MBC3 and MBC4 splint, 10 units/uL T4 DNA ligase, 50 mM Tris-HCl, 10 mM MgCl2, 1 mM ATP, and 10% PEG8000. After completion of adapter ligation, the i7 adapter was primed, followed by reverse transcription with template switching and PCR amplification as described in Example 13. The library was sequenced, and RNA modifications were identified and localized to specific loci via bioinformatic deconvolution of the MBCs appended to each RNA fragment (FIGS. 20B and 20C). This workflow was able to detect m6A and m5C with a specificity similar to that reported for encoding by reverse transcription (example 13).

Example 16: A-Tailing and Encoding Example

In this example, a universal sequence for encoding by primer extension was introduced by A-tailing of the 3' end of RNA (FIG. 21A), thus obviating the need for a single stranded spacer ligation (example 12)A-tailing reactions are known to be higher yielding than single stranded ligations and unbiased, which benefits the assay sensitivity by means of providing better transcriptome coverage.

1.5 kb IVT RNA was fragmented to 150 bases by incubating in 1× T4 RNA ligase I buffer (New England Biolabs) at 90C for 20 min. The 3' ends of RNA were dephosphorylated by addition of T4 Polynucleotide Kinase (cat. no. T4PK-200, MCLab) in the presence of RNase inhibitor (cat. no. AM2694, Thermo Fisher) at 37C for 30 min. The reaction was supplemented with 5 units of E. coli Poly(A) Polymerase (cat. no. M0276L, New England Biolabs), 0.95 mM ATP, 0.05 mM dATP, and 1× E. coli Poly(A) Polymerase buffer, then incubated for 10 min at 37° C. The A-tailed RNA was purified by 1.8× volumes of RNAClean XP beads.

To detect m6A in an RNA sample, a bead was prepared that displays Ab05 (m6A) and a reporter antibody conjugated to an adapter containing a barcode that identifies m6A (MBC000) (/5AmMC6/T/iSp18//iSp18//iSp18//iSp18/ AGACGTGTGCTCTTCCGATCTNNNNNNNNACT AATTTTTTTTTTTTVN) (SEQ ID NO: 35). The adapter architecture comprised a poly(dT) sequence that hybridizes to A-tailed RNA, the MBC (underlined), a UMI (NNNNNNNN) and the i7 Illumina adapter (sequence 5' of the UMI).

For each sample, the bead was loaded, and IP of A-tailed RNA fragments was performed using the same method as in Example 13. Briefly, beads, 0.05 to 50 ng of RNA, and 10 units/uL of RNase inhibitor were incubated in 1×PBST. After incubation, the beads were washed and reverse transcribed by elongation of the immobilized Illumina i7 adapter. Template switching with a TSO introduced the Illumina i5 adapter necessary for PCR amplification and sequencing. After completion of the reaction, the supernatant was amplified by PCR using standard Illumina index primers (1 uM forward primer, 1 uM reverse primer, NEBNext Ultra II Q5 (cat. no. M0544X, New England Biolabs) for 10-13 cycles (30 sec at 98° C., then n cycles of 10 sec at 98° C., 75 sec at 65° C., and final extension for 5 min at 65° C.). The library was sequenced, and RNA modifications were identified and localized to specific loci via bioinformatic deconvolution of the MBCs appended to each RNA fragment.

FIG. 21B shows the sequencing results obtained for the described barcoding method using 0.5 ng of pooled IVT as input. In this example, the IVT RNA pool consisted of 70% unmodified PhiX RNA, 10% m6A-modified FLuc-RNA, 10% inosine-modified Lambda RNA and 10% m5C-modified M13 RNA. The plots show that the MBC was associated with the correct genome.

Example 17: Multiplexed Detection of m6A, Inosine and m5C in mRNA Using Encoding by Reverse Transcription, Template Switching and a Streptavidin Bead This example describes an end-to-end library preparation workflow with an integrated barcoding step for the detection of RNA modifications in an mRNA enriched sample derived from a human lung carcinoma immortalized cell line (A549, cat. No. 636141, Takara). Barcoding is accomplished by bidirectional extension of the RNA target and the adapter using a reverse transcriptase (FIG. 17A).

To detect m5C, m6A and inosine in an RNA sample, a minimum of three different bead types was required. Biotinylated adapters and Protein G were bound to streptavidin-coated beads (cat. No. 65305, Thermo Fisher) followed by affinity binding of modification-specific antibodies (FIG. 1D). The first bead type displayed an anti-m6A (cat. no. MA5-3303, Thermo Fisher) and an adapter containing MBC-111 (/5Biosg//iSp18//iSp18//iSp18//iSp18/CTA-CACGACGCTCTTCCGATCTNNNNNNNNNNNN GACACCACACTCAGT) (SEQ ID NO: 36). A second bead type exhibited an anti-inosine (cat. no. PM098, MBL) and an adapter containing MBC-112 (/5Biosg//iSp18//iSp18// iSp18//iSp18/CTACACGACGCTCTTCC-GATCTNNNNNNNNNNNN TCAAGCGCACTCAGT) (SEQ ID NO: 37). A third bead type featured an anti-m5C (cat. no. MA5-24694, Thermo Fisher) and an adapter containing MBC-113 (/5Biosg//iSp18//iSp18//iSp18//iSp18/ CTACACGACGCTCTTCCGATCTNNNNNNNNNNNN AGCGATTCACTCAGT) (SEQ ID NO: 38).

The adapters contained the spacer sequence (bold letters at the 3' end), the MBC (underlined), a UMI (NNNNNNNNNNN) and the i5 Illumina adapter (sequence 5' of the UMI).

Per sample, equal volumes of each loaded bead type were combined and used as substrates for IP. The first assay step is an IP of the spacer ligated RNA prepared according to example 12. The bead pool is mixed with 10 uL of 50 ng of RNA and 10 units/uL of RNase inhibitor in 1×TBST and incubated for 30 min. After incubation, the beads were washed with 1×TBST buffer and resuspended in 1× Superscript IV reverse transcription buffer (cat. no. 18090050, Thermo Fisher). Washing removed non-specifically bound RNA and preserved the specific RNA modification-antibody complexes. A reverse transcriptase elongated the 3' end of the RNA targets, thereby copying the MBC and i5 adapter, and simultaneously synthesized cDNA by extending the 3' end of the adapter.

The IP beads were added to the reverse transcription reaction (1× Superscript IV buffer, 0.5 u/uL Superase-In, 5 u/uL Superscript IV reverse transcriptase, 1 mM dNTPs, 2 uM template switching oligo, "TSO" (AGACGTGTGCTCTTCCGATCTrGrGrG) (SEQ ID NO: 9) and incubated for 15 min at 23C, followed by 60 min at 50° C. After completion of the reaction, the beads were washed with 1×TBST, RNA removed by denaturation with 0.1N NaOH, and neutralized by additional washes with 1×TBST. The cDNA attached to beads was amplified by PCR by adding the beads directly to the reaction mixture containing standard Illumina index primers (0.5 uM forward primer, 0.5 uM reverse primer, NEBNext Ultra II Q5 (cat.

no. M0544X, New England Biolabs) for 17-19 cycles (30 sec at 98° C., then n cycles of 10 sec at 98° C., 75 sec at 65° C., and 5 min at 65° C.).

Figure 23C:
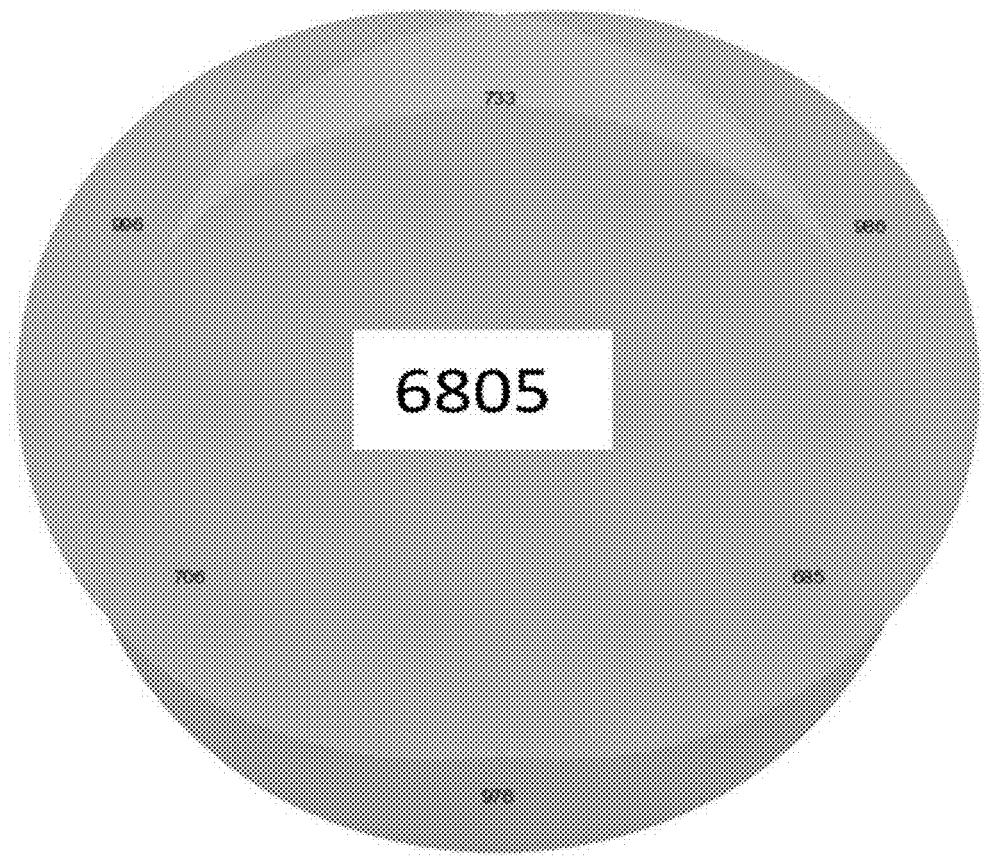
Figure 23C:
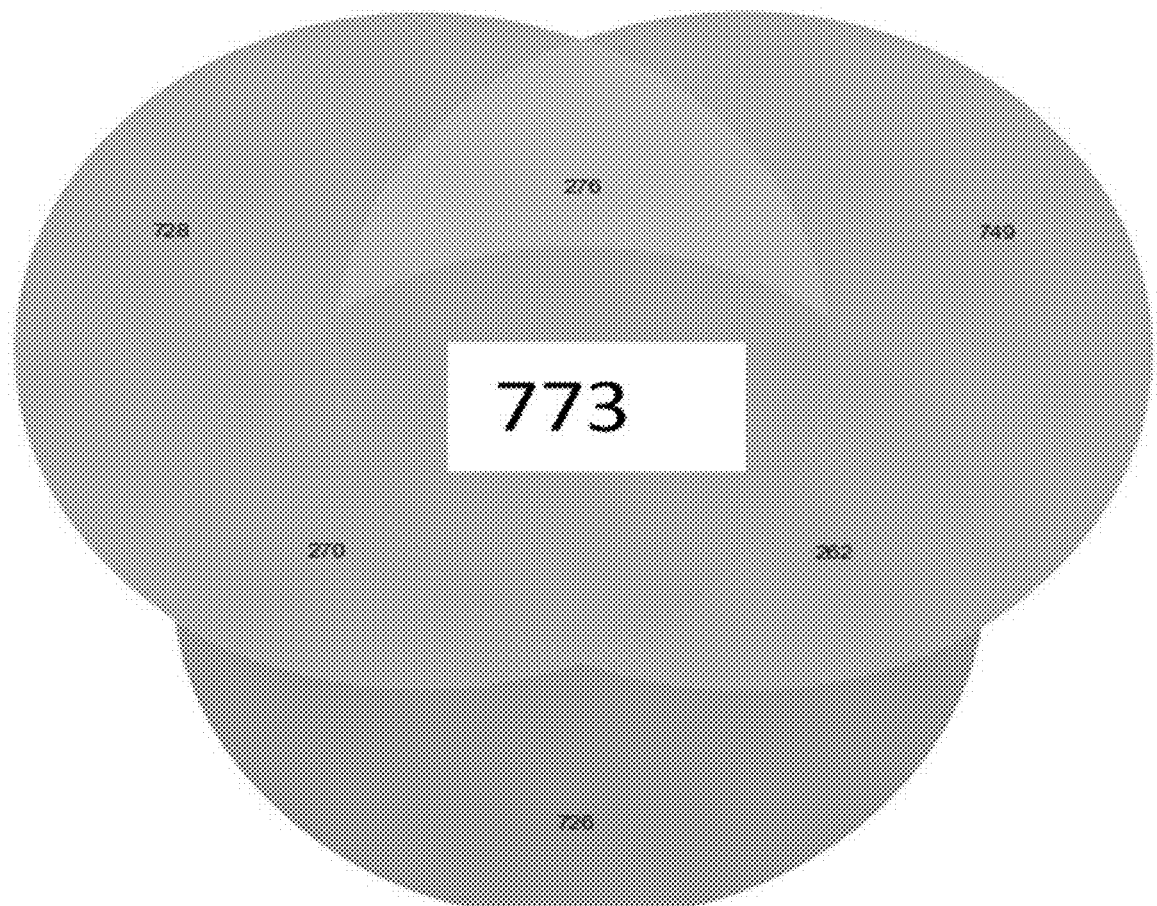
Figure 23C:
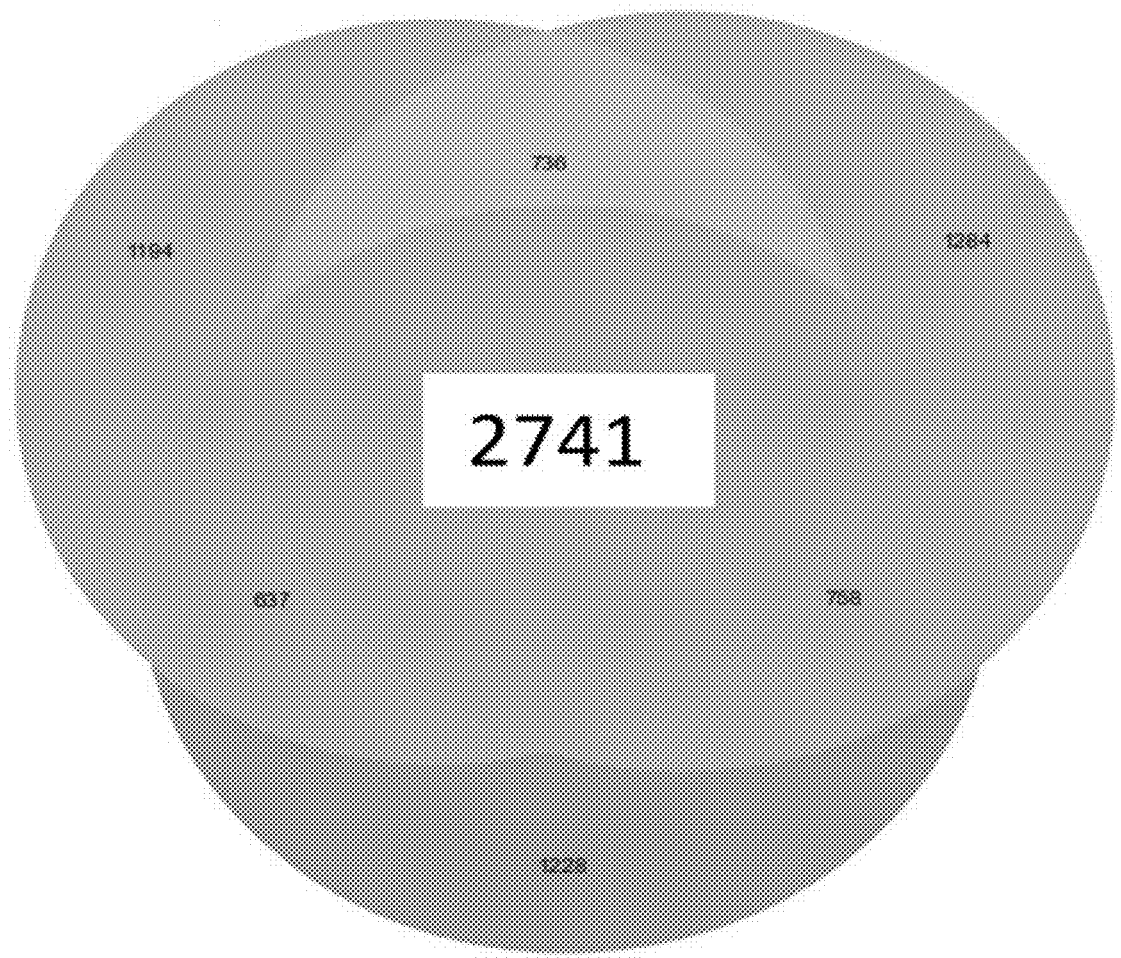

The library was sequenced on an Illumina sequencer and RNA modifications were identified and localized to specific loci via bioinformatic deconvolution of the MBCs appended to each RNA fragment. FIG. 23A shows the global barcode representation for technical triplicates of IP RNA and a non-enriched (input) sample. As expected, the IP samples show enrichment of MBC111 reads as m6A modifications in mRNA are known to occur 5-10× more frequently than inosine or m5C. Reads were aligned and stack-up of reads for each barcode were compared between IP and input samples and peaks were called with MACS2. FIG. 23B shows the location of called peaks within genes. The shift in peak call for MBC111-m6A towards the 3' end matches the known bias of m6A modifications to occur toward the 3' UTR (untranslated region). FIG. 23C shows the number of peaks called for each modification and each replicate sample in a Venn diagram. The number of high confidence peaks, i.e., peaks that occurred in all three replicates, were 6,805 for m6A, 773 for inosine and 2741 for m5C, which is in line with the number of modification sites reported for these modifications by other methods.

Example 18: Detection of m6A Using an Antibody-Protein A-Tn5 Complex

This example describes the use of an immobilized conjugate comprising an antibody and proteinA-Tn5 fusion protein for the tagmentation of DNA-RNA heteroduplexes specifically at the site of a m6A modification (FIG. 1H). The tagmentation reaction introduces a barcode that identifies the RNA modification. The advantage of this format is that the transposase is directly associated with the antibody, which limits the tagmentation activity to the RNA modification site.

m6A-specific beads were prepared by forming a conjugate comprising m6A antibody and protein A-Tn5 molecules (Diagnode, cat. no. C01070002) in solution and then immobilizing the conjugate on protein G beads (FIGS. 1H and 24A). Like protein G, protein A binds strongly to a Fc region of antibodies, thus immobilizing Tn5 on the bead in direct proximity of the m6A antibody binding pocket. Each Tn5 dimer was loaded with a pair of mosaic-end (ME) adapters, both containing a barcode indicative of m6A (i7 ME adapter: 5'Phos-CTGTCTCTTATACACATCT (SEQ ID NO: 16) hybridized to CAAGCAGAAGACGGCATACGAGAT-NNNNNNNN-GTCTCGTGGGCTCG-GAGATGTGTATAAGAGACAG (SEQ ID NO: 39); i5 ME adapter: 5'Phos-CTGTCTCTTATACACATCT (SEQ ID NO: 16) hybridized to AATGATACGGCGAC-CACCGAGATCTACAC-NNNNNNNN-TCGTCGGCAGCGTCAGATGTGTATAAGAGACAG (SEQ ID NO: 40).

First, RNA containing a mixture of unmodified and m6A-modified A-tailed IVT RNA (c. f. example 11) was reverse transcribed using Superscript IV reverse transcriptase and a poly-dT oligo primer. The DNA-RNA heteroduplexes were then added to the beads in IP buffer (50 mM HEPES pH 7.5, 300 mM NaCl, 0.1 mM EDTA, 0.05% Tween®-20) and allowed to immunoprecipitate for 30 min. During this step, the m6A antibody selectively bound the m6A modified RNA. The beads were washed and a $Mg^{2+}$-containing tagmentation buffer (10 mM Tris-HCl pH 8.5, 5 mM MgCl2, 10% DMF) was added to initiate the tagmentation reaction. The tagmented DNA-RNA heteroduplexes were gap filled and PCR amplified using a reaction mixture containing standard Illumina index primers or library amplification primers (0.5 uM forward primer, 0.5 uM reverse primer, NEBNext Ultra II Q5 (cat. no. M0544X, New England Biolabs) for 17-19 cycles (5 min at 72° C., 2 min at 98° C., then n cycles of 10 sec at 98° C.-75 sec at 65° C., and final extension for 5 min at 65° C.). The library was sequenced on an Illumina sequencer and RNA modifications were identified and localized to specific loci via bioinformatic deconvolution of the barcodes appended to each RNA fragment.

FIG. 24B compares the read coverage plots for the input (control) and the immunoprecipitated samples. The m6A modified region shows significant read enrichment in the immunoprecipitated samples, whereas other regions are depleted relative to the RNA input. To determine the optimal protein A-Tn5 loading ratio, the experiment was conducted with a 2×, 4× or 8× excess of protein A-Tn5 over antibody. All conditions exhibited specific enrichment of m6A, however, because the library yield was negatively impacted by higher protein A-Tn5 ratios without improved specificity, we conclude that a 2-4× excess of protein A-Tn5 is ideal. Taken together, these experiments establish that a combination of IP by an antibody-pA-Tn5 complex followed by tagmentation is effective at detecting m6A in a complex pool of RNA.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

What is claimed is:

1. A method for detecting a plurality of non-canonical features in a plurality of target nucleic acids, the method comprising:
(i) providing a plurality of target nucleic acids by reverse transcribing target RNA molecules to form DNA-RNA heteroduplex molecules or providing target double-stranded DNA molecules;
(ii) contacting a solution comprising the plurality of target nucleic acids with a composition comprising:
a substrate,
a binding domain coupled to the substrate via a first linker or a secondary recognition element,
mosaic end (ME) adapters coupled to the substrate via a second linker or recognition element, and
a transposase,
wherein the transposase is loaded to the immobilized ME adapters,
wherein the binding domain binds specifically to a non-canonical feature of a DNA or an RNA,
wherein at least one of the ME adapters comprises a nucleic acid barcode sequence unique to the non-canonical feature; or
the substrate,
the binding domain coupled to the substrate via a linker or secondary recognition element, and
the transposase coupled to the binding domain,
wherein the transposase is loaded with ME adapters,
wherein the binding domain binds specifically to a non-canonical feature of a DNA or an RNA,
wherein at least one of the ME adapters comprises a nucleic acid barcode sequence unique to the non-canonical feature;
(iii) transferring, using transposase, two adapters, at least one of them comprising the nucleic acid barcode, to a double-stranded target nucleic acid comprising the non-canonical feature to generate barcoded target nucleic acids,
(iv) amplifying the barcoded target nucleic acids; and
(v) sequencing the barcoded target nucleic acids,
wherein steps (ii) and (iii) are performed concurrently or sequentially.

2. The method of claim 1, wherein step (ii) is performed in the absence of $Mg^{2+}$ ions, wherein step (ii) is performed before step (iii).

3. The method of claim 1, wherein step (iii) further comprises adding $Mg^{2+}$ ions, wherein step (iii) is performed after step (ii).

4. The method of claim 1, wherein the nucleic acid barcode is transferred to the target nucleic acid by enzymatic transposition or wherein the transposase is Tn5 transposase.

5. The method of claim 1, wherein the ME adapters comprising the barcode are immobilized on the substrate via their 5' ends.

6. The method of claim 1, wherein the non-canonical features are selected from the group consisting of: one or more modified nucleosides, one or more nucleic acid lesions, and one or more structural elements.

7. The method of claim 6, wherein the one or more modified nucleosides comprise a chemical derivative of pseudouridine generated by attaching a chemical moiety to a pseudouridine prior to step (i).

8. The method of claim 6, wherein the one or more modified nucleosides are selected from 3-methylcytidine (m3C), 5-methylcytidine (m5C), N4-acetylcytidine (ac4C), pseudouridine (ψ), 1-methyladenosine (m1A), N6-methyladenosine (m6A), inosine (I), 7-methylguanosine (m7G), dihydrouridine (D), 3-methyluridine (m3U), 5-methyluridine (m5U), 1-methylguanosine (m1G), N2-methylguanosine (m2G), 5-methyldeoxycytidine (m5dC), N4-methyldeoxycytidine, 5-hydroxymethylcytidine (5-hmC), 5-hydroxymethyldeoxycytidine (5hmdC), 5-carboxydeoxycytidine (5cadC), 5-formylcytidine (5fC), 5-formyldeoxycytidine (5fdC), 6-methyldeoxyadenosine, N7-methylguanosine (m7G), 2,7,2'-methylguanosine, or ribose methylation (Nm);

wherein the one or more nucleic acid lesions are selected from 8-oxo-guanine (8-oxoG), one or more abasic sites, cis-platin crosslinks, benzo (a) pyrene diol epoxide (BPDE)-adducts, cyclobutene pyrimidine dimers (CPD), pyrimidine-pyrimidone (6-4) photoproduct (6-4PP), 6-Omethylguanine (O6-MedG), or O6-(Carboxymethyl)-2'-deoxyguanosine (O6-CMdG); and/or wherein the one or more structural elements are selected from a hairpin, loop, Z-DNA structure, G-quadruplex, triplex, i-motif, bulge, triplex, three-way junction, cruciform structure, tetraloop, ribose zipper, or pseudoknot.

9. A method for detecting a plurality of non-canonical features in a plurality of target nucleic acids, the method comprising:
(i) contacting a solution comprising the plurality of target nucleic acids with one or more compositions,
wherein the one or more compositions are each independently selected from:
(a) a composition comprising:
a substrate,
a binding domain coupled to the substrate via a first linker or via a recognition element, and
an adapter coupled to the recognition element or to the substrate via a second linker,
wherein the binding domain is configured to bind specifically to a non-canonical feature of a DNA or an RNA;
wherein the adapter comprises a nucleic acid barcode sequence unique to the non-canonical feature;
(b) a composition comprising:
a substrate,
a binding domain coupled to the substrate via a first linker or via a plurality of recognition elements, and
an adapter coupled to one or more of the plurality of recognition elements or to the substrate via a second linker,
wherein the binding domain is configured to bind specifically to a non-canonical feature of a DNA or an RNA;
wherein the adapter comprises a nucleic acid barcode sequence unique to the non-canonical feature; or
a combination of (a) and (b);
(ii) performing one of (a1) and (b1):
(a1) transferring the nucleic acid barcode to a target nucleic acid comprising the non-canonical feature to generate a barcoded target nucleic acid,
(b1) generating a barcoded copy of the target nucleic acid comprising the non-canonical feature;
(iii) amplifying the barcoded target nucleic acids; and
(iv) sequencing the barcoded target nucleic acids,
wherein steps (i) and (ii) are performed sequentially or concurrently.

10. The method of claim 9, wherein the nucleic acid barcode is transferred to the target nucleic acid by enzymatic transfer or by chemical ligation.

11. The method of claim 9, wherein the nucleic acid barcode is transferred to the target nucleic acid enzymatically by single stranded ligation, splint ligation, primer extension, reverse transcription, or double-stranded ligation.

12. The method of claim 9, further comprising ligating a universal nucleic acid sequence to the 3' or 5' end or both ends of the target nucleic acid before step (i).

13. The method of claim 9, further comprising tailing the 3' end of the target nucleic acid enzymatically with a plurality of a single type of nucleotide before step (i).

14. The method of claim 9, wherein the enzymatic transfer of the nucleic acid barcode to the target nucleic acid is performed by Avian Myeloblastosis Virus (AMV) Reverse Transcriptase, Moloney Murine Leukemia Virus (MMLV) Reverse Transcriptase or a group II intron-encoded Reverse Transcriptase, or derivatives thereof.

15. The method of claim 9, wherein the 3' end of the adapter is configured to bind to the 3' end of the target nucleic acid and step (ii) further comprises introducing a modification specific barcode, wherein the 3' end of the adapter comprises a 3' spacer sequence and binds site-specifically to a complementary synthetic spacer sequence displayed by the target nucleic acid and one or both of the 3' end of the adapter and the 3' end of the target nucleic acid are extended by reverse transcriptase or a DNA polymerase.

16. The method of claim 9, wherein an adapter with 3' degenerate bases primes the target nucleic acid randomly and step (ii) further comprises introducing a modification-specific barcode, wherein the 3' end of the adapter is extended by reverse transcriptase or a DNA polymerase.

17. The method of claim 9, wherein the barcoded target nucleic acid is immobilized on the substrate via its 5' end.

18. The method of claim 9, wherein the barcoded target nucleic acid is immobilized on the substrate via its 3' end.

19. The method of claim 9, wherein the amplifying step (iii) is performed on the substrate's surface.

20. The method of claim 9, further comprising forming clusters of identical copies of the target nucleic acid in step (iii).

21. The method of claim 20, further comprising in situ sequencing of the clusters of identical copies of target nucleic acid on the substrate in step (iv).

22. The method of claim 9, wherein the plurality of non-canonical features are selected from the group consisting of: one or more modified nucleosides, one or more nucleic acid lesions, and one or more structural elements.

23. The method of claim 22, wherein the one or more modified nucleosides are selected from a chemical derivative of pseudouridine generated by attaching a chemical moiety to pseudouridine prior to step (i).

24. The method of claim 22, wherein the one or more modified nucleosides are selected from 3-methylcytidine (m3C), 5-methylcytidine (m5C), N4-acetylcytidine (ac4C), pseudouridine (ψ), 1-methyladenosine (m1A), N6-methyladenosine (m6A), inosine (I), 7-methylguanosine (m7G), dihydrouridine (D), 3-methyluridine (m3U), 5-methyluridine (m5U), 1-methylguanosine (m1G), N2-methylguanosine (m2G), 5-methyldeoxycytidine (m5dC), N4-methyldeoxycytidine, 5-hydroxymethylcytidine (5-hmC), 5-hydroxymethyldeoxycytidine (5hmdC), 5-carboxydeoxycytidine (5cadC), 5-formylcytidine (5fC), 5-formyldeoxycytidine (5fdC), 6-methyldeoxyadenosine, N7-methylguanosine (m7G), 2,7,2'-methylguanosine, or ribose methylation (Nm);

wherein the one or more nucleic acid lesions are selected from 8-oxo-guanine (8-oxoG), one or more abasic sites, cis-platin crosslinks, benzo (a) pyrene diol epoxide (BPDE)-adducts, cyclobutene pyrimidine dimers (CPD), pyrimidine-pyrimidone (6-4) photoproduct (6-4PP), 6-Omethylguanine (O6-MedG), or O6-(Carboxymethyl)-2'-deoxyguanosine (O6-CMdG); and/or wherein the one or more structural elements are selected from a hairpin, loop, Z-DNA structure, G-quadruplex, triplex, i-motif, bulge, triplex, three-way junction, cruciform structure, tetraloop, ribose zipper, or pseudoknot.

25. The method of claim 9, wherein the plurality of target nucleic acids in step (i) have a nucleic acid lesion resulting from bulky adduct formation or base alkylation by an exogenous agent.

26. The method of claim 9, wherein the non-canonical feature is a pseudouridine.

27. The method of claim 25, wherein the exogenous agent is an alkylating agent.

28. The method of claim 9, wherein the substrate comprises a functionalized or patterned surface.

29. A method for detecting a plurality of non-canonical features in a plurality of target nucleic acids, the method comprising:
  (i) contacting a solution comprising the plurality of target nucleic acids with a plurality of compositions;
    wherein the plurality of compositions are each independently selected from:
      (a) a composition comprising:
        a substrate;
        a binding domain coupled to the substrate via a first linker or via a recognition element; and
        an adapter coupled to the recognition element or to the substrate via a second linker,
        wherein the binding domain is configured to bind specifically to a non-canonical feature of a DNA or an RNA;
        wherein the adapter comprises a nucleic acid barcode sequence unique to the non-canonical feature;
      (b) a composition comprising:
        a substrate,
        a recognition element coupled to the substrate via a first linker, and
        an adapter coupled to the recognition element or to the substrate via a second linker, and
        a binding domain,
        wherein the binding domain is configured to bind specifically to a non-canonical feature of a DNA or an RNA, and wherein the binding domain is immobilized by the recognition element, and
        wherein the adapter comprises a nucleic acid barcode sequence unique to the non-canonical feature;
      (c) a composition comprising:
        a substrate,
        a recognition element,
        a binding domain coupled to the substrate via a secondary recognition element,
        an adapter coupled to the substrate via a linker,
        wherein the binding domain is configured to bind specifically to a non-canonical feature of a DNA or an RNA, and
        wherein the adapter comprises a nucleic acid barcode sequence unique to the non-canonical feature;
      (d) a composition comprising:
        a substrate,
        a recognition element coupled to the substrate,
        a binding domain coupled to the substrate via a linker,
        an adapter coupled to the substrate via the recognition element,
        wherein the binding domain is configured to bind specifically to a non-canonical feature of a DNA or an RNA, and
        wherein the adapter comprises a nucleic acid barcode sequence unique to the non-canonical feature;
      (e) a composition comprising:
        a substrate,
        a binding domain coupled to the substrate via a first linker or via a plurality of recognition elements, and
        an adapter coupled to one or more of the plurality of recognition elements or to the substrate via a second linker,
        wherein the binding domain is configured to bind specifically to a non-canonical feature of a DNA or an RNA;
        wherein the adapter comprises a nucleic acid barcode sequence unique to the non-canonical feature; or
      any combination of (a) to (e);
    wherein the number of the plurality of compositions contacted in step (i) is equal to or greater than the number of non-canonical features,
    wherein the binding domains of the plurality of compositions each bind to different non-canonical features of a DNA or RNA or wherein multiple binding domains bind to the same non-canonical feature of a DNA or RNA; and
    wherein the adapters of the plurality of compositions each comprise a nucleic acid barcode sequence unique to the non-canonical feature bound specifically by the binding domain of that composition or unique to the binding domain;
  (ii) performing one of the following:
    (a1) transferring the nucleic acid barcode sequences of each of the plurality of compositions to a plurality of target nucleic acids, or
    (b1) generating barcoded copies of the plurality of target nucleic acids;
  (iii) amplifying the barcoded target nucleic acids; and
  (iv) sequencing the barcoded target nucleic acids.

30. The method of claim 29, wherein the adapter is provided in a ratio of 1 to 15 fold excess over the binding domain, and/or
  wherein the composition (a), the composition (b), the composition (c), the composition (d), the composition (e), or each of compositions (a) to (e) comprise two or more substrates.

* * * * *